United States Patent
Overmyer et al.

(10) Patent No.: US 10,743,873 B2
(45) Date of Patent: Aug. 18, 2020

(54) DRIVE ARRANGEMENTS FOR ARTICULATABLE SURGICAL INSTRUMENTS

(71) Applicant: Ethicon LLC, Guaynabo, PR (US)

(72) Inventors: Mark D. Overmyer, Cincinnati, OH (US); Chester O. Baxter, III, Loveland, OH (US); Frederick E. Shelton, IV, Hillsboro, OH (US); Jerome R. Morgan, Cincinnati, OH (US)

(73) Assignee: Ethicon LLC, Guaynabo, PR (US)

( * ) Notice: Subject to any disclaimer, the term of this patent is extended or adjusted under 35 U.S.C. 154(b) by 203 days.

(21) Appl. No.: 15/807,038

(22) Filed: Nov. 8, 2017

(65) Prior Publication Data

US 2018/0110518 A1 Apr. 26, 2018

Related U.S. Application Data

(63) Continuation of application No. 14/575,139, filed on Dec. 18, 2014, now Pat. No. 9,844,375.

(51) Int. Cl.
*A61B 17/072* (2006.01)
*A61B 17/00* (2006.01)
*A61B 17/29* (2006.01)

(52) U.S. Cl.
CPC ............... *A61B 17/07207* (2013.01); *A61B 2017/00017* (2013.01); *A61B 2017/00367* (2013.01);
(Continued)

(58) Field of Classification Search
CPC .............................................. A61B 17/07207
(Continued)

(56) References Cited

U.S. PATENT DOCUMENTS 66,052 A 6/1867 Smith
662,587 A 11/1900 Blake
(Continued)

FOREIGN PATENT DOCUMENTS

AU 2012200594 A1 2/2012
AU 2011218702 B2 6/2013
(Continued)

OTHER PUBLICATIONS

ASTM procedure D2240-00, "Standard Test Method for Rubber Property-Durometer Hardness," (Published Aug. 2000).
(Continued)

*Primary Examiner* — Nathaniel C Chukwurah

(57) ABSTRACT

A shaft assembly for a surgical instrument that includes a movable drive member. In at least one form, the surgical instrument includes a spine assembly that is couplable to the surgical instrument and has a surgical end effector coupled thereto by an articulation joint. The shaft assembly in one form includes a proximal firing member and an intermediate firing member that is coupled to a distal firing member. The distal firing member is configured for selective travel through the surgical end effector. At least one articulation driver is coupled to the surgical end effector to apply articulation motions thereto. A clutch assembly interfaces with the primary and intermediate firing members and the articulation driver such that when in an articulation orientation, movement of the drive member results in movement of the articulation driver and when in a firing orientation, movement of the drive member results in movement of the intermediate and distal firing members. A separate articulation motor may be employed to actuate the articulation driver.

22 Claims, 30 Drawing Sheets

(52) U.S. Cl.
CPC ............ *A61B 2017/00371* (2013.01); *A61B 2017/00398* (2013.01); *A61B 2017/00464* (2013.01); *A61B 2017/07271* (2013.01); *A61B 2017/07285* (2013.01); *A61B 2017/2927* (2013.01); *A61B 2017/2947* (2013.01)

(58) Field of Classification Search
USPC .................................................. 227/180.1
See application file for complete search history.

(56) References Cited

U.S. PATENT DOCUMENTS

| | | |
|---|---|---|
| 670,748 A | 3/1901 | Weddeler |
| 719,487 A | 2/1903 | Minor |
| 804,229 A | 11/1905 | Hutchinson |
| 951,393 A | 3/1910 | Hahn |
| 1,188,721 A | 6/1916 | Bittner |
| 1,306,107 A | 6/1919 | Elliott |
| 1,314,601 A | 9/1919 | McCaskey |
| 1,677,337 A | 7/1928 | Grove |
| 1,794,907 A | 3/1931 | Kelly |
| 1,849,427 A | 3/1932 | Hook |
| 1,944,116 A | 1/1934 | Stratman |
| 1,954,048 A | 4/1934 | Jeffrey et al. |
| 2,037,727 A | 4/1936 | La Chapelle |
| 2,132,295 A | 10/1938 | Hawkins |
| 2,161,632 A | 6/1939 | Nattenheimer |
| D120,434 S | 5/1940 | Gold |
| 2,211,117 A | 8/1940 | Hess |
| 2,214,870 A | 9/1940 | West |
| 2,224,882 A | 12/1940 | Peck |
| 2,318,379 A | 5/1943 | Davis et al. |
| 2,329,440 A | 9/1943 | La Place |
| 2,377,581 A | 6/1945 | Shaffrey |
| 2,406,389 A | 8/1946 | Lee |
| 2,441,096 A | 5/1948 | Happe |
| 2,448,741 A | 9/1948 | Scott et al. |
| 2,450,527 A | 10/1948 | Smith |
| 2,507,872 A | 5/1950 | Unsinger |
| 2,526,902 A | 10/1950 | Rublee |
| 2,527,256 A | 10/1950 | Jackson |
| 2,578,686 A | 12/1951 | Fish |
| 2,638,901 A | 5/1953 | Sugarbaker |
| 2,674,149 A | 4/1954 | Benson |
| 2,701,489 A | 2/1955 | Osborn |
| 2,711,461 A | 6/1955 | Happe |
| 2,742,955 A | 4/1956 | Dominguez |
| 2,804,848 A | 9/1957 | O'Farrell et al. |
| 2,808,482 A | 10/1957 | Zanichkowsky et al. |
| 2,853,074 A | 9/1958 | Olson |
| 2,856,192 A | 10/1958 | Schuster |
| 2,887,004 A | 5/1959 | Stewart |
| 2,957,353 A | 10/1960 | Lewis |
| 2,959,974 A | 11/1960 | Emrick |
| 3,032,769 A | 5/1962 | Palmer |
| 3,060,972 A | 10/1962 | Sheldon |
| 3,075,062 A | 1/1963 | Iaccarino |
| 3,078,465 A | 2/1963 | Bobrov |
| 3,079,606 A | 3/1963 | Bobrov et al. |
| 3,080,564 A | 3/1963 | Strekopitov et al. |
| 3,166,072 A | 1/1965 | Sullivan, Jr. |
| 3,180,236 A | 4/1965 | Beckett |
| 3,196,869 A | 7/1965 | Scholl |
| 3,204,731 A | 9/1965 | Bent et al. |
| 3,266,494 A | 8/1966 | Brownrigg et al. |
| 3,269,630 A | 8/1966 | Fleischer |
| 3,269,631 A | 8/1966 | Takaro |
| 3,275,211 A | 9/1966 | Hirsch et al. |
| 3,317,103 A | 5/1967 | Cullen et al. |
| 3,317,105 A | 5/1967 | Astafjev et al. |
| 3,357,296 A | 12/1967 | Lefever |
| 3,359,978 A | 12/1967 | Smith, Jr. |
| 3,377,893 A | 4/1968 | Shorb |
| 3,480,193 A | 11/1969 | Ralston |
| 3,490,675 A | 1/1970 | Green et al. |
| 3,494,533 A | 2/1970 | Green et al. |
| 3,499,591 A | 3/1970 | Green |
| 3,503,396 A | 3/1970 | Pierie et al. |
| 3,509,629 A | 5/1970 | Kidokoro |
| 3,551,987 A | 1/1971 | Wilkinson |
| 3,568,675 A | 3/1971 | Harvey |
| 3,572,159 A | 3/1971 | Tschanz |
| 3,583,393 A | 6/1971 | Takahashi |
| 3,589,589 A | 6/1971 | Akopov |
| 3,598,943 A | 8/1971 | Barrett |
| 3,608,549 A | 9/1971 | Merrill |
| 3,618,842 A | 11/1971 | Bryan |
| 3,638,652 A | 2/1972 | Kelley |
| 3,640,317 A | 2/1972 | Panfili |
| 3,643,851 A | 2/1972 | Green et al. |
| 3,650,453 A | 3/1972 | Smith, Jr. |
| 3,661,666 A | 5/1972 | Foster et al. |
| 3,662,939 A | 5/1972 | Bryan |
| 3,688,966 A | 9/1972 | Perkins et al. |
| 3,695,646 A | 10/1972 | Mommsen |
| 3,709,221 A | 1/1973 | Riely |
| 3,717,294 A | 2/1973 | Green |
| 3,726,755 A | 4/1973 | Shannon |
| 3,727,904 A | 4/1973 | Gabbey |
| 3,734,207 A | 5/1973 | Fishbein |
| 3,740,994 A | 6/1973 | De Carlo, Jr. |
| 3,744,495 A | 7/1973 | Johnson |
| 3,746,002 A | 7/1973 | Haller |
| 3,747,603 A | 7/1973 | Adler |
| 3,747,692 A | 7/1973 | Davidson |
| 3,751,902 A | 8/1973 | Kingsbury et al. |
| 3,752,161 A | 8/1973 | Bent |
| 3,799,151 A | 3/1974 | Fukaumi et al. |
| 3,808,452 A | 4/1974 | Hutchinson |
| 3,815,476 A | 6/1974 | Green et al. |
| 3,819,100 A | 6/1974 | Noiles et al. |
| 3,821,919 A | 7/1974 | Knohl |
| 3,826,978 A | 7/1974 | Kelly |
| 3,836,171 A | 9/1974 | Hayashi et al. |
| 3,837,555 A | 9/1974 | Green |
| 3,841,474 A | 10/1974 | Maier |
| 3,851,196 A | 11/1974 | Hinds |
| 3,863,639 A | 2/1975 | Kleaveland |
| 3,863,940 A | 2/1975 | Cummings |
| 3,883,624 A | 5/1975 | McKenzie et al. |
| 3,885,491 A | 5/1975 | Curtis |
| 3,892,228 A | 7/1975 | Mitsui |
| 3,894,174 A | 7/1975 | Cartun |
| 3,902,247 A | 9/1975 | Fleer et al. |
| 3,940,844 A | 3/1976 | Colby et al. |
| 3,944,163 A | 3/1976 | Hayashi et al. |
| 3,950,686 A | 4/1976 | Randall |
| 3,952,747 A | 4/1976 | Kimmell, Jr. |
| 3,955,581 A | 5/1976 | Spasiano et al. |
| 3,959,879 A | 6/1976 | Sellers |
| RE28,932 E | 8/1976 | Noiles et al. |
| 3,972,734 A | 8/1976 | King |
| 3,981,051 A | 9/1976 | Brumlik |
| 4,025,216 A | 5/1977 | Hives |
| 4,027,746 A | 6/1977 | Kine |
| 4,034,143 A | 7/1977 | Sweet |
| 4,038,987 A | 8/1977 | Komiya |
| 4,054,108 A | 10/1977 | Gill |
| 4,060,089 A | 11/1977 | Noiles |
| 4,066,133 A | 1/1978 | Voss |
| 4,085,337 A | 4/1978 | Moeller |
| 4,100,820 A | 7/1978 | Evett |
| 4,106,446 A | 8/1978 | Yamada et al. |
| 4,106,620 A | 8/1978 | Brimmer et al. |
| 4,108,211 A | 8/1978 | Tanaka |
| 4,111,206 A | 9/1978 | Vishnevsky et al. |
| 4,127,227 A | 11/1978 | Green |
| 4,129,059 A | 12/1978 | Van Eck |
| 4,132,146 A | 1/1979 | Uhlig |
| 4,135,517 A | 1/1979 | Reale |
| 4,154,122 A | 5/1979 | Severin |
| 4,169,990 A | 10/1979 | Lerdman |
| 4,180,285 A | 12/1979 | Reneau |
| 4,185,701 A | 1/1980 | Boys |

(56) References Cited

U.S. PATENT DOCUMENTS

| | | |
|---|---|---|
| 4,190,042 A | 2/1980 | Sinnreich |
| 4,198,734 A | 4/1980 | Brumlik |
| 4,198,982 A | 4/1980 | Fortner et al. |
| 4,207,898 A | 6/1980 | Becht |
| 4,213,562 A | 7/1980 | Garrett et al. |
| 4,226,242 A | 10/1980 | Jarvik |
| 4,239,431 A | 12/1980 | Davini |
| 4,241,861 A | 12/1980 | Fleischer |
| 4,244,372 A | 1/1981 | Kapitanov et al. |
| 4,250,436 A | 2/1981 | Weissman |
| 4,261,244 A | 4/1981 | Becht et al. |
| 4,272,002 A | 6/1981 | Moshofsky |
| 4,272,662 A | 6/1981 | Simpson |
| 4,274,304 A | 6/1981 | Curtiss |
| 4,274,398 A | 6/1981 | Scott, Jr. |
| 4,275,813 A | 6/1981 | Noiles |
| 4,278,091 A | 7/1981 | Borzone |
| 4,289,131 A | 9/1981 | Mueller |
| 4,289,133 A | 9/1981 | Rothfuss |
| 4,290,542 A | 9/1981 | Fedotov et al. |
| D261,356 S | 10/1981 | Robinson |
| 4,293,604 A | 10/1981 | Campbell |
| 4,296,654 A | 10/1981 | Mercer |
| 4,296,881 A | 10/1981 | Lee |
| 4,304,236 A | 12/1981 | Conta et al. |
| 4,305,539 A | 12/1981 | Korolkov et al. |
| 4,312,363 A | 1/1982 | Rothfuss et al. |
| 4,312,685 A | 1/1982 | Riedl |
| 4,317,451 A | 3/1982 | Cerwin et al. |
| 4,319,576 A | 3/1982 | Rothfuss |
| 4,321,002 A | 3/1982 | Froehlich |
| 4,321,746 A | 3/1982 | Grinage |
| 4,328,839 A | 5/1982 | Lyons et al. |
| 4,331,277 A | 5/1982 | Green |
| 4,340,331 A | 7/1982 | Savino |
| 4,347,450 A | 8/1982 | Colligan |
| 4,348,603 A | 9/1982 | Huber |
| 4,349,028 A | 9/1982 | Green |
| 4,350,151 A | 9/1982 | Scott |
| 4,353,371 A | 10/1982 | Cosman |
| 4,357,940 A | 11/1982 | Muller |
| 4,361,057 A | 11/1982 | Kochera |
| 4,366,544 A | 12/1982 | Shima et al. |
| 4,369,013 A | 1/1983 | Abildgaard et al. |
| 4,373,147 A | 2/1983 | Carlson, Jr. |
| 4,376,380 A | 3/1983 | Burgess |
| 4,379,457 A | 4/1983 | Gravener et al. |
| 4,380,312 A | 4/1983 | Landrus |
| 4,382,326 A | 5/1983 | Rabuse |
| 4,383,634 A | 5/1983 | Green |
| 4,393,728 A | 7/1983 | Larson et al. |
| 4,394,613 A | 7/1983 | Cole |
| 4,396,139 A | 8/1983 | Hall et al. |
| 4,397,311 A | 8/1983 | Kanshin et al. |
| 4,402,445 A | 9/1983 | Green |
| 4,406,621 A | 9/1983 | Bailey |
| 4,408,692 A | 10/1983 | Sigel et al. |
| 4,409,057 A | 10/1983 | Molenda et al. |
| 4,415,112 A | 11/1983 | Green |
| 4,416,276 A | 11/1983 | Newton et al. |
| 4,417,890 A | 11/1983 | Dennehey et al. |
| 4,423,456 A | 12/1983 | Zaidenweber |
| 4,428,376 A | 1/1984 | Mericle |
| 4,429,695 A | 2/1984 | Green |
| 4,430,997 A | 2/1984 | DiGiovanni et al. |
| 4,434,796 A | 3/1984 | Karapetian et al. |
| 4,438,659 A | 3/1984 | Desplats |
| 4,442,964 A | 4/1984 | Becht |
| 4,448,194 A | 5/1984 | DiGiovanni et al. |
| 4,451,743 A | 5/1984 | Suzuki et al. |
| 4,452,376 A | 6/1984 | Klieman et al. |
| 4,454,887 A | 6/1984 | Kruger |
| 4,461,305 A | 7/1984 | Cibley |
| 4,467,805 A | 8/1984 | Fukuda |
| 4,468,597 A | 8/1984 | Baumard et al. |
| 4,469,481 A | 9/1984 | Kobayashi |
| 4,470,414 A | 9/1984 | Imagawa et al. |
| 4,471,780 A | 9/1984 | Menges et al. |
| 4,471,781 A | 9/1984 | Di Giovanni et al. |
| 4,473,077 A | 9/1984 | Noiles et al. |
| 4,475,679 A | 10/1984 | Fleury, Jr. |
| 4,478,220 A | 10/1984 | Di Giovanni et al. |
| 4,480,641 A | 11/1984 | Failla et al. |
| 4,483,562 A | 11/1984 | Schoolman |
| 4,485,816 A | 12/1984 | Krumme |
| 4,485,817 A | 12/1984 | Swiggett |
| 4,486,928 A | 12/1984 | Tucker et al. |
| 4,488,523 A | 12/1984 | Shichman |
| 4,489,875 A | 12/1984 | Crawford et al. |
| 4,493,983 A | 1/1985 | Taggert |
| 4,494,057 A | 1/1985 | Hotta |
| 4,499,895 A | 2/1985 | Takayama |
| 4,500,024 A | 2/1985 | DiGiovanni et al. |
| D278,081 S | 3/1985 | Green |
| 4,503,842 A | 3/1985 | Takayama |
| 4,505,272 A | 3/1985 | Utyamyshev et al. |
| 4,505,273 A | 3/1985 | Braun et al. |
| 4,505,414 A | 3/1985 | Filipi |
| 4,506,671 A | 3/1985 | Green |
| 4,512,038 A | 4/1985 | Alexander et al. |
| 4,520,817 A | 6/1985 | Green |
| 4,522,327 A | 6/1985 | Korthoff et al. |
| 4,526,174 A | 7/1985 | Froehlich |
| 4,527,724 A | 7/1985 | Chow et al. |
| 4,530,357 A | 7/1985 | Pawloski et al. |
| 4,530,453 A | 7/1985 | Green |
| 4,531,522 A | 7/1985 | Bedi et al. |
| 4,532,927 A | 8/1985 | Miksza, Jr. |
| 4,540,202 A | 9/1985 | Amphoux et al. |
| 4,548,202 A | 10/1985 | Duncan |
| 4,556,058 A | 12/1985 | Green |
| 4,560,915 A | 12/1985 | Soultanian |
| 4,565,109 A | 1/1986 | Tsay |
| 4,565,189 A | 1/1986 | Mabuchi |
| 4,566,620 A | 1/1986 | Green et al. |
| 4,569,346 A | 2/1986 | Poirier |
| 4,569,469 A | 2/1986 | Mongeon et al. |
| 4,571,213 A | 2/1986 | Ishimoto |
| 4,573,468 A | 3/1986 | Conta et al. |
| 4,573,469 A | 3/1986 | Golden et al. |
| 4,573,622 A | 3/1986 | Green et al. |
| 4,576,165 A | 3/1986 | Green et al. |
| 4,576,167 A | 3/1986 | Noiles |
| 4,580,712 A | 4/1986 | Green |
| 4,585,153 A | 4/1986 | Failla et al. |
| 4,586,501 A | 5/1986 | Claracq |
| 4,586,502 A | 5/1986 | Bedi et al. |
| 4,589,416 A | 5/1986 | Green |
| 4,589,582 A | 5/1986 | Bilotti |
| 4,589,870 A | 5/1986 | Citrin et al. |
| 4,591,085 A | 5/1986 | Di Giovanni |
| RE32,214 E | 7/1986 | Schramm |
| 4,597,753 A | 7/1986 | Turley |
| 4,600,037 A | 7/1986 | Hatten |
| 4,604,786 A | 8/1986 | Howie, Jr. |
| 4,605,001 A | 8/1986 | Rothfuss et al. |
| 4,605,004 A | 8/1986 | Di Giovanni et al. |
| 4,606,343 A | 8/1986 | Conta et al. |
| 4,607,636 A | 8/1986 | Kula et al. |
| 4,607,638 A | 8/1986 | Crainich |
| 4,608,981 A | 9/1986 | Rothfuss et al. |
| 4,610,250 A | 9/1986 | Green |
| 4,610,383 A | 9/1986 | Rothfuss et al. |
| 4,612,933 A | 9/1986 | Brinkerhoff et al. |
| D286,180 S | 10/1986 | Korthoff |
| D286,442 S | 10/1986 | Korthoff et al. |
| 4,617,893 A | 10/1986 | Donner et al. |
| 4,617,914 A | 10/1986 | Ueda |
| 4,619,262 A | 10/1986 | Taylor |
| 4,619,391 A | 10/1986 | Sharkany et al. |
| D287,278 S | 12/1986 | Spreckelmeier |
| 4,628,459 A | 12/1986 | Shinohara et al. |
| 4,628,636 A | 12/1986 | Folger |
| 4,629,107 A | 12/1986 | Fedotov et al. |

(56) References Cited

U.S. PATENT DOCUMENTS

| | | |
|---|---|---|
| 4,632,290 A | 12/1986 | Green et al. |
| 4,633,861 A | 1/1987 | Chow et al. |
| 4,633,874 A | 1/1987 | Chow et al. |
| 4,634,419 A | 1/1987 | Kreizman et al. |
| 4,635,638 A | 1/1987 | Weintraub et al. |
| 4,641,076 A | 2/1987 | Linden |
| 4,642,618 A | 2/1987 | Johnson et al. |
| 4,643,173 A | 2/1987 | Bell et al. |
| 4,643,731 A | 2/1987 | Eckenhoff |
| 4,646,722 A | 3/1987 | Silverstein et al. |
| 4,646,745 A | 3/1987 | Noiles |
| 4,652,820 A | 3/1987 | Maresca |
| 4,654,028 A | 3/1987 | Suma |
| 4,655,222 A | 4/1987 | Florez et al. |
| 4,662,555 A | 5/1987 | Thornton |
| 4,663,874 A | 5/1987 | Sano et al. |
| 4,664,305 A | 5/1987 | Blake, III et al. |
| 4,665,916 A | 5/1987 | Green |
| 4,667,674 A | 5/1987 | Korthoff et al. |
| 4,669,647 A | 6/1987 | Storace |
| 4,671,278 A | 6/1987 | Chin |
| 4,671,280 A | 6/1987 | Dorband et al. |
| 4,671,445 A | 6/1987 | Barker et al. |
| 4,672,964 A | 6/1987 | Dee et al. |
| 4,675,944 A | 6/1987 | Wells |
| 4,676,245 A | 6/1987 | Fukuda |
| 4,679,460 A | 7/1987 | Yoshigai |
| 4,679,719 A | 7/1987 | Kramer |
| 4,684,051 A | 8/1987 | Akopov et al. |
| 4,688,555 A | 8/1987 | Wardle |
| 4,691,703 A | 9/1987 | Auth et al. |
| 4,693,248 A | 9/1987 | Failla |
| 4,698,579 A | 10/1987 | Richter et al. |
| 4,700,703 A | 10/1987 | Resnick et al. |
| 4,705,038 A | 11/1987 | Sjostrom et al. |
| 4,708,141 A | 11/1987 | Inoue et al. |
| 4,709,120 A | 11/1987 | Pearson |
| 4,715,520 A | 12/1987 | Roehr, Jr. et al. |
| 4,719,917 A | 1/1988 | Barrows et al. |
| 4,721,099 A | 1/1988 | Chikama |
| 4,722,340 A | 2/1988 | Takayama et al. |
| 4,724,840 A | 2/1988 | McVay et al. |
| 4,727,308 A | 2/1988 | Huljak et al. |
| 4,728,020 A | 3/1988 | Green et al. |
| 4,728,876 A | 3/1988 | Mongeon et al. |
| 4,729,260 A | 3/1988 | Dudden |
| 4,730,726 A | 3/1988 | Holzwarth |
| 4,741,336 A | 5/1988 | Failla et al. |
| 4,743,214 A | 5/1988 | Tai-Cheng |
| 4,744,363 A | 5/1988 | Hasson |
| 4,747,820 A | 5/1988 | Hornlein et al. |
| 4,750,902 A | 6/1988 | Wuchinich et al. |
| 4,752,024 A | 6/1988 | Green et al. |
| 4,754,909 A | 7/1988 | Barker et al. |
| 4,761,326 A | 8/1988 | Barnes et al. |
| 4,763,669 A | 8/1988 | Jaeger |
| 4,767,044 A | 8/1988 | Green |
| D297,764 S | 9/1988 | Hunt et al. |
| 4,773,420 A | 9/1988 | Green |
| 4,777,780 A | 10/1988 | Holzwarth |
| 4,781,186 A | 11/1988 | Simpson et al. |
| 4,784,137 A | 11/1988 | Kulik et al. |
| 4,787,387 A | 11/1988 | Burbank, III et al. |
| 4,788,485 A | 11/1988 | Kawagishi et al. |
| D298,967 S | 12/1988 | Hunt |
| 4,790,225 A | 12/1988 | Moody et al. |
| 4,790,314 A | 12/1988 | Weaver |
| 4,805,617 A | 2/1989 | Bedi et al. |
| 4,805,823 A | 2/1989 | Rothfuss |
| 4,807,628 A | 2/1989 | Peters et al. |
| 4,809,695 A | 3/1989 | Gwathmey et al. |
| 4,815,460 A | 3/1989 | Porat et al. |
| 4,817,643 A | 4/1989 | Olson |
| 4,817,847 A | 4/1989 | Redtenbacher et al. |
| 4,819,853 A | 4/1989 | Green |
| 4,821,939 A | 4/1989 | Green |
| 4,827,911 A | 5/1989 | Broadwin et al. |
| 4,828,542 A | 5/1989 | Hermann |
| 4,828,944 A | 5/1989 | Yabe et al. |
| 4,830,855 A | 5/1989 | Stewart |
| 4,832,158 A | 5/1989 | Farrar et al. |
| 4,833,937 A | 5/1989 | Nagano |
| 4,834,720 A | 5/1989 | Blinkhorn |
| 4,838,859 A | 6/1989 | Strassmann |
| 4,844,068 A | 7/1989 | Arata et al. |
| 4,848,637 A | 7/1989 | Pruitt |
| 4,856,078 A | 8/1989 | Konopka |
| 4,860,644 A | 8/1989 | Kohl et al. |
| 4,862,891 A | 9/1989 | Smith |
| 4,863,423 A | 9/1989 | Wallace |
| 4,865,030 A | 9/1989 | Polyak |
| 4,868,530 A | 9/1989 | Ahs |
| 4,869,414 A | 9/1989 | Green et al. |
| 4,869,415 A | 9/1989 | Fox |
| 4,873,977 A | 10/1989 | Avant et al. |
| 4,875,486 A | 10/1989 | Rapoport et al. |
| 4,880,015 A | 11/1989 | Nierman |
| 4,890,613 A | 1/1990 | Golden et al. |
| 4,892,244 A | 1/1990 | Fox et al. |
| 4,893,622 A | 1/1990 | Green et al. |
| 4,894,051 A | 1/1990 | Shiber |
| 4,896,584 A | 1/1990 | Stoll et al. |
| 4,896,678 A | 1/1990 | Ogawa |
| 4,900,303 A | 2/1990 | Lemelson |
| 4,903,697 A | 2/1990 | Resnick et al. |
| 4,909,789 A | 3/1990 | Taguchi et al. |
| 4,915,100 A | 4/1990 | Green |
| 4,919,679 A | 4/1990 | Averill et al. |
| 4,921,479 A | 5/1990 | Grayzel |
| 4,925,082 A | 5/1990 | Kim |
| 4,928,699 A | 5/1990 | Sasai |
| 4,930,503 A | 6/1990 | Pruitt |
| 4,930,674 A | 6/1990 | Barak |
| 4,931,047 A | 6/1990 | Broadwin et al. |
| 4,931,737 A | 6/1990 | Hishiki |
| 4,932,960 A | 6/1990 | Green et al. |
| 4,933,800 A | 6/1990 | Yang |
| 4,933,843 A | 6/1990 | Scheller et al. |
| D309,350 S | 7/1990 | Sutherland et al. |
| 4,938,408 A | 7/1990 | Bedi et al. |
| 4,941,623 A | 7/1990 | Pruitt |
| 4,943,182 A | 7/1990 | Hoblingre |
| 4,944,443 A | 7/1990 | Oddsen et al. |
| 4,946,067 A | 8/1990 | Kelsall |
| 4,948,327 A | 8/1990 | Crupi, Jr. |
| 4,949,707 A | 8/1990 | LeVahn et al. |
| 4,951,860 A | 8/1990 | Peters et al. |
| 4,951,861 A | 8/1990 | Schulze et al. |
| 4,954,960 A | 9/1990 | Lo et al. |
| 4,955,959 A | 9/1990 | Tompkins et al. |
| 4,957,212 A | 9/1990 | Duck et al. |
| 4,962,877 A | 10/1990 | Hervas |
| 4,964,559 A | 10/1990 | Deniega et al. |
| 4,964,863 A | 10/1990 | Kanshin et al. |
| 4,965,709 A | 10/1990 | Ngo |
| 4,970,656 A | 11/1990 | Lo et al. |
| 4,973,274 A | 11/1990 | Hirukawa |
| 4,973,302 A | 11/1990 | Armour et al. |
| 4,978,049 A | 12/1990 | Green |
| 4,978,333 A | 12/1990 | Broadwin et al. |
| 4,979,952 A | 12/1990 | Kubota et al. |
| 4,984,564 A | 1/1991 | Yuen |
| 4,986,808 A | 1/1991 | Broadwin et al. |
| 4,987,049 A | 1/1991 | Komamura et al. |
| 4,988,334 A | 1/1991 | Hornlein et al. |
| 4,995,877 A | 2/1991 | Ams et al. |
| 4,995,959 A | 2/1991 | Metzner |
| 4,996,975 A | 3/1991 | Nakamura |
| 5,001,649 A | 3/1991 | Lo et al. |
| 5,002,543 A | 3/1991 | Bradshaw et al. |
| 5,002,553 A | 3/1991 | Shiber |
| 5,005,754 A | 4/1991 | Van Overloop |
| 5,009,661 A | 4/1991 | Michelson |
| 5,012,411 A | 4/1991 | Policastro et al. |

(56) References Cited

U.S. PATENT DOCUMENTS

| | | |
|---|---|---|
| 5,014,898 A | 5/1991 | Heidrich |
| 5,014,899 A | 5/1991 | Presty et al. |
| 5,015,227 A | 5/1991 | Broadwin et al. |
| 5,018,515 A | 5/1991 | Gilman |
| 5,018,657 A | 5/1991 | Pedlick et al. |
| 5,024,652 A | 6/1991 | Dumenek et al. |
| 5,024,671 A | 6/1991 | Tu et al. |
| 5,025,559 A | 6/1991 | McCullough |
| 5,027,834 A | 7/1991 | Pruitt |
| 5,030,226 A | 7/1991 | Green et al. |
| 5,031,814 A | 7/1991 | Tompkins et al. |
| 5,035,040 A | 7/1991 | Kerrigan et al. |
| 5,038,109 A | 8/1991 | Goble et al. |
| 5,038,247 A | 8/1991 | Kelley et al. |
| 5,040,715 A | 8/1991 | Green et al. |
| 5,042,707 A | 8/1991 | Taheri |
| 5,061,269 A | 10/1991 | Muller |
| 5,062,491 A | 11/1991 | Takeshima et al. |
| 5,062,563 A | 11/1991 | Green et al. |
| 5,065,929 A | 11/1991 | Schulze et al. |
| 5,071,052 A | 12/1991 | Rodak et al. |
| 5,071,430 A | 12/1991 | de Salis et al. |
| 5,074,454 A | 12/1991 | Peters |
| 5,077,506 A | 12/1991 | Krause |
| 5,079,006 A | 1/1992 | Urquhart |
| 5,080,556 A | 1/1992 | Carreno |
| 5,083,695 A | 1/1992 | Foslien et al. |
| 5,084,057 A | 1/1992 | Green et al. |
| 5,088,979 A | 2/1992 | Filipi et al. |
| 5,088,997 A | 2/1992 | Delahuerga et al. |
| 5,089,606 A | 2/1992 | Cole et al. |
| 5,094,247 A | 3/1992 | Hernandez et al. |
| 5,098,004 A | 3/1992 | Kerrigan |
| 5,098,360 A | 3/1992 | Hirota |
| 5,100,042 A | 3/1992 | Gravener et al. |
| 5,100,420 A | 3/1992 | Green et al. |
| 5,104,025 A | 4/1992 | Main et al. |
| 5,104,397 A | 4/1992 | Vasconcelos et al. |
| 5,104,400 A | 4/1992 | Berguer et al. |
| 5,106,008 A | 4/1992 | Tompkins et al. |
| 5,108,368 A | 4/1992 | Hammerslag et al. |
| 5,109,722 A | 5/1992 | Hufnagle et al. |
| 5,111,987 A | 5/1992 | Moeinzadeh et al. |
| 5,116,349 A | 5/1992 | Aranyi |
| D327,323 S | 6/1992 | Hunt |
| 5,119,009 A | 6/1992 | McCaleb et al. |
| 5,122,156 A | 6/1992 | Granger et al. |
| 5,124,990 A | 6/1992 | Williamson |
| 5,129,570 A | 7/1992 | Schulze et al. |
| 5,137,198 A | 8/1992 | Nobis et al. |
| 5,139,513 A | 8/1992 | Segato |
| 5,141,144 A | 8/1992 | Foslien et al. |
| 5,142,932 A | 9/1992 | Moya et al. |
| 5,155,941 A | 10/1992 | Takahashi et al. |
| 5,156,315 A | 10/1992 | Green et al. |
| 5,156,609 A | 10/1992 | Nakao et al. |
| 5,156,614 A | 10/1992 | Green et al. |
| 5,158,222 A | 10/1992 | Green et al. |
| 5,158,567 A | 10/1992 | Green |
| D330,699 S | 11/1992 | Gill |
| 5,163,598 A | 11/1992 | Peters et al. |
| 5,168,605 A | 12/1992 | Bartlett |
| 5,170,925 A | 12/1992 | Madden et al. |
| 5,171,247 A | 12/1992 | Hughett et al. |
| 5,171,249 A | 12/1992 | Stefanchik et al. |
| 5,171,253 A | 12/1992 | Klieman |
| 5,173,053 A | 12/1992 | Swanson et al. |
| 5,173,133 A | 12/1992 | Morin et al. |
| 5,176,677 A | 1/1993 | Wuchinich |
| 5,176,688 A | 1/1993 | Narayan et al. |
| 5,187,422 A | 2/1993 | Izenbaard et al. |
| 5,188,102 A | 2/1993 | Idemoto et al. |
| 5,188,111 A | 2/1993 | Yates et al. |
| 5,190,517 A | 3/1993 | Zieve et al. |
| 5,190,544 A | 3/1993 | Chapman et al. |
| 5,190,560 A | 3/1993 | Woods et al. |
| 5,190,657 A | 3/1993 | Heagle et al. |
| 5,192,288 A | 3/1993 | Thompson et al. |
| 5,193,731 A | 3/1993 | Aranyi |
| 5,195,505 A | 3/1993 | Josefsen |
| 5,195,968 A | 3/1993 | Lundquist et al. |
| 5,197,648 A | 3/1993 | Gingold |
| 5,197,649 A | 3/1993 | Bessler et al. |
| 5,197,966 A | 3/1993 | Sommerkamp |
| 5,197,970 A | 3/1993 | Green et al. |
| 5,200,280 A | 4/1993 | Karasa |
| 5,201,750 A | 4/1993 | Hocherl et al. |
| 5,205,459 A | 4/1993 | Brinkerhoff et al. |
| 5,207,672 A | 5/1993 | Roth et al. |
| 5,207,697 A | 5/1993 | Carusillo et al. |
| 5,209,747 A | 5/1993 | Knoepfler |
| 5,209,756 A | 5/1993 | Seedhom et al. |
| 5,211,649 A | 5/1993 | Kohler et al. |
| 5,211,655 A | 5/1993 | Hasson |
| 5,217,457 A | 6/1993 | Delahuerga et al. |
| 5,217,478 A | 6/1993 | Rexroth |
| 5,219,111 A | 6/1993 | Bilotti et al. |
| 5,220,269 A | 6/1993 | Chen et al. |
| 5,221,036 A | 6/1993 | Takase |
| 5,221,281 A | 6/1993 | Klicek |
| 5,222,945 A | 6/1993 | Basnight |
| 5,222,963 A | 6/1993 | Brinkerhoff et al. |
| 5,222,975 A | 6/1993 | Crainich |
| 5,222,976 A | 6/1993 | Yoon |
| 5,223,675 A | 6/1993 | Taft |
| D338,729 S | 8/1993 | Sprecklemeier et al. |
| 5,234,447 A | 8/1993 | Kaster et al. |
| 5,236,269 A | 8/1993 | Handy |
| 5,236,424 A | 8/1993 | Imran |
| 5,236,440 A | 8/1993 | Hlavacek |
| 5,239,981 A | 8/1993 | Anapliotis |
| 5,240,163 A | 8/1993 | Stein et al. |
| 5,242,456 A | 9/1993 | Nash et al. |
| 5,242,457 A | 9/1993 | Akopov et al. |
| 5,244,462 A | 9/1993 | Delahuerga et al. |
| 5,246,156 A | 9/1993 | Rothfuss et al. |
| 5,246,443 A | 9/1993 | Mai |
| 5,253,793 A | 10/1993 | Green et al. |
| 5,258,007 A | 11/1993 | Spetzler et al. |
| 5,258,008 A | 11/1993 | Wilk |
| 5,258,009 A | 11/1993 | Conners |
| 5,258,010 A | 11/1993 | Green et al. |
| 5,258,012 A | 11/1993 | Luscombe et al. |
| 5,259,366 A | 11/1993 | Reydel et al. |
| 5,259,835 A | 11/1993 | Clark et al. |
| 5,260,637 A | 11/1993 | Pizzi |
| 5,261,135 A | 11/1993 | Mitchell |
| 5,261,877 A | 11/1993 | Fine et al. |
| 5,261,922 A | 11/1993 | Hood |
| 5,263,629 A | 11/1993 | Trumbull et al. |
| 5,263,937 A | 11/1993 | Shipp |
| 5,263,973 A | 11/1993 | Cook |
| 5,264,218 A | 11/1993 | Rogozinski |
| 5,268,622 A | 12/1993 | Philipp |
| 5,271,543 A | 12/1993 | Grant et al. |
| 5,271,544 A | 12/1993 | Fox et al. |
| RE34,519 E | 1/1994 | Fox et al. |
| 5,275,322 A | 1/1994 | Brinkerhoff et al. |
| 5,275,323 A | 1/1994 | Schulze et al. |
| 5,275,608 A | 1/1994 | Forman et al. |
| 5,279,416 A | 1/1994 | Malec et al. |
| 5,281,216 A | 1/1994 | Klicek |
| 5,282,806 A | 2/1994 | Haber et al. |
| 5,282,829 A | 2/1994 | Hermes |
| 5,284,128 A | 2/1994 | Hart |
| 5,285,381 A | 2/1994 | Iskarous et al. |
| 5,285,945 A | 2/1994 | Brinkerhoff et al. |
| 5,286,253 A | 2/1994 | Fucci |
| 5,289,963 A | 3/1994 | McGarry et al. |
| 5,290,271 A | 3/1994 | Jernberg |
| 5,290,310 A | 3/1994 | Makower et al. |
| 5,292,053 A | 3/1994 | Bilotti et al. |
| 5,293,024 A | 3/1994 | Sugahara et al. |
| 5,297,714 A | 3/1994 | Kramer |

(56) References Cited

U.S. PATENT DOCUMENTS

| | | |
|---|---|---|
| 5,304,204 A | 4/1994 | Bregen |
| D347,474 S | 5/1994 | Olson |
| 5,307,976 A | 5/1994 | Olson et al. |
| 5,308,576 A | 5/1994 | Green et al. |
| 5,309,387 A | 5/1994 | Mori et al. |
| 5,309,927 A | 5/1994 | Welch |
| 5,312,023 A | 5/1994 | Green et al. |
| 5,312,024 A | 5/1994 | Grant et al. |
| 5,312,329 A | 5/1994 | Beaty et al. |
| 5,313,935 A | 5/1994 | Kortenbach et al. |
| 5,313,967 A | 5/1994 | Lieber et al. |
| 5,314,424 A | 5/1994 | Nicholas |
| 5,314,445 A | 5/1994 | Heidmueller nee Degwitz et al. |
| 5,314,466 A | 5/1994 | Stern et al. |
| 5,318,221 A | 6/1994 | Green et al. |
| 5,320,627 A | 6/1994 | Sorensen et al. |
| D348,930 S | 7/1994 | Olson |
| 5,326,013 A | 7/1994 | Green et al. |
| 5,329,923 A | 7/1994 | Lundquist |
| 5,330,487 A | 7/1994 | Thornton et al. |
| 5,330,502 A | 7/1994 | Hassler et al. |
| 5,331,971 A | 7/1994 | Bales et al. |
| 5,332,142 A | 7/1994 | Robinson et al. |
| 5,333,422 A | 8/1994 | Warren et al. |
| 5,333,772 A | 8/1994 | Rothfuss et al. |
| 5,333,773 A | 8/1994 | Main et al. |
| 5,334,183 A | 8/1994 | Wuchinich |
| 5,336,130 A | 8/1994 | Ray |
| 5,336,229 A | 8/1994 | Noda |
| 5,336,232 A | 8/1994 | Green et al. |
| 5,339,799 A | 8/1994 | Kami et al. |
| 5,341,724 A | 8/1994 | Vatel |
| 5,341,807 A | 8/1994 | Nardella |
| 5,341,810 A | 8/1994 | Dardel |
| 5,342,380 A | 8/1994 | Hood |
| 5,342,381 A | 8/1994 | Tidemand |
| 5,342,385 A | 8/1994 | Norelli et al. |
| 5,342,395 A | 8/1994 | Jarrett et al. |
| 5,342,396 A | 8/1994 | Cook |
| 5,343,382 A | 8/1994 | Hale et al. |
| 5,343,391 A | 8/1994 | Mushabac |
| 5,344,059 A | 9/1994 | Green et al. |
| 5,344,060 A | 9/1994 | Gravener et al. |
| 5,344,454 A | 9/1994 | Clarke et al. |
| 5,346,504 A | 9/1994 | Ortiz et al. |
| 5,348,259 A | 9/1994 | Blanco et al. |
| 5,350,355 A | 9/1994 | Sklar |
| 5,350,388 A | 9/1994 | Epstein |
| 5,350,391 A | 9/1994 | Iacovelli |
| 5,350,400 A | 9/1994 | Esposito et al. |
| 5,352,229 A | 10/1994 | Goble et al. |
| 5,352,235 A | 10/1994 | Koros et al. |
| 5,352,238 A | 10/1994 | Green et al. |
| 5,354,250 A | 10/1994 | Christensen |
| 5,354,303 A | 10/1994 | Spaeth et al. |
| 5,356,006 A | 10/1994 | Alpern et al. |
| 5,356,064 A | 10/1994 | Green et al. |
| 5,358,506 A | 10/1994 | Green et al. |
| 5,358,510 A | 10/1994 | Luscombe et al. |
| 5,359,231 A | 10/1994 | Flowers et al. |
| D352,780 S | 11/1994 | Glaeser et al. |
| 5,359,993 A | 11/1994 | Slater et al. |
| 5,360,305 A | 11/1994 | Kerrigan |
| 5,360,428 A | 11/1994 | Hutchinson, Jr. |
| 5,361,902 A | 11/1994 | Abidin et al. |
| 5,364,001 A | 11/1994 | Bryan |
| 5,364,002 A | 11/1994 | Green et al. |
| 5,364,003 A | 11/1994 | Williamson, IV |
| 5,366,133 A | 11/1994 | Geiste |
| 5,366,134 A | 11/1994 | Green et al. |
| 5,366,479 A | 11/1994 | McGarry et al. |
| 5,368,015 A | 11/1994 | Wilk |
| 5,368,592 A | 11/1994 | Stern et al. |
| 5,369,565 A | 11/1994 | Chen et al. |
| 5,370,645 A | 12/1994 | Klicek et al. |
| 5,372,124 A | 12/1994 | Takayama et al. |
| 5,372,596 A | 12/1994 | Klicek et al. |
| 5,372,602 A | 12/1994 | Burke |
| 5,374,277 A | 12/1994 | Hassler |
| 5,375,588 A | 12/1994 | Yoon |
| 5,376,095 A | 12/1994 | Ortiz |
| 5,379,933 A | 1/1995 | Green et al. |
| 5,381,649 A | 1/1995 | Webb |
| 5,381,782 A | 1/1995 | DeLaRama et al. |
| 5,381,943 A | 1/1995 | Allen et al. |
| 5,382,247 A | 1/1995 | Cimino et al. |
| 5,383,460 A | 1/1995 | Jang et al. |
| 5,383,880 A | 1/1995 | Hooven |
| 5,383,881 A | 1/1995 | Green et al. |
| 5,383,882 A | 1/1995 | Buess et al. |
| 5,383,888 A | 1/1995 | Zvenyatsky et al. |
| 5,383,895 A | 1/1995 | Holmes et al. |
| 5,388,568 A | 2/1995 | van der Heide |
| 5,389,098 A | 2/1995 | Tsuruta et al. |
| 5,389,102 A | 2/1995 | Green et al. |
| 5,389,104 A | 2/1995 | Hahnen et al. |
| 5,391,180 A | 2/1995 | Tovey et al. |
| 5,392,979 A | 2/1995 | Green et al. |
| 5,395,030 A | 3/1995 | Kuramoto et al. |
| 5,395,033 A | 3/1995 | Byrne et al. |
| 5,395,034 A | 3/1995 | Allen et al. |
| 5,395,312 A | 3/1995 | Desai |
| 5,395,384 A | 3/1995 | Duthoit et al. |
| 5,397,046 A | 3/1995 | Savage et al. |
| 5,397,324 A | 3/1995 | Carroll et al. |
| 5,400,267 A | 3/1995 | Denen et al. |
| 5,403,276 A | 4/1995 | Schechter et al. |
| 5,403,312 A | 4/1995 | Yates et al. |
| 5,404,106 A | 4/1995 | Matsuda |
| 5,404,870 A | 4/1995 | Brinkerhoff et al. |
| 5,404,960 A | 4/1995 | Wada et al. |
| 5,405,072 A | 4/1995 | Zlock et al. |
| 5,405,073 A | 4/1995 | Porter |
| 5,405,344 A | 4/1995 | Williamson et al. |
| 5,405,360 A | 4/1995 | Tovey |
| 5,407,293 A | 4/1995 | Crainich |
| 5,408,409 A | 4/1995 | Glassman et al. |
| 5,409,498 A | 4/1995 | Braddock et al. |
| 5,409,703 A | 4/1995 | McAnalley et al. |
| D357,981 S | 5/1995 | Green et al. |
| 5,411,481 A | 5/1995 | Allen et al. |
| 5,411,508 A | 5/1995 | Bessler et al. |
| 5,413,107 A | 5/1995 | Oakley et al. |
| 5,413,267 A | 5/1995 | Solyntjes et al. |
| 5,413,268 A | 5/1995 | Green et al. |
| 5,413,272 A | 5/1995 | Green et al. |
| 5,413,573 A | 5/1995 | Koivukangas |
| 5,415,334 A | 5/1995 | Williamson et al. |
| 5,415,335 A | 5/1995 | Knodell, Jr. |
| 5,417,203 A | 5/1995 | Tovey et al. |
| 5,417,361 A | 5/1995 | Williamson, IV |
| 5,419,766 A | 5/1995 | Chang et al. |
| 5,421,829 A | 6/1995 | Olichney et al. |
| 5,422,567 A | 6/1995 | Matsunaga |
| 5,423,471 A | 6/1995 | Mastri et al. |
| 5,423,809 A | 6/1995 | Klicek |
| 5,423,835 A | 6/1995 | Green et al. |
| 5,425,745 A | 6/1995 | Green et al. |
| 5,427,298 A | 6/1995 | Tegtmeier |
| 5,431,322 A | 7/1995 | Green et al. |
| 5,431,323 A | 7/1995 | Smith et al. |
| 5,431,654 A | 7/1995 | Nic |
| 5,431,668 A | 7/1995 | Burbank, III et al. |
| 5,433,721 A | 7/1995 | Hooven et al. |
| 5,437,681 A | 8/1995 | Meade et al. |
| 5,438,302 A | 8/1995 | Goble |
| 5,438,997 A | 8/1995 | Sieben et al. |
| 5,439,155 A | 8/1995 | Viola |
| 5,439,156 A | 8/1995 | Grant et al. |
| 5,439,479 A | 8/1995 | Shichman et al. |
| 5,441,191 A | 8/1995 | Linden |
| 5,441,193 A | 8/1995 | Gravener |
| 5,441,483 A | 8/1995 | Avitall |
| 5,441,494 A | 8/1995 | Ortiz |

(56) References Cited

U.S. PATENT DOCUMENTS

| | | |
|---|---|---|
| 5,441,499 A | 8/1995 | Fritzsch |
| 5,443,197 A | 8/1995 | Malis et al. |
| 5,443,463 A | 8/1995 | Stern et al. |
| 5,444,113 A | 8/1995 | Sinclair et al. |
| 5,445,155 A | 8/1995 | Sieben |
| 5,445,304 A | 8/1995 | Plyley et al. |
| 5,445,604 A | 8/1995 | Lang |
| 5,445,644 A | 8/1995 | Pietrafitta et al. |
| 5,446,646 A | 8/1995 | Miyazaki |
| 5,447,265 A | 9/1995 | Vidal et al. |
| 5,447,417 A | 9/1995 | Kuhl et al. |
| 5,447,513 A | 9/1995 | Davison et al. |
| 5,449,355 A | 9/1995 | Rhum et al. |
| 5,449,365 A | 9/1995 | Green et al. |
| 5,449,370 A | 9/1995 | Vaitekunas |
| 5,452,836 A | 9/1995 | Huitema et al. |
| 5,452,837 A | 9/1995 | Williamson, IV et al. |
| 5,454,378 A | 10/1995 | Palmer et al. |
| 5,454,822 A | 10/1995 | Schob et al. |
| 5,454,827 A | 10/1995 | Aust et al. |
| 5,456,401 A | 10/1995 | Green et al. |
| 5,456,917 A | 10/1995 | Wise et al. |
| 5,458,279 A | 10/1995 | Plyley |
| 5,458,579 A | 10/1995 | Chodorow et al. |
| 5,462,215 A | 10/1995 | Viola et al. |
| 5,464,013 A | 11/1995 | Lemelson |
| 5,464,144 A | 11/1995 | Guy et al. |
| 5,464,300 A | 11/1995 | Crainich |
| 5,465,819 A | 11/1995 | Weilant et al. |
| 5,465,894 A | 11/1995 | Clark et al. |
| 5,465,895 A | 11/1995 | Knodel et al. |
| 5,465,896 A | 11/1995 | Allen et al. |
| 5,466,020 A | 11/1995 | Page et al. |
| 5,467,911 A | 11/1995 | Tsuruta et al. |
| 5,468,253 A | 11/1995 | Bezwada et al. |
| 5,470,006 A | 11/1995 | Rodak |
| 5,470,007 A | 11/1995 | Plyley et al. |
| 5,470,008 A | 11/1995 | Rodak |
| 5,470,009 A | 11/1995 | Rodak |
| 5,470,010 A | 11/1995 | Rothfuss et al. |
| 5,471,129 A | 11/1995 | Mann |
| 5,472,132 A | 12/1995 | Savage et al. |
| 5,472,442 A | 12/1995 | Klicek |
| 5,473,204 A | 12/1995 | Temple |
| 5,474,057 A | 12/1995 | Makower et al. |
| 5,474,223 A | 12/1995 | Viola et al. |
| 5,474,566 A | 12/1995 | Alesi et al. |
| 5,474,570 A | 12/1995 | Kockerling et al. |
| 5,476,206 A | 12/1995 | Green et al. |
| 5,476,479 A | 12/1995 | Green et al. |
| 5,476,481 A | 12/1995 | Schondorf |
| 5,478,003 A | 12/1995 | Green et al. |
| 5,478,354 A | 12/1995 | Tovey et al. |
| 5,480,089 A | 1/1996 | Blewett |
| 5,480,409 A | 1/1996 | Riza |
| 5,482,197 A | 1/1996 | Green et al. |
| 5,483,952 A | 1/1996 | Aranyi |
| 5,484,095 A | 1/1996 | Green et al. |
| 5,484,398 A | 1/1996 | Stoddard |
| 5,484,451 A | 1/1996 | Akopov et al. |
| 5,485,947 A | 1/1996 | Olson et al. |
| 5,485,952 A | 1/1996 | Fontayne |
| 5,487,499 A | 1/1996 | Sorrentino et al. |
| 5,487,500 A | 1/1996 | Knodel et al. |
| 5,489,058 A | 2/1996 | Plyley et al. |
| 5,489,256 A | 2/1996 | Adair |
| 5,489,290 A | 2/1996 | Furnish |
| 5,490,819 A | 2/1996 | Nicholas et al. |
| 5,492,671 A | 2/1996 | Krafft |
| 5,496,312 A | 3/1996 | Klicek |
| 5,496,317 A | 3/1996 | Goble et al. |
| 5,497,933 A | 3/1996 | DeFonzo et al. |
| 5,498,164 A | 3/1996 | Ward et al. |
| 5,498,838 A | 3/1996 | Furman |
| 5,501,654 A | 3/1996 | Failla et al. |
| 5,503,320 A | 4/1996 | Webster et al. |
| 5,503,635 A | 4/1996 | Sauer et al. |
| 5,503,638 A | 4/1996 | Cooper et al. |
| 5,505,363 A | 4/1996 | Green et al. |
| 5,507,425 A | 4/1996 | Ziglioli |
| 5,507,426 A | 4/1996 | Young et al. |
| 5,509,596 A | 4/1996 | Green et al. |
| 5,509,916 A | 4/1996 | Taylor |
| 5,511,564 A | 4/1996 | Wilk |
| 5,514,129 A | 5/1996 | Smith |
| 5,514,149 A | 5/1996 | Green et al. |
| 5,514,157 A | 5/1996 | Nicholas et al. |
| 5,518,163 A | 5/1996 | Hooven |
| 5,518,164 A | 5/1996 | Hooven |
| 5,520,609 A | 5/1996 | Moll et al. |
| 5,520,634 A | 5/1996 | Fox et al. |
| 5,520,678 A | 5/1996 | Heckele et al. |
| 5,520,700 A | 5/1996 | Beyar et al. |
| 5,522,817 A | 6/1996 | Sander et al. |
| 5,522,831 A | 6/1996 | Sleister et al. |
| 5,527,264 A | 6/1996 | Moll et al. |
| 5,527,320 A | 6/1996 | Carruthers et al. |
| 5,529,235 A | 6/1996 | Boiarski et al. |
| D372,086 S | 7/1996 | Grasso et al. |
| 5,531,305 A | 7/1996 | Roberts et al. |
| 5,531,744 A | 7/1996 | Nardella et al. |
| 5,531,856 A | 7/1996 | Moll et al. |
| 5,533,521 A | 7/1996 | Granger |
| 5,533,581 A | 7/1996 | Barth et al. |
| 5,533,661 A | 7/1996 | Main et al. |
| 5,535,934 A | 7/1996 | Boiarski et al. |
| 5,535,935 A | 7/1996 | Vidal et al. |
| 5,535,937 A | 7/1996 | Boiarski et al. |
| 5,540,375 A | 7/1996 | Bolanos et al. |
| 5,540,705 A | 7/1996 | Meade et al. |
| 5,541,376 A | 7/1996 | Ladtkow et al. |
| 5,541,489 A | 7/1996 | Dunstan |
| 5,542,594 A | 8/1996 | McKean et al. |
| 5,542,949 A | 8/1996 | Yoon |
| 5,543,119 A | 8/1996 | Sutter et al. |
| 5,543,695 A | 8/1996 | Culp et al. |
| 5,544,802 A | 8/1996 | Crainich |
| 5,547,117 A | 8/1996 | Hamblin et al. |
| 5,549,583 A | 8/1996 | Sanford et al. |
| 5,549,621 A | 8/1996 | Bessler et al. |
| 5,549,627 A | 8/1996 | Kieturakis |
| 5,549,628 A | 8/1996 | Cooper et al. |
| 5,549,637 A | 8/1996 | Crainich |
| 5,551,622 A | 9/1996 | Yoon |
| 5,553,624 A | 9/1996 | Francese et al. |
| 5,553,675 A | 9/1996 | Pitzen et al. |
| 5,553,765 A | 9/1996 | Knodel et al. |
| 5,554,148 A | 9/1996 | Aebischer et al. |
| 5,554,169 A | 9/1996 | Green et al. |
| 5,556,020 A | 9/1996 | Hou |
| 5,556,416 A | 9/1996 | Clark et al. |
| 5,558,533 A | 9/1996 | Hashizawa et al. |
| 5,558,665 A | 9/1996 | Kieturakis |
| 5,558,671 A | 9/1996 | Yates |
| 5,560,530 A | 10/1996 | Bolanos et al. |
| 5,560,532 A | 10/1996 | DeFonzo et al. |
| 5,561,881 A | 10/1996 | Klinger et al. |
| 5,562,239 A | 10/1996 | Boiarski et al. |
| 5,562,241 A | 10/1996 | Knodel et al. |
| 5,562,682 A | 10/1996 | Oberlin et al. |
| 5,562,690 A | 10/1996 | Green et al. |
| 5,562,701 A | 10/1996 | Huitema et al. |
| 5,562,702 A | 10/1996 | Huitema et al. |
| 5,563,481 A | 10/1996 | Krause |
| 5,564,615 A | 10/1996 | Bishop et al. |
| 5,569,161 A | 10/1996 | Ebling et al. |
| 5,569,270 A | 10/1996 | Weng |
| 5,569,284 A | 10/1996 | Young et al. |
| 5,571,090 A | 11/1996 | Sherts |
| 5,571,100 A | 11/1996 | Goble et al. |
| 5,571,116 A | 11/1996 | Bolanos et al. |
| 5,571,285 A | 11/1996 | Chow et al. |
| 5,571,488 A | 11/1996 | Beerstecher et al. |
| 5,573,169 A | 11/1996 | Green et al. |

(56) References Cited

U.S. PATENT DOCUMENTS

| | | |
|---|---|---|
| 5,573,543 A | 11/1996 | Akopov et al. |
| 5,574,431 A | 11/1996 | McKeown et al. |
| 5,575,054 A | 11/1996 | Klinzing et al. |
| 5,575,789 A | 11/1996 | Bell et al. |
| 5,575,799 A | 11/1996 | Bolanos et al. |
| 5,575,803 A | 11/1996 | Cooper et al. |
| 5,575,805 A | 11/1996 | Li |
| 5,577,654 A | 11/1996 | Bishop |
| 5,578,052 A | 11/1996 | Koros et al. |
| 5,579,978 A | 12/1996 | Green et al. |
| 5,580,067 A | 12/1996 | Hamblin et al. |
| 5,582,611 A | 12/1996 | Tsuruta et al. |
| 5,582,617 A | 12/1996 | Klieman et al. |
| 5,582,907 A | 12/1996 | Pall |
| 5,583,114 A | 12/1996 | Barrows et al. |
| 5,584,425 A | 12/1996 | Savage et al. |
| 5,586,711 A | 12/1996 | Plyley et al. |
| 5,588,579 A | 12/1996 | Schnut et al. |
| 5,588,580 A | 12/1996 | Paul et al. |
| 5,588,581 A | 12/1996 | Conlon et al. |
| 5,591,170 A | 1/1997 | Spievack et al. |
| 5,591,187 A | 1/1997 | Dekel |
| 5,597,107 A | 1/1997 | Knodel et al. |
| 5,599,151 A | 2/1997 | Daum et al. |
| 5,599,279 A | 2/1997 | Slotman et al. |
| 5,599,344 A | 2/1997 | Paterson |
| 5,599,350 A | 2/1997 | Schulze et al. |
| 5,599,852 A | 2/1997 | Scopelianos et al. |
| 5,601,224 A | 2/1997 | Bishop et al. |
| 5,601,573 A | 2/1997 | Fogelberg et al. |
| 5,601,604 A | 2/1997 | Vincent |
| 5,602,449 A | 2/1997 | Krause et al. |
| 5,603,443 A | 2/1997 | Clark et al. |
| 5,605,272 A | 2/1997 | Witt et al. |
| 5,605,273 A | 2/1997 | Hamblin et al. |
| 5,607,094 A | 3/1997 | Clark et al. |
| 5,607,095 A | 3/1997 | Smith et al. |
| 5,607,433 A | 3/1997 | Polla et al. |
| 5,607,450 A | 3/1997 | Zvenyatsky et al. |
| 5,607,474 A | 3/1997 | Athanasiou et al. |
| 5,609,285 A | 3/1997 | Grant et al. |
| 5,609,601 A | 3/1997 | Kolesa et al. |
| 5,611,709 A | 3/1997 | McAnulty |
| 5,613,499 A | 3/1997 | Palmer et al. |
| 5,613,937 A | 3/1997 | Garrison et al. |
| 5,613,966 A | 3/1997 | Makower et al. |
| 5,614,887 A | 3/1997 | Buchbinder |
| 5,615,820 A | 4/1997 | Viola |
| 5,618,294 A | 4/1997 | Aust et al. |
| 5,618,303 A | 4/1997 | Marlow et al. |
| 5,618,307 A | 4/1997 | Donlon et al. |
| 5,619,992 A | 4/1997 | Guthrie et al. |
| 5,620,289 A | 4/1997 | Curry |
| 5,620,326 A | 4/1997 | Younker |
| 5,620,452 A | 4/1997 | Yoon |
| 5,624,398 A | 4/1997 | Smith et al. |
| 5,624,452 A | 4/1997 | Yates |
| 5,626,587 A | 5/1997 | Bishop et al. |
| 5,626,595 A | 5/1997 | Sklar et al. |
| 5,628,446 A | 5/1997 | Geiste et al. |
| 5,628,743 A | 5/1997 | Cimino |
| 5,628,745 A | 5/1997 | Bek |
| 5,630,539 A | 5/1997 | Plyley et al. |
| 5,630,540 A | 5/1997 | Blewett |
| 5,630,541 A | 5/1997 | Williamson, IV et al. |
| 5,630,782 A | 5/1997 | Adair |
| 5,631,973 A | 5/1997 | Green |
| 5,632,432 A | 5/1997 | Schulze et al. |
| 5,632,433 A | 5/1997 | Grant et al. |
| 5,633,374 A | 5/1997 | Humphrey et al. |
| 5,634,584 A | 6/1997 | Okorocha et al. |
| 5,636,779 A | 6/1997 | Palmer |
| 5,636,780 A | 6/1997 | Green et al. |
| 5,638,582 A | 6/1997 | Klatt et al. |
| 5,639,008 A | 6/1997 | Gallagher et al. |
| D381,077 S | 7/1997 | Hunt |
| 5,643,291 A | 7/1997 | Pier et al. |
| 5,643,293 A | 7/1997 | Kogasaka et al. |
| 5,643,294 A | 7/1997 | Tovey et al. |
| 5,643,319 A | 7/1997 | Green et al. |
| 5,645,209 A | 7/1997 | Green et al. |
| 5,647,526 A | 7/1997 | Green et al. |
| 5,647,869 A | 7/1997 | Goble et al. |
| 5,649,937 A | 7/1997 | Bito et al. |
| 5,649,956 A | 7/1997 | Jensen et al. |
| 5,651,491 A | 7/1997 | Heaton et al. |
| 5,651,762 A | 7/1997 | Bridges |
| 5,651,821 A | 7/1997 | Uchida |
| 5,653,373 A | 8/1997 | Green et al. |
| 5,653,374 A | 8/1997 | Young et al. |
| 5,653,677 A | 8/1997 | Okada et al. |
| 5,653,721 A | 8/1997 | Knodel et al. |
| 5,653,748 A | 8/1997 | Strecker |
| 5,655,698 A | 8/1997 | Yoon |
| 5,657,417 A | 8/1997 | Di Troia |
| 5,657,429 A | 8/1997 | Wang et al. |
| 5,657,921 A | 8/1997 | Young et al. |
| 5,658,238 A | 8/1997 | Suzuki et al. |
| 5,658,281 A | 8/1997 | Heard |
| 5,658,298 A | 8/1997 | Vincent et al. |
| 5,658,300 A | 8/1997 | Bito et al. |
| 5,658,307 A | 8/1997 | Exconde |
| 5,662,258 A | 9/1997 | Knodel et al. |
| 5,662,260 A | 9/1997 | Yoon |
| 5,662,662 A | 9/1997 | Bishop et al. |
| 5,662,667 A | 9/1997 | Knodel |
| 5,665,085 A | 9/1997 | Nardella |
| 5,667,517 A | 9/1997 | Hooven |
| 5,667,526 A | 9/1997 | Levin |
| 5,667,527 A | 9/1997 | Cook |
| 5,667,864 A | 9/1997 | Landoll |
| 5,669,544 A | 9/1997 | Schulze et al. |
| 5,669,904 A | 9/1997 | Platt, Jr. et al. |
| 5,669,907 A | 9/1997 | Platt, Jr. et al. |
| 5,669,918 A | 9/1997 | Balazs et al. |
| 5,672,945 A | 9/1997 | Krause |
| 5,673,840 A | 10/1997 | Schulze et al. |
| 5,673,841 A | 10/1997 | Schulze et al. |
| 5,673,842 A | 10/1997 | Bittner et al. |
| 5,674,286 A | 10/1997 | D'Alessio et al. |
| 5,678,748 A | 10/1997 | Plyley et al. |
| 5,680,981 A | 10/1997 | Mililli et al. |
| 5,680,982 A | 10/1997 | Schulze et al. |
| 5,680,983 A | 10/1997 | Plyley et al. |
| 5,681,341 A | 10/1997 | Lunsford et al. |
| 5,683,349 A | 11/1997 | Makower et al. |
| 5,685,474 A | 11/1997 | Seeber |
| 5,686,090 A | 11/1997 | Schilder et al. |
| 5,688,270 A | 11/1997 | Yates et al. |
| 5,690,269 A | 11/1997 | Bolanos et al. |
| 5,690,675 A | 11/1997 | Sawyer et al. |
| 5,692,668 A | 12/1997 | Schulze et al. |
| 5,693,020 A | 12/1997 | Rauh |
| 5,693,042 A | 12/1997 | Boiarski et al. |
| 5,693,051 A | 12/1997 | Schulze et al. |
| 5,695,494 A | 12/1997 | Becker |
| 5,695,502 A | 12/1997 | Pier et al. |
| 5,695,504 A | 12/1997 | Gifford, III et al. |
| 5,695,524 A | 12/1997 | Kelley et al. |
| 5,697,542 A | 12/1997 | Knodel et al. |
| 5,697,543 A | 12/1997 | Burdorff |
| 5,697,909 A | 12/1997 | Eggers et al. |
| 5,697,943 A | 12/1997 | Sauer et al. |
| 5,700,270 A | 12/1997 | Peyser et al. |
| 5,700,276 A | 12/1997 | Benecke |
| 5,702,387 A | 12/1997 | Arts et al. |
| 5,702,408 A | 12/1997 | Wales et al. |
| 5,702,409 A | 12/1997 | Rayburn et al. |
| 5,704,087 A | 1/1998 | Strub |
| 5,704,534 A | 1/1998 | Huitema et al. |
| 5,706,997 A | 1/1998 | Green et al. |
| 5,706,998 A | 1/1998 | Plyley et al. |
| 5,707,392 A | 1/1998 | Kortenbach |
| 5,709,334 A | 1/1998 | Sorrentino et al. |

(56) References Cited

U.S. PATENT DOCUMENTS

| | | |
|---|---|---|
| 5,709,335 A | 1/1998 | Heck |
| 5,709,680 A | 1/1998 | Yates et al. |
| 5,709,706 A | 1/1998 | Kienzle et al. |
| 5,711,472 A | 1/1998 | Bryan |
| 5,712,460 A | 1/1998 | Carr et al. |
| 5,713,128 A | 2/1998 | Schrenk et al. |
| 5,713,505 A | 2/1998 | Huitema |
| 5,713,895 A | 2/1998 | Lontine et al. |
| 5,713,896 A | 2/1998 | Nardella |
| 5,713,920 A | 2/1998 | Bezwada et al. |
| 5,715,604 A | 2/1998 | Lanzoni |
| 5,715,987 A | 2/1998 | Kelley et al. |
| 5,715,988 A | 2/1998 | Palmer |
| 5,716,366 A | 2/1998 | Yates |
| 5,718,359 A | 2/1998 | Palmer et al. |
| 5,718,360 A | 2/1998 | Green et al. |
| 5,718,548 A | 2/1998 | Cotellessa |
| 5,718,714 A | 2/1998 | Livneh |
| 5,720,744 A | 2/1998 | Eggleston et al. |
| D393,067 S | 3/1998 | Geary et al. |
| 5,724,025 A | 3/1998 | Tavori |
| 5,725,536 A | 3/1998 | Oberlin et al. |
| 5,725,554 A | 3/1998 | Simon et al. |
| 5,728,110 A | 3/1998 | Vidal et al. |
| 5,728,113 A | 3/1998 | Sherts |
| 5,728,121 A | 3/1998 | Bimbo et al. |
| 5,730,758 A | 3/1998 | Allgeyer |
| 5,732,821 A | 3/1998 | Stone et al. |
| 5,732,871 A | 3/1998 | Clark et al. |
| 5,732,872 A | 3/1998 | Bolduc et al. |
| 5,733,308 A | 3/1998 | Daugherty et al. |
| 5,735,445 A | 4/1998 | Vidal et al. |
| 5,735,848 A | 4/1998 | Yates et al. |
| 5,735,874 A | 4/1998 | Measamer et al. |
| 5,738,474 A | 4/1998 | Blewett |
| 5,738,629 A | 4/1998 | Moll et al. |
| 5,738,648 A | 4/1998 | Lands et al. |
| 5,741,271 A | 4/1998 | Nakao et al. |
| 5,743,456 A | 4/1998 | Jones et al. |
| 5,747,953 A | 5/1998 | Philipp |
| 5,749,889 A | 5/1998 | Bacich et al. |
| 5,749,893 A | 5/1998 | Vidal et al. |
| 5,749,896 A | 5/1998 | Cook |
| 5,749,968 A | 5/1998 | Melanson et al. |
| 5,752,644 A | 5/1998 | Bolanos et al. |
| 5,752,965 A | 5/1998 | Francis et al. |
| 5,752,970 A | 5/1998 | Yoon |
| 5,752,973 A | 5/1998 | Kieturakis |
| 5,755,717 A | 5/1998 | Yates et al. |
| 5,758,814 A | 6/1998 | Gallagher et al. |
| 5,762,255 A | 6/1998 | Chrisman et al. |
| 5,762,256 A | 6/1998 | Mastri et al. |
| 5,765,565 A | 6/1998 | Adair |
| 5,766,188 A | 6/1998 | Igaki |
| 5,766,205 A | 6/1998 | Zvenyatsky et al. |
| 5,769,303 A | 6/1998 | Knodel et al. |
| 5,769,748 A | 6/1998 | Eyerly et al. |
| 5,769,791 A | 6/1998 | Benaron et al. |
| 5,769,892 A | 6/1998 | Kingwell |
| 5,772,379 A | 6/1998 | Evensen |
| 5,772,578 A | 6/1998 | Heimberger et al. |
| 5,772,659 A | 6/1998 | Becker et al. |
| 5,773,991 A | 6/1998 | Chen |
| 5,776,130 A | 7/1998 | Buysse et al. |
| 5,778,939 A | 7/1998 | Hok-Yin |
| 5,779,130 A | 7/1998 | Alesi et al. |
| 5,779,131 A | 7/1998 | Knodel et al. |
| 5,779,132 A | 7/1998 | Knodel et al. |
| 5,782,396 A | 7/1998 | Mastri et al. |
| 5,782,397 A | 7/1998 | Koukline |
| 5,782,748 A | 7/1998 | Palmer et al. |
| 5,782,749 A | 7/1998 | Riza |
| 5,782,859 A | 7/1998 | Nicholas et al. |
| 5,784,934 A | 7/1998 | Izumisawa |
| 5,785,232 A | 7/1998 | Vidal et al. |
| 5,785,647 A | 7/1998 | Tompkins et al. |
| 5,787,897 A | 8/1998 | Kieturakis |
| 5,791,231 A | 8/1998 | Cohn et al. |
| 5,792,135 A | 8/1998 | Madhani et al. |
| 5,792,162 A | 8/1998 | Jolly et al. |
| 5,792,165 A | 8/1998 | Klieman et al. |
| 5,792,573 A | 8/1998 | Pitzen et al. |
| 5,794,834 A | 8/1998 | Hamblin et al. |
| 5,796,188 A | 8/1998 | Bays |
| 5,797,536 A | 8/1998 | Smith et al. |
| 5,797,537 A | 8/1998 | Oberlin et al. |
| 5,797,538 A | 8/1998 | Heaton et al. |
| 5,797,637 A | 8/1998 | Ervin |
| 5,797,900 A | 8/1998 | Madhani et al. |
| 5,797,906 A | 8/1998 | Rhum et al. |
| 5,797,927 A | 8/1998 | Yoon |
| 5,797,941 A | 8/1998 | Schulze et al. |
| 5,797,959 A | 8/1998 | Castro et al. |
| 5,799,857 A | 9/1998 | Robertson et al. |
| 5,800,379 A | 9/1998 | Edwards |
| 5,800,423 A | 9/1998 | Jensen |
| 5,804,726 A | 9/1998 | Geib et al. |
| 5,804,936 A | 9/1998 | Brodsky et al. |
| 5,806,676 A | 9/1998 | Wasgien |
| 5,807,376 A | 9/1998 | Viola et al. |
| 5,807,378 A | 9/1998 | Jensen et al. |
| 5,807,393 A | 9/1998 | Williamson, IV et al. |
| 5,809,441 A | 9/1998 | McKee |
| 5,810,721 A | 9/1998 | Mueller et al. |
| 5,810,811 A | 9/1998 | Yates et al. |
| 5,810,846 A | 9/1998 | Virnich et al. |
| 5,810,855 A | 9/1998 | Rayburn et al. |
| 5,812,188 A | 9/1998 | Adair |
| 5,813,813 A | 9/1998 | Daum et al. |
| 5,814,055 A | 9/1998 | Knodel et al. |
| 5,814,057 A | 9/1998 | Oi et al. |
| 5,816,471 A | 10/1998 | Plyley et al. |
| 5,817,084 A | 10/1998 | Jensen |
| 5,817,091 A | 10/1998 | Nardella et al. |
| 5,817,093 A | 10/1998 | Williamson, IV et al. |
| 5,817,109 A | 10/1998 | McGarry et al. |
| 5,817,119 A | 10/1998 | Klieman et al. |
| 5,820,009 A | 10/1998 | Melling et al. |
| 5,823,066 A | 10/1998 | Huitema et al. |
| 5,824,333 A | 10/1998 | Scopelianos et al. |
| 5,826,776 A | 10/1998 | Schulze et al. |
| 5,827,271 A | 10/1998 | Buysse et al. |
| 5,827,298 A | 10/1998 | Hart et al. |
| 5,827,323 A | 10/1998 | Klieman et al. |
| 5,829,662 A | 11/1998 | Allen et al. |
| 5,830,598 A | 11/1998 | Patterson |
| 5,833,690 A | 11/1998 | Yates et al. |
| 5,833,695 A | 11/1998 | Yoon |
| 5,833,696 A | 11/1998 | Whitfield et al. |
| 5,836,503 A | 11/1998 | Ehrenfels et al. |
| 5,836,960 A | 11/1998 | Kolesa et al. |
| 5,839,369 A | 11/1998 | Chatterjee et al. |
| 5,839,639 A | 11/1998 | Sauer et al. |
| 5,841,284 A | 11/1998 | Takahashi |
| 5,843,021 A | 12/1998 | Edwards et al. |
| 5,843,096 A | 12/1998 | Igaki et al. |
| 5,843,097 A | 12/1998 | Mayenberger et al. |
| 5,843,122 A | 12/1998 | Riza |
| 5,843,132 A | 12/1998 | Ilvento |
| 5,843,169 A | 12/1998 | Taheri |
| 5,846,254 A | 12/1998 | Schulze et al. |
| 5,847,566 A | 12/1998 | Marritt et al. |
| 5,849,011 A | 12/1998 | Jones et al. |
| 5,849,020 A | 12/1998 | Long et al. |
| 5,849,023 A | 12/1998 | Mericle |
| 5,851,179 A | 12/1998 | Ritson et al. |
| 5,851,212 A | 12/1998 | Zirps et al. |
| 5,853,366 A | 12/1998 | Dowlatshahi |
| 5,855,311 A | 1/1999 | Hamblin et al. |
| 5,855,583 A | 1/1999 | Wang et al. |
| 5,860,581 A | 1/1999 | Robertson et al. |
| 5,860,975 A | 1/1999 | Goble et al. |
| 5,865,361 A | 2/1999 | Milliman et al. |
| 5,865,638 A | 2/1999 | Trafton |

(56) References Cited

U.S. PATENT DOCUMENTS

| | | |
|---|---|---|
| 5,868,361 A | 2/1999 | Rinderer |
| 5,868,760 A | 2/1999 | McGuckin, Jr. |
| 5,868,790 A | 2/1999 | Vincent et al. |
| 5,871,135 A | 2/1999 | Williamson, IV et al. |
| 5,873,885 A | 2/1999 | Weidenbenner |
| 5,876,401 A | 3/1999 | Schulze et al. |
| 5,878,193 A | 3/1999 | Wang et al. |
| 5,878,607 A | 3/1999 | Nunes et al. |
| 5,878,937 A | 3/1999 | Green et al. |
| 5,878,938 A | 3/1999 | Bittner et al. |
| 5,881,777 A | 3/1999 | Bassi et al. |
| 5,891,094 A | 4/1999 | Masterson et al. |
| 5,891,160 A | 4/1999 | Williamson, IV et al. |
| 5,891,558 A | 4/1999 | Bell et al. |
| 5,893,506 A | 4/1999 | Powell |
| 5,893,835 A | 4/1999 | Witt et al. |
| 5,893,878 A | 4/1999 | Pierce |
| 5,894,979 A | 4/1999 | Powell |
| 5,897,552 A | 4/1999 | Edwards et al. |
| 5,897,562 A | 4/1999 | Bolanos et al. |
| 5,899,824 A | 5/1999 | Kurtz et al. |
| 5,899,914 A | 5/1999 | Zirps et al. |
| 5,901,895 A | 5/1999 | Heaton et al. |
| 5,902,312 A | 5/1999 | Frater et al. |
| 5,903,117 A | 5/1999 | Gregory |
| 5,904,647 A | 5/1999 | Ouchi |
| 5,904,693 A | 5/1999 | Dicesare et al. |
| 5,904,702 A | 5/1999 | Ek et al. |
| 5,906,577 A | 5/1999 | Beane et al. |
| 5,906,625 A | 5/1999 | Bito et al. |
| 5,907,211 A | 5/1999 | Hall et al. |
| 5,908,402 A | 6/1999 | Blythe |
| 5,908,427 A | 6/1999 | McKean et al. |
| 5,909,062 A | 6/1999 | Krietzman |
| 5,911,353 A | 6/1999 | Bolanos et al. |
| 5,915,616 A | 6/1999 | Viola et al. |
| 5,916,225 A | 6/1999 | Kugel |
| 5,918,791 A | 7/1999 | Sorrentino et al. |
| 5,919,198 A | 7/1999 | Graves, Jr. et al. |
| 5,921,956 A | 7/1999 | Grinberg et al. |
| 5,924,864 A | 7/1999 | Loge et al. |
| 5,928,137 A | 7/1999 | Green |
| 5,928,256 A | 7/1999 | Riza |
| 5,931,847 A | 8/1999 | Bittner et al. |
| 5,931,853 A | 8/1999 | McEwen et al. |
| 5,937,951 A | 8/1999 | Izuchukwu et al. |
| 5,938,667 A | 8/1999 | Peyser et al. |
| 5,941,442 A | 8/1999 | Geiste et al. |
| 5,941,890 A | 8/1999 | Voegele et al. |
| 5,944,172 A | 8/1999 | Hannula |
| 5,944,715 A | 8/1999 | Goble et al. |
| 5,946,978 A | 9/1999 | Yamashita |
| 5,947,984 A | 9/1999 | Whipple |
| 5,947,996 A | 9/1999 | Logeman |
| 5,948,030 A | 9/1999 | Miller et al. |
| 5,948,429 A | 9/1999 | Bell et al. |
| 5,951,301 A | 9/1999 | Younker |
| 5,951,516 A | 9/1999 | Bunyan |
| 5,951,552 A | 9/1999 | Long et al. |
| 5,951,574 A | 9/1999 | Stefanchik et al. |
| 5,951,575 A | 9/1999 | Bolduc et al. |
| 5,951,581 A | 9/1999 | Saadat et al. |
| 5,954,259 A | 9/1999 | Viola et al. |
| 5,957,831 A | 9/1999 | Adair |
| 5,964,394 A | 10/1999 | Robertson |
| 5,964,774 A | 10/1999 | McKean et al. |
| 5,966,126 A | 10/1999 | Szabo |
| 5,971,916 A | 10/1999 | Koren |
| 5,973,221 A | 10/1999 | Collyer et al. |
| D416,089 S | 11/1999 | Barton et al. |
| 5,976,122 A | 11/1999 | Madhani et al. |
| 5,977,746 A | 11/1999 | Hershberger et al. |
| 5,980,248 A | 11/1999 | Kusakabe et al. |
| 5,984,949 A | 11/1999 | Levin |
| 5,988,479 A | 11/1999 | Palmer |
| 5,990,379 A | 11/1999 | Gregory |
| 5,993,466 A | 11/1999 | Yoon |
| 5,997,528 A | 12/1999 | Bisch et al. |
| 5,997,552 A | 12/1999 | Person et al. |
| 6,001,108 A | 12/1999 | Wang et al. |
| 6,003,517 A | 12/1999 | Sheffield et al. |
| 6,004,319 A | 12/1999 | Goble et al. |
| 6,004,335 A | 12/1999 | Vaitekunas et al. |
| 6,007,521 A | 12/1999 | Bidwell et al. |
| 6,010,054 A | 1/2000 | Johnson et al. |
| 6,010,513 A | 1/2000 | Tormala et al. |
| 6,010,520 A | 1/2000 | Pattison |
| 6,012,494 A | 1/2000 | Balazs |
| 6,013,076 A | 1/2000 | Goble et al. |
| 6,015,406 A | 1/2000 | Goble et al. |
| 6,015,417 A | 1/2000 | Reynolds, Jr. |
| 6,017,322 A | 1/2000 | Snoke et al. |
| 6,017,354 A | 1/2000 | Culp et al. |
| 6,017,356 A | 1/2000 | Frederick et al. |
| 6,018,227 A | 1/2000 | Kumar et al. |
| 6,019,745 A | 2/2000 | Gray |
| 6,022,352 A | 2/2000 | Vandewalle |
| 6,023,641 A | 2/2000 | Thompson |
| 6,024,708 A | 2/2000 | Bales et al. |
| 6,024,741 A | 2/2000 | Williamson, IV et al. |
| 6,024,748 A | 2/2000 | Manzo et al. |
| 6,024,750 A | 2/2000 | Mastri et al. |
| 6,024,764 A | 2/2000 | Schroeppel |
| 6,027,501 A | 2/2000 | Goble et al. |
| 6,030,384 A | 2/2000 | Nezhat |
| 6,032,849 A | 3/2000 | Mastri et al. |
| 6,033,105 A | 3/2000 | Barker et al. |
| 6,033,378 A | 3/2000 | Lundquist et al. |
| 6,033,399 A | 3/2000 | Gines |
| 6,033,427 A | 3/2000 | Lee |
| 6,036,641 A | 3/2000 | Taylor et al. |
| 6,036,667 A | 3/2000 | Manna et al. |
| 6,037,724 A | 3/2000 | Buss et al. |
| 6,037,927 A | 3/2000 | Rosenberg |
| 6,039,733 A | 3/2000 | Buysse et al. |
| 6,039,734 A | 3/2000 | Goble |
| 6,042,601 A | 3/2000 | Smith |
| 6,042,607 A | 3/2000 | Williamson, IV et al. |
| 6,043,626 A | 3/2000 | Snyder et al. |
| 6,045,560 A | 4/2000 | McKean et al. |
| 6,047,861 A | 4/2000 | Vidal et al. |
| 6,049,145 A | 4/2000 | Austin et al. |
| 6,050,172 A | 4/2000 | Corves et al. |
| 6,050,472 A | 4/2000 | Shibata |
| 6,050,989 A | 4/2000 | Fox et al. |
| 6,050,990 A | 4/2000 | Tankovich et al. |
| 6,050,996 A | 4/2000 | Schmaltz et al. |
| 6,053,390 A | 4/2000 | Green et al. |
| 6,053,899 A | 4/2000 | Slanda et al. |
| 6,053,922 A | 4/2000 | Krause et al. |
| 6,054,142 A | 4/2000 | Li et al. |
| 6,055,062 A | 4/2000 | Dina et al. |
| RE36,720 E | 5/2000 | Green et al. |
| 6,056,735 A | 5/2000 | Okada et al. |
| 6,056,746 A | 5/2000 | Goble et al. |
| 6,059,806 A | 5/2000 | Hoegerle |
| 6,062,360 A | 5/2000 | Shields |
| 6,063,020 A | 5/2000 | Jones et al. |
| 6,063,025 A | 5/2000 | Bridges et al. |
| 6,063,050 A | 5/2000 | Manna et al. |
| 6,063,095 A | 5/2000 | Wang et al. |
| 6,063,097 A | 5/2000 | Oi et al. |
| 6,063,098 A | 5/2000 | Houser et al. |
| 6,065,679 A | 5/2000 | Levie et al. |
| 6,065,919 A | 5/2000 | Peck |
| 6,066,132 A | 5/2000 | Chen et al. |
| 6,066,151 A | 5/2000 | Miyawaki et al. |
| 6,068,627 A | 5/2000 | Orszulak et al. |
| 6,071,233 A | 6/2000 | Ishikawa et al. |
| 6,074,386 A | 6/2000 | Goble et al. |
| 6,074,401 A | 6/2000 | Gardiner et al. |
| 6,077,280 A | 6/2000 | Fossum |
| 6,077,286 A | 6/2000 | Cuschieri et al. |
| 6,077,290 A | 6/2000 | Marini |

(56) References Cited

U.S. PATENT DOCUMENTS

| | | |
|---|---|---|
| 6,079,606 A | 6/2000 | Milliman et al. |
| 6,080,181 A | 6/2000 | Jensen et al. |
| 6,082,577 A | 7/2000 | Coates et al. |
| 6,083,191 A | 7/2000 | Rose |
| 6,083,223 A | 7/2000 | Baker |
| 6,083,234 A | 7/2000 | Nicholas et al. |
| 6,083,242 A | 7/2000 | Cook |
| 6,086,544 A | 7/2000 | Hibner et al. |
| 6,086,600 A | 7/2000 | Kortenbach |
| 6,090,106 A | 7/2000 | Goble et al. |
| 6,093,186 A | 7/2000 | Goble |
| 6,099,537 A | 8/2000 | Sugai et al. |
| 6,099,551 A | 8/2000 | Gabbay |
| 6,102,271 A | 8/2000 | Longo et al. |
| 6,102,926 A | 8/2000 | Tartaglia et al. |
| 6,104,162 A | 8/2000 | Sainsbury et al. |
| 6,104,304 A | 8/2000 | Clark et al. |
| 6,106,511 A | 8/2000 | Jensen |
| 6,109,500 A | 8/2000 | Alli et al. |
| 6,110,187 A | 8/2000 | Donlon |
| 6,113,618 A | 9/2000 | Nic |
| 6,117,148 A | 9/2000 | Ravo et al. |
| 6,117,158 A | 9/2000 | Measamer et al. |
| 6,119,913 A | 9/2000 | Adams et al. |
| 6,120,433 A | 9/2000 | Mizuno et al. |
| 6,120,462 A | 9/2000 | Hibner et al. |
| 6,123,241 A | 9/2000 | Walter et al. |
| 6,123,701 A | 9/2000 | Nezhat |
| H1904 H | 10/2000 | Yates et al. |
| 6,126,058 A | 10/2000 | Adams et al. |
| 6,126,359 A | 10/2000 | Dittrich et al. |
| 6,126,670 A | 10/2000 | Walker et al. |
| 6,131,789 A | 10/2000 | Schulze et al. |
| 6,131,790 A | 10/2000 | Piraka |
| 6,132,368 A | 10/2000 | Cooper |
| 6,134,962 A | 10/2000 | Sugitani |
| 6,139,546 A | 10/2000 | Koenig et al. |
| 6,142,149 A | 11/2000 | Steen |
| 6,142,933 A | 11/2000 | Longo et al. |
| 6,147,135 A | 11/2000 | Yuan et al. |
| 6,149,660 A | 11/2000 | Laufer et al. |
| 6,151,323 A | 11/2000 | O'Connell et al. |
| 6,152,935 A | 11/2000 | Kammerer et al. |
| 6,155,473 A | 12/2000 | Tompkins et al. |
| 6,156,056 A | 12/2000 | Kearns et al. |
| 6,157,169 A | 12/2000 | Lee |
| 6,159,146 A | 12/2000 | El Gazayerli |
| 6,159,200 A | 12/2000 | Verdura et al. |
| 6,159,224 A | 12/2000 | Yoon |
| 6,162,208 A | 12/2000 | Hipps |
| 6,162,220 A | 12/2000 | Nezhat |
| 6,162,537 A | 12/2000 | Martin et al. |
| 6,165,175 A | 12/2000 | Wampler et al. |
| 6,165,184 A | 12/2000 | Verdura et al. |
| 6,165,188 A | 12/2000 | Saadat et al. |
| 6,167,185 A | 12/2000 | Smiley et al. |
| 6,168,605 B1 | 1/2001 | Measamer et al. |
| 6,171,305 B1 | 1/2001 | Sherman |
| 6,171,316 B1 | 1/2001 | Kovac et al. |
| 6,171,330 B1 | 1/2001 | Benchetrit |
| 6,173,074 B1 | 1/2001 | Russo |
| 6,174,308 B1 | 1/2001 | Goble et al. |
| 6,174,309 B1 | 1/2001 | Wrublewski et al. |
| 6,174,318 B1 | 1/2001 | Bates et al. |
| 6,175,290 B1 | 1/2001 | Forsythe et al. |
| 6,179,195 B1 | 1/2001 | Adams et al. |
| 6,179,776 B1 | 1/2001 | Adams et al. |
| 6,181,105 B1 | 1/2001 | Cutolo et al. |
| 6,182,673 B1 | 2/2001 | Kindermann et al. |
| 6,185,356 B1 | 2/2001 | Parker et al. |
| 6,186,142 B1 | 2/2001 | Schmidt et al. |
| 6,187,003 B1 | 2/2001 | Buysse et al. |
| 6,190,386 B1 | 2/2001 | Rydell |
| 6,193,129 B1 | 2/2001 | Bittner et al. |
| 6,197,042 B1 | 3/2001 | Ginn et al. |
| 6,200,330 B1 | 3/2001 | Benderev et al. |
| 6,202,914 B1 | 3/2001 | Geiste et al. |
| 6,206,894 B1 | 3/2001 | Thompson et al. |
| 6,206,897 B1 | 3/2001 | Jamiolkowski et al. |
| 6,206,903 B1 | 3/2001 | Ramans |
| 6,206,904 B1 | 3/2001 | Ouchi |
| 6,209,414 B1 | 4/2001 | Uneme |
| 6,210,403 B1 | 4/2001 | Klicek |
| 6,211,626 B1 | 4/2001 | Lys et al. |
| 6,213,999 B1 | 4/2001 | Platt, Jr. et al. |
| 6,214,028 B1 | 4/2001 | Yoon et al. |
| 6,220,368 B1 | 4/2001 | Ark et al. |
| 6,221,007 B1 | 4/2001 | Green |
| 6,221,023 B1 | 4/2001 | Matsuba et al. |
| 6,223,100 B1 | 4/2001 | Green |
| 6,223,835 B1 | 5/2001 | Habedank et al. |
| 6,224,617 B1 | 5/2001 | Saadat et al. |
| 6,228,080 B1 | 5/2001 | Gines |
| 6,228,081 B1 | 5/2001 | Goble |
| 6,228,083 B1 | 5/2001 | Lands et al. |
| 6,228,084 B1 | 5/2001 | Kirwan, Jr. |
| 6,228,089 B1 | 5/2001 | Wahrburg |
| 6,228,098 B1 | 5/2001 | Kayan et al. |
| 6,231,565 B1 | 5/2001 | Tovey et al. |
| 6,234,178 B1 | 5/2001 | Goble et al. |
| 6,237,604 B1 | 5/2001 | Burnside et al. |
| 6,238,384 B1 | 5/2001 | Peer |
| 6,241,139 B1 | 6/2001 | Milliman et al. |
| 6,241,140 B1 | 6/2001 | Adams et al. |
| 6,241,723 B1 | 6/2001 | Heim et al. |
| 6,245,084 B1 | 6/2001 | Mark et al. |
| 6,248,116 B1 | 6/2001 | Chevillon et al. |
| 6,248,117 B1 | 6/2001 | Blatter |
| 6,249,076 B1 | 6/2001 | Madden et al. |
| 6,249,105 B1 | 6/2001 | Andrews et al. |
| 6,250,532 B1 | 6/2001 | Green et al. |
| 6,251,485 B1 | 6/2001 | Harris et al. |
| D445,745 S | 7/2001 | Norman |
| 6,254,534 B1 | 7/2001 | Butler et al. |
| 6,254,619 B1 | 7/2001 | Garabet et al. |
| 6,254,642 B1 | 7/2001 | Taylor |
| 6,258,107 B1 | 7/2001 | Balazs et al. |
| 6,261,286 B1 | 7/2001 | Goble et al. |
| 6,261,679 B1 | 7/2001 | Chen et al. |
| 6,264,086 B1 | 7/2001 | McGuckin, Jr. |
| 6,264,087 B1 | 7/2001 | Whitman |
| 6,264,617 B1 | 7/2001 | Bales et al. |
| 6,270,508 B1 | 8/2001 | Klieman et al. |
| 6,270,916 B1 | 8/2001 | Sink et al. |
| 6,273,252 B1 | 8/2001 | Mitchell |
| 6,273,876 B1 | 8/2001 | Klima et al. |
| 6,273,897 B1 | 8/2001 | Dalessandro et al. |
| 6,277,114 B1 | 8/2001 | Bullivant et al. |
| 6,280,407 B1 | 8/2001 | Manna et al. |
| 6,283,981 B1 | 9/2001 | Beaupre |
| 6,293,927 B1 | 9/2001 | McGuckin, Jr. |
| 6,293,942 B1 | 9/2001 | Goble et al. |
| 6,296,640 B1 | 10/2001 | Wampler et al. |
| 6,302,311 B1 | 10/2001 | Adams et al. |
| 6,302,743 B1 | 10/2001 | Chiu et al. |
| 6,305,891 B1 | 10/2001 | Burlingame |
| 6,306,134 B1 | 10/2001 | Goble et al. |
| 6,306,149 B1 | 10/2001 | Meade |
| 6,306,424 B1 | 10/2001 | Vyakarnam et al. |
| 6,309,397 B1 | 10/2001 | Julian et al. |
| 6,309,400 B2 | 10/2001 | Beaupre |
| 6,309,403 B1 | 10/2001 | Minor et al. |
| 6,312,435 B1 | 11/2001 | Wallace et al. |
| 6,315,184 B1 | 11/2001 | Whitman |
| 6,319,510 B1 | 11/2001 | Yates |
| 6,320,123 B1 | 11/2001 | Reimers |
| 6,322,494 B1 | 11/2001 | Bullivant et al. |
| 6,324,339 B1 | 11/2001 | Hudson et al. |
| 6,325,799 B1 | 12/2001 | Goble |
| 6,325,805 B1 | 12/2001 | Ogilvie et al. |
| 6,325,810 B1 | 12/2001 | Hamilton et al. |
| 6,328,498 B1 | 12/2001 | Mersch |
| 6,330,965 B1 | 12/2001 | Milliman et al. |
| 6,331,181 B1 | 12/2001 | Tierney et al. |

(56) References Cited

U.S. PATENT DOCUMENTS

| | | |
|---|---|---|
| 6,331,761 B1 | 12/2001 | Kumar et al. |
| 6,333,029 B1 | 12/2001 | Vyakarnam et al. |
| 6,334,860 B1 | 1/2002 | Dorn |
| 6,334,861 B1 | 1/2002 | Chandler et al. |
| 6,336,926 B1 | 1/2002 | Goble |
| 6,338,737 B1 | 1/2002 | Toledano |
| 6,343,731 B1 | 2/2002 | Adams et al. |
| 6,346,077 B1 | 2/2002 | Taylor et al. |
| 6,348,061 B1 | 2/2002 | Whitman |
| D454,951 S | 3/2002 | Bon |
| 6,352,503 B1 | 3/2002 | Matsui et al. |
| 6,352,532 B1 | 3/2002 | Kramer et al. |
| 6,355,699 B1 | 3/2002 | Vyakarnam et al. |
| 6,356,072 B1 | 3/2002 | Chass |
| 6,358,224 B1 | 3/2002 | Tims et al. |
| 6,358,263 B2 | 3/2002 | Mark et al. |
| 6,358,459 B1 | 3/2002 | Ziegler et al. |
| 6,364,877 B1 | 4/2002 | Goble et al. |
| 6,364,888 B1 | 4/2002 | Niemeyer et al. |
| 6,366,441 B1 | 4/2002 | Ozawa et al. |
| 6,370,981 B2 | 4/2002 | Watarai |
| 6,371,114 B1 | 4/2002 | Schmidt et al. |
| 6,373,152 B1 | 4/2002 | Wang et al. |
| 6,377,011 B1 | 4/2002 | Ben-Ur |
| 6,383,201 B1 | 5/2002 | Dong |
| 6,387,092 B1 | 5/2002 | Burnside et al. |
| 6,387,113 B1 | 5/2002 | Hawkins et al. |
| 6,387,114 B2 | 5/2002 | Adams |
| 6,391,038 B2 | 5/2002 | Vargas et al. |
| 6,392,854 B1 | 5/2002 | O'Gorman |
| 6,394,998 B1 | 5/2002 | Wallace et al. |
| 6,398,779 B1 | 6/2002 | Buysse et al. |
| 6,398,781 B1 | 6/2002 | Goble et al. |
| 6,398,797 B2 | 6/2002 | Bombard et al. |
| 6,402,766 B2 | 6/2002 | Bowman et al. |
| 6,406,440 B1 | 6/2002 | Stefanchik |
| 6,406,472 B1 | 6/2002 | Jensen |
| 6,409,724 B1 | 6/2002 | Penny et al. |
| H2037 H | 7/2002 | Yates et al. |
| 6,412,639 B1 | 7/2002 | Hickey |
| 6,413,274 B1 | 7/2002 | Pedros |
| 6,415,542 B1 | 7/2002 | Bates et al. |
| 6,416,486 B1 | 7/2002 | Wampler |
| 6,416,509 B1 | 7/2002 | Goble et al. |
| 6,419,695 B1 | 7/2002 | Gabbay |
| 6,423,079 B1 | 7/2002 | Blake, III |
| 6,424,885 B1 | 7/2002 | Niemeyer et al. |
| RE37,814 E | 8/2002 | Allgeyer |
| 6,428,070 B1 | 8/2002 | Takanashi et al. |
| 6,428,487 B1 | 8/2002 | Burdorff et al. |
| 6,429,611 B1 | 8/2002 | Li |
| 6,430,298 B1 | 8/2002 | Kettl et al. |
| 6,432,065 B1 | 8/2002 | Burdorff et al. |
| 6,436,097 B1 | 8/2002 | Nardella |
| 6,436,107 B1 | 8/2002 | Wang et al. |
| 6,436,110 B2 | 8/2002 | Bowman et al. |
| 6,436,115 B1 | 8/2002 | Beaupre |
| 6,436,122 B1 | 8/2002 | Frank et al. |
| 6,439,439 B1 | 8/2002 | Rickard et al. |
| 6,439,446 B1 | 8/2002 | Perry et al. |
| 6,440,146 B2 | 8/2002 | Nicholas et al. |
| 6,441,577 B2 | 8/2002 | Blumenkranz et al. |
| D462,758 S | 9/2002 | Epstein et al. |
| 6,443,973 B1 | 9/2002 | Whitman |
| 6,445,530 B1 | 9/2002 | Baker |
| 6,447,518 B1 | 9/2002 | Krause et al. |
| 6,447,523 B1 | 9/2002 | Middleman et al. |
| 6,447,799 B1 | 9/2002 | Ullman |
| 6,447,864 B2 | 9/2002 | Johnson et al. |
| 6,450,391 B1 | 9/2002 | Kayan et al. |
| 6,450,989 B2 | 9/2002 | Dubrul et al. |
| 6,454,781 B1 | 9/2002 | Witt et al. |
| 6,457,625 B1 | 10/2002 | Tormala et al. |
| 6,458,077 B1 | 10/2002 | Boebel et al. |
| 6,458,147 B1 | 10/2002 | Cruise et al. |
| 6,460,627 B1 | 10/2002 | Below et al. |
| 6,468,275 B1 | 10/2002 | Wampler et al. |
| 6,468,286 B2 | 10/2002 | Mastri et al. |
| 6,471,106 B1 | 10/2002 | Reining |
| 6,471,659 B2 | 10/2002 | Eggers et al. |
| 6,478,210 B2 | 11/2002 | Adams et al. |
| 6,482,200 B2 | 11/2002 | Shippert |
| 6,482,217 B1 | 11/2002 | Pintor et al. |
| 6,485,490 B2 | 11/2002 | Wampler et al. |
| 6,485,503 B2 | 11/2002 | Jacobs et al. |
| 6,485,667 B1 | 11/2002 | Tan |
| 6,486,286 B1 | 11/2002 | McGall et al. |
| 6,488,196 B1 | 12/2002 | Fenton, Jr. |
| 6,488,197 B1 | 12/2002 | Whitman |
| 6,488,659 B1 | 12/2002 | Rosenman |
| 6,491,201 B1 | 12/2002 | Whitman |
| 6,491,690 B1 | 12/2002 | Goble et al. |
| 6,491,701 B2 | 12/2002 | Tierney et al. |
| 6,491,702 B2 | 12/2002 | Heilbrun et al. |
| 6,492,785 B1 | 12/2002 | Kasten et al. |
| 6,494,882 B1 | 12/2002 | Lebouitz et al. |
| 6,494,885 B1 | 12/2002 | Dhindsa |
| 6,494,888 B1 | 12/2002 | Laufer et al. |
| 6,494,896 B1 | 12/2002 | D'Alessio et al. |
| 6,498,480 B1 | 12/2002 | Manara |
| 6,500,176 B1 | 12/2002 | Truckai et al. |
| 6,500,194 B2 | 12/2002 | Benderev et al. |
| 6,503,139 B2 | 1/2003 | Coral |
| 6,503,257 B2 | 1/2003 | Grant et al. |
| 6,503,259 B2 | 1/2003 | Huxel et al. |
| 6,505,768 B2 | 1/2003 | Whitman |
| 6,506,197 B1 | 1/2003 | Rollero et al. |
| 6,510,854 B2 | 1/2003 | Goble |
| 6,511,468 B1 | 1/2003 | Cragg et al. |
| 6,512,360 B1 | 1/2003 | Goto et al. |
| 6,514,252 B2 | 2/2003 | Nezhat et al. |
| 6,516,073 B1 | 2/2003 | Schulz et al. |
| 6,517,528 B1 | 2/2003 | Pantages et al. |
| 6,517,535 B2 | 2/2003 | Edwards |
| 6,517,565 B1 | 2/2003 | Whitman et al. |
| 6,517,566 B1 | 2/2003 | Hovland et al. |
| 6,520,971 B1 | 2/2003 | Perry et al. |
| 6,520,972 B2 | 2/2003 | Peters |
| 6,522,101 B2 | 2/2003 | Malackowski |
| 6,524,180 B1 | 2/2003 | Simms et al. |
| 6,525,499 B2 | 2/2003 | Naganuma |
| 6,527,782 B2 | 3/2003 | Hogg et al. |
| 6,527,785 B2 | 3/2003 | Sancoff et al. |
| 6,530,942 B2 | 3/2003 | Fogarty et al. |
| 6,532,958 B1 | 3/2003 | Buan et al. |
| 6,533,157 B1 | 3/2003 | Whitman |
| 6,533,723 B1 | 3/2003 | Lockery et al. |
| 6,533,784 B2 | 3/2003 | Truckai et al. |
| 6,535,764 B2 | 3/2003 | Imran et al. |
| 6,539,297 B2 | 3/2003 | Weiberle et al. |
| D473,239 S | 4/2003 | Cockerill |
| 6,539,816 B2 | 4/2003 | Kogiso et al. |
| 6,540,737 B2 | 4/2003 | Bacher et al. |
| 6,543,456 B1 | 4/2003 | Freeman |
| 6,545,384 B1 | 4/2003 | Pelrine et al. |
| 6,547,786 B1 | 4/2003 | Goble |
| 6,550,546 B2 | 4/2003 | Thurler et al. |
| 6,551,333 B2 | 4/2003 | Kuhns et al. |
| 6,554,861 B2 | 4/2003 | Knox et al. |
| 6,555,770 B2 | 4/2003 | Kawase |
| 6,558,378 B2 | 5/2003 | Sherman et al. |
| 6,558,379 B1 | 5/2003 | Batchelor et al. |
| 6,558,429 B2 | 5/2003 | Taylor |
| 6,561,187 B2 | 5/2003 | Schmidt et al. |
| 6,565,560 B1 | 5/2003 | Goble et al. |
| 6,566,619 B2 | 5/2003 | Gillman et al. |
| 6,569,085 B2 | 5/2003 | Kortenbach et al. |
| 6,569,171 B2 | 5/2003 | DeGuillebon et al. |
| 6,578,751 B2 | 6/2003 | Hartwick |
| 6,582,364 B2 | 6/2003 | Butler et al. |
| 6,582,427 B1 | 6/2003 | Goble et al. |
| 6,582,441 B1 | 6/2003 | He et al. |
| 6,583,533 B2 | 6/2003 | Pelrine et al. |
| 6,585,144 B2 | 7/2003 | Adams et al. |

(56) References Cited

U.S. PATENT DOCUMENTS

| | | |
|---|---|---|
| 6,585,664 B2 | 7/2003 | Burdorff et al. |
| 6,586,898 B2 | 7/2003 | King et al. |
| 6,587,750 B2 | 7/2003 | Gerbi et al. |
| 6,588,277 B2 | 7/2003 | Giordano et al. |
| 6,588,643 B2 | 7/2003 | Bolduc et al. |
| 6,588,931 B2 | 7/2003 | Betzner et al. |
| 6,589,118 B1 | 7/2003 | Soma et al. |
| 6,589,164 B1 | 7/2003 | Flaherty |
| 6,592,538 B1 | 7/2003 | Hotchkiss et al. |
| 6,592,597 B2 | 7/2003 | Grant et al. |
| 6,594,552 B1 | 7/2003 | Nowlin et al. |
| 6,596,296 B1 | 7/2003 | Nelson et al. |
| 6,596,304 B1 | 7/2003 | Bayon et al. |
| 6,596,432 B2 | 7/2003 | Kawakami et al. |
| 6,599,295 B1 | 7/2003 | Tornier et al. |
| 6,599,323 B2 | 7/2003 | Melican et al. |
| D478,665 S | 8/2003 | Isaacs et al. |
| D478,986 S | 8/2003 | Johnston et al. |
| 6,601,749 B2 | 8/2003 | Sullivan et al. |
| 6,602,252 B2 | 8/2003 | Mollenauer |
| 6,602,262 B2 | 8/2003 | Griego et al. |
| 6,603,050 B2 | 8/2003 | Heaton |
| 6,605,078 B2 | 8/2003 | Adams |
| 6,605,669 B2 | 8/2003 | Awokola et al. |
| 6,605,911 B1 | 8/2003 | Klesing |
| 6,607,475 B2 | 8/2003 | Doyle et al. |
| 6,611,793 B1 | 8/2003 | Burnside et al. |
| 6,613,069 B2 | 9/2003 | Boyd et al. |
| 6,616,686 B2 | 9/2003 | Coleman et al. |
| 6,619,529 B2 | 9/2003 | Green et al. |
| 6,620,111 B2 | 9/2003 | Stephens et al. |
| 6,620,161 B2 | 9/2003 | Schulze et al. |
| 6,620,166 B1 | 9/2003 | Wenstrom, Jr. et al. |
| 6,625,517 B1 | 9/2003 | Bogdanov et al. |
| 6,626,834 B2 | 9/2003 | Dunne et al. |
| H2086 H | 10/2003 | Amsler |
| 6,629,630 B2 | 10/2003 | Adams |
| 6,629,974 B2 | 10/2003 | Penny et al. |
| 6,629,988 B2 | 10/2003 | Weadock |
| 6,635,838 B1 | 10/2003 | Kornelson |
| 6,636,412 B2 | 10/2003 | Smith |
| 6,638,108 B2 | 10/2003 | Tachi |
| 6,638,285 B2 | 10/2003 | Gabbay |
| 6,638,297 B1 | 10/2003 | Huitema |
| RE38,335 E | 11/2003 | Aust et al. |
| 6,641,528 B2 | 11/2003 | Torii |
| 6,644,532 B2 | 11/2003 | Green et al. |
| 6,645,201 B1 | 11/2003 | Utley et al. |
| 6,646,307 B1 | 11/2003 | Yu et al. |
| 6,648,816 B2 | 11/2003 | Irion et al. |
| 6,648,901 B2 | 11/2003 | Fleischman et al. |
| 6,652,595 B1 | 11/2003 | Nicolo |
| D484,243 S | 12/2003 | Ryan et al. |
| D484,595 S | 12/2003 | Ryan et al. |
| D484,596 S | 12/2003 | Ryan et al. |
| 6,656,177 B2 | 12/2003 | Truckai et al. |
| 6,656,193 B2 | 12/2003 | Grant et al. |
| 6,659,940 B2 | 12/2003 | Adler |
| 6,660,008 B1 | 12/2003 | Foerster et al. |
| 6,663,623 B1 | 12/2003 | Oyama et al. |
| 6,663,641 B1 | 12/2003 | Kovac et al. |
| 6,666,854 B1 | 12/2003 | Lange |
| 6,666,860 B1 | 12/2003 | Takahashi |
| 6,666,875 B1 | 12/2003 | Sakurai et al. |
| 6,667,825 B2 | 12/2003 | Lu et al. |
| 6,669,073 B2 | 12/2003 | Milliman et al. |
| 6,670,806 B2 | 12/2003 | Wendt et al. |
| 6,671,185 B2 | 12/2003 | Duval |
| D484,977 S | 1/2004 | Ryan et al. |
| 6,676,660 B2 | 1/2004 | Wampler et al. |
| 6,677,687 B2 | 1/2004 | Ho et al. |
| 6,679,269 B2 | 1/2004 | Swanson |
| 6,679,410 B2 | 1/2004 | Wursch et al. |
| 6,681,978 B2 | 1/2004 | Geiste et al. |
| 6,681,979 B2 | 1/2004 | Whitman |
| 6,682,527 B2 | 1/2004 | Strul |
| 6,682,528 B2 | 1/2004 | Frazier et al. |
| 6,682,544 B2 | 1/2004 | Mastri et al. |
| 6,685,698 B2 | 2/2004 | Morley et al. |
| 6,685,727 B2 | 2/2004 | Fisher et al. |
| 6,689,153 B1 | 2/2004 | Skiba |
| 6,692,507 B2 | 2/2004 | Pugsley et al. |
| 6,692,692 B2 | 2/2004 | Stetzel |
| 6,695,198 B2 | 2/2004 | Adams et al. |
| 6,695,199 B2 | 2/2004 | Whitman |
| 6,695,774 B2 | 2/2004 | Hale et al. |
| 6,695,849 B2 | 2/2004 | Michelson |
| 6,696,814 B2 | 2/2004 | Henderson et al. |
| 6,697,048 B2 | 2/2004 | Rosenberg et al. |
| 6,698,643 B2 | 3/2004 | Whitman |
| 6,699,177 B1 | 3/2004 | Wang et al. |
| 6,699,214 B2 | 3/2004 | Gellman |
| 6,699,235 B2 | 3/2004 | Wallace et al. |
| 6,704,210 B1 | 3/2004 | Myers |
| 6,705,503 B1 | 3/2004 | Pedicini et al. |
| 6,709,445 B2 | 3/2004 | Boebel et al. |
| 6,712,773 B1 | 3/2004 | Viola |
| 6,716,223 B2 | 4/2004 | Leopold et al. |
| 6,716,232 B1 | 4/2004 | Vidal et al. |
| 6,716,233 B1 | 4/2004 | Whitman |
| 6,720,734 B2 | 4/2004 | Norris |
| 6,722,550 B1 | 4/2004 | Ricordi et al. |
| 6,722,552 B2 | 4/2004 | Fenton, Jr. |
| 6,723,087 B2 | 4/2004 | O'Neill et al. |
| 6,723,091 B2 | 4/2004 | Goble et al. |
| 6,723,109 B2 | 4/2004 | Solingen |
| 6,726,697 B2 | 4/2004 | Nicholas et al. |
| 6,726,706 B2 | 4/2004 | Dominguez |
| 6,729,119 B2 | 5/2004 | Schnipke et al. |
| 6,731,976 B2 | 5/2004 | Penn et al. |
| 6,736,825 B2 | 5/2004 | Blatter et al. |
| 6,736,854 B2 | 5/2004 | Vadurro et al. |
| 6,740,030 B2 | 5/2004 | Martone et al. |
| 6,743,230 B2 | 6/2004 | Lutze et al. |
| 6,744,385 B2 | 6/2004 | Kazuya et al. |
| 6,747,121 B2 | 6/2004 | Gogolewski |
| 6,747,300 B2 | 6/2004 | Nadd et al. |
| 6,749,560 B1 | 6/2004 | Konstorum et al. |
| 6,749,600 B1 | 6/2004 | Levy |
| 6,752,768 B2 | 6/2004 | Burdorff et al. |
| 6,752,816 B2 | 6/2004 | Culp et al. |
| 6,754,959 B1 | 6/2004 | Guiette, III et al. |
| 6,755,195 B1 | 6/2004 | Lemke et al. |
| 6,755,338 B2 | 6/2004 | Hahnen et al. |
| 6,755,843 B2 | 6/2004 | Chung et al. |
| 6,756,705 B2 | 6/2004 | Pulford, Jr. |
| 6,758,846 B2 | 7/2004 | Goble et al. |
| 6,761,685 B2 | 7/2004 | Adams et al. |
| 6,762,339 B1 | 7/2004 | Klun et al. |
| 6,764,445 B2 | 7/2004 | Ramans et al. |
| 6,766,957 B2 | 7/2004 | Matsuura et al. |
| 6,767,352 B2 | 7/2004 | Field et al. |
| 6,767,356 B2 | 7/2004 | Kanner et al. |
| 6,769,590 B2 | 8/2004 | Vresh et al. |
| 6,769,594 B2 | 8/2004 | Orban, III |
| 6,770,027 B2 | 8/2004 | Banik et al. |
| 6,770,070 B1 | 8/2004 | Balbierz |
| 6,770,072 B1 | 8/2004 | Truckai et al. |
| 6,770,078 B2 | 8/2004 | Bonutti |
| 6,773,409 B2 | 8/2004 | Truckai et al. |
| 6,773,437 B2 | 8/2004 | Ogilvie et al. |
| 6,773,438 B1 | 8/2004 | Knodel et al. |
| 6,775,575 B2 | 8/2004 | Bommannan et al. |
| 6,777,838 B2 | 8/2004 | Miekka et al. |
| 6,780,151 B2 | 8/2004 | Grabover et al. |
| 6,780,180 B1 | 8/2004 | Goble et al. |
| 6,783,524 B2 | 8/2004 | Anderson et al. |
| 6,786,382 B1 | 9/2004 | Hoffman |
| 6,786,864 B2 | 9/2004 | Matsuura et al. |
| 6,786,896 B1 | 9/2004 | Madhani et al. |
| 6,788,018 B1 | 9/2004 | Blumenkranz |
| 6,790,173 B2 | 9/2004 | Saadat et al. |
| 6,793,652 B1 | 9/2004 | Whitman et al. |
| 6,793,661 B2 | 9/2004 | Hamilton et al. |

(56) References Cited

U.S. PATENT DOCUMENTS

| | | |
|---|---|---|
| 6,793,663 B2 | 9/2004 | Kneifel et al. |
| 6,793,669 B2 | 9/2004 | Nakamura et al. |
| 6,796,921 B1 | 9/2004 | Buck et al. |
| 6,799,669 B2 | 10/2004 | Fukumura et al. |
| 6,802,822 B1 | 10/2004 | Dodge |
| 6,802,843 B2 | 10/2004 | Truckai et al. |
| 6,802,844 B2 | 10/2004 | Ferree |
| 6,805,273 B2 | 10/2004 | Bilotti et al. |
| 6,806,808 B1 | 10/2004 | Watters et al. |
| 6,808,525 B2 | 10/2004 | Latterell et al. |
| 6,810,359 B2 | 10/2004 | Sakaguchi |
| 6,814,154 B2 | 11/2004 | Chou |
| 6,814,741 B2 | 11/2004 | Bowman et al. |
| 6,817,508 B1 | 11/2004 | Racenet et al. |
| 6,817,509 B2 | 11/2004 | Geiste et al. |
| 6,817,974 B2 | 11/2004 | Cooper et al. |
| 6,818,018 B1 | 11/2004 | Sawhney |
| 6,820,791 B2 | 11/2004 | Adams |
| 6,821,273 B2 | 11/2004 | Mollenauer |
| 6,821,282 B2 | 11/2004 | Perry et al. |
| 6,821,284 B2 | 11/2004 | Sturtz et al. |
| 6,827,246 B2 | 12/2004 | Sullivan et al. |
| 6,827,712 B2 | 12/2004 | Tovey et al. |
| 6,827,725 B2 | 12/2004 | Batchelor et al. |
| 6,828,902 B2 | 12/2004 | Casden |
| 6,830,174 B2 | 12/2004 | Hillstead et al. |
| 6,831,629 B2 | 12/2004 | Nishino et al. |
| 6,832,998 B2 | 12/2004 | Goble |
| 6,834,001 B2 | 12/2004 | Myono |
| 6,835,173 B2 | 12/2004 | Couvillon, Jr. |
| 6,835,199 B2 | 12/2004 | McGuckin, Jr. et al. |
| 6,835,336 B2 | 12/2004 | Watt |
| 6,836,611 B2 | 12/2004 | Popovic et al. |
| 6,837,846 B2 | 1/2005 | Jaffe et al. |
| 6,837,883 B2 | 1/2005 | Moll et al. |
| 6,838,493 B2 | 1/2005 | Williams et al. |
| 6,840,423 B2 | 1/2005 | Adams et al. |
| 6,840,938 B1 | 1/2005 | Morley et al. |
| 6,841,967 B2 | 1/2005 | Kim et al. |
| 6,843,403 B2 | 1/2005 | Whitman |
| 6,843,789 B2 | 1/2005 | Goble |
| 6,843,793 B2 | 1/2005 | Brock et al. |
| 6,846,307 B2 | 1/2005 | Whitman et al. |
| 6,846,308 B2 | 1/2005 | Whitman et al. |
| 6,846,309 B2 | 1/2005 | Whitman et al. |
| 6,847,190 B2 | 1/2005 | Schaefer et al. |
| 6,849,071 B2 | 2/2005 | Whitman et al. |
| 6,850,817 B1 | 2/2005 | Green |
| 6,852,122 B2 | 2/2005 | Rush |
| 6,852,330 B2 | 2/2005 | Bowman et al. |
| 6,853,879 B2 | 2/2005 | Sunaoshi |
| 6,858,005 B2 | 2/2005 | Ohline et al. |
| 6,859,882 B2 | 2/2005 | Fung |
| RE38,708 E | 3/2005 | Bolanos et al. |
| D502,994 S | 3/2005 | Blake, III |
| 6,861,142 B1 | 3/2005 | Wilkie et al. |
| 6,861,954 B2 | 3/2005 | Levin |
| 6,863,668 B2 | 3/2005 | Gillespie et al. |
| 6,863,694 B1 | 3/2005 | Boyce et al. |
| 6,863,924 B2 | 3/2005 | Ranganathan et al. |
| 6,866,178 B2 | 3/2005 | Adams et al. |
| 6,866,668 B2 | 3/2005 | Giannetti et al. |
| 6,866,671 B2 | 3/2005 | Tierney et al. |
| 6,867,248 B1 | 3/2005 | Martin et al. |
| 6,869,430 B2 | 3/2005 | Balbierz et al. |
| 6,869,435 B2 | 3/2005 | Blake, III |
| 6,872,214 B2 | 3/2005 | Sonnenschein et al. |
| 6,874,669 B2 | 4/2005 | Adams et al. |
| 6,877,647 B2 | 4/2005 | Green et al. |
| 6,878,106 B1 | 4/2005 | Herrmann |
| 6,884,392 B2 | 4/2005 | Malkin et al. |
| 6,884,428 B2 | 4/2005 | Binette et al. |
| 6,886,730 B2 | 5/2005 | Fujisawa et al. |
| 6,887,710 B2 | 5/2005 | Call et al. |
| 6,889,116 B2 | 5/2005 | Jinno |
| 6,893,435 B2 | 5/2005 | Goble |
| 6,894,140 B2 | 5/2005 | Roby |
| 6,895,176 B2 | 5/2005 | Archer et al. |
| 6,899,538 B2 | 5/2005 | Matoba |
| 6,899,593 B1 | 5/2005 | Moeller et al. |
| 6,899,915 B2 | 5/2005 | Yelick et al. |
| 6,905,057 B2 | 6/2005 | Swayze et al. |
| 6,905,497 B2 | 6/2005 | Truckai et al. |
| 6,905,498 B2 | 6/2005 | Hooven |
| 6,908,472 B2 | 6/2005 | Wiener et al. |
| 6,911,033 B2 | 6/2005 | de Guillebon et al. |
| 6,911,916 B1 | 6/2005 | Wang et al. |
| 6,913,579 B2 | 7/2005 | Truckai et al. |
| 6,913,608 B2 | 7/2005 | Liddicoat et al. |
| 6,913,613 B2 | 7/2005 | Schwarz et al. |
| 6,921,397 B2 | 7/2005 | Corcoran et al. |
| 6,921,412 B1 | 7/2005 | Black et al. |
| 6,923,093 B2 | 8/2005 | Ullah |
| 6,923,803 B2 | 8/2005 | Goble |
| 6,923,819 B2 | 8/2005 | Meade et al. |
| 6,925,849 B2 | 8/2005 | Jairam |
| 6,926,716 B2 | 8/2005 | Baker et al. |
| 6,928,902 B1 | 8/2005 | Eyssallenne |
| 6,929,641 B2 | 8/2005 | Goble et al. |
| 6,929,644 B2 | 8/2005 | Truckai et al. |
| 6,931,830 B2 | 8/2005 | Liao |
| 6,932,218 B2 | 8/2005 | Kosann et al. |
| 6,932,810 B2 | 8/2005 | Ryan |
| 6,936,042 B2 | 8/2005 | Wallace et al. |
| 6,936,948 B2 | 8/2005 | Bell et al. |
| D509,297 S | 9/2005 | Wells |
| D509,589 S | 9/2005 | Wells |
| 6,938,706 B2 | 9/2005 | Ng |
| 6,939,358 B2 | 9/2005 | Palacios et al. |
| 6,942,662 B2 | 9/2005 | Goble et al. |
| 6,942,674 B2 | 9/2005 | Belef et al. |
| 6,945,444 B2 | 9/2005 | Gresham et al. |
| 6,945,981 B2 | 9/2005 | Donofrio et al. |
| 6,951,562 B2 | 10/2005 | Zwirnmann |
| 6,953,138 B1 | 10/2005 | Dworak et al. |
| 6,953,139 B2 | 10/2005 | Milliman et al. |
| 6,953,461 B2 | 10/2005 | McClurken et al. |
| 6,957,758 B2 | 10/2005 | Aranyi |
| 6,958,035 B2 | 10/2005 | Friedman et al. |
| 6,959,851 B2 | 11/2005 | Heinrich |
| 6,959,852 B2 | 11/2005 | Shelton, IV et al. |
| 6,960,107 B1 | 11/2005 | Schaub et al. |
| 6,960,163 B2 | 11/2005 | Ewers et al. |
| 6,960,220 B2 | 11/2005 | Marino et al. |
| 6,962,587 B2 | 11/2005 | Johnson et al. |
| 6,963,792 B1 | 11/2005 | Green |
| 6,964,363 B2 | 11/2005 | Wales et al. |
| 6,966,907 B2 | 11/2005 | Goble |
| 6,966,909 B2 | 11/2005 | Marshall et al. |
| 6,968,908 B2 | 11/2005 | Tokunaga et al. |
| 6,969,385 B2 | 11/2005 | Moreyra |
| 6,969,395 B2 | 11/2005 | Eskuri |
| 6,971,988 B2 | 12/2005 | Orban, III |
| 6,972,199 B2 | 12/2005 | Lebouitz et al. |
| 6,974,435 B2 | 12/2005 | Daw et al. |
| 6,974,462 B2 | 12/2005 | Sater |
| 6,978,921 B2 | 12/2005 | Shelton, IV et al. |
| 6,978,922 B2 | 12/2005 | Bilotti et al. |
| 6,981,628 B2 | 1/2006 | Wales |
| 6,981,941 B2 | 1/2006 | Whitman et al. |
| 6,981,978 B2 | 1/2006 | Gannoe |
| 6,984,203 B2 | 1/2006 | Tartaglia et al. |
| 6,984,231 B2 | 1/2006 | Goble et al. |
| 6,986,451 B1 | 1/2006 | Mastri et al. |
| 6,988,649 B2 | 1/2006 | Shelton, IV et al. |
| 6,988,650 B2 | 1/2006 | Schwemberger et al. |
| 6,989,034 B2 | 1/2006 | Hammer et al. |
| 6,990,731 B2 | 1/2006 | Haytayan |
| 6,990,796 B2 | 1/2006 | Schnipke et al. |
| 6,993,200 B2 | 1/2006 | Tastl et al. |
| 6,993,413 B2 | 1/2006 | Sunaoshi |
| 6,994,708 B2 | 2/2006 | Manzo |
| 6,995,729 B2 | 2/2006 | Govari et al. |
| 6,996,433 B2 | 2/2006 | Burbank et al. |

(56) References Cited

U.S. PATENT DOCUMENTS

| | | |
|---|---|---|
| 6,997,931 B2 | 2/2006 | Sauer et al. |
| 6,997,935 B2 | 2/2006 | Anderson et al. |
| 6,998,736 B2 | 2/2006 | Lee et al. |
| 6,998,816 B2 | 2/2006 | Wieck et al. |
| 7,000,818 B2 | 2/2006 | Shelton, IV et al. |
| 7,000,819 B2 | 2/2006 | Swayze et al. |
| 7,000,911 B2 | 2/2006 | McCormick et al. |
| 7,001,380 B2 | 2/2006 | Goble |
| 7,001,408 B2 | 2/2006 | Knodel et al. |
| 7,004,174 B2 | 2/2006 | Eggers et al. |
| 7,007,176 B2 | 2/2006 | Goodfellow et al. |
| 7,008,433 B2 | 3/2006 | Voellmicke et al. |
| 7,008,435 B2 | 3/2006 | Cummins |
| 7,009,039 B2 | 3/2006 | Yayon et al. |
| 7,011,657 B2 | 3/2006 | Truckai et al. |
| 7,014,640 B2 | 3/2006 | Kemppainen et al. |
| 7,018,357 B2 | 3/2006 | Emmons |
| 7,018,390 B2 | 3/2006 | Turovskiy et al. |
| 7,021,669 B1 | 4/2006 | Lindermeir et al. |
| 7,022,131 B1 | 4/2006 | Derowe et al. |
| 7,023,159 B2 | 4/2006 | Gorti et al. |
| 7,025,064 B2 | 4/2006 | Wang et al. |
| 7,025,732 B2 | 4/2006 | Thompson et al. |
| 7,025,743 B2 | 4/2006 | Mann et al. |
| 7,025,774 B2 | 4/2006 | Freeman et al. |
| 7,025,775 B2 | 4/2006 | Gadberry et al. |
| 7,028,570 B2 | 4/2006 | Ohta et al. |
| 7,029,435 B2 | 4/2006 | Nakao |
| 7,029,439 B2 | 4/2006 | Roberts et al. |
| 7,030,904 B2 | 4/2006 | Adair et al. |
| 7,032,798 B2 | 4/2006 | Whitman et al. |
| 7,032,799 B2 | 4/2006 | Viola et al. |
| 7,033,356 B2 | 4/2006 | Latterell et al. |
| 7,035,716 B2 | 4/2006 | Harris et al. |
| 7,035,762 B2 | 4/2006 | Menard et al. |
| 7,036,680 B1 | 5/2006 | Flannery |
| 7,037,314 B2 | 5/2006 | Armstrong |
| 7,037,344 B2 | 5/2006 | Kagan et al. |
| 7,041,088 B2 | 5/2006 | Nawrocki et al. |
| 7,041,102 B2 | 5/2006 | Truckai et al. |
| 7,041,868 B2 | 5/2006 | Greene et al. |
| 7,043,852 B2 | 5/2006 | Hayashida et al. |
| 7,044,350 B2 | 5/2006 | Kameyama et al. |
| 7,044,352 B2 | 5/2006 | Shelton, IV et al. |
| 7,044,353 B2 | 5/2006 | Mastri et al. |
| 7,046,082 B2 | 5/2006 | Komiya et al. |
| 7,048,165 B2 | 5/2006 | Haramiishi |
| 7,048,687 B1 | 5/2006 | Reuss et al. |
| 7,048,745 B2 | 5/2006 | Tierney et al. |
| 7,052,454 B2 | 5/2006 | Taylor |
| 7,052,494 B2 | 5/2006 | Goble et al. |
| 7,052,499 B2 | 5/2006 | Steger et al. |
| 7,055,730 B2 | 6/2006 | Ehrenfels et al. |
| 7,055,731 B2 | 6/2006 | Shelton, IV et al. |
| 7,056,284 B2 | 6/2006 | Martone et al. |
| 7,056,330 B2 | 6/2006 | Gayton |
| 7,059,331 B2 | 6/2006 | Adams et al. |
| 7,059,508 B2 | 6/2006 | Shelton, IV et al. |
| 7,063,671 B2 | 6/2006 | Couvillon, Jr. |
| 7,063,712 B2 | 6/2006 | Vargas et al. |
| 7,064,509 B1 | 6/2006 | Fu et al. |
| 7,066,879 B2 | 6/2006 | Fowler et al. |
| 7,066,944 B2 | 6/2006 | Laufer et al. |
| 7,067,038 B2 | 6/2006 | Trokhan et al. |
| 7,070,083 B2 | 7/2006 | Jankowski |
| 7,070,559 B2 | 7/2006 | Adams et al. |
| 7,070,597 B2 | 7/2006 | Truckai et al. |
| 7,071,287 B2 | 7/2006 | Rhine et al. |
| 7,075,770 B1 | 7/2006 | Smith |
| 7,077,856 B2 | 7/2006 | Whitman |
| 7,080,769 B2 | 7/2006 | Vresh et al. |
| 7,081,114 B2 | 7/2006 | Rashidi |
| 7,083,073 B2 | 8/2006 | Yoshie et al. |
| 7,083,075 B2 | 8/2006 | Swayze et al. |
| 7,083,571 B2 | 8/2006 | Wang et al. |
| 7,083,615 B2 | 8/2006 | Peterson et al. |
| 7,083,619 B2 | 8/2006 | Truckai et al. |
| 7,083,620 B2 | 8/2006 | Jahns et al. |
| 7,083,626 B2 | 8/2006 | Hart et al. |
| 7,086,267 B2 | 8/2006 | Dworak et al. |
| 7,087,049 B2 | 8/2006 | Nowlin et al. |
| 7,087,054 B2 | 8/2006 | Truckai et al. |
| 7,087,071 B2 | 8/2006 | Nicholas et al. |
| 7,090,637 B2 | 8/2006 | Danitz et al. |
| 7,090,673 B2 | 8/2006 | Dycus et al. |
| 7,090,683 B2 | 8/2006 | Brock et al. |
| 7,090,684 B2 | 8/2006 | McGuckin, Jr. et al. |
| 7,091,191 B2 | 8/2006 | Laredo et al. |
| 7,091,412 B2 | 8/2006 | Wang et al. |
| 7,093,492 B2 | 8/2006 | Treiber et al. |
| 7,094,202 B2 | 8/2006 | Nobis et al. |
| 7,094,247 B2 | 8/2006 | Monassevitch et al. |
| 7,094,916 B2 | 8/2006 | DeLuca et al. |
| 7,096,972 B2 | 8/2006 | Orozco, Jr. |
| 7,097,089 B2 | 8/2006 | Marczyk |
| 7,097,644 B2 | 8/2006 | Long |
| 7,097,650 B2 | 8/2006 | Weller et al. |
| 7,098,794 B2 | 8/2006 | Lindsay et al. |
| 7,100,949 B2 | 9/2006 | Williams et al. |
| 7,101,187 B1 | 9/2006 | Deconinck et al. |
| 7,101,371 B2 | 9/2006 | Dycus et al. |
| 7,101,394 B2 | 9/2006 | Hamm et al. |
| 7,104,741 B2 | 9/2006 | Krohn |
| 7,108,695 B2 | 9/2006 | Witt et al. |
| 7,108,701 B2 | 9/2006 | Evens et al. |
| 7,108,709 B2 | 9/2006 | Cummins |
| 7,111,768 B2 | 9/2006 | Cummins et al. |
| 7,111,769 B2 | 9/2006 | Wales et al. |
| 7,112,214 B2 | 9/2006 | Peterson et al. |
| RE39,358 E | 10/2006 | Goble |
| 7,114,642 B2 | 10/2006 | Whitman |
| 7,116,100 B1 | 10/2006 | Mock et al. |
| 7,118,020 B2 | 10/2006 | Lee et al. |
| 7,118,528 B1 | 10/2006 | Piskun |
| 7,118,563 B2 | 10/2006 | Weckwerth et al. |
| 7,118,582 B1 | 10/2006 | Wang et al. |
| 7,119,534 B2 | 10/2006 | Butzmann |
| 7,121,446 B2 | 10/2006 | Arad et al. |
| 7,121,773 B2 | 10/2006 | Mikiya et al. |
| 7,122,028 B2 | 10/2006 | Looper et al. |
| 7,125,403 B2 | 10/2006 | Julian et al. |
| 7,125,409 B2 | 10/2006 | Truckai et al. |
| 7,126,303 B2 | 10/2006 | Farritor et al. |
| 7,126,879 B2 | 10/2006 | Snyder |
| 7,128,253 B2 | 10/2006 | Mastri et al. |
| 7,128,254 B2 | 10/2006 | Shelton, IV et al. |
| 7,128,748 B2 | 10/2006 | Mooradian et al. |
| 7,131,445 B2 | 11/2006 | Amoah |
| 7,133,601 B2 | 11/2006 | Phillips et al. |
| 7,134,364 B2 | 11/2006 | Kageler et al. |
| 7,134,587 B2 | 11/2006 | Schwemberger et al. |
| 7,135,027 B2 | 11/2006 | Delmotte |
| 7,137,980 B2 | 11/2006 | Buysse et al. |
| 7,137,981 B2 | 11/2006 | Long |
| 7,139,016 B2 | 11/2006 | Squilla et al. |
| 7,140,527 B2 | 11/2006 | Ehrenfels et al. |
| 7,140,528 B2 | 11/2006 | Shelton, IV |
| 7,141,055 B2 | 11/2006 | Abrams et al. |
| 7,143,923 B2 | 12/2006 | Shelton, IV et al. |
| 7,143,924 B2 | 12/2006 | Scirica et al. |
| 7,143,925 B2 | 12/2006 | Shelton, IV et al. |
| 7,143,926 B2 | 12/2006 | Shelton, IV et al. |
| 7,146,191 B2 | 12/2006 | Kerner et al. |
| 7,147,138 B2 | 12/2006 | Shelton, IV |
| 7,147,139 B2 | 12/2006 | Schwemberger et al. |
| 7,147,140 B2 | 12/2006 | Wukusick et al. |
| 7,147,637 B2 | 12/2006 | Goble |
| 7,147,648 B2 | 12/2006 | Lin |
| 7,147,650 B2 | 12/2006 | Lee |
| 7,150,748 B2 | 12/2006 | Ebbutt et al. |
| 7,153,300 B2 | 12/2006 | Goble |
| 7,153,314 B2 | 12/2006 | Laufer et al. |
| 7,155,316 B2 | 12/2006 | Sutherland et al. |
| 7,156,863 B2 | 1/2007 | Sonnenschein et al. |

(56) References Cited

U.S. PATENT DOCUMENTS

| | | |
|---|---|---|
| 7,159,750 B2 | 1/2007 | Racenet et al. |
| 7,160,296 B2 | 1/2007 | Pearson et al. |
| 7,160,299 B2 | 1/2007 | Baily |
| 7,161,036 B2 | 1/2007 | Oikawa et al. |
| 7,161,580 B2 | 1/2007 | Bailey et al. |
| 7,162,758 B2 | 1/2007 | Skinner |
| 7,163,563 B2 | 1/2007 | Schwartz et al. |
| 7,166,133 B2 | 1/2007 | Evans et al. |
| 7,168,604 B2 | 1/2007 | Milliman et al. |
| 7,170,910 B2 | 1/2007 | Chen et al. |
| 7,171,279 B2 | 1/2007 | Buckingham et al. |
| 7,172,104 B2 | 2/2007 | Scirica et al. |
| 7,172,593 B2 | 2/2007 | Trieu et al. |
| 7,172,615 B2 | 2/2007 | Morriss et al. |
| 7,174,202 B2 | 2/2007 | Bladen et al. |
| 7,174,636 B2 | 2/2007 | Lowe |
| 7,177,533 B2 | 2/2007 | McFarlin et al. |
| 7,179,223 B2 | 2/2007 | Motoki et al. |
| 7,179,267 B2 | 2/2007 | Nolan et al. |
| 7,182,239 B1 | 2/2007 | Myers |
| 7,182,763 B2 | 2/2007 | Nardella |
| 7,183,737 B2 | 2/2007 | Kitagawa |
| 7,187,960 B2 | 3/2007 | Abreu |
| 7,188,758 B2 | 3/2007 | Viola et al. |
| 7,189,207 B2 | 3/2007 | Viola |
| 7,190,147 B2 | 3/2007 | Gileff et al. |
| 7,193,199 B2 | 3/2007 | Jang |
| 7,195,627 B2 | 3/2007 | Amoah et al. |
| 7,196,911 B2 | 3/2007 | Takano et al. |
| D541,418 S | 4/2007 | Schechter et al. |
| 7,199,537 B2 | 4/2007 | Okamura et al. |
| 7,199,545 B2 | 4/2007 | Oleynikov et al. |
| 7,202,576 B1 | 4/2007 | Dechene et al. |
| 7,202,653 B2 | 4/2007 | Pai |
| 7,204,404 B2 | 4/2007 | Nguyen et al. |
| 7,204,835 B2 | 4/2007 | Latterell et al. |
| 7,206,626 B2 | 4/2007 | Quaid, III |
| 7,207,233 B2 | 4/2007 | Wadge |
| 7,207,471 B2 | 4/2007 | Heinrich et al. |
| 7,207,472 B2 | 4/2007 | Wukusick et al. |
| 7,207,556 B2 | 4/2007 | Saitoh et al. |
| 7,208,005 B2 | 4/2007 | Frecker et al. |
| 7,210,609 B2 | 5/2007 | Leiboff et al. |
| 7,211,081 B2 | 5/2007 | Goble |
| 7,211,084 B2 | 5/2007 | Goble et al. |
| 7,211,092 B2 | 5/2007 | Hughett |
| 7,211,979 B2 | 5/2007 | Khatib et al. |
| 7,213,736 B2 | 5/2007 | Wales et al. |
| 7,214,224 B2 | 5/2007 | Goble |
| 7,215,517 B2 | 5/2007 | Takamatsu |
| 7,217,285 B2 | 5/2007 | Vargas et al. |
| 7,220,260 B2 | 5/2007 | Fleming et al. |
| 7,220,272 B2 | 5/2007 | Weadock |
| 7,225,959 B2 | 6/2007 | Patton et al. |
| 7,225,963 B2 | 6/2007 | Scirica |
| 7,225,964 B2 | 6/2007 | Mastri et al. |
| 7,226,450 B2 | 6/2007 | Athanasiou et al. |
| 7,228,505 B2 | 6/2007 | Shimazu et al. |
| 7,229,408 B2 | 6/2007 | Douglas et al. |
| 7,234,624 B2 | 6/2007 | Gresham et al. |
| 7,235,072 B2 | 6/2007 | Sartor et al. |
| 7,235,089 B1 | 6/2007 | McGuckin, Jr. |
| 7,235,302 B2 | 6/2007 | Jing et al. |
| 7,237,708 B1 | 7/2007 | Guy et al. |
| 7,238,195 B2 | 7/2007 | Viola |
| 7,238,901 B2 | 7/2007 | Kim et al. |
| 7,239,657 B1 | 7/2007 | Gunnarsson |
| 7,241,288 B2 | 7/2007 | Braun |
| 7,241,289 B2 | 7/2007 | Braun |
| 7,246,734 B2 | 7/2007 | Shelton, IV |
| 7,247,161 B2 | 7/2007 | Johnston et al. |
| 7,249,267 B2 | 7/2007 | Chapuis |
| 7,252,641 B2 | 8/2007 | Thompson et al. |
| 7,252,660 B2 | 8/2007 | Kunz |
| 7,255,012 B2 | 8/2007 | Hedtke |
| 7,255,696 B2 | 8/2007 | Goble et al. |
| 7,256,695 B2 | 8/2007 | Hamel et al. |
| 7,258,262 B2 | 8/2007 | Mastri et al. |
| 7,258,546 B2 | 8/2007 | Beier et al. |
| 7,260,431 B2 | 8/2007 | Libbus et al. |
| 7,265,374 B2 | 9/2007 | Lee et al. |
| 7,267,677 B2 | 9/2007 | Johnson et al. |
| 7,267,679 B2 | 9/2007 | McGuckin, Jr. et al. |
| 7,272,002 B2 | 9/2007 | Drapeau |
| 7,273,483 B2 | 9/2007 | Wiener et al. |
| D552,623 S | 10/2007 | Vong et al. |
| 7,275,674 B2 | 10/2007 | Racenet et al. |
| 7,276,044 B2 | 10/2007 | Ferry et al. |
| 7,276,068 B2 | 10/2007 | Johnson et al. |
| 7,278,562 B2 | 10/2007 | Mastri et al. |
| 7,278,563 B1 | 10/2007 | Green |
| 7,278,949 B2 | 10/2007 | Bader |
| 7,278,994 B2 | 10/2007 | Goble |
| 7,282,048 B2 | 10/2007 | Goble et al. |
| 7,283,096 B2 | 10/2007 | Geisheimer et al. |
| 7,286,850 B2 | 10/2007 | Frielink et al. |
| 7,287,682 B1 | 10/2007 | Ezzat et al. |
| 7,289,139 B2 | 10/2007 | Amling et al. |
| 7,293,685 B2 | 11/2007 | Ehrenfels et al. |
| 7,295,893 B2 | 11/2007 | Sunaoshi |
| 7,295,907 B2 | 11/2007 | Lu et al. |
| 7,296,722 B2 | 11/2007 | Ivanko |
| 7,296,724 B2 | 11/2007 | Green et al. |
| 7,297,149 B2 | 11/2007 | Vitali et al. |
| 7,300,373 B2 | 11/2007 | Jinno et al. |
| 7,300,431 B2 | 11/2007 | Dubrovsky |
| 7,300,450 B2 | 11/2007 | Vleugels et al. |
| 7,303,106 B2 | 12/2007 | Milliman et al. |
| 7,303,107 B2 | 12/2007 | Milliman et al. |
| 7,303,108 B2 | 12/2007 | Shelton, IV |
| 7,303,502 B2 | 12/2007 | Thompson |
| 7,303,556 B2 | 12/2007 | Metzger |
| 7,306,597 B2 | 12/2007 | Manzo |
| 7,308,998 B2 | 12/2007 | Mastri et al. |
| 7,311,238 B2 | 12/2007 | Liu |
| 7,313,430 B2 | 12/2007 | Urquhart et al. |
| 7,314,473 B2 | 1/2008 | Jinno et al. |
| 7,322,859 B2 | 1/2008 | Evans |
| 7,322,975 B2 | 1/2008 | Goble et al. |
| 7,322,994 B2 | 1/2008 | Nicholas et al. |
| 7,324,572 B2 | 1/2008 | Chang |
| 7,326,203 B2 | 2/2008 | Papineau et al. |
| 7,326,213 B2 | 2/2008 | Benderev et al. |
| 7,328,828 B2 | 2/2008 | Ortiz et al. |
| 7,328,829 B2 | 2/2008 | Arad et al. |
| 7,330,004 B2 | 2/2008 | DeJonge et al. |
| 7,331,340 B2 | 2/2008 | Barney |
| 7,331,343 B2 | 2/2008 | Schmidt et al. |
| 7,331,403 B2 | 2/2008 | Berry et al. |
| 7,331,406 B2 | 2/2008 | Wottreng, Jr. et al. |
| 7,331,969 B1 | 2/2008 | Inganas et al. |
| 7,334,717 B2 | 2/2008 | Rethy et al. |
| 7,334,718 B2 | 2/2008 | McAlister et al. |
| 7,335,199 B2 | 2/2008 | Goble et al. |
| 7,335,401 B2 | 2/2008 | Finke et al. |
| 7,336,045 B2 | 2/2008 | Clermonts |
| 7,336,048 B2 | 2/2008 | Lohr |
| 7,336,184 B2 | 2/2008 | Smith et al. |
| 7,337,774 B2 | 3/2008 | Webb |
| 7,338,505 B2 | 3/2008 | Belson |
| 7,338,513 B2 | 3/2008 | Lee et al. |
| 7,341,554 B2 | 3/2008 | Sekine et al. |
| 7,341,555 B2 | 3/2008 | Ootawara et al. |
| 7,341,591 B2 | 3/2008 | Grinberg |
| 7,343,920 B2 | 3/2008 | Toby et al. |
| 7,344,532 B2 | 3/2008 | Goble et al. |
| 7,344,533 B2 | 3/2008 | Pearson et al. |
| 7,346,344 B2 | 3/2008 | Fontaine |
| 7,346,406 B2 | 3/2008 | Brotto et al. |
| 7,348,763 B1 | 3/2008 | Reinhart et al. |
| 7,348,875 B2 | 3/2008 | Hughes et al. |
| RE40,237 E | 4/2008 | Bilotti et al. |
| 7,351,258 B2 | 4/2008 | Ricotta et al. |
| 7,354,447 B2 | 4/2008 | Shelton, IV et al. |

(56) References Cited

U.S. PATENT DOCUMENTS

| | | |
|---|---|---|
| 7,354,502 B2 | 4/2008 | Polat et al. |
| 7,357,287 B2 | 4/2008 | Shelton, IV et al. |
| 7,357,806 B2 | 4/2008 | Rivera et al. |
| 7,361,168 B2 | 4/2008 | Makower et al. |
| 7,361,195 B2 | 4/2008 | Schwartz et al. |
| 7,362,062 B2 | 4/2008 | Schneider et al. |
| 7,364,060 B2 | 4/2008 | Milliman |
| 7,364,061 B2 | 4/2008 | Swayze et al. |
| 7,367,485 B2 | 5/2008 | Shelton, IV et al. |
| 7,368,124 B2 | 5/2008 | Chun et al. |
| 7,371,210 B2 | 5/2008 | Brock et al. |
| 7,371,403 B2 | 5/2008 | McCarthy et al. |
| 7,375,493 B2 | 5/2008 | Calhoon et al. |
| 7,377,918 B2 | 5/2008 | Amoah |
| 7,377,928 B2 | 5/2008 | Zubik et al. |
| 7,378,817 B2 | 5/2008 | Calhoon et al. |
| RE40,388 E | 6/2008 | Gines |
| 7,380,695 B2 | 6/2008 | Doll et al. |
| 7,380,696 B2 | 6/2008 | Shelton, IV et al. |
| 7,384,403 B2 | 6/2008 | Sherman |
| 7,384,417 B2 | 6/2008 | Cucin |
| 7,386,365 B2 | 6/2008 | Nixon |
| 7,386,730 B2 | 6/2008 | Uchikubo |
| 7,388,217 B2 | 6/2008 | Buschbeck et al. |
| 7,388,484 B2 | 6/2008 | Hsu |
| 7,391,173 B2 | 6/2008 | Schena |
| 7,394,190 B2 | 7/2008 | Huang |
| 7,396,356 B2 | 7/2008 | Mollenauer |
| 7,397,364 B2 | 7/2008 | Govari |
| 7,398,707 B2 | 7/2008 | Morley et al. |
| 7,398,907 B2 | 7/2008 | Racenet et al. |
| 7,398,908 B2 | 7/2008 | Holsten et al. |
| 7,400,107 B2 | 7/2008 | Schneider et al. |
| 7,400,752 B2 | 7/2008 | Zacharias |
| 7,401,000 B2 | 7/2008 | Nakamura |
| 7,401,721 B2 | 7/2008 | Holsten et al. |
| 7,404,449 B2 | 7/2008 | Bermingham et al. |
| 7,404,508 B2 | 7/2008 | Smith et al. |
| 7,404,509 B2 | 7/2008 | Ortiz et al. |
| 7,404,822 B2 | 7/2008 | Viart et al. |
| 7,407,074 B2 | 8/2008 | Ortiz et al. |
| 7,407,075 B2 | 8/2008 | Holsten et al. |
| 7,407,076 B2 | 8/2008 | Racenet et al. |
| 7,407,077 B2 | 8/2008 | Ortiz et al. |
| 7,407,078 B2 | 8/2008 | Shelton, IV et al. |
| 7,408,310 B2 | 8/2008 | Hong et al. |
| 7,410,085 B2 | 8/2008 | Wolf et al. |
| 7,410,086 B2 | 8/2008 | Ortiz et al. |
| 7,410,483 B2 | 8/2008 | Danitz et al. |
| 7,413,563 B2 | 8/2008 | Corcoran et al. |
| 7,416,101 B2 | 8/2008 | Shelton, IV et al. |
| 7,418,078 B2 | 8/2008 | Blanz et al. |
| RE40,514 E | 9/2008 | Mastri et al. |
| 7,419,080 B2 | 9/2008 | Smith et al. |
| 7,419,081 B2 | 9/2008 | Ehrenfels et al. |
| 7,419,321 B2 | 9/2008 | Tereschouk |
| 7,419,495 B2 | 9/2008 | Menn et al. |
| 7,422,136 B1 | 9/2008 | Marczyk |
| 7,422,138 B2 | 9/2008 | Bilotti et al. |
| 7,422,139 B2 | 9/2008 | Shelton, IV et al. |
| 7,424,965 B2 | 9/2008 | Racenet et al. |
| 7,427,607 B2 | 9/2008 | Suzuki |
| D578,644 S | 10/2008 | Shumer et al. |
| 7,430,772 B2 | 10/2008 | Van Es |
| 7,431,188 B1 | 10/2008 | Marczyk |
| 7,431,189 B2 | 10/2008 | Shelton, IV et al. |
| 7,431,230 B2 | 10/2008 | McPherson et al. |
| 7,431,694 B2 | 10/2008 | Stefanchik et al. |
| 7,431,730 B2 | 10/2008 | Viola |
| 7,434,715 B2 | 10/2008 | Shelton, IV et al. |
| 7,434,717 B2 | 10/2008 | Shelton, IV et al. |
| 7,435,249 B2 | 10/2008 | Buysse et al. |
| 7,438,209 B1 | 10/2008 | Hess et al. |
| 7,438,718 B2 | 10/2008 | Milliman et al. |
| 7,439,354 B2 | 10/2008 | Lenges et al. |
| 7,441,684 B2 | 10/2008 | Shelton, IV et al. |
| 7,441,685 B1 | 10/2008 | Boudreaux |
| 7,442,201 B2 | 10/2008 | Pugsley et al. |
| 7,443,547 B2 | 10/2008 | Moreno et al. |
| 7,446,131 B1 | 11/2008 | Liu et al. |
| 7,448,525 B2 | 11/2008 | Shelton, IV et al. |
| 7,450,010 B1 | 11/2008 | Gravelle et al. |
| 7,451,904 B2 | 11/2008 | Shelton, IV |
| 7,455,208 B2 | 11/2008 | Wales et al. |
| 7,455,676 B2 | 11/2008 | Holsten et al. |
| 7,455,682 B2 | 11/2008 | Viola |
| D582,934 S | 12/2008 | Byeon |
| 7,461,767 B2 | 12/2008 | Viola et al. |
| 7,462,187 B2 | 12/2008 | Johnston et al. |
| 7,464,845 B2 | 12/2008 | Chou |
| 7,464,846 B2 | 12/2008 | Shelton, IV et al. |
| 7,464,847 B2 | 12/2008 | Viola et al. |
| 7,464,848 B2 | 12/2008 | Green et al. |
| 7,464,849 B2 | 12/2008 | Shelton, IV et al. |
| 7,467,740 B2 | 12/2008 | Shelton, IV et al. |
| 7,467,849 B2 | 12/2008 | Silverbrook et al. |
| 7,472,814 B2 | 1/2009 | Mastri et al. |
| 7,472,815 B2 | 1/2009 | Shelton, IV et al. |
| 7,472,816 B2 | 1/2009 | Holsten et al. |
| 7,473,221 B2 | 1/2009 | Ewers et al. |
| 7,473,253 B2 | 1/2009 | Dycus et al. |
| 7,473,263 B2 | 1/2009 | Johnston et al. |
| 7,476,237 B2 | 1/2009 | Taniguchi et al. |
| 7,479,608 B2 | 1/2009 | Smith |
| 7,481,347 B2 | 1/2009 | Roy |
| 7,481,348 B2 | 1/2009 | Marczyk |
| 7,481,349 B2 | 1/2009 | Holsten et al. |
| 7,481,824 B2 | 1/2009 | Boudreaux et al. |
| 7,485,124 B2 | 2/2009 | Kuhns et al. |
| 7,485,133 B2 | 2/2009 | Cannon et al. |
| 7,485,142 B2 | 2/2009 | Milo |
| 7,487,899 B2 | 2/2009 | Shelton, IV et al. |
| 7,489,055 B2 | 2/2009 | Jeong et al. |
| 7,490,749 B2 | 2/2009 | Schall et al. |
| 7,491,232 B2 | 2/2009 | Bolduc et al. |
| 7,494,039 B2 | 2/2009 | Racenet et al. |
| 7,494,460 B2 | 2/2009 | Haarstad et al. |
| 7,494,499 B2 | 2/2009 | Nagase et al. |
| 7,494,501 B2 | 2/2009 | Ahlberg et al. |
| 7,500,979 B2 | 3/2009 | Hueil et al. |
| 7,501,198 B2 | 3/2009 | Barley et al. |
| 7,503,474 B2 | 3/2009 | Hillstead et al. |
| 7,506,790 B2 | 3/2009 | Shelton, IV |
| 7,506,791 B2 | 3/2009 | Omaits et al. |
| 7,507,202 B2 | 3/2009 | Schoellhorn |
| 7,510,107 B2 | 3/2009 | Timm et al. |
| 7,510,534 B2 | 3/2009 | Burdorff et al. |
| 7,510,566 B2 | 3/2009 | Jacobs et al. |
| 7,513,407 B1 | 4/2009 | Chang |
| 7,513,408 B2 | 4/2009 | Shelton, IV et al. |
| 7,517,356 B2 | 4/2009 | Heinrich |
| 7,524,320 B2 | 4/2009 | Tierney et al. |
| 7,527,632 B2 | 5/2009 | Houghton et al. |
| 7,530,984 B2 | 5/2009 | Sonnenschein et al. |
| 7,530,985 B2 | 5/2009 | Takemoto et al. |
| 7,533,906 B2 | 5/2009 | Luettgen et al. |
| 7,534,259 B2 | 5/2009 | Lashinski et al. |
| 7,540,867 B2 | 6/2009 | Jinno et al. |
| 7,540,872 B2 | 6/2009 | Schechter et al. |
| 7,542,807 B2 | 6/2009 | Bertolero et al. |
| 7,543,730 B1 | 6/2009 | Marczyk |
| 7,546,939 B2 | 6/2009 | Adams et al. |
| 7,546,940 B2 | 6/2009 | Milliman et al. |
| 7,547,287 B2 | 6/2009 | Boecker et al. |
| 7,547,312 B2 | 6/2009 | Bauman et al. |
| 7,549,563 B2 | 6/2009 | Mather et al. |
| 7,549,564 B2 | 6/2009 | Boudreaux |
| 7,549,998 B2 | 6/2009 | Braun |
| 7,552,854 B2 | 6/2009 | Wixey et al. |
| 7,553,173 B2 | 6/2009 | Kowalick |
| 7,553,275 B2 | 6/2009 | Padget et al. |
| 7,554,343 B2 | 6/2009 | Bromfield |
| 7,556,185 B2 | 7/2009 | Viola |
| 7,556,186 B2 | 7/2009 | Milliman |

(56) References Cited

U.S. PATENT DOCUMENTS

| | | |
|---|---|---|
| 7,556,647 B2 | 7/2009 | Drews et al. |
| 7,559,449 B2 | 7/2009 | Viola |
| 7,559,450 B2 | 7/2009 | Wales et al. |
| 7,559,452 B2 | 7/2009 | Wales et al. |
| 7,559,937 B2 | 7/2009 | de la Torre et al. |
| 7,561,637 B2 | 7/2009 | Jonsson et al. |
| 7,562,910 B2 | 7/2009 | Kertesz et al. |
| 7,563,269 B2 | 7/2009 | Hashiguchi |
| 7,563,862 B2 | 7/2009 | Sieg et al. |
| 7,565,993 B2 | 7/2009 | Milliman et al. |
| 7,566,300 B2 | 7/2009 | Devierre et al. |
| 7,567,045 B2 | 7/2009 | Fristedt |
| 7,568,603 B2 | 8/2009 | Shelton, IV et al. |
| 7,568,604 B2 | 8/2009 | Ehrenfels et al. |
| 7,568,619 B2 | 8/2009 | Todd et al. |
| 7,575,144 B2 | 8/2009 | Ortiz et al. |
| 7,578,825 B2 | 8/2009 | Huebner |
| D600,712 S | 9/2009 | LaManna et al. |
| 7,583,063 B2 | 9/2009 | Dooley |
| 7,584,880 B2 | 9/2009 | Racenet et al. |
| 7,586,289 B2 | 9/2009 | Andruk et al. |
| 7,588,174 B2 | 9/2009 | Holsten et al. |
| 7,588,175 B2 | 9/2009 | Timm et al. |
| 7,588,177 B2 | 9/2009 | Racenet |
| 7,591,783 B2 | 9/2009 | Boulais et al. |
| 7,591,818 B2 | 9/2009 | Bertolero et al. |
| 7,593,766 B2 | 9/2009 | Faber et al. |
| 7,595,642 B2 | 9/2009 | Doyle |
| 7,597,229 B2 | 10/2009 | Boudreaux et al. |
| 7,597,230 B2 | 10/2009 | Racenet et al. |
| 7,597,693 B2 | 10/2009 | Garrison |
| 7,597,699 B2 | 10/2009 | Rogers |
| 7,598,972 B2 | 10/2009 | Tomita |
| 7,600,663 B2 | 10/2009 | Green |
| 7,604,118 B2 | 10/2009 | Iio et al. |
| 7,604,150 B2 | 10/2009 | Boudreaux |
| 7,604,151 B2 | 10/2009 | Hess et al. |
| 7,604,668 B2 | 10/2009 | Farnsworth et al. |
| 7,607,557 B2 | 10/2009 | Shelton, IV et al. |
| 7,608,091 B2 | 10/2009 | Goldfarb et al. |
| D604,325 S | 11/2009 | Ebeling et al. |
| 7,611,038 B2 | 11/2009 | Racenet et al. |
| 7,611,474 B2 | 11/2009 | Hibner et al. |
| 7,615,003 B2 | 11/2009 | Stefanchik et al. |
| 7,615,006 B2 | 11/2009 | Abe |
| 7,615,067 B2 | 11/2009 | Lee et al. |
| 7,617,961 B2 | 11/2009 | Viola |
| D605,201 S | 12/2009 | Lorenz et al. |
| D607,010 S | 12/2009 | Kocmick |
| 7,624,902 B2 | 12/2009 | Marczyk et al. |
| 7,624,903 B2 | 12/2009 | Green et al. |
| 7,625,370 B2 | 12/2009 | Hart et al. |
| 7,630,841 B2 | 12/2009 | Comisky et al. |
| 7,631,793 B2 | 12/2009 | Rethy et al. |
| 7,631,794 B2 | 12/2009 | Rethy et al. |
| 7,635,074 B2 | 12/2009 | Olson et al. |
| 7,635,922 B2 | 12/2009 | Becker |
| 7,637,409 B2 | 12/2009 | Marczyk |
| 7,637,410 B2 | 12/2009 | Marczyk |
| 7,638,958 B2 | 12/2009 | Philipp et al. |
| 7,641,091 B2 | 1/2010 | Olson et al. |
| 7,641,092 B2 | 1/2010 | Kruszynski et al. |
| 7,641,093 B2 | 1/2010 | Doll et al. |
| 7,641,095 B2 | 1/2010 | Viola |
| 7,641,671 B2 | 1/2010 | Crainich |
| 7,644,783 B2 | 1/2010 | Roberts et al. |
| 7,644,848 B2 | 1/2010 | Swayze et al. |
| 7,645,230 B2 | 1/2010 | Mikkaichi et al. |
| 7,648,055 B2 | 1/2010 | Marczyk |
| 7,648,457 B2 | 1/2010 | Stefanchik et al. |
| 7,648,519 B2 | 1/2010 | Lee et al. |
| 7,650,185 B2 | 1/2010 | Maile et al. |
| 7,651,017 B2 | 1/2010 | Ortiz et al. |
| 7,651,498 B2 | 1/2010 | Shifrin et al. |
| 7,654,431 B2 | 2/2010 | Hueil et al. |
| 7,655,004 B2 | 2/2010 | Long |
| 7,655,288 B2 | 2/2010 | Bauman et al. |
| 7,655,584 B2 | 2/2010 | Biran et al. |
| 7,656,131 B2 | 2/2010 | Embrey et al. |
| 7,658,311 B2 | 2/2010 | Boudreaux |
| 7,658,312 B2 | 2/2010 | Vidal et al. |
| 7,658,705 B2 | 2/2010 | Melvin et al. |
| 7,659,219 B2 | 2/2010 | Biran et al. |
| 7,661,448 B2 | 2/2010 | Kim et al. |
| 7,662,161 B2 | 2/2010 | Briganti et al. |
| 7,665,646 B2 | 2/2010 | Prommersberger |
| 7,665,647 B2 | 2/2010 | Shelton, IV et al. |
| 7,666,195 B2 | 2/2010 | Kelleher et al. |
| 7,669,746 B2 | 3/2010 | Shelton, IV |
| 7,669,747 B2 | 3/2010 | Weisenburgh, II et al. |
| 7,670,334 B2 | 3/2010 | Hueil et al. |
| 7,673,780 B2 | 3/2010 | Shelton, IV et al. |
| 7,673,781 B2 | 3/2010 | Swayze et al. |
| 7,673,782 B2 | 3/2010 | Hess et al. |
| 7,673,783 B2 | 3/2010 | Morgan et al. |
| 7,674,253 B2 | 3/2010 | Fisher et al. |
| 7,674,255 B2 | 3/2010 | Braun |
| 7,674,263 B2 | 3/2010 | Ryan |
| 7,674,270 B2 | 3/2010 | Layer |
| 7,682,307 B2 | 3/2010 | Danitz et al. |
| 7,682,367 B2 | 3/2010 | Shah et al. |
| 7,682,686 B2 | 3/2010 | Curro et al. |
| 7,686,201 B2 | 3/2010 | Csiky |
| 7,686,804 B2 | 3/2010 | Johnson et al. |
| 7,686,826 B2 | 3/2010 | Lee et al. |
| 7,688,028 B2 | 3/2010 | Phillips et al. |
| 7,691,098 B2 | 4/2010 | Wallace et al. |
| 7,691,103 B2 | 4/2010 | Fernandez et al. |
| 7,691,106 B2 | 4/2010 | Schenberger et al. |
| 7,694,864 B2 | 4/2010 | Okada et al. |
| 7,694,865 B2 | 4/2010 | Scirica |
| 7,695,485 B2 | 4/2010 | Whitman et al. |
| 7,695,493 B2 | 4/2010 | Saadat et al. |
| 7,699,204 B2 | 4/2010 | Viola |
| 7,699,835 B2 | 4/2010 | Lee et al. |
| 7,699,844 B2 | 4/2010 | Utley et al. |
| 7,699,846 B2 | 4/2010 | Ryan |
| 7,699,856 B2 | 4/2010 | Van Wyk et al. |
| 7,699,859 B2 | 4/2010 | Bombard et al. |
| 7,699,860 B2 | 4/2010 | Huitema et al. |
| 7,699,868 B2 | 4/2010 | Frank et al. |
| 7,703,653 B2 | 4/2010 | Shah et al. |
| 7,705,559 B2 | 4/2010 | Powell et al. |
| 7,708,180 B2 | 5/2010 | Murray et al. |
| 7,708,181 B2 | 5/2010 | Cole et al. |
| 7,708,182 B2 | 5/2010 | Viola |
| 7,708,758 B2 | 5/2010 | Lee et al. |
| 7,708,768 B2 | 5/2010 | Danek et al. |
| 7,712,182 B2 | 5/2010 | Zeiler et al. |
| 7,713,190 B2 | 5/2010 | Brock et al. |
| 7,713,542 B2 | 5/2010 | Xu et al. |
| 7,714,239 B2 | 5/2010 | Smith |
| 7,714,334 B2 | 5/2010 | Lin |
| 7,717,312 B2 | 5/2010 | Beetel |
| 7,717,313 B2 | 5/2010 | Criscuolo et al. |
| 7,717,846 B2 | 5/2010 | Zirps et al. |
| 7,717,873 B2 | 5/2010 | Swick |
| 7,717,915 B2 | 5/2010 | Miyazawa |
| 7,717,926 B2 | 5/2010 | Whitfield et al. |
| 7,718,180 B2 | 5/2010 | Karp |
| 7,718,556 B2 | 5/2010 | Matsuda et al. |
| 7,721,930 B2 | 5/2010 | McKenna et al. |
| 7,721,931 B2 | 5/2010 | Shelton, IV et al. |
| 7,721,932 B2 | 5/2010 | Cole et al. |
| 7,721,933 B2 | 5/2010 | Ehrenfels et al. |
| 7,721,934 B2 | 5/2010 | Shelton, IV et al. |
| 7,721,936 B2 | 5/2010 | Shalton, IV et al. |
| 7,722,527 B2 | 5/2010 | Bouchier et al. |
| 7,722,607 B2 | 5/2010 | Dumbauld et al. |
| 7,722,610 B2 | 5/2010 | Viola et al. |
| 7,725,214 B2 | 5/2010 | Diolaiti |
| 7,726,171 B2 | 6/2010 | Langlotz et al. |
| 7,726,537 B2 | 6/2010 | Olson et al. |
| 7,726,538 B2 | 6/2010 | Holsten et al. |

(56) References Cited

U.S. PATENT DOCUMENTS

| | | |
|---|---|---|
| 7,726,539 B2 | 6/2010 | Holsten et al. |
| 7,727,954 B2 | 6/2010 | McKay |
| 7,728,553 B2 | 6/2010 | Carrier et al. |
| 7,729,742 B2 | 6/2010 | Govari |
| 7,731,072 B2 | 6/2010 | Timm et al. |
| 7,731,073 B2 | 6/2010 | Wixey et al. |
| 7,731,724 B2 | 6/2010 | Huitema et al. |
| 7,735,703 B2 | 6/2010 | Morgan et al. |
| 7,736,254 B2 | 6/2010 | Schena |
| 7,736,306 B2 | 6/2010 | Brustad et al. |
| 7,736,374 B2 | 6/2010 | Vaughan et al. |
| 7,738,971 B2 | 6/2010 | Swayze et al. |
| 7,740,159 B2 | 6/2010 | Shelton, IV et al. |
| 7,742,036 B2 | 6/2010 | Grant et al. |
| 7,743,960 B2 | 6/2010 | Whitman et al. |
| 7,744,624 B2 | 6/2010 | Bettuchi |
| 7,744,627 B2 | 6/2010 | Orban, III et al. |
| 7,744,628 B2 | 6/2010 | Viola |
| 7,747,146 B2 | 6/2010 | Milano et al. |
| 7,748,587 B2 | 7/2010 | Haramiishi et al. |
| 7,748,632 B2 | 7/2010 | Coleman et al. |
| 7,749,204 B2 | 7/2010 | Dhanaraj et al. |
| 7,749,240 B2 | 7/2010 | Takahashi et al. |
| 7,751,870 B2 | 7/2010 | Whitman |
| 7,753,245 B2 | 7/2010 | Boudreaux et al. |
| 7,753,246 B2 | 7/2010 | Scirica |
| 7,757,924 B2 | 7/2010 | Gerbi et al. |
| 7,758,594 B2 | 7/2010 | Lamson et al. |
| 7,758,612 B2 | 7/2010 | Shipp |
| 7,762,462 B2 | 7/2010 | Gelbman |
| 7,762,998 B2 | 7/2010 | Birk et al. |
| 7,766,207 B2 | 8/2010 | Mather et al. |
| 7,766,209 B2 | 8/2010 | Baxter, III et al. |
| 7,766,210 B2 | 8/2010 | Shelton, IV et al. |
| 7,766,821 B2 | 8/2010 | Brunnen et al. |
| 7,766,894 B2 | 8/2010 | Weitzner et al. |
| 7,770,658 B2 | 8/2010 | Ito et al. |
| 7,770,773 B2 | 8/2010 | Whitman et al. |
| 7,770,774 B2 | 8/2010 | Mastri et al. |
| 7,770,775 B2 | 8/2010 | Shelton, IV et al. |
| 7,770,776 B2 | 8/2010 | Chen et al. |
| 7,771,396 B2 | 8/2010 | Stefanchik et al. |
| 7,772,720 B2 | 8/2010 | McGee et al. |
| 7,772,725 B2 | 8/2010 | Siman-Tov |
| 7,775,972 B2 | 8/2010 | Brock et al. |
| 7,776,037 B2 | 8/2010 | Odom |
| 7,776,060 B2 | 8/2010 | Mooradian et al. |
| 7,776,065 B2 | 8/2010 | Griffiths et al. |
| 7,778,004 B2 | 8/2010 | Nerheim et al. |
| 7,779,737 B2 | 8/2010 | Newman, Jr. et al. |
| 7,780,054 B2 | 8/2010 | Wales |
| 7,780,055 B2 | 8/2010 | Scirica et al. |
| 7,780,309 B2 | 8/2010 | McMillan et al. |
| 7,780,663 B2 | 8/2010 | Yates et al. |
| 7,780,685 B2 | 8/2010 | Hunt et al. |
| 7,784,662 B2 | 8/2010 | Wales et al. |
| 7,784,663 B2 | 8/2010 | Shelton, IV |
| 7,787,256 B2 | 8/2010 | Chan et al. |
| 7,789,283 B2 | 9/2010 | Shah |
| 7,789,875 B2 | 9/2010 | Brock et al. |
| 7,789,883 B2 | 9/2010 | Takashino et al. |
| 7,789,889 B2 | 9/2010 | Zubik et al. |
| 7,793,812 B2 | 9/2010 | Moore et al. |
| 7,794,475 B2 | 9/2010 | Hess et al. |
| 7,798,386 B2 | 9/2010 | Schall et al. |
| 7,799,039 B2 | 9/2010 | Shelton, IV et al. |
| 7,799,044 B2 | 9/2010 | Johnston et al. |
| 7,799,965 B2 | 9/2010 | Patel et al. |
| 7,803,151 B2 | 9/2010 | Whitman |
| 7,806,871 B2 | 10/2010 | Li et al. |
| 7,806,891 B2 | 10/2010 | Nowlin et al. |
| 7,810,690 B2 | 10/2010 | Bilotti et al. |
| 7,810,691 B2 | 10/2010 | Boyden et al. |
| 7,810,692 B2 | 10/2010 | Hall et al. |
| 7,810,693 B2 | 10/2010 | Broehl et al. |
| 7,811,275 B2 | 10/2010 | Birk et al. |
| 7,814,816 B2 | 10/2010 | Alberti et al. |
| 7,815,092 B2 | 10/2010 | Whitman et al. |
| 7,815,565 B2 | 10/2010 | Stefanchik et al. |
| 7,815,662 B2 | 10/2010 | Spivey et al. |
| 7,819,296 B2 | 10/2010 | Hueil et al. |
| 7,819,297 B2 | 10/2010 | Doll et al. |
| 7,819,298 B2 | 10/2010 | Hall et al. |
| 7,819,299 B2 | 10/2010 | Shelton, IV et al. |
| 7,819,799 B2 | 10/2010 | Merril et al. |
| 7,819,884 B2 | 10/2010 | Lee et al. |
| 7,819,885 B2 | 10/2010 | Cooper |
| 7,819,886 B2 | 10/2010 | Whitfield et al. |
| 7,823,592 B2 | 11/2010 | Bettuchi et al. |
| 7,823,760 B2 | 11/2010 | Zemlok et al. |
| 7,824,401 B2 | 11/2010 | Manzo et al. |
| 7,824,422 B2 | 11/2010 | Benchetrit |
| 7,824,426 B2 | 11/2010 | Racenet et al. |
| 7,828,189 B2 | 11/2010 | Holsten et al. |
| 7,828,794 B2 | 11/2010 | Sartor |
| 7,828,808 B2 | 11/2010 | Hinman et al. |
| 7,831,292 B2 | 11/2010 | Quaid et al. |
| 7,832,408 B2 | 11/2010 | Shelton, IV et al. |
| 7,832,611 B2 | 11/2010 | Boyden et al. |
| 7,832,612 B2 | 11/2010 | Baxter, III et al. |
| 7,833,234 B2 | 11/2010 | Bailly et al. |
| 7,835,823 B2 | 11/2010 | Sillman et al. |
| 7,836,400 B2 | 11/2010 | May et al. |
| 7,837,079 B2 | 11/2010 | Holsten et al. |
| 7,837,080 B2 | 11/2010 | Schwemberger |
| 7,837,081 B2 | 11/2010 | Holsten et al. |
| 7,837,425 B2 | 11/2010 | Saeki et al. |
| 7,837,685 B2 | 11/2010 | Weinberg et al. |
| 7,837,687 B2 | 11/2010 | Harp |
| 7,837,694 B2 | 11/2010 | Tethrake et al. |
| 7,838,789 B2 | 11/2010 | Stoffers et al. |
| 7,839,109 B2 | 11/2010 | Carmen, Jr. et al. |
| 7,841,503 B2 | 11/2010 | Sonnenschein et al. |
| 7,842,025 B2 | 11/2010 | Coleman et al. |
| 7,842,028 B2 | 11/2010 | Lee |
| 7,843,158 B2 | 11/2010 | Prisco |
| 7,845,533 B2 | 12/2010 | Marczyk et al. |
| 7,845,534 B2 | 12/2010 | Viola et al. |
| 7,845,535 B2 | 12/2010 | Scircia |
| 7,845,536 B2 | 12/2010 | Viola et al. |
| 7,845,537 B2 | 12/2010 | Shelton, IV et al. |
| 7,845,538 B2 | 12/2010 | Whitman |
| 7,846,085 B2 | 12/2010 | Silverman et al. |
| 7,846,149 B2 | 12/2010 | Jankowski |
| 7,848,066 B2 | 12/2010 | Yanagishima |
| 7,850,623 B2 | 12/2010 | Griffin et al. |
| 7,850,642 B2 | 12/2010 | Moll et al. |
| 7,850,982 B2 | 12/2010 | Stopek et al. |
| 7,853,813 B2 | 12/2010 | Lee |
| 7,854,735 B2 | 12/2010 | Houser et al. |
| 7,854,736 B2 | 12/2010 | Ryan |
| 7,857,183 B2 | 12/2010 | Shelton, IV |
| 7,857,184 B2 | 12/2010 | Viola |
| 7,857,185 B2 | 12/2010 | Swayze et al. |
| 7,857,186 B2 | 12/2010 | Baxter, III et al. |
| 7,857,813 B2 | 12/2010 | Schmitz et al. |
| 7,861,906 B2 | 1/2011 | Doll et al. |
| 7,862,502 B2 | 1/2011 | Pool et al. |
| 7,862,546 B2 | 1/2011 | Conlon et al. |
| 7,862,579 B2 | 1/2011 | Ortiz et al. |
| 7,866,525 B2 | 1/2011 | Scirica |
| 7,866,527 B2 | 1/2011 | Hall et al. |
| 7,866,528 B2 | 1/2011 | Olson et al. |
| 7,870,989 B2 | 1/2011 | Viola et al. |
| 7,871,418 B2 | 1/2011 | Thompson et al. |
| 7,871,440 B2 | 1/2011 | Schwartz et al. |
| 7,875,055 B2 | 1/2011 | Cichocki, Jr. |
| 7,879,063 B2 | 2/2011 | Khosravi |
| 7,879,070 B2 | 2/2011 | Ortiz et al. |
| 7,883,461 B2 | 2/2011 | Albrecht et al. |
| 7,883,465 B2 | 2/2011 | Donofrio et al. |
| 7,886,951 B2 | 2/2011 | Hessler |
| 7,886,952 B2 | 2/2011 | Scirica et al. |
| 7,887,530 B2 | 2/2011 | Zemlok et al. |

(56) References Cited

U.S. PATENT DOCUMENTS

| | | |
|---|---|---|
| 7,887,535 B2 | 2/2011 | Lands et al. |
| 7,887,536 B2 | 2/2011 | Johnson et al. |
| 7,887,563 B2 | 2/2011 | Cummins |
| 7,891,531 B1 | 2/2011 | Ward |
| 7,891,532 B2 | 2/2011 | Mastri et al. |
| 7,892,200 B2 | 2/2011 | Birk et al. |
| 7,892,245 B2 | 2/2011 | Liddicoat et al. |
| 7,893,586 B2 | 2/2011 | West et al. |
| 7,896,214 B2 | 3/2011 | Farascioni |
| 7,896,215 B2 | 3/2011 | Adams et al. |
| 7,896,869 B2 | 3/2011 | DiSilvestro et al. |
| 7,896,877 B2 | 3/2011 | Hall et al. |
| 7,896,895 B2 | 3/2011 | Boudreaux et al. |
| 7,896,897 B2 | 3/2011 | Gresham et al. |
| 7,896,900 B2 | 3/2011 | Frank et al. |
| 7,898,198 B2 | 3/2011 | Murphree |
| 7,900,805 B2 | 3/2011 | Shelton, IV et al. |
| 7,900,806 B2 | 3/2011 | Chen et al. |
| 7,901,381 B2 | 3/2011 | Birk et al. |
| 7,905,380 B2 | 3/2011 | Shelton, IV et al. |
| 7,905,381 B2 | 3/2011 | Baxter, III et al. |
| 7,905,881 B2 | 3/2011 | Masuda et al. |
| 7,905,889 B2 | 3/2011 | Catanese, III et al. |
| 7,905,890 B2 | 3/2011 | Whitfield et al. |
| 7,905,902 B2 | 3/2011 | Huitema et al. |
| 7,909,039 B2 | 3/2011 | Hur |
| 7,909,191 B2 | 3/2011 | Baker et al. |
| 7,909,220 B2 | 3/2011 | Viola |
| 7,909,221 B2 | 3/2011 | Viola et al. |
| 7,909,224 B2 | 3/2011 | Prommersberger |
| 7,913,891 B2 | 3/2011 | Doll et al. |
| 7,913,893 B2 | 3/2011 | Mastri et al. |
| 7,914,521 B2 | 3/2011 | Wang et al. |
| 7,914,543 B2 | 3/2011 | Roth et al. |
| 7,914,551 B2 | 3/2011 | Ortiz et al. |
| 7,918,230 B2 | 4/2011 | Whitman et al. |
| 7,918,376 B1 | 4/2011 | Knodel et al. |
| 7,918,377 B2 | 4/2011 | Measamer et al. |
| 7,918,845 B2 | 4/2011 | Saadat et al. |
| 7,918,848 B2 | 4/2011 | Lau et al. |
| 7,918,861 B2 | 4/2011 | Brock et al. |
| 7,918,867 B2 | 4/2011 | Dana et al. |
| 7,922,061 B2 | 4/2011 | Shelton, IV et al. |
| 7,922,063 B2 | 4/2011 | Zemlok et al. |
| 7,922,743 B2 | 4/2011 | Heinrich et al. |
| 7,923,144 B2 | 4/2011 | Kohn et al. |
| 7,926,691 B2 | 4/2011 | Viola et al. |
| 7,926,692 B2 | 4/2011 | Racenet et al. |
| 7,927,328 B2 | 4/2011 | Orszulak et al. |
| 7,928,281 B2 | 4/2011 | Augustine |
| 7,930,040 B1 | 4/2011 | Kelsch et al. |
| 7,930,065 B2 | 4/2011 | Larkin et al. |
| 7,931,660 B2 | 4/2011 | Aranyi et al. |
| 7,931,695 B2 | 4/2011 | Ringeisen |
| 7,931,877 B2 | 4/2011 | Steffens et al. |
| 7,934,630 B2 | 5/2011 | Shelton, IV et al. |
| 7,934,631 B2 | 5/2011 | Balbierz et al. |
| 7,934,896 B2 | 5/2011 | Schnier |
| 7,935,130 B2 | 5/2011 | Williams |
| 7,935,773 B2 | 5/2011 | Hadba et al. |
| 7,936,142 B2 | 5/2011 | Otsuka et al. |
| 7,938,307 B2 | 5/2011 | Bettuchi |
| 7,941,865 B2 | 5/2011 | Seman, Jr. et al. |
| 7,942,303 B2 | 5/2011 | Shah |
| 7,942,890 B2 | 5/2011 | D'Agostino et al. |
| 7,944,175 B2 | 5/2011 | Mori et al. |
| 7,945,792 B2 | 5/2011 | Cherpantier |
| 7,945,798 B2 | 5/2011 | Carlson et al. |
| 7,946,453 B2 | 5/2011 | Voegele et al. |
| 7,947,011 B2 | 5/2011 | Birk et al. |
| 7,950,560 B2 | 5/2011 | Zemlok et al. |
| 7,950,561 B2 | 5/2011 | Aranyi |
| 7,951,071 B2 | 5/2011 | Whitman et al. |
| 7,951,166 B2 | 5/2011 | Orban, III et al. |
| 7,954,682 B2 | 6/2011 | Giordano et al. |
| 7,954,684 B2 | 6/2011 | Boudreaux |
| 7,954,685 B2 | 6/2011 | Viola |
| 7,954,686 B2 | 6/2011 | Baxter, III et al. |
| 7,954,687 B2 | 6/2011 | Zemlok et al. |
| 7,955,253 B2 | 6/2011 | Ewers et al. |
| 7,955,257 B2 | 6/2011 | Frasier et al. |
| 7,955,322 B2 | 6/2011 | Devengenzo et al. |
| 7,955,327 B2 | 6/2011 | Sartor et al. |
| 7,955,380 B2 | 6/2011 | Chu et al. |
| 7,959,050 B2 | 6/2011 | Smith et al. |
| 7,959,051 B2 | 6/2011 | Smith et al. |
| 7,959,052 B2 | 6/2011 | Sonnenschein et al. |
| 7,963,432 B2 | 6/2011 | Knodel et al. |
| 7,963,433 B2 | 6/2011 | Whitman et al. |
| 7,963,913 B2 | 6/2011 | Devengenzo et al. |
| 7,963,963 B2 | 6/2011 | Francischelli et al. |
| 7,963,964 B2 | 6/2011 | Santilli et al. |
| 7,964,206 B2 | 6/2011 | Suokas et al. |
| 7,966,236 B2 | 6/2011 | Noriega et al. |
| 7,966,269 B2 | 6/2011 | Bauer et al. |
| 7,966,799 B2 | 6/2011 | Morgan et al. |
| 7,967,178 B2 | 6/2011 | Scirica et al. |
| 7,967,179 B2 | 6/2011 | Olson et al. |
| 7,967,180 B2 | 6/2011 | Scirica |
| 7,967,181 B2 | 6/2011 | Viola et al. |
| 7,967,791 B2 | 6/2011 | Franer et al. |
| 7,967,839 B2 | 6/2011 | Flock et al. |
| 7,972,298 B2 | 7/2011 | Wallace et al. |
| 7,972,315 B2 | 7/2011 | Birk et al. |
| 7,976,213 B2 | 7/2011 | Bertolotti et al. |
| 7,976,563 B2 | 7/2011 | Summerer |
| 7,979,137 B2 | 7/2011 | Tracey et al. |
| 7,980,443 B2 | 7/2011 | Scheib et al. |
| 7,981,132 B2 | 7/2011 | Dubrul et al. |
| 7,987,405 B2 | 7/2011 | Turner et al. |
| 7,988,015 B2 | 8/2011 | Mason, II et al. |
| 7,988,026 B2 | 8/2011 | Knodel et al. |
| 7,988,027 B2 | 8/2011 | Olson et al. |
| 7,988,028 B2 | 8/2011 | Farascioni et al. |
| 7,988,779 B2 | 8/2011 | Disalvo et al. |
| 7,992,757 B2 | 8/2011 | Wheeler et al. |
| 7,993,360 B2 | 8/2011 | Hacker et al. |
| 7,994,670 B2 | 8/2011 | Ji |
| 7,997,054 B2 | 8/2011 | Bertsch et al. |
| 7,997,468 B2 | 8/2011 | Farascioni |
| 7,997,469 B2 | 8/2011 | Olson et al. |
| 8,002,696 B2 | 8/2011 | Suzuki |
| 8,002,784 B2 | 8/2011 | Jinno et al. |
| 8,002,785 B2 | 8/2011 | Weiss et al. |
| 8,002,795 B2 | 8/2011 | Beetel |
| 8,006,365 B2 | 8/2011 | Levin et al. |
| 8,006,885 B2 | 8/2011 | Marczyk |
| 8,006,889 B2 | 8/2011 | Adams et al. |
| 8,007,370 B2 | 8/2011 | Hirsch et al. |
| 8,007,465 B2 | 8/2011 | Birk et al. |
| 8,007,479 B2 | 8/2011 | Birk et al. |
| 8,007,511 B2 | 8/2011 | Brock et al. |
| 8,007,513 B2 | 8/2011 | Nalagatla et al. |
| 8,008,598 B2 | 8/2011 | Whitman et al. |
| 8,010,180 B2 | 8/2011 | Quaid et al. |
| 8,011,550 B2 | 9/2011 | Aranyi et al. |
| 8,011,551 B2 | 9/2011 | Marczyk et al. |
| 8,011,553 B2 | 9/2011 | Mastri et al. |
| 8,011,555 B2 | 9/2011 | Tarinelli et al. |
| 8,012,170 B2 | 9/2011 | Whitman et al. |
| 8,016,176 B2 | 9/2011 | Kasvikis et al. |
| 8,016,177 B2 | 9/2011 | Bettuchi et al. |
| 8,016,178 B2 | 9/2011 | Olson et al. |
| 8,016,849 B2 | 9/2011 | Wenchell |
| 8,016,855 B2 | 9/2011 | Whitman et al. |
| 8,016,858 B2 | 9/2011 | Whitman |
| 8,016,881 B2 | 9/2011 | Furst |
| 8,020,742 B2 | 9/2011 | Marczyk |
| 8,020,743 B2 | 9/2011 | Shelton, IV |
| 8,021,375 B2 | 9/2011 | Aldrich et al. |
| 8,025,199 B2 | 9/2011 | Whitman et al. |
| 8,025,896 B2 | 9/2011 | Malaviya et al. |
| 8,028,882 B2 | 10/2011 | Viola |
| 8,028,883 B2 | 10/2011 | Stopek |

(56) References Cited

U.S. PATENT DOCUMENTS

| | | |
|---|---|---|
| 8,028,884 B2 | 10/2011 | Sniffin et al. |
| 8,028,885 B2 | 10/2011 | Smith et al. |
| 8,029,510 B2 | 10/2011 | Hoegerle |
| 8,031,069 B2 | 10/2011 | Cohn et al. |
| 8,033,438 B2 | 10/2011 | Scirica |
| 8,033,439 B2 | 10/2011 | Racenet et al. |
| 8,033,440 B2 | 10/2011 | Wenchell et al. |
| 8,033,442 B2 | 10/2011 | Racenet et al. |
| 8,034,077 B2 | 10/2011 | Smith et al. |
| 8,034,337 B2 | 10/2011 | Simard |
| 8,034,363 B2 | 10/2011 | Li et al. |
| 8,035,487 B2 | 10/2011 | Malackowski |
| 8,037,591 B2 | 10/2011 | Spivey et al. |
| 8,038,045 B2 | 10/2011 | Bettuchi et al. |
| 8,038,046 B2 | 10/2011 | Smith et al. |
| 8,038,686 B2 | 10/2011 | Huitema et al. |
| 8,043,207 B2 | 10/2011 | Adams |
| 8,043,328 B2 | 10/2011 | Hahnen et al. |
| 8,044,536 B2 | 10/2011 | Nguyen et al. |
| 8,044,604 B2 | 10/2011 | Hagino et al. |
| 8,047,236 B2 | 11/2011 | Perry |
| 8,048,503 B2 | 11/2011 | Farnsworth et al. |
| 8,052,636 B2 | 11/2011 | Moll et al. |
| 8,056,787 B2 | 11/2011 | Boudreaux et al. |
| 8,056,788 B2 | 11/2011 | Mastri et al. |
| 8,056,789 B1 | 11/2011 | White et al. |
| 8,057,508 B2 | 11/2011 | Shelton, IV |
| 8,058,771 B2 | 11/2011 | Giordano et al. |
| 8,060,250 B2 | 11/2011 | Reiland et al. |
| 8,061,014 B2 | 11/2011 | Smith et al. |
| 8,061,576 B2 | 11/2011 | Cappola |
| 8,062,236 B2 | 11/2011 | Soltz |
| 8,062,306 B2 | 11/2011 | Nobis et al. |
| 8,062,330 B2 | 11/2011 | Prommersberger et al. |
| 8,063,619 B2 | 11/2011 | Zhu et al. |
| 8,066,158 B2 | 11/2011 | Vogel et al. |
| 8,066,166 B2 | 11/2011 | Demmy et al. |
| 8,066,167 B2 | 11/2011 | Measamer et al. |
| 8,066,168 B2 | 11/2011 | Vidal et al. |
| 8,066,720 B2 | 11/2011 | Knodel et al. |
| D650,074 S | 12/2011 | Hunt et al. |
| D650,789 S | 12/2011 | Arnold |
| 8,070,033 B2 | 12/2011 | Milliman et al. |
| 8,070,034 B1 | 12/2011 | Knodel |
| 8,070,035 B2 | 12/2011 | Holsten et al. |
| 8,070,743 B2 | 12/2011 | Kagan et al. |
| 8,074,858 B2 | 12/2011 | Marczyk |
| 8,074,859 B2 | 12/2011 | Kostrzewski |
| 8,074,861 B2 | 12/2011 | Ehrenfels et al. |
| 8,075,476 B2 | 12/2011 | Vargas |
| 8,075,571 B2 | 12/2011 | Vitali et al. |
| 8,079,950 B2 | 12/2011 | Stern et al. |
| 8,079,989 B2 | 12/2011 | Birk et al. |
| 8,080,004 B2 | 12/2011 | Downey et al. |
| 8,083,118 B2 | 12/2011 | Milliman et al. |
| 8,083,119 B2 | 12/2011 | Prommersberger |
| 8,083,120 B2 | 12/2011 | Shelton, IV et al. |
| 8,084,001 B2 | 12/2011 | Burns et al. |
| 8,084,969 B2 | 12/2011 | David et al. |
| 8,085,013 B2 | 12/2011 | Wei et al. |
| 8,087,562 B1 | 1/2012 | Manoux et al. |
| 8,087,563 B2 | 1/2012 | Milliman et al. |
| 8,089,509 B2 | 1/2012 | Chatenever et al. |
| 8,091,753 B2 | 1/2012 | Viola |
| 8,091,756 B2 | 1/2012 | Viola |
| 8,092,443 B2 | 1/2012 | Bischoff |
| 8,092,932 B2 | 1/2012 | Phillips et al. |
| 8,093,572 B2 | 1/2012 | Kuduvalli |
| 8,096,458 B2 | 1/2012 | Hessler |
| 8,096,459 B2 | 1/2012 | Ortiz et al. |
| 8,097,017 B2 | 1/2012 | Viola |
| 8,100,310 B2 | 1/2012 | Zemlok |
| 8,100,824 B2 | 1/2012 | Hegeman et al. |
| 8,100,872 B2 | 1/2012 | Patel |
| 8,102,138 B2 | 1/2012 | Sekine et al. |
| 8,102,278 B2 | 1/2012 | Deck et al. |
| 8,105,350 B2 | 1/2012 | Lee et al. |
| 8,107,925 B2 | 1/2012 | Natsuno et al. |
| 8,108,033 B2 | 1/2012 | Drew et al. |
| 8,108,072 B2 | 1/2012 | Zhao et al. |
| 8,109,426 B2 | 2/2012 | Milliman et al. |
| 8,110,208 B1 | 2/2012 | Hen |
| 8,113,405 B2 | 2/2012 | Milliman |
| 8,113,407 B2 | 2/2012 | Holsten et al. |
| 8,113,408 B2 | 2/2012 | Wenchell et al. |
| 8,113,410 B2 | 2/2012 | Hall et al. |
| 8,114,017 B2 | 2/2012 | Bacher |
| 8,114,100 B2 | 2/2012 | Smith et al. |
| 8,118,206 B2 | 2/2012 | Zand et al. |
| 8,118,207 B2 | 2/2012 | Racenet et al. |
| 8,120,301 B2 | 2/2012 | Goldberg et al. |
| 8,122,128 B2 | 2/2012 | Burke, II et al. |
| 8,123,103 B2 | 2/2012 | Milliman |
| 8,123,523 B2 | 2/2012 | Carron et al. |
| 8,123,766 B2 | 2/2012 | Bauman et al. |
| 8,123,767 B2 | 2/2012 | Bauman et al. |
| 8,125,168 B2 | 2/2012 | Johnson et al. |
| 8,127,975 B2 | 3/2012 | Olson et al. |
| 8,127,976 B2 | 3/2012 | Scirica et al. |
| 8,128,624 B2 | 3/2012 | Couture et al. |
| 8,128,643 B2 | 3/2012 | Aranyi et al. |
| 8,128,645 B2 | 3/2012 | Sonnenschein et al. |
| 8,128,662 B2 | 3/2012 | Altarac et al. |
| 8,132,703 B2 | 3/2012 | Milliman et al. |
| 8,132,705 B2 | 3/2012 | Viola et al. |
| 8,132,706 B2 | 3/2012 | Marczyk et al. |
| 8,133,500 B2 | 3/2012 | Ringeisen et al. |
| 8,134,306 B2 | 3/2012 | Drader et al. |
| 8,136,711 B2 | 3/2012 | Beardsley et al. |
| 8,136,712 B2 | 3/2012 | Zingman |
| 8,136,713 B2 | 3/2012 | Hathaway et al. |
| 8,137,339 B2 | 3/2012 | Jinno et al. |
| 8,140,417 B2 | 3/2012 | Shibata |
| 8,141,762 B2 | 3/2012 | Bedi et al. |
| 8,141,763 B2 | 3/2012 | Milliman |
| 8,142,200 B2 | 3/2012 | Crunkilton et al. |
| 8,142,425 B2 | 3/2012 | Eggers |
| 8,142,461 B2 | 3/2012 | Houser et al. |
| 8,142,515 B2 | 3/2012 | Therin et al. |
| 8,143,520 B2 | 3/2012 | Cutler |
| 8,146,790 B2 | 4/2012 | Milliman |
| 8,147,421 B2 | 4/2012 | Farquhar et al. |
| 8,147,456 B2 | 4/2012 | Fisher et al. |
| 8,147,485 B2 | 4/2012 | Wham et al. |
| 8,152,041 B2 | 4/2012 | Kostrzewski |
| 8,152,756 B2 | 4/2012 | Webster et al. |
| 8,154,239 B2 | 4/2012 | Katsuki et al. |
| 8,157,145 B2 | 4/2012 | Shelton, IV et al. |
| 8,157,148 B2 | 4/2012 | Scirica |
| 8,157,151 B2 | 4/2012 | Ingmanson et al. |
| 8,157,152 B2 | 4/2012 | Holsten et al. |
| 8,157,153 B2 | 4/2012 | Shelton, IV et al. |
| 8,157,793 B2 | 4/2012 | Omori et al. |
| 8,161,977 B2 | 4/2012 | Shelton, IV et al. |
| 8,162,138 B2 | 4/2012 | Bettenhausen et al. |
| 8,162,197 B2 | 4/2012 | Mastri et al. |
| 8,162,668 B2 | 4/2012 | Toly |
| 8,162,933 B2 | 4/2012 | Francischelli et al. |
| 8,162,965 B2 | 4/2012 | Reschke et al. |
| 8,167,185 B2 | 5/2012 | Shelton, IV et al. |
| 8,167,622 B2 | 5/2012 | Zhou |
| 8,167,895 B2 | 5/2012 | D'Agostino et al. |
| 8,167,898 B1 | 5/2012 | Schaller et al. |
| 8,170,241 B2 | 5/2012 | Roe et al. |
| 8,172,004 B2 | 5/2012 | Ho |
| 8,172,120 B2 | 5/2012 | Boyden et al. |
| 8,172,122 B2 | 5/2012 | Kasvikis et al. |
| 8,172,124 B2 | 5/2012 | Shelton, IV et al. |
| 8,177,776 B2 | 5/2012 | Humayun et al. |
| 8,177,797 B2 | 5/2012 | Shimoji et al. |
| 8,179,705 B2 | 5/2012 | Chapuis |
| 8,180,458 B2 | 5/2012 | Kane et al. |
| 8,181,839 B2 | 5/2012 | Beetel |
| 8,181,840 B2 | 5/2012 | Milliman |

(56) References Cited

U.S. PATENT DOCUMENTS

| | | |
|---|---|---|
| 8,182,422 B2 | 5/2012 | Bayer et al. |
| 8,182,444 B2 | 5/2012 | Uber, III et al. |
| 8,183,807 B2 | 5/2012 | Tsai et al. |
| 8,186,555 B2 | 5/2012 | Shelton, IV et al. |
| 8,186,556 B2 | 5/2012 | Viola |
| 8,186,558 B2 | 5/2012 | Sapienza |
| 8,186,560 B2 | 5/2012 | Hess et al. |
| 8,191,752 B2 | 6/2012 | Scirica |
| 8,192,350 B2 | 6/2012 | Ortiz et al. |
| 8,192,460 B2 | 6/2012 | Orban, III et al. |
| 8,192,651 B2 | 6/2012 | Young et al. |
| 8,196,795 B2 | 6/2012 | Moore et al. |
| 8,196,796 B2 | 6/2012 | Shelton, IV et al. |
| 8,197,501 B2 | 6/2012 | Shadeck et al. |
| 8,197,502 B2 | 6/2012 | Smith et al. |
| 8,197,837 B2 | 6/2012 | Jamiolkowski et al. |
| 8,201,720 B2 | 6/2012 | Hessler |
| 8,201,721 B2 | 6/2012 | Zemlok et al. |
| 8,202,549 B2 | 6/2012 | Stucky et al. |
| 8,205,779 B2 | 6/2012 | Ma et al. |
| 8,205,780 B2 | 6/2012 | Sorrentino et al. |
| 8,205,781 B2 | 6/2012 | Baxter, III et al. |
| 8,210,411 B2 | 7/2012 | Yates et al. |
| 8,210,414 B2 | 7/2012 | Bettuchi et al. |
| 8,210,415 B2 | 7/2012 | Ward |
| 8,210,416 B2 | 7/2012 | Milliman et al. |
| 8,210,721 B2 | 7/2012 | Chen et al. |
| 8,211,125 B2 | 7/2012 | Spivey |
| 8,214,019 B2 | 7/2012 | Govari et al. |
| 8,215,531 B2 | 7/2012 | Shelton, IV et al. |
| 8,215,532 B2 | 7/2012 | Marczyk |
| 8,215,533 B2 | 7/2012 | Viola et al. |
| 8,220,468 B2 | 7/2012 | Cooper et al. |
| 8,220,688 B2 | 7/2012 | Laurent et al. |
| 8,220,690 B2 | 7/2012 | Hess et al. |
| 8,221,402 B2 | 7/2012 | Francischelli et al. |
| 8,221,424 B2 | 7/2012 | Cha |
| 8,221,433 B2 | 7/2012 | Lozier et al. |
| 8,225,799 B2 | 7/2012 | Bettuchi |
| 8,225,979 B2 | 7/2012 | Farascioni et al. |
| 8,226,553 B2 | 7/2012 | Shelton, IV et al. |
| 8,226,635 B2 | 7/2012 | Petrie et al. |
| 8,226,675 B2 | 7/2012 | Houser et al. |
| 8,226,715 B2 | 7/2012 | Hwang et al. |
| 8,227,946 B2 | 7/2012 | Kim |
| 8,228,020 B2 | 7/2012 | Shin et al. |
| 8,228,048 B2 | 7/2012 | Spencer |
| 8,229,549 B2 | 7/2012 | Whitman et al. |
| 8,231,040 B2 | 7/2012 | Zemlok et al. |
| 8,231,042 B2 | 7/2012 | Hessler et al. |
| 8,231,043 B2 | 7/2012 | Tarinelli et al. |
| 8,235,272 B2 | 8/2012 | Nicholas et al. |
| 8,236,010 B2 | 8/2012 | Ortiz et al. |
| 8,236,011 B2 | 8/2012 | Harris et al. |
| 8,236,020 B2 | 8/2012 | Smith et al. |
| 8,237,388 B2 | 8/2012 | Jinno et al. |
| 8,240,537 B2 | 8/2012 | Marczyk |
| 8,241,271 B2 | 8/2012 | Millman et al. |
| 8,241,284 B2 | 8/2012 | Dycus et al. |
| 8,241,308 B2 | 8/2012 | Kortenbach et al. |
| 8,241,322 B2 | 8/2012 | Whitman et al. |
| 8,245,594 B2 | 8/2012 | Rogers et al. |
| 8,245,898 B2 | 8/2012 | Smith et al. |
| 8,245,899 B2 | 8/2012 | Swensgard et al. |
| 8,245,900 B2 | 8/2012 | Scirica |
| 8,245,901 B2 | 8/2012 | Stopek |
| 8,246,608 B2 | 8/2012 | Omori et al. |
| 8,246,637 B2 | 8/2012 | Viola et al. |
| 8,252,009 B2 | 8/2012 | Weller et al. |
| 8,256,654 B2 | 9/2012 | Bettuchi et al. |
| 8,256,655 B2 | 9/2012 | Sniffin et al. |
| 8,256,656 B2 | 9/2012 | Milliman et al. |
| 8,257,251 B2 | 9/2012 | Shelton, IV et al. |
| 8,257,356 B2 | 9/2012 | Bleich et al. |
| 8,257,386 B2 | 9/2012 | Lee et al. |
| 8,257,391 B2 | 9/2012 | Orban, III et al. |
| 8,257,634 B2 | 9/2012 | Scirica |
| 8,258,745 B2 | 9/2012 | Smith et al. |
| 8,261,958 B1 | 9/2012 | Knodel |
| 8,262,560 B2 | 9/2012 | Whitman |
| 8,262,655 B2 | 9/2012 | Ghabrial et al. |
| 8,267,300 B2 | 9/2012 | Boudreaux |
| 8,267,924 B2 | 9/2012 | Zemlok et al. |
| 8,267,946 B2 | 9/2012 | Whitfield et al. |
| 8,267,951 B2 | 9/2012 | Whayne et al. |
| 8,268,344 B2 | 9/2012 | Ma et al. |
| 8,269,121 B2 | 9/2012 | Smith |
| 8,272,553 B2 | 9/2012 | Mastri et al. |
| 8,272,554 B2 | 9/2012 | Whitman et al. |
| 8,272,918 B2 | 9/2012 | Lam |
| 8,273,404 B2 | 9/2012 | Dave et al. |
| 8,276,594 B2 | 10/2012 | Shah |
| 8,276,801 B2 | 10/2012 | Zemlok et al. |
| 8,276,802 B2 | 10/2012 | Kostrzewski |
| 8,277,473 B2 | 10/2012 | Sunaoshi et al. |
| 8,281,446 B2 | 10/2012 | Moskovich |
| 8,281,973 B2 | 10/2012 | Wenchell et al. |
| 8,281,974 B2 | 10/2012 | Hessler et al. |
| 8,282,654 B2 | 10/2012 | Ferrari et al. |
| 8,285,367 B2 | 10/2012 | Hyde et al. |
| 8,286,723 B2 | 10/2012 | Puzio et al. |
| 8,286,845 B2 | 10/2012 | Perry et al. |
| 8,286,846 B2 | 10/2012 | Smith et al. |
| 8,286,847 B2 | 10/2012 | Taylor |
| 8,287,487 B2 | 10/2012 | Estes |
| 8,287,522 B2 | 10/2012 | Moses et al. |
| 8,287,561 B2 | 10/2012 | Nunez et al. |
| 8,288,984 B2 | 10/2012 | Yang |
| 8,289,403 B2 | 10/2012 | Dobashi et al. |
| 8,292,147 B2 | 10/2012 | Viola |
| 8,292,148 B2 | 10/2012 | Viola |
| 8,292,150 B2 | 10/2012 | Bryant |
| 8,292,151 B2 | 10/2012 | Viola |
| 8,292,152 B2 | 10/2012 | Milliman et al. |
| 8,292,155 B2 | 10/2012 | Shelton, IV et al. |
| 8,292,157 B2 | 10/2012 | Smith et al. |
| 8,292,158 B2 | 10/2012 | Sapienza |
| 8,292,801 B2 | 10/2012 | Dejima et al. |
| 8,292,888 B2 | 10/2012 | Whitman |
| 8,292,906 B2 | 10/2012 | Taylor et al. |
| 8,294,399 B2 | 10/2012 | Suzuki et al. |
| 8,298,161 B2 | 10/2012 | Vargas |
| 8,298,189 B2 | 10/2012 | Fisher et al. |
| 8,298,233 B2 | 10/2012 | Mueller |
| 8,298,677 B2 | 10/2012 | Wiesner et al. |
| 8,302,323 B2 | 11/2012 | Fortier et al. |
| 8,303,621 B2 | 11/2012 | Miyamoto et al. |
| 8,308,040 B2 | 11/2012 | Huang et al. |
| 8,308,041 B2 | 11/2012 | Kostrzewski |
| 8,308,042 B2 | 11/2012 | Aranyi |
| 8,308,043 B2 | 11/2012 | Bindra et al. |
| 8,308,046 B2 | 11/2012 | Prommersberger |
| 8,308,659 B2 | 11/2012 | Scheibe et al. |
| 8,308,725 B2 | 11/2012 | Bell et al. |
| 8,310,188 B2 | 11/2012 | Nakai |
| 8,313,496 B2 | 11/2012 | Sauer et al. |
| 8,313,499 B2 | 11/2012 | Magnusson et al. |
| 8,313,509 B2 | 11/2012 | Kostrzewski |
| 8,317,070 B2 | 11/2012 | Hueil et al. |
| 8,317,071 B1 | 11/2012 | Knodel |
| 8,317,074 B2 | 11/2012 | Ortiz et al. |
| 8,317,437 B2 | 11/2012 | Merkley et al. |
| 8,317,744 B2 | 11/2012 | Kirschenman |
| 8,317,790 B2 | 11/2012 | Bell et al. |
| 8,319,002 B2 | 11/2012 | Daniels et al. |
| 8,322,455 B2 | 12/2012 | Shelton, IV et al. |
| 8,322,589 B2 | 12/2012 | Boudreaux |
| 8,322,590 B2 | 12/2012 | Patel et al. |
| 8,322,901 B2 | 12/2012 | Michelotti |
| 8,323,789 B2 | 12/2012 | Rozhin et al. |
| 8,328,061 B2 | 12/2012 | Kasvikis |
| 8,328,062 B2 | 12/2012 | Viola |
| 8,328,063 B2 | 12/2012 | Milliman et al. |
| 8,328,064 B2 | 12/2012 | Racenet et al. |

(56) References Cited

U.S. PATENT DOCUMENTS

| | | |
|---|---|---|
| 8,328,802 B2 | 12/2012 | Deville et al. |
| 8,328,823 B2 | 12/2012 | Aranyi et al. |
| 8,333,313 B2 | 12/2012 | Boudreaux et al. |
| 8,333,691 B2 | 12/2012 | Schaaf |
| 8,333,764 B2 | 12/2012 | Francischelli et al. |
| 8,333,779 B2 | 12/2012 | Smith et al. |
| 8,334,468 B2 | 12/2012 | Palmer et al. |
| 8,336,753 B2 | 12/2012 | Olson et al. |
| 8,336,754 B2 | 12/2012 | Cappola et al. |
| 8,342,377 B2 | 1/2013 | Milliman et al. |
| 8,342,378 B2 | 1/2013 | Marczyk et al. |
| 8,342,379 B2 | 1/2013 | Whitman et al. |
| 8,342,380 B2 | 1/2013 | Viola |
| 8,343,150 B2 | 1/2013 | Artale |
| 8,347,978 B2 | 1/2013 | Forster et al. |
| 8,348,118 B2 | 1/2013 | Segura |
| 8,348,123 B2 | 1/2013 | Scirica et al. |
| 8,348,124 B2 | 1/2013 | Scirica |
| 8,348,125 B2 | 1/2013 | Viola et al. |
| 8,348,126 B2 | 1/2013 | Olson et al. |
| 8,348,127 B2 | 1/2013 | Marczyk |
| 8,348,129 B2 | 1/2013 | Bedi et al. |
| 8,348,130 B2 | 1/2013 | Shah et al. |
| 8,348,131 B2 | 1/2013 | Omaits et al. |
| 8,348,837 B2 | 1/2013 | Wenchell |
| 8,348,959 B2 | 1/2013 | Wolford et al. |
| 8,348,972 B2 | 1/2013 | Soltz et al. |
| 8,349,987 B2 | 1/2013 | Kapiamba et al. |
| 8,352,004 B2 | 1/2013 | Mannheimer et al. |
| 8,353,437 B2 | 1/2013 | Boudreaux |
| 8,353,438 B2 | 1/2013 | Baxter, III et al. |
| 8,353,439 B2 | 1/2013 | Baxter, III et al. |
| 8,356,740 B1 | 1/2013 | Knodel |
| 8,357,144 B2 | 1/2013 | Whitman et al. |
| 8,357,158 B2 | 1/2013 | McKenna et al. |
| 8,357,161 B2 | 1/2013 | Mueller |
| 8,359,174 B2 | 1/2013 | Nakashima et al. |
| 8,360,296 B2 | 1/2013 | Zingman |
| 8,360,297 B2 | 1/2013 | Shelton, IV et al. |
| 8,360,298 B2 | 1/2013 | Farascioni et al. |
| 8,360,299 B2 | 1/2013 | Zemlok et al. |
| 8,361,501 B2 | 1/2013 | DiTizio et al. |
| D676,866 S | 2/2013 | Chaudhri |
| 8,365,972 B2 | 2/2013 | Aranyi et al. |
| 8,365,973 B1 | 2/2013 | White et al. |
| 8,365,975 B1 | 2/2013 | Manoux et al. |
| 8,365,976 B2 | 2/2013 | Hess et al. |
| 8,366,559 B2 | 2/2013 | Papenfuss et al. |
| 8,366,719 B2 | 2/2013 | Markey et al. |
| 8,366,787 B2 | 2/2013 | Brown et al. |
| 8,369,056 B2 | 2/2013 | Senriuchi et al. |
| 8,371,393 B2 | 2/2013 | Higuchi et al. |
| 8,371,491 B2 | 2/2013 | Huitema et al. |
| 8,371,492 B2 | 2/2013 | Aranyi et al. |
| 8,371,493 B2 | 2/2013 | Aranyi et al. |
| 8,371,494 B2 | 2/2013 | Racenet et al. |
| 8,372,094 B2 | 2/2013 | Bettuchi et al. |
| 8,376,865 B2 | 2/2013 | Forster et al. |
| 8,377,029 B2 | 2/2013 | Nagao et al. |
| 8,377,044 B2 | 2/2013 | Coe et al. |
| 8,381,828 B2 | 2/2013 | Whitman et al. |
| 8,382,773 B2 | 2/2013 | Whitfield et al. |
| 8,382,790 B2 | 2/2013 | Uenohara et al. |
| D677,273 S | 3/2013 | Randall et al. |
| 8,387,848 B2 | 3/2013 | Johnson et al. |
| 8,388,633 B2 | 3/2013 | Rousseau et al. |
| 8,389,588 B2 | 3/2013 | Ringeisen et al. |
| 8,393,513 B2 | 3/2013 | Jankowski |
| 8,393,514 B2 | 3/2013 | Shelton, IV et al. |
| 8,393,516 B2 | 3/2013 | Kostrzewski |
| 8,397,832 B2 | 3/2013 | Blickle et al. |
| 8,397,971 B2 | 3/2013 | Yates et al. |
| 8,397,973 B1 | 3/2013 | Hausen |
| 8,398,633 B2 | 3/2013 | Mueller |
| 8,398,669 B2 | 3/2013 | Kim |
| 8,398,673 B2 | 3/2013 | Hinchliffe et al. |
| 8,398,674 B2 | 3/2013 | Prestel |
| 8,400,851 B2 | 3/2013 | Byun |
| 8,403,138 B2 | 3/2013 | Weisshaupt et al. |
| 8,403,195 B2 | 3/2013 | Beardsley et al. |
| 8,403,196 B2 | 3/2013 | Beardsley et al. |
| 8,403,198 B2 | 3/2013 | Sorrentino et al. |
| 8,403,832 B2 | 3/2013 | Cunningham et al. |
| 8,403,926 B2 | 3/2013 | Nobis et al. |
| 8,403,945 B2 | 3/2013 | Whitfield et al. |
| 8,403,946 B2 | 3/2013 | Whitfield et al. |
| 8,403,950 B2 | 3/2013 | Palmer et al. |
| 8,408,439 B2 | 4/2013 | Huang et al. |
| 8,408,442 B2 | 4/2013 | Racenet et al. |
| 8,409,079 B2 | 4/2013 | Okamoto et al. |
| 8,409,174 B2 | 4/2013 | Omori |
| 8,409,175 B2 | 4/2013 | Lee et al. |
| 8,409,222 B2 | 4/2013 | Whitfield et al. |
| 8,409,223 B2 | 4/2013 | Sorrentino et al. |
| 8,411,500 B2 | 4/2013 | Gapihan et al. |
| 8,413,661 B2 | 4/2013 | Rousseau et al. |
| 8,413,870 B2 | 4/2013 | Pastorelli et al. |
| 8,413,871 B2 | 4/2013 | Racenet et al. |
| 8,413,872 B2 | 4/2013 | Patel |
| 8,414,469 B2 | 4/2013 | Diolaiti |
| 8,414,577 B2 | 4/2013 | Boudreaux et al. |
| 8,414,598 B2 | 4/2013 | Brock et al. |
| 8,418,073 B2 | 4/2013 | Mohr et al. |
| 8,418,906 B2 | 4/2013 | Farascioni et al. |
| 8,418,907 B2 | 4/2013 | Johnson et al. |
| 8,418,908 B1 | 4/2013 | Beardsley |
| 8,418,909 B2 | 4/2013 | Kostrzewski |
| 8,419,635 B2 | 4/2013 | Shelton, IV et al. |
| 8,419,717 B2 | 4/2013 | Diolaiti et al. |
| 8,419,747 B2 | 4/2013 | Hinman et al. |
| 8,419,754 B2 | 4/2013 | Laby et al. |
| 8,423,182 B2 | 4/2013 | Robinson et al. |
| 8,424,737 B2 | 4/2013 | Scirica |
| 8,424,739 B2 | 4/2013 | Racenet et al. |
| 8,424,740 B2 | 4/2013 | Shelton, IV et al. |
| 8,424,741 B2 | 4/2013 | McGuckin, Jr. et al. |
| 8,425,600 B2 | 4/2013 | Maxwell |
| 8,427,430 B2 | 4/2013 | Lee et al. |
| 8,430,292 B2 | 4/2013 | Patel et al. |
| 8,430,892 B2 | 4/2013 | Bindra et al. |
| 8,430,898 B2 | 4/2013 | Wiener et al. |
| 8,435,257 B2 | 5/2013 | Smith et al. |
| 8,439,246 B1 | 5/2013 | Knodel |
| 8,444,036 B2 | 5/2013 | Shelton, IV |
| 8,444,037 B2 | 5/2013 | Nicholas et al. |
| 8,444,549 B2 | 5/2013 | Viola et al. |
| 8,449,536 B2 | 5/2013 | Selig |
| 8,449,560 B2 | 5/2013 | Roth et al. |
| 8,453,904 B2 | 6/2013 | Eskaros et al. |
| 8,453,906 B2 | 6/2013 | Huang et al. |
| 8,453,907 B2 | 6/2013 | Laurent et al. |
| 8,453,908 B2 | 6/2013 | Bedi et al. |
| 8,453,912 B2 | 6/2013 | Mastri et al. |
| 8,453,914 B2 | 6/2013 | Laurent et al. |
| 8,454,495 B2 | 6/2013 | Kawano et al. |
| 8,454,551 B2 | 6/2013 | Allen et al. |
| 8,454,628 B2 | 6/2013 | Smith et al. |
| 8,454,640 B2 | 6/2013 | Johnston et al. |
| 8,457,757 B2 | 6/2013 | Cauller et al. |
| 8,459,520 B2 | 6/2013 | Giordano et al. |
| 8,459,521 B2 | 6/2013 | Zemlok et al. |
| 8,459,524 B2 | 6/2013 | Pribanic et al. |
| 8,459,525 B2 | 6/2013 | Yates et al. |
| 8,464,922 B2 | 6/2013 | Marczyk |
| 8,464,923 B2 | 6/2013 | Shelton, IV |
| 8,464,924 B2 | 6/2013 | Gresham et al. |
| 8,464,925 B2 | 6/2013 | Hull et al. |
| 8,465,475 B2 | 6/2013 | Isbell, Jr. |
| 8,465,502 B2 | 6/2013 | Zergiebel |
| 8,465,515 B2 | 6/2013 | Drew et al. |
| 8,469,254 B2 | 6/2013 | Czernik et al. |
| 8,469,946 B2 | 6/2013 | Sugita |
| 8,469,973 B2 | 6/2013 | Meade et al. |
| 8,470,355 B2 | 6/2013 | Skalla et al. |

(56) References Cited

U.S. PATENT DOCUMENTS

| | | |
|---|---|---|
| D686,240 S | 7/2013 | Lin |
| 8,474,677 B2 | 7/2013 | Woodard, Jr. et al. |
| 8,475,453 B2 | 7/2013 | Marczyk et al. |
| 8,475,454 B1 | 7/2013 | Alshemari |
| 8,475,474 B2 | 7/2013 | Bombard et al. |
| 8,479,968 B2 | 7/2013 | Hodgkinson et al. |
| 8,479,969 B2 | 7/2013 | Shelton, IV |
| 8,480,703 B2 | 7/2013 | Nicholas et al. |
| 8,483,509 B2 | 7/2013 | Matsuzaka |
| 8,485,412 B2 | 7/2013 | Shelton, IV et al. |
| 8,485,413 B2 | 7/2013 | Scheib et al. |
| 8,485,970 B2 | 7/2013 | Widenhouse et al. |
| 8,487,199 B2 | 7/2013 | Palmer et al. |
| 8,487,487 B2 | 7/2013 | Dietz et al. |
| 8,490,851 B2 | 7/2013 | Blier et al. |
| 8,490,853 B2 | 7/2013 | Criscuolo et al. |
| 8,491,581 B2 | 7/2013 | Deville et al. |
| 8,491,603 B2 | 7/2013 | Yeung et al. |
| 8,496,153 B2 | 7/2013 | Demmy et al. |
| 8,496,154 B2 | 7/2013 | Marczyk et al. |
| 8,496,156 B2 | 7/2013 | Sniffin et al. |
| 8,496,683 B2 | 7/2013 | Prommersberger et al. |
| 8,498,691 B2 | 7/2013 | Moll et al. |
| 8,499,992 B2 | 8/2013 | Whitman et al. |
| 8,499,993 B2 | 8/2013 | Shelton, IV et al. |
| 8,500,721 B2 | 8/2013 | Jinno |
| 8,500,762 B2 | 8/2013 | Sholev et al. |
| 8,502,091 B2 | 8/2013 | Palmer et al. |
| 8,505,799 B2 | 8/2013 | Viola et al. |
| 8,505,801 B2 | 8/2013 | Ehrenfels et al. |
| 8,506,555 B2 | 8/2013 | Ruiz Morales |
| 8,506,557 B2 | 8/2013 | Zemlok et al. |
| 8,506,580 B2 | 8/2013 | Zergiebel et al. |
| 8,506,581 B2 | 8/2013 | Wingardner, III et al. |
| 8,511,308 B2 | 8/2013 | Hecox et al. |
| 8,512,359 B2 | 8/2013 | Whitman et al. |
| 8,512,402 B2 | 8/2013 | Marczyk et al. |
| 8,517,239 B2 | 8/2013 | Scheib et al. |
| 8,517,241 B2 | 8/2013 | Nicholas et al. |
| 8,517,243 B2 | 8/2013 | Giordano et al. |
| 8,517,244 B2 | 8/2013 | Shelton, IV et al. |
| 8,518,024 B2 | 8/2013 | Williams et al. |
| 8,521,273 B2 | 8/2013 | Kliman |
| 8,523,042 B2 | 9/2013 | Masiakos et al. |
| 8,523,043 B2 | 9/2013 | Ullrich et al. |
| 8,523,881 B2 | 9/2013 | Cabiri et al. |
| 8,523,900 B2 | 9/2013 | Jinno et al. |
| 8,529,588 B2 | 9/2013 | Ahlberg et al. |
| 8,529,600 B2 | 9/2013 | Woodard, Jr. et al. |
| 8,529,819 B2 | 9/2013 | Ostapoff et al. |
| 8,532,747 B2 | 9/2013 | Nock et al. |
| 8,534,527 B2 | 9/2013 | Brendel et al. |
| 8,534,528 B2 | 9/2013 | Shelton, IV |
| 8,535,304 B2 | 9/2013 | Sklar et al. |
| 8,535,340 B2 | 9/2013 | Allen |
| 8,539,866 B2 | 9/2013 | Nayak et al. |
| 8,540,128 B2 | 9/2013 | Shelton, IV et al. |
| 8,540,129 B2 | 9/2013 | Baxter, III et al. |
| 8,540,130 B2 | 9/2013 | Moore et al. |
| 8,540,131 B2 | 9/2013 | Swayze |
| 8,540,133 B2 | 9/2013 | Bedi et al. |
| 8,540,733 B2 | 9/2013 | Whitman et al. |
| 8,540,735 B2 | 9/2013 | Mitelberg et al. |
| 8,550,984 B2 | 10/2013 | Takemoto |
| 8,551,076 B2 | 10/2013 | Duval et al. |
| 8,555,660 B2 | 10/2013 | Takenaka et al. |
| 8,556,151 B2 | 10/2013 | Viola |
| 8,556,918 B2 | 10/2013 | Bauman et al. |
| 8,556,935 B1 | 10/2013 | Knodel et al. |
| 8,560,147 B2 | 10/2013 | Taylor et al. |
| 8,561,617 B2 | 10/2013 | Lindh et al. |
| 8,561,870 B2 | 10/2013 | Baxter, III et al. |
| 8,561,871 B2 | 10/2013 | Rajappa et al. |
| 8,561,873 B2 | 10/2013 | Ingmanson et al. |
| 8,562,592 B2 | 10/2013 | Conlon et al. |
| 8,562,598 B2 | 10/2013 | Falkenstein et al. |
| 8,567,656 B2 | 10/2013 | Shelton, IV et al. |
| 8,568,416 B2 | 10/2013 | Schmitz et al. |
| 8,568,425 B2 | 10/2013 | Ross et al. |
| D692,916 S | 11/2013 | Granchi et al. |
| 8,573,459 B2 | 11/2013 | Smith et al. |
| 8,573,461 B2 | 11/2013 | Shelton, IV et al. |
| 8,573,462 B2 | 11/2013 | Smith et al. |
| 8,573,465 B2 | 11/2013 | Shelton, IV |
| 8,574,199 B2 | 11/2013 | von Bulow et al. |
| 8,574,263 B2 | 11/2013 | Mueller |
| 8,575,880 B2 | 11/2013 | Grantz |
| 8,575,895 B2 | 11/2013 | Garrastacho et al. |
| 8,579,176 B2 | 11/2013 | Smith et al. |
| 8,579,178 B2 | 11/2013 | Holsten et al. |
| 8,579,897 B2 | 11/2013 | Vakharia et al. |
| 8,579,937 B2 | 11/2013 | Gresham |
| 8,584,919 B2 | 11/2013 | Hueil et al. |
| 8,584,920 B2 | 11/2013 | Hodgkinson |
| 8,584,921 B2 | 11/2013 | Scirica |
| 8,585,583 B2 | 11/2013 | Sakaguchi et al. |
| 8,585,721 B2 | 11/2013 | Kirsch |
| 8,590,760 B2 | 11/2013 | Cummins et al. |
| 8,590,762 B2 | 11/2013 | Hess et al. |
| 8,590,764 B2 | 11/2013 | Hartwick et al. |
| 8,596,515 B2 | 12/2013 | Okoniewski |
| 8,597,745 B2 | 12/2013 | Farnsworth et al. |
| 8,599,450 B2 | 12/2013 | Kubo et al. |
| 8,602,125 B2 | 12/2013 | King |
| 8,602,287 B2 | 12/2013 | Yates et al. |
| 8,602,288 B2 | 12/2013 | Shelton, IV et al. |
| 8,603,077 B2 | 12/2013 | Cooper et al. |
| 8,603,089 B2 | 12/2013 | Viola |
| 8,603,110 B2 | 12/2013 | Maruyama et al. |
| 8,603,135 B2 | 12/2013 | Mueller |
| 8,608,043 B2 | 12/2013 | Scirica |
| 8,608,044 B2 | 12/2013 | Hueil et al. |
| 8,608,045 B2 | 12/2013 | Smith et al. |
| 8,608,046 B2 | 12/2013 | Laurent et al. |
| 8,608,745 B2 | 12/2013 | Guzman et al. |
| 8,613,383 B2 | 12/2013 | Beckman et al. |
| 8,616,427 B2 | 12/2013 | Viola |
| 8,616,431 B2 | 12/2013 | Timm et al. |
| 8,622,274 B2 | 1/2014 | Yates et al. |
| 8,622,275 B2 | 1/2014 | Baxter, III et al. |
| 8,627,993 B2 | 1/2014 | Smith et al. |
| 8,627,994 B2 | 1/2014 | Zemlok et al. |
| 8,627,995 B2 | 1/2014 | Smith et al. |
| 8,628,518 B2 | 1/2014 | Blumenkranz et al. |
| 8,628,544 B2 | 1/2014 | Farascioni |
| 8,628,545 B2 | 1/2014 | Cabrera et al. |
| 8,631,987 B2 | 1/2014 | Shelton, IV et al. |
| 8,631,992 B1 | 1/2014 | Hausen et al. |
| 8,631,993 B2 | 1/2014 | Kostrzewski |
| 8,632,462 B2 | 1/2014 | Yoo et al. |
| 8,632,525 B2 | 1/2014 | Kerr et al. |
| 8,632,535 B2 | 1/2014 | Shelton, IV et al. |
| 8,632,539 B2 | 1/2014 | Twomey et al. |
| 8,632,563 B2 | 1/2014 | Nagase et al. |
| 8,636,187 B2 | 1/2014 | Hueil et al. |
| 8,636,190 B2 | 1/2014 | Zemlok et al. |
| 8,636,191 B2 | 1/2014 | Meagher |
| 8,636,193 B2 | 1/2014 | Whitman et al. |
| 8,636,736 B2 | 1/2014 | Yates et al. |
| 8,636,766 B2 | 1/2014 | Milliman et al. |
| 8,639,936 B2 | 1/2014 | Hu et al. |
| 8,640,788 B2 | 2/2014 | Dachs, II et al. |
| 8,646,674 B2 | 2/2014 | Schulte et al. |
| 8,647,258 B2 | 2/2014 | Aranyi et al. |
| 8,652,120 B2 | 2/2014 | Giordano et al. |
| 8,652,151 B2 | 2/2014 | Lehman et al. |
| 8,652,155 B2 | 2/2014 | Houser et al. |
| 8,657,174 B2 | 2/2014 | Yates et al. |
| 8,657,175 B2 | 2/2014 | Sonnenschein et al. |
| 8,657,176 B2 | 2/2014 | Shelton, IV et al. |
| 8,657,177 B2 | 2/2014 | Scirica et al. |
| 8,657,178 B2 | 2/2014 | Hueil et al. |
| 8,657,482 B2 | 2/2014 | Malackowski et al. |
| 8,657,808 B2 | 2/2014 | McPherson et al. |

(56) References Cited

U.S. PATENT DOCUMENTS

| | | |
|---|---|---|
| 8,657,814 B2 | 2/2014 | Werneth et al. |
| 8,657,821 B2 | 2/2014 | Palermo |
| D701,238 S | 3/2014 | Lai et al. |
| 8,662,370 B2 | 3/2014 | Takei |
| 8,663,106 B2 | 3/2014 | Stivoric et al. |
| 8,663,192 B2 | 3/2014 | Hester et al. |
| 8,663,245 B2 | 3/2014 | Francischelli et al. |
| 8,663,262 B2 | 3/2014 | Smith et al. |
| 8,663,270 B2 | 3/2014 | Donnigan et al. |
| 8,664,792 B2 | 3/2014 | Rebsdorf |
| 8,668,129 B2 | 3/2014 | Olson |
| 8,668,130 B2 | 3/2014 | Hess et al. |
| 8,672,206 B2 | 3/2014 | Aranyi et al. |
| 8,672,207 B2 | 3/2014 | Shelton, IV et al. |
| 8,672,208 B2 | 3/2014 | Hess et al. |
| 8,672,922 B2 | 3/2014 | Loh et al. |
| 8,672,935 B2 | 3/2014 | Okada et al. |
| 8,672,951 B2 | 3/2014 | Smith et al. |
| 8,673,210 B2 | 3/2014 | Deshays |
| 8,675,820 B2 | 3/2014 | Baic et al. |
| 8,678,263 B2 | 3/2014 | Viola |
| 8,678,994 B2 | 3/2014 | Sonnenschein et al. |
| 8,679,093 B2 | 3/2014 | Farra |
| 8,679,098 B2 | 3/2014 | Hart |
| 8,679,137 B2 | 3/2014 | Bauman et al. |
| 8,679,154 B2 | 3/2014 | Smith et al. |
| 8,679,156 B2 | 3/2014 | Smith et al. |
| 8,679,454 B2 | 3/2014 | Guire et al. |
| 8,684,248 B2 | 4/2014 | Milliman |
| 8,684,249 B2 | 4/2014 | Racenet et al. |
| 8,684,250 B2 | 4/2014 | Bettuchi et al. |
| 8,684,253 B2 | 4/2014 | Giordano et al. |
| 8,684,962 B2 | 4/2014 | Kirschenman et al. |
| 8,685,004 B2 | 4/2014 | Zemlock et al. |
| 8,685,020 B2 | 4/2014 | Weizman et al. |
| 8,690,893 B2 | 4/2014 | Deitch et al. |
| 8,695,866 B2 | 4/2014 | Leimbach et al. |
| 8,696,665 B2 | 4/2014 | Hunt et al. |
| 8,701,958 B2 | 4/2014 | Shelton, IV et al. |
| 8,701,959 B2 | 4/2014 | Shah |
| 8,708,210 B2 | 4/2014 | Zemlok et al. |
| 8,708,211 B2 | 4/2014 | Zemlok et al. |
| 8,708,213 B2 | 4/2014 | Shelton, IV et al. |
| 8,714,352 B2 | 5/2014 | Farascioni et al. |
| 8,714,429 B2 | 5/2014 | Demmy |
| 8,714,430 B2 | 5/2014 | Natarajan et al. |
| 8,715,256 B2 | 5/2014 | Greener |
| 8,715,302 B2 | 5/2014 | Ibrahim et al. |
| 8,720,766 B2 | 5/2014 | Hess et al. |
| 8,721,630 B2 | 5/2014 | Ortiz et al. |
| 8,721,666 B2 | 5/2014 | Schroeder et al. |
| 8,727,197 B2 | 5/2014 | Hess et al. |
| 8,727,199 B2 | 5/2014 | Wenchell |
| 8,727,200 B2 | 5/2014 | Roy |
| 8,727,961 B2 | 5/2014 | Ziv |
| 8,728,099 B2 | 5/2014 | Cohn et al. |
| 8,728,119 B2 | 5/2014 | Cummins |
| 8,733,470 B2 | 5/2014 | Matthias et al. |
| 8,733,612 B2 | 5/2014 | Ma |
| 8,733,613 B2 | 5/2014 | Huitema et al. |
| 8,733,614 B2 | 5/2014 | Ross et al. |
| 8,734,336 B2 | 5/2014 | Bonadio et al. |
| 8,734,359 B2 | 5/2014 | Ibanez et al. |
| 8,734,478 B2 | 5/2014 | Widenhouse et al. |
| 8,734,831 B2 | 5/2014 | Kim et al. |
| 8,739,033 B2 | 5/2014 | Rosenberg |
| 8,739,417 B2 | 6/2014 | Tokunaga et al. |
| 8,740,034 B2 | 6/2014 | Morgan et al. |
| 8,740,037 B2 | 6/2014 | Shelton, IV et al. |
| 8,740,038 B2 | 6/2014 | Shelton, IV et al. |
| 8,740,987 B2 | 6/2014 | Geremakis et al. |
| 8,746,529 B2 | 6/2014 | Shelton, IV et al. |
| 8,746,530 B2 | 6/2014 | Giordano et al. |
| 8,746,533 B2 | 6/2014 | Whitman et al. |
| 8,746,535 B2 | 6/2014 | Shelton, IV et al. |
| 8,747,238 B2 | 6/2014 | Shelton, IV et al. |
| 8,747,441 B2 | 6/2014 | Konieczynski et al. |
| 8,752,264 B2 | 6/2014 | Ackley et al. |
| 8,752,699 B2 | 6/2014 | Morgan et al. |
| 8,752,747 B2 | 6/2014 | Shelton, IV et al. |
| 8,752,748 B2 | 6/2014 | Whitman et al. |
| 8,752,749 B2 | 6/2014 | Moore et al. |
| 8,753,664 B2 | 6/2014 | Dao et al. |
| 8,757,287 B2 | 6/2014 | Mak et al. |
| 8,757,465 B2 | 6/2014 | Woodard, Jr. et al. |
| 8,758,235 B2 | 6/2014 | Jaworek |
| 8,758,366 B2 | 6/2014 | McLean et al. |
| 8,758,391 B2 | 6/2014 | Swayze et al. |
| 8,758,438 B2 | 6/2014 | Boyce et al. |
| 8,763,875 B2 | 7/2014 | Morgan et al. |
| 8,763,877 B2 | 7/2014 | Schall et al. |
| 8,763,879 B2 | 7/2014 | Shelton, IV et al. |
| 8,764,732 B2 | 7/2014 | Hartwell |
| 8,770,458 B2 | 7/2014 | Scirica |
| 8,770,459 B2 | 7/2014 | Racenet et al. |
| 8,770,460 B2 | 7/2014 | Belzer |
| 8,771,169 B2 | 7/2014 | Whitman et al. |
| 8,771,260 B2 | 7/2014 | Conlon et al. |
| 8,777,004 B2 | 7/2014 | Shelton, IV et al. |
| 8,777,082 B2 | 7/2014 | Scirica |
| 8,777,083 B2 | 7/2014 | Racenet et al. |
| 8,777,898 B2 | 7/2014 | Suon et al. |
| 8,783,541 B2 | 7/2014 | Shelton, IV et al. |
| 8,783,542 B2 | 7/2014 | Riestenberg et al. |
| 8,783,543 B2 | 7/2014 | Shelton, IV et al. |
| 8,784,304 B2 | 7/2014 | Mikkaichi et al. |
| 8,784,404 B2 | 7/2014 | Doyle et al. |
| 8,784,415 B2 | 7/2014 | Malackowski et al. |
| 8,789,737 B2 | 7/2014 | Hodgkinson et al. |
| 8,789,739 B2 | 7/2014 | Swensgard |
| 8,789,740 B2 | 7/2014 | Baxter, III et al. |
| 8,789,741 B2 | 7/2014 | Baxter, III et al. |
| 8,790,658 B2 | 7/2014 | Cigarini et al. |
| 8,790,684 B2 | 7/2014 | Dave et al. |
| D711,905 S | 8/2014 | Morrison et al. |
| 8,794,496 B2 | 8/2014 | Scirica |
| 8,794,497 B2 | 8/2014 | Zingman |
| 8,795,276 B2 | 8/2014 | Dietz et al. |
| 8,795,308 B2 | 8/2014 | Valin |
| 8,795,324 B2 | 8/2014 | Kawai et al. |
| 8,796,995 B2 | 8/2014 | Cunanan et al. |
| 8,800,681 B2 | 8/2014 | Rousson et al. |
| 8,800,837 B2 | 8/2014 | Zemlok |
| 8,800,838 B2 | 8/2014 | Shelton, IV |
| 8,800,839 B2 | 8/2014 | Beetel |
| 8,800,840 B2 | 8/2014 | Jankowski |
| 8,800,841 B2 | 8/2014 | Ellerhorst et al. |
| 8,801,710 B2 | 8/2014 | Ullrich et al. |
| 8,801,734 B2 | 8/2014 | Shelton, IV et al. |
| 8,801,735 B2 | 8/2014 | Shelton, IV et al. |
| 8,801,752 B2 | 8/2014 | Fortier et al. |
| 8,801,801 B2 | 8/2014 | Datta et al. |
| 8,806,973 B2 | 8/2014 | Ross et al. |
| 8,807,414 B2 | 8/2014 | Ross et al. |
| 8,808,161 B2 | 8/2014 | Gregg et al. |
| 8,808,164 B2 | 8/2014 | Hoffman et al. |
| 8,808,274 B2 | 8/2014 | Hartwell |
| 8,808,294 B2 | 8/2014 | Fox et al. |
| 8,808,308 B2 | 8/2014 | Boukhny et al. |
| 8,808,311 B2 | 8/2014 | Heinrich et al. |
| 8,808,325 B2 | 8/2014 | Hess et al. |
| 8,810,197 B2 | 8/2014 | Juergens |
| 8,811,017 B2 | 8/2014 | Fujii et al. |
| 8,813,866 B2 | 8/2014 | Suzuki |
| 8,814,024 B2 | 8/2014 | Woodard, Jr. et al. |
| 8,814,025 B2 | 8/2014 | Miller et al. |
| 8,814,836 B2 | 8/2014 | Ignon et al. |
| 8,815,594 B2 | 8/2014 | Harris et al. |
| 8,818,523 B2 | 8/2014 | Olson et al. |
| 8,820,603 B2 | 9/2014 | Shelton, IV et al. |
| 8,820,605 B2 | 9/2014 | Shelton, IV |
| 8,820,606 B2 | 9/2014 | Hodgkinson |
| 8,820,607 B2 | 9/2014 | Marczyk |
| 8,820,608 B2 | 9/2014 | Miyamoto |

(56) References Cited

U.S. PATENT DOCUMENTS

| | | |
|---|---|---|
| 8,821,514 B2 | 9/2014 | Aranyi |
| 8,822,934 B2 | 9/2014 | Sayeh et al. |
| 8,825,164 B2 | 9/2014 | Tweden et al. |
| 8,827,133 B2 | 9/2014 | Shelton, IV et al. |
| 8,827,134 B2 | 9/2014 | Viola et al. |
| 8,827,903 B2 | 9/2014 | Shelton, IV et al. |
| 8,831,779 B2 | 9/2014 | Ortmaier et al. |
| 8,833,219 B2 | 9/2014 | Pierce |
| 8,833,630 B2 | 9/2014 | Milliman |
| 8,833,632 B2 | 9/2014 | Swensgard |
| 8,834,353 B2 | 9/2014 | Dejima et al. |
| 8,834,465 B2 | 9/2014 | Ramstein et al. |
| 8,834,498 B2 | 9/2014 | Byrum et al. |
| 8,834,518 B2 | 9/2014 | Faller et al. |
| 8,840,003 B2 | 9/2014 | Morgan et al. |
| 8,840,603 B2 | 9/2014 | Shelton, IV et al. |
| 8,840,609 B2 | 9/2014 | Stuebe |
| 8,840,876 B2 | 9/2014 | Eemeta et al. |
| 8,844,789 B2 | 9/2014 | Shelton, IV et al. |
| 8,844,790 B2 | 9/2014 | Demmy et al. |
| 8,851,215 B2 | 10/2014 | Goto |
| 8,851,354 B2 | 10/2014 | Swensgard et al. |
| 8,852,174 B2 | 10/2014 | Burbank |
| 8,852,185 B2 | 10/2014 | Twomey |
| 8,852,199 B2 | 10/2014 | Deslauriers et al. |
| 8,852,218 B2 | 10/2014 | Hughett, Sr. et al. |
| 8,857,693 B2 | 10/2014 | Schuckmann et al. |
| 8,857,694 B2 | 10/2014 | Shelton, IV et al. |
| 8,858,538 B2 | 10/2014 | Belson et al. |
| 8,858,571 B2 | 10/2014 | Shelton, IV et al. |
| 8,858,590 B2 | 10/2014 | Shelton, IV et al. |
| 8,864,007 B2 | 10/2014 | Widenhouse et al. |
| 8,864,009 B2 | 10/2014 | Shelton, IV et al. |
| 8,864,010 B2 | 10/2014 | Williams |
| 8,864,750 B2 | 10/2014 | Ross et al. |
| 8,870,050 B2 | 10/2014 | Hodgkinson |
| 8,870,912 B2 | 10/2014 | Brisson et al. |
| 8,875,971 B2 | 11/2014 | Hall et al. |
| 8,875,972 B2 | 11/2014 | Weisenburgh, II et al. |
| 8,876,857 B2 | 11/2014 | Burbank |
| 8,876,858 B2 | 11/2014 | Braun |
| 8,887,979 B2 | 11/2014 | Mastri et al. |
| 8,888,688 B2 | 11/2014 | Julian et al. |
| 8,888,695 B2 | 11/2014 | Piskun et al. |
| 8,888,792 B2 | 11/2014 | Harris et al. |
| 8,888,809 B2 | 11/2014 | Davison et al. |
| 8,893,946 B2 | 11/2014 | Boudreaux et al. |
| 8,893,949 B2 | 11/2014 | Shelton, IV et al. |
| 8,894,647 B2 | 11/2014 | Beardsley et al. |
| 8,894,654 B2 | 11/2014 | Anderson |
| 8,899,460 B2 | 12/2014 | Wojcicki |
| 8,899,461 B2 | 12/2014 | Farascioni |
| 8,899,462 B2 | 12/2014 | Kostrzewski et al. |
| 8,899,463 B2 | 12/2014 | Schall et al. |
| 8,899,464 B2 | 12/2014 | Hueil et al. |
| 8,899,465 B2 | 12/2014 | Shelton, IV et al. |
| 8,899,466 B2 | 12/2014 | Baxter, III et al. |
| 8,900,267 B2 | 12/2014 | Woolfson et al. |
| 8,905,287 B2 | 12/2014 | Racenet et al. |
| 8,905,977 B2 | 12/2014 | Shelton et al. |
| 8,910,846 B2 | 12/2014 | Viola |
| 8,911,426 B2 | 12/2014 | Coppeta et al. |
| 8,911,448 B2 | 12/2014 | Stein |
| 8,911,460 B2 | 12/2014 | Neurohr et al. |
| 8,911,471 B2 | 12/2014 | Spivey et al. |
| 8,912,746 B2 | 12/2014 | Reid et al. |
| 8,920,433 B2 | 12/2014 | Barrier et al. |
| 8,920,435 B2 | 12/2014 | Smith et al. |
| 8,920,438 B2 | 12/2014 | Aranyi et al. |
| 8,920,443 B2 | 12/2014 | Hiles et al. |
| 8,920,444 B2 | 12/2014 | Hiles et al. |
| 8,922,163 B2 | 12/2014 | Macdonald |
| 8,925,782 B2 | 1/2015 | Shelton, IV |
| 8,925,783 B2 | 1/2015 | Zemlok et al. |
| 8,925,788 B2 | 1/2015 | Hess et al. |
| 8,926,506 B2 | 1/2015 | Widenhouse et al. |
| 8,926,598 B2 | 1/2015 | Mollere et al. |
| 8,931,576 B2 | 1/2015 | Iwata |
| 8,931,679 B2 | 1/2015 | Kostrzewski |
| 8,931,680 B2 | 1/2015 | Milliman |
| 8,931,682 B2 | 1/2015 | Timm et al. |
| 8,936,614 B2 | 1/2015 | Allen, IV |
| 8,939,343 B2 | 1/2015 | Milliman et al. |
| 8,939,344 B2 | 1/2015 | Olson et al. |
| 8,945,095 B2 | 2/2015 | Blumenkranz et al. |
| 8,945,163 B2 | 2/2015 | Voegele et al. |
| 8,955,732 B2 | 2/2015 | Zemlok et al. |
| 8,956,342 B1 | 2/2015 | Russo et al. |
| 8,956,390 B2 | 2/2015 | Shah et al. |
| 8,958,860 B2 | 2/2015 | Banerjee et al. |
| 8,960,519 B2 | 2/2015 | Whitman et al. |
| 8,960,520 B2 | 2/2015 | McCuen |
| 8,960,521 B2 | 2/2015 | Kostrzewski |
| 8,961,191 B2 | 2/2015 | Hanshew |
| 8,961,504 B2 | 2/2015 | Hoarau et al. |
| 8,963,714 B2 | 2/2015 | Medhal et al. |
| D725,674 S | 3/2015 | Jung et al. |
| 8,967,443 B2 | 3/2015 | McCuen |
| 8,967,444 B2 | 3/2015 | Beetel |
| 8,967,446 B2 | 3/2015 | Beardsley et al. |
| 8,967,448 B2 | 3/2015 | Carter et al. |
| 8,968,276 B2 | 3/2015 | Zemlok et al. |
| 8,968,308 B2 | 3/2015 | Homer et al. |
| 8,968,312 B2 | 3/2015 | Marczyk et al. |
| 8,968,337 B2 | 3/2015 | Whitfield et al. |
| 8,968,340 B2 | 3/2015 | Chowaniec et al. |
| 8,968,355 B2 | 3/2015 | Malkowski et al. |
| 8,968,358 B2 | 3/2015 | Reschke |
| 8,970,507 B2 | 3/2015 | Holbein et al. |
| 8,973,803 B2 | 3/2015 | Hall et al. |
| 8,973,804 B2 | 3/2015 | Hess et al. |
| 8,973,805 B2 | 3/2015 | Scirica et al. |
| 8,974,440 B2 | 3/2015 | Farritor et al. |
| 8,974,542 B2 | 3/2015 | Fujimoto et al. |
| 8,974,932 B2 | 3/2015 | McGahan et al. |
| 8,978,954 B2 | 3/2015 | Shelton, IV et al. |
| 8,978,955 B2 | 3/2015 | Aronhalt et al. |
| 8,978,956 B2 | 3/2015 | Schall et al. |
| 8,979,843 B2 | 3/2015 | Timm et al. |
| 8,979,890 B2 | 3/2015 | Boudreaux |
| 8,982,195 B2 | 3/2015 | Claus et al. |
| 8,985,429 B2 | 3/2015 | Balek et al. |
| 8,986,302 B2 | 3/2015 | Aldridge et al. |
| 8,989,903 B2 | 3/2015 | Weir et al. |
| 8,991,676 B2 | 3/2015 | Hess et al. |
| 8,991,677 B2 | 3/2015 | Moore et al. |
| 8,991,678 B2 | 3/2015 | Wellman et al. |
| 8,992,042 B2 | 3/2015 | Eichenholz |
| 8,992,422 B2 | 3/2015 | Spivey et al. |
| 8,992,565 B2 | 3/2015 | Brisson et al. |
| 8,996,165 B2 | 3/2015 | Wang et al. |
| 8,998,058 B2 | 4/2015 | Moore et al. |
| 8,998,059 B2 | 4/2015 | Smith et al. |
| 8,998,060 B2 | 4/2015 | Bruewer et al. |
| 8,998,061 B2 | 4/2015 | Williams et al. |
| 8,998,939 B2 | 4/2015 | Price et al. |
| 9,000,720 B2 | 4/2015 | Stulen et al. |
| 9,002,518 B2 | 4/2015 | Manzo et al. |
| 9,004,339 B1 | 4/2015 | Park |
| 9,005,230 B2 | 4/2015 | Yates et al. |
| 9,005,238 B2 | 4/2015 | DeSantis et al. |
| 9,005,243 B2 | 4/2015 | Stopek et al. |
| 9,010,606 B2 | 4/2015 | Aranyi et al. |
| 9,010,608 B2 | 4/2015 | Casasanta, Jr. et al. |
| 9,010,611 B2 | 4/2015 | Ross et al. |
| 9,011,437 B2 | 4/2015 | Woodruff et al. |
| 9,011,439 B2 | 4/2015 | Shalaby et al. |
| 9,011,471 B2 | 4/2015 | Timm et al. |
| 9,016,539 B2 | 4/2015 | Kostrzewski et al. |
| 9,016,540 B2 | 4/2015 | Whitman et al. |
| 9,016,541 B2 | 4/2015 | Viola et al. |
| 9,016,542 B2 | 4/2015 | Shelton, IV et al. |
| 9,016,545 B2 | 4/2015 | Aranyi et al. |
| 9,017,331 B2 | 4/2015 | Fox |

(56) References Cited

U.S. PATENT DOCUMENTS

| | | |
|---|---|---|
| 9,017,355 B2 | 4/2015 | Smith et al. |
| 9,017,369 B2 | 4/2015 | Renger et al. |
| 9,017,371 B2 | 4/2015 | Whitman et al. |
| 9,021,684 B2 | 5/2015 | Lenker et al. |
| 9,023,014 B2 | 5/2015 | Chowaniec et al. |
| 9,023,069 B2 | 5/2015 | Kasvikis et al. |
| 9,023,071 B2 | 5/2015 | Miller et al. |
| 9,026,347 B2 | 5/2015 | Gadh et al. |
| 9,027,817 B2 | 5/2015 | Milliman et al. |
| 9,028,494 B2 | 5/2015 | Shelton, IV et al. |
| 9,028,495 B2 | 5/2015 | Mueller et al. |
| 9,028,510 B2 | 5/2015 | Miyamoto et al. |
| 9,028,511 B2 | 5/2015 | Weller et al. |
| 9,028,519 B2 | 5/2015 | Yates et al. |
| 9,030,169 B2 | 5/2015 | Christensen et al. |
| 9,033,203 B2 | 5/2015 | Woodard, Jr. et al. |
| 9,033,204 B2 | 5/2015 | Shelton, IV et al. |
| 9,034,505 B2 | 5/2015 | Detry et al. |
| 9,038,881 B1 | 5/2015 | Schaller et al. |
| 9,039,690 B2 | 5/2015 | Kersten et al. |
| 9,039,694 B2 | 5/2015 | Ross et al. |
| 9,039,720 B2 | 5/2015 | Madan |
| 9,043,027 B2 | 5/2015 | Durant et al. |
| 9,044,227 B2 | 6/2015 | Shelton, IV et al. |
| 9,044,228 B2 | 6/2015 | Woodard, Jr. et al. |
| 9,044,229 B2 | 6/2015 | Scheib et al. |
| 9,044,230 B2 | 6/2015 | Morgan et al. |
| 9,044,241 B2 | 6/2015 | Barner et al. |
| 9,044,261 B2 | 6/2015 | Houser |
| 9,044,281 B2 | 6/2015 | Pool et al. |
| 9,050,083 B2 | 6/2015 | Yates et al. |
| 9,050,084 B2 | 6/2015 | Schmid et al. |
| 9,050,100 B2 | 6/2015 | Yates et al. |
| 9,050,120 B2 | 6/2015 | Swarup et al. |
| 9,050,123 B2 | 6/2015 | Krause et al. |
| 9,050,176 B2 | 6/2015 | Datta et al. |
| 9,050,192 B2 | 6/2015 | Mansmann |
| 9,055,941 B2 | 6/2015 | Schmid et al. |
| 9,055,942 B2 | 6/2015 | Balbierz et al. |
| 9,055,943 B2 | 6/2015 | Zemlok et al. |
| 9,055,944 B2 | 6/2015 | Hodgkinson et al. |
| 9,055,961 B2 | 6/2015 | Manzo et al. |
| 9,060,770 B2 | 6/2015 | Shelton, IV et al. |
| 9,060,776 B2 | 6/2015 | Yates et al. |
| 9,060,794 B2 | 6/2015 | Kang et al. |
| 9,060,894 B2 | 6/2015 | Wubbeling |
| 9,061,392 B2 | 6/2015 | Forgues et al. |
| 9,072,515 B2 | 7/2015 | Hall et al. |
| 9,072,523 B2 | 7/2015 | Houser et al. |
| 9,072,535 B2 | 7/2015 | Shelton, IV et al. |
| 9,072,536 B2 | 7/2015 | Shelton, IV et al. |
| 9,078,653 B2 | 7/2015 | Leimbach et al. |
| 9,078,654 B2 | 7/2015 | Whitman et al. |
| 9,084,601 B2 | 7/2015 | Moore et al. |
| 9,084,602 B2 | 7/2015 | Gleiman |
| 9,086,875 B2 | 7/2015 | Harrat et al. |
| 9,089,326 B2 | 7/2015 | Krumanaker et al. |
| 9,089,330 B2 | 7/2015 | Widenhouse et al. |
| 9,089,352 B2 | 7/2015 | Jeong |
| 9,089,360 B2 | 7/2015 | Messerly et al. |
| 9,091,588 B2 | 7/2015 | Lefler |
| D736,792 S | 8/2015 | Brinda et al. |
| 9,095,339 B2 | 8/2015 | Moore et al. |
| 9,095,346 B2 | 8/2015 | Houser et al. |
| 9,095,362 B2 | 8/2015 | Dachs, II et al. |
| 9,095,367 B2 | 8/2015 | Olson et al. |
| 9,096,033 B2 | 8/2015 | Holop et al. |
| 9,099,863 B2 | 8/2015 | Smith et al. |
| 9,099,877 B2 | 8/2015 | Banos et al. |
| 9,101,358 B2 | 8/2015 | Kerr et al. |
| 9,101,385 B2 | 8/2015 | Shelton, IV et al. |
| 9,101,475 B2 | 8/2015 | Wei et al. |
| 9,107,663 B2 | 8/2015 | Swensgard |
| 9,107,690 B2 | 8/2015 | Bales, Jr. et al. |
| 9,110,587 B2 | 8/2015 | Kim et al. |
| 9,113,862 B2 | 8/2015 | Morgan et al. |
| 9,113,864 B2 | 8/2015 | Morgan et al. |
| 9,113,865 B2 | 8/2015 | Shelton, IV et al. |
| 9,113,868 B2 | 8/2015 | Felder et al. |
| 9,113,873 B2 | 8/2015 | Marczyk et al. |
| 9,113,874 B2 | 8/2015 | Shelton, IV et al. |
| 9,113,876 B2 | 8/2015 | Zemlok et al. |
| 9,113,879 B2 | 8/2015 | Felder et al. |
| 9,113,880 B2 | 8/2015 | Zemlok et al. |
| 9,113,881 B2 | 8/2015 | Scirica |
| 9,113,883 B2 | 8/2015 | Aronhalt et al. |
| 9,113,884 B2 | 8/2015 | Shelton, IV et al. |
| 9,113,887 B2 | 8/2015 | Behnke, II et al. |
| 9,119,615 B2 | 9/2015 | Felder et al. |
| 9,119,657 B2 | 9/2015 | Shelton, IV et al. |
| 9,119,898 B2 | 9/2015 | Bayon et al. |
| 9,119,957 B2 | 9/2015 | Gantz et al. |
| 9,123,286 B2 | 9/2015 | Park |
| 9,124,097 B2 | 9/2015 | Cruz |
| 9,125,654 B2 | 9/2015 | Aronhalt et al. |
| 9,125,662 B2 | 9/2015 | Shelton, IV |
| 9,126,317 B2 | 9/2015 | Lawton et al. |
| 9,131,835 B2 | 9/2015 | Widenhouse et al. |
| 9,131,940 B2 | 9/2015 | Huitema et al. |
| 9,131,950 B2 | 9/2015 | Matthew |
| 9,131,957 B2 | 9/2015 | Skarbnik et al. |
| 9,138,225 B2 | 9/2015 | Huang et al. |
| 9,138,226 B2 | 9/2015 | Racenet et al. |
| 9,144,455 B2 | 9/2015 | Kennedy et al. |
| D741,882 S | 10/2015 | Shmilov et al. |
| 9,149,274 B2 | 10/2015 | Spivey et al. |
| 9,149,324 B2 | 10/2015 | Huang et al. |
| 9,149,325 B2 | 10/2015 | Worrell et al. |
| 9,153,994 B2 | 10/2015 | Wood et al. |
| 9,161,753 B2 | 10/2015 | Prior |
| 9,161,769 B2 | 10/2015 | Stoddard et al. |
| 9,161,803 B2 | 10/2015 | Yates et al. |
| 9,161,807 B2 | 10/2015 | Garrison |
| 9,168,038 B2 | 10/2015 | Shelton, IV et al. |
| 9,168,039 B1 | 10/2015 | Knodel |
| 9,168,042 B2 | 10/2015 | Milliman |
| 9,168,054 B2 | 10/2015 | Turner et al. |
| 9,168,144 B2 | 10/2015 | Rivin et al. |
| 9,179,911 B2 | 11/2015 | Morgan et al. |
| 9,179,912 B2 | 11/2015 | Yates et al. |
| 9,180,223 B2 | 11/2015 | Yu et al. |
| 9,182,244 B2 | 11/2015 | Luke et al. |
| 9,186,046 B2 | 11/2015 | Ramamurthy et al. |
| 9,186,137 B2 | 11/2015 | Farascioni et al. |
| 9,186,140 B2 | 11/2015 | Hiles et al. |
| 9,186,142 B2 | 11/2015 | Fanelli et al. |
| 9,186,143 B2 | 11/2015 | Timm et al. |
| 9,186,148 B2 | 11/2015 | Felder et al. |
| 9,186,221 B2 | 11/2015 | Burbank |
| 9,192,380 B2 | 11/2015 | (Tarinelli) Racenet et al. |
| 9,192,384 B2 | 11/2015 | Bettuchi |
| 9,192,430 B2 | 11/2015 | Rachlin et al. |
| 9,192,434 B2 | 11/2015 | Twomey et al. |
| 9,193,045 B2 | 11/2015 | Saur et al. |
| 9,197,079 B2 | 11/2015 | Yip et al. |
| D744,528 S | 12/2015 | Agrawal |
| 9,198,642 B2 | 12/2015 | Storz |
| 9,198,644 B2 | 12/2015 | Balek et al. |
| 9,198,661 B2 | 12/2015 | Swensgard |
| 9,198,662 B2 | 12/2015 | Barton et al. |
| 9,198,683 B2 | 12/2015 | Friedman et al. |
| 9,204,830 B2 | 12/2015 | Zand et al. |
| 9,204,877 B2 | 12/2015 | Whitman et al. |
| 9,204,878 B2 | 12/2015 | Hall et al. |
| 9,204,879 B2 | 12/2015 | Shelton, IV |
| 9,204,880 B2 | 12/2015 | Baxter, III et al. |
| 9,204,923 B2 | 12/2015 | Manzo et al. |
| 9,204,924 B2 | 12/2015 | Marczyk et al. |
| 9,211,120 B2 | 12/2015 | Scheib et al. |
| 9,211,121 B2 | 12/2015 | Hall et al. |
| 9,211,122 B2 | 12/2015 | Hagerty et al. |
| 9,216,013 B2 | 12/2015 | Scirica et al. |
| 9,216,019 B2 | 12/2015 | Schmid et al. |
| 9,216,020 B2 | 12/2015 | Zhang et al. |

(56) References Cited

U.S. PATENT DOCUMENTS

| | | |
|---|---|---|
| 9,216,030 B2 | 12/2015 | Fan et al. |
| 9,216,062 B2 | 12/2015 | Duque et al. |
| 9,220,500 B2 | 12/2015 | Swayze et al. |
| 9,220,501 B2 | 12/2015 | Baxter, III et al. |
| 9,220,502 B2 | 12/2015 | Zemlok et al. |
| 9,220,508 B2 | 12/2015 | Dannaher |
| 9,220,559 B2 | 12/2015 | Worrell et al. |
| 9,220,570 B2 | 12/2015 | Kim et al. |
| D746,854 S | 1/2016 | Shardlow et al. |
| 9,226,750 B2 | 1/2016 | Weir et al. |
| 9,226,751 B2 | 1/2016 | Shelton, IV et al. |
| 9,226,754 B2 | 1/2016 | D'Agostino et al. |
| 9,226,761 B2 | 1/2016 | Burbank |
| 9,226,767 B2 | 1/2016 | Stulen et al. |
| 9,232,941 B2 | 1/2016 | Mandakolathur Vasudevan et al. |
| 9,232,945 B2 | 1/2016 | Zingman |
| 9,232,979 B2 | 1/2016 | Parihar et al. |
| 9,233,610 B2 | 1/2016 | Kim et al. |
| 9,237,891 B2 | 1/2016 | Shelton, IV |
| 9,237,892 B2 | 1/2016 | Hodgkinson |
| 9,237,895 B2 | 1/2016 | McCarthy et al. |
| 9,237,900 B2 | 1/2016 | Boudreaux et al. |
| 9,237,921 B2 | 1/2016 | Messerly et al. |
| 9,239,064 B2 | 1/2016 | Helbig et al. |
| 9,240,740 B2 | 1/2016 | Zeng et al. |
| 9,241,711 B2 | 1/2016 | Ivanko |
| 9,241,712 B2 | 1/2016 | Zemlok et al. |
| 9,241,714 B2 | 1/2016 | Timm et al. |
| 9,241,716 B2 | 1/2016 | Whitman |
| 9,241,731 B2 | 1/2016 | Boudreaux et al. |
| 9,244,524 B2 | 1/2016 | Inoue et al. |
| D748,668 S | 2/2016 | Kim et al. |
| D749,623 S | 2/2016 | Gray et al. |
| D750,122 S | 2/2016 | Shardlow et al. |
| D750,129 S | 2/2016 | Kwon |
| 9,254,131 B2 | 2/2016 | Soltz et al. |
| 9,259,274 B2 | 2/2016 | Prisco |
| 9,259,275 B2 | 2/2016 | Burbank |
| 9,261,172 B2 | 2/2016 | Solomon et al. |
| 9,265,500 B2 | 2/2016 | Sorrentino et al. |
| 9,265,516 B2 | 2/2016 | Casey et al. |
| 9,265,585 B2 | 2/2016 | Wingardner et al. |
| 9,271,718 B2 | 3/2016 | Milad et al. |
| 9,271,727 B2 | 3/2016 | McGuckin, Jr. et al. |
| 9,271,753 B2 | 3/2016 | Butler et al. |
| 9,271,799 B2 | 3/2016 | Shelton, IV et al. |
| 9,272,406 B2 | 3/2016 | Aronhalt et al. |
| 9,274,095 B2 | 3/2016 | Humayun et al. |
| 9,277,919 B2 | 3/2016 | Timmer et al. |
| 9,277,922 B2 | 3/2016 | Carter et al. |
| 9,277,969 B2 | 3/2016 | Brannan et al. |
| 9,282,962 B2 | 3/2016 | Schmid et al. |
| 9,282,963 B2 | 3/2016 | Bryant |
| 9,282,966 B2 | 3/2016 | Shelton, IV et al. |
| 9,282,974 B2 | 3/2016 | Shelton, IV |
| 9,283,028 B2 | 3/2016 | Johnson |
| 9,283,045 B2 | 3/2016 | Rhee et al. |
| 9,283,054 B2 | 3/2016 | Morgan et al. |
| 9,289,206 B2 | 3/2016 | Hess et al. |
| 9,289,207 B2 | 3/2016 | Shelton, IV |
| 9,289,210 B2 | 3/2016 | Baxter, III et al. |
| 9,289,211 B2 | 3/2016 | Williams et al. |
| 9,289,212 B2 | 3/2016 | Shelton, IV et al. |
| 9,289,225 B2 | 3/2016 | Shelton, IV et al. |
| 9,289,256 B2 | 3/2016 | Shelton, IV et al. |
| 9,293,757 B2 | 3/2016 | Toussaint et al. |
| 9,295,464 B2 | 3/2016 | Shelton, IV et al. |
| 9,295,465 B2 | 3/2016 | Farascioni |
| 9,295,466 B2 | 3/2016 | Hodgkinson et al. |
| 9,295,467 B2 | 3/2016 | Scirica |
| 9,295,468 B2 | 3/2016 | Heinrich et al. |
| 9,295,514 B2 | 3/2016 | Shelton, IV et al. |
| 9,295,522 B2 | 3/2016 | Kostrzewski |
| 9,295,565 B2 | 3/2016 | McLean |
| 9,295,784 B2 | 3/2016 | Eggert et al. |
| D753,167 S | 4/2016 | Yu et al. |
| 9,301,691 B2 | 4/2016 | Hufnagel et al. |
| 9,301,752 B2 | 4/2016 | Mandakolathur Vasudevan et al. |
| 9,301,753 B2 | 4/2016 | Aldridge et al. |
| 9,301,755 B2 | 4/2016 | Shelton, IV et al. |
| 9,301,759 B2 | 4/2016 | Spivey et al. |
| 9,307,965 B2 | 4/2016 | Ming et al. |
| 9,307,986 B2 | 4/2016 | Hall et al. |
| 9,307,987 B2 | 4/2016 | Swensgard et al. |
| 9,307,988 B2 | 4/2016 | Shelton, IV |
| 9,307,989 B2 | 4/2016 | Shelton, IV et al. |
| 9,307,994 B2 | 4/2016 | Gresham et al. |
| 9,308,009 B2 | 4/2016 | Madan et al. |
| 9,308,011 B2 | 4/2016 | Chao et al. |
| 9,308,646 B2 | 4/2016 | Lim et al. |
| 9,313,915 B2 | 4/2016 | Niu et al. |
| 9,314,246 B2 | 4/2016 | Shelton, IV et al. |
| 9,314,247 B2 | 4/2016 | Shelton, IV et al. |
| 9,314,261 B2 | 4/2016 | Bales, Jr. et al. |
| 9,314,339 B2 | 4/2016 | Mansmann |
| 9,314,908 B2 | 4/2016 | Tanimoto et al. |
| 9,320,518 B2 | 4/2016 | Henderson et al. |
| 9,320,520 B2 | 4/2016 | Shelton, IV et al. |
| 9,320,521 B2 | 4/2016 | Shelton, IV et al. |
| 9,320,523 B2 | 4/2016 | Shelton, IV et al. |
| 9,325,516 B2 | 4/2016 | Pera et al. |
| D755,196 S | 5/2016 | Meyers et al. |
| D756,373 S | 5/2016 | Raskin et al. |
| D756,377 S | 5/2016 | Connolly et al. |
| D757,028 S | 5/2016 | Goldenberg et al. |
| 9,326,767 B2 | 5/2016 | Koch et al. |
| 9,326,768 B2 | 5/2016 | Shelton, IV |
| 9,326,769 B2 | 5/2016 | Shelton, IV et al. |
| 9,326,770 B2 | 5/2016 | Shelton, IV et al. |
| 9,326,771 B2 | 5/2016 | Baxter, III et al. |
| 9,326,788 B2 | 5/2016 | Batross et al. |
| 9,326,812 B2 | 5/2016 | Waaler et al. |
| 9,327,061 B2 | 5/2016 | Govil et al. |
| 9,331,721 B2 | 5/2016 | Martinez Nuevo et al. |
| 9,332,890 B2 | 5/2016 | Ozawa |
| 9,332,974 B2 | 5/2016 | Henderson et al. |
| 9,332,984 B2 | 5/2016 | Weaner et al. |
| 9,332,987 B2 | 5/2016 | Leimbach et al. |
| 9,333,040 B2 | 5/2016 | Shellenberger et al. |
| 9,333,082 B2 | 5/2016 | Wei et al. |
| 9,337,668 B2 | 5/2016 | Yip |
| 9,339,226 B2 | 5/2016 | van der Walt et al. |
| 9,345,477 B2 | 5/2016 | Anim et al. |
| 9,345,479 B2 | 5/2016 | (Tarinelli) Racenet et al. |
| 9,345,480 B2 | 5/2016 | Hessler et al. |
| 9,345,481 B2 | 5/2016 | Hall et al. |
| 9,345,503 B2 | 5/2016 | Ishida et al. |
| 9,351,726 B2 | 5/2016 | Leimbach et al. |
| 9,351,727 B2 | 5/2016 | Leimbach et al. |
| 9,351,728 B2 | 5/2016 | Sniffin et al. |
| 9,351,730 B2 | 5/2016 | Schmid et al. |
| 9,351,731 B2 | 5/2016 | Carter et al. |
| 9,351,732 B2 | 5/2016 | Hodgkinson |
| D758,433 S | 6/2016 | Lee et al. |
| D759,063 S | 6/2016 | Chen |
| 9,358,003 B2 | 6/2016 | Hall et al. |
| 9,358,005 B2 | 6/2016 | Shelton, IV et al. |
| 9,358,015 B2 | 6/2016 | Sorrentino et al. |
| 9,358,031 B2 | 6/2016 | Manzo |
| 9,364,217 B2 | 6/2016 | Kostrzewski et al. |
| 9,364,219 B2 | 6/2016 | Olson et al. |
| 9,364,220 B2 | 6/2016 | Williams |
| 9,364,226 B2 | 6/2016 | Zemlok et al. |
| 9,364,229 B2 | 6/2016 | D'Agostino et al. |
| 9,364,230 B2 | 6/2016 | Shelton, IV et al. |
| 9,364,231 B2 | 6/2016 | Wenchell |
| 9,364,233 B2 | 6/2016 | Alexander, III et al. |
| 9,364,279 B2 | 6/2016 | Houser et al. |
| 9,368,991 B2 | 6/2016 | Qahouq |
| 9,370,341 B2 | 6/2016 | Ceniccola et al. |
| 9,370,358 B2 | 6/2016 | Shelton, IV et al. |
| 9,370,364 B2 | 6/2016 | Smith et al. |
| 9,375,206 B2 | 6/2016 | Vidal et al. |
| 9,375,218 B2 | 6/2016 | Wheeler et al. |

(56) References Cited

U.S. PATENT DOCUMENTS

| | | |
|---|---|---|
| 9,375,230 B2 | 6/2016 | Ross et al. |
| 9,375,232 B2 | 6/2016 | Hunt et al. |
| 9,375,255 B2 | 6/2016 | Houser et al. |
| D761,309 S | 7/2016 | Lee et al. |
| 9,381,058 B2 | 7/2016 | Houser et al. |
| 9,383,881 B2 | 7/2016 | Day et al. |
| 9,386,983 B2 | 7/2016 | Swensgard et al. |
| 9,386,984 B2 | 7/2016 | Aronhalt et al. |
| 9,386,985 B2 | 7/2016 | Koch, Jr. et al. |
| 9,386,988 B2 | 7/2016 | Baxter, III et al. |
| 9,387,003 B2 | 7/2016 | Kaercher et al. |
| 9,393,015 B2 | 7/2016 | Laurent et al. |
| 9,393,017 B2 | 7/2016 | Flanagan et al. |
| 9,393,018 B2 | 7/2016 | Wang et al. |
| 9,396,669 B2 | 7/2016 | Karkanias et al. |
| 9,398,911 B2 | 7/2016 | Auld |
| D763,277 S | 8/2016 | Ahmed et al. |
| D764,498 S | 8/2016 | Capela et al. |
| 9,402,604 B2 | 8/2016 | Williams et al. |
| 9,402,625 B2 | 8/2016 | Coleman et al. |
| 9,402,626 B2 | 8/2016 | Ortiz et al. |
| 9,402,627 B2 | 8/2016 | Stevenson et al. |
| 9,402,629 B2 | 8/2016 | Ehrenfels et al. |
| 9,402,679 B2 | 8/2016 | Ginnebaugh et al. |
| 9,408,604 B2 | 8/2016 | Shelton, IV et al. |
| 9,408,606 B2 | 8/2016 | Shelton, IV |
| 9,408,622 B2 | 8/2016 | Stulen et al. |
| 9,411,370 B2 | 8/2016 | Benni et al. |
| 9,413,128 B2 | 8/2016 | Tien et al. |
| 9,414,838 B2 | 8/2016 | Shelton, IV et al. |
| 9,414,849 B2 | 8/2016 | Nagashimada |
| 9,414,880 B2 | 8/2016 | Monson et al. |
| 9,420,967 B2 | 8/2016 | Zand et al. |
| 9,421,003 B2 | 8/2016 | Williams et al. |
| 9,421,014 B2 | 8/2016 | Ingmanson et al. |
| 9,421,030 B2 | 8/2016 | Cole et al. |
| 9,421,060 B2 | 8/2016 | Monson et al. |
| 9,421,062 B2 | 8/2016 | Houser et al. |
| 9,427,223 B2 | 8/2016 | Park et al. |
| 9,427,231 B2 | 8/2016 | Racenet et al. |
| D767,624 S | 9/2016 | Lee et al. |
| 9,433,411 B2 | 9/2016 | Racenet et al. |
| 9,433,414 B2 | 9/2016 | Chen et al. |
| 9,433,419 B2 | 9/2016 | Gonzalez et al. |
| 9,433,420 B2 | 9/2016 | Hodgkinson |
| 9,439,649 B2 | 9/2016 | Shelton, IV et al. |
| 9,439,650 B2 | 9/2016 | McGuckin, Jr. et al. |
| 9,439,651 B2 | 9/2016 | Smith et al. |
| 9,439,668 B2 | 9/2016 | Timm et al. |
| 9,445,808 B2 | 9/2016 | Woodard, Jr. et al. |
| 9,445,813 B2 | 9/2016 | Shelton, IV et al. |
| 9,445,816 B2 | 9/2016 | Swayze et al. |
| 9,445,817 B2 | 9/2016 | Bettuchi |
| 9,446,226 B2 | 9/2016 | Zilberman |
| 9,451,938 B2 | 9/2016 | Overes et al. |
| 9,451,958 B2 | 9/2016 | Shelton, IV et al. |
| D768,152 S | 10/2016 | Gutierrez et al. |
| D768,156 S | 10/2016 | Frincke |
| D769,315 S | 10/2016 | Scotti |
| D769,930 S | 10/2016 | Agrawal |
| 9,461,340 B2 | 10/2016 | Li et al. |
| 9,463,040 B2 | 10/2016 | Jeong et al. |
| 9,463,260 B2 | 10/2016 | Stopek |
| 9,468,438 B2 | 10/2016 | Baber et al. |
| 9,468,447 B2 | 10/2016 | Aman et al. |
| 9,470,297 B2 | 10/2016 | Aranyi et al. |
| 9,471,969 B2 | 10/2016 | Zeng et al. |
| 9,474,506 B2 | 10/2016 | Magnin et al. |
| 9,474,523 B2 | 10/2016 | Meade et al. |
| 9,474,540 B2 | 10/2016 | Stokes et al. |
| 9,475,180 B2 | 10/2016 | Eshleman et al. |
| D770,476 S | 11/2016 | Jitkoff et al. |
| D770,515 S | 11/2016 | Cho et al. |
| D771,116 S | 11/2016 | Dellinger et al. |
| D772,905 S | 11/2016 | Ingenlath |
| 9,480,476 B2 | 11/2016 | Aldridge et al. |
| 9,480,492 B2 | 11/2016 | Aranyi et al. |
| 9,483,095 B2 | 11/2016 | Tran et al. |
| 9,486,186 B2 | 11/2016 | Fiebig et al. |
| 9,486,213 B2 | 11/2016 | Altman et al. |
| 9,486,214 B2 | 11/2016 | Shelton, IV |
| 9,486,302 B2 | 11/2016 | Boey et al. |
| 9,488,197 B2 | 11/2016 | Wi |
| 9,492,146 B2 | 11/2016 | Kostrzewski et al. |
| 9,492,167 B2 | 11/2016 | Shelton, IV et al. |
| 9,492,170 B2 | 11/2016 | Bear et al. |
| 9,492,189 B2 | 11/2016 | Williams et al. |
| 9,492,192 B2 | 11/2016 | To et al. |
| 9,498,213 B2 | 11/2016 | Marczyk et al. |
| 9,498,219 B2 | 11/2016 | Moore et al. |
| 9,498,231 B2 | 11/2016 | Haider et al. |
| 9,504,455 B2 | 11/2016 | Whitman et al. |
| 9,504,483 B2 | 11/2016 | Houser et al. |
| 9,504,521 B2 | 11/2016 | Deutmeyer et al. |
| D774,547 S | 12/2016 | Capela et al. |
| D775,336 S | 12/2016 | Shelton, IV et al. |
| 9,510,827 B2 | 12/2016 | Kostrzewski |
| 9,510,828 B2 | 12/2016 | Yates et al. |
| 9,510,830 B2 | 12/2016 | Shelton, IV et al. |
| 9,510,846 B2 | 12/2016 | Sholev et al. |
| 9,510,895 B2 | 12/2016 | Houser et al. |
| 9,510,925 B2 | 12/2016 | Hotter et al. |
| 9,517,063 B2 | 12/2016 | Swayze et al. |
| 9,517,068 B2 | 12/2016 | Shelton, IV et al. |
| 9,517,326 B2 | 12/2016 | Hinman et al. |
| 9,521,996 B2 | 12/2016 | Armstrong |
| 9,522,003 B2 | 12/2016 | Weir et al. |
| 9,522,029 B2 | 12/2016 | Yates et al. |
| 9,526,481 B2 | 12/2016 | Storz et al. |
| 9,526,499 B2 | 12/2016 | Kostrzewski et al. |
| 9,526,563 B2 | 12/2016 | Twomey |
| 9,526,564 B2 | 12/2016 | Rusin |
| D776,683 S | 1/2017 | Gobinski et al. |
| D777,773 S | 1/2017 | Shi |
| 9,532,783 B2 | 1/2017 | Swayze et al. |
| 9,539,726 B2 | 1/2017 | Simaan et al. |
| 9,545,253 B2 | 1/2017 | Worrell et al. |
| 9,545,258 B2 | 1/2017 | Smith et al. |
| 9,549,732 B2 | 1/2017 | Yates et al. |
| 9,549,735 B2 | 1/2017 | Shelton, IV et al. |
| 9,554,794 B2 | 1/2017 | Baber et al. |
| 9,554,796 B2 | 1/2017 | Kostrzewski |
| 9,554,812 B2 | 1/2017 | Inkpen et al. |
| 9,559,624 B2 | 1/2017 | Philipp |
| 9,561,013 B2 | 2/2017 | Tsuchiya |
| 9,561,030 B2 | 2/2017 | Zhang et al. |
| 9,561,031 B2 | 2/2017 | Heinrich et al. |
| 9,561,032 B2 | 2/2017 | Shelton, IV et al. |
| 9,561,038 B2 | 2/2017 | Shelton, IV et al. |
| 9,561,045 B2 | 2/2017 | Hinman et al. |
| 9,566,061 B2 | 2/2017 | Aronhalt et al. |
| 9,566,062 B2 | 2/2017 | Boudreaux |
| 9,566,065 B2 | 2/2017 | Knodel |
| 9,566,067 B2 | 2/2017 | Milliman et al. |
| 9,572,574 B2 | 2/2017 | Shelton, IV et al. |
| 9,572,576 B2 | 2/2017 | Hodgkinson et al. |
| 9,572,577 B2 | 2/2017 | Lloyd et al. |
| 9,572,592 B2 | 2/2017 | Price et al. |
| 9,574,644 B2 | 2/2017 | Parihar |
| 9,579,088 B2 | 2/2017 | Farritor et al. |
| D780,803 S | 3/2017 | Gill et al. |
| D781,879 S | 3/2017 | Butcher et al. |
| D782,530 S | 3/2017 | Paek et al. |
| 9,585,550 B2 | 3/2017 | Abel et al. |
| 9,585,657 B2 | 3/2017 | Shelton, IV et al. |
| 9,585,658 B2 | 3/2017 | Shelton, IV |
| 9,585,659 B2 | 3/2017 | Viola et al. |
| 9,585,660 B2 | 3/2017 | Laurent et al. |
| 9,585,662 B2 | 3/2017 | Shelton, IV et al. |
| 9,585,663 B2 | 3/2017 | Shelton, IV et al. |
| 9,585,672 B2 | 3/2017 | Bastia |
| 9,590,433 B2 | 3/2017 | Li |
| 9,592,050 B2 | 3/2017 | Schmid et al. |
| 9,592,052 B2 | 3/2017 | Shelton, IV |

(56) References Cited

U.S. PATENT DOCUMENTS

| | | |
|---|---|---|
| 9,592,053 B2 | 3/2017 | Shelton, IV et al. |
| 9,592,054 B2 | 3/2017 | Schmid et al. |
| 9,597,073 B2 | 3/2017 | Sorrentino et al. |
| 9,597,075 B2 | 3/2017 | Shelton, IV et al. |
| 9,597,080 B2 | 3/2017 | Milliman et al. |
| 9,597,104 B2 | 3/2017 | Nicholas et al. |
| 9,597,143 B2 | 3/2017 | Madan et al. |
| 9,603,595 B2 | 3/2017 | Shelton, IV et al. |
| 9,603,598 B2 | 3/2017 | Shelton, IV et al. |
| 9,603,599 B2 | 3/2017 | Miller et al. |
| 9,603,991 B2 | 3/2017 | Shelton, IV et al. |
| D783,658 S | 4/2017 | Hurst et al. |
| 9,610,068 B2 | 4/2017 | Kappel et al. |
| 9,610,080 B2 | 4/2017 | Whitfield et al. |
| 9,614,258 B2 | 4/2017 | Takahashi et al. |
| 9,615,826 B2 | 4/2017 | Shelton, IV et al. |
| 9,622,745 B2 | 4/2017 | Ingmanson et al. |
| 9,629,623 B2 | 4/2017 | Lytle, IV et al. |
| 9,629,626 B2 | 4/2017 | Soltz et al. |
| 9,629,627 B2 | 4/2017 | Kostrzewski et al. |
| 9,629,628 B2 | 4/2017 | Aranyi |
| 9,629,629 B2 | 4/2017 | Leimbach et al. |
| 9,629,652 B2 | 4/2017 | Mumaw et al. |
| 9,629,814 B2 | 4/2017 | Widenhouse et al. |
| D786,280 S | 5/2017 | Ma |
| D786,896 S | 5/2017 | Kim et al. |
| D787,547 S | 5/2017 | Basargin et al. |
| D788,123 S | 5/2017 | Shan et al. |
| D788,140 S | 5/2017 | Hemsley et al. |
| 9,636,111 B2 | 5/2017 | Wenchell |
| 9,636,113 B2 | 5/2017 | Wenchell |
| 9,636,850 B2 | 5/2017 | Stopek (nee Prommersberger) et al. |
| 9,641,122 B2 | 5/2017 | Romanowich et al. |
| 9,642,620 B2 | 5/2017 | Baxter, III et al. |
| 9,649,096 B2 | 5/2017 | Sholev |
| 9,649,110 B2 | 5/2017 | Parihar et al. |
| 9,649,111 B2 | 5/2017 | Shelton, IV et al. |
| 9,655,613 B2 | 5/2017 | Schaller |
| 9,655,614 B2 | 5/2017 | Swensgard et al. |
| 9,655,615 B2 | 5/2017 | Knodel et al. |
| 9,655,616 B2 | 5/2017 | Aranyi |
| 9,655,624 B2 | 5/2017 | Shelton, IV et al. |
| 9,662,108 B2 | 5/2017 | Williams |
| 9,662,110 B2 | 5/2017 | Huang et al. |
| 9,662,116 B2 | 5/2017 | Smith et al. |
| 9,662,131 B2 | 5/2017 | Omori et al. |
| D788,792 S | 6/2017 | Alessandri et al. |
| D789,384 S | 6/2017 | Lin et al. |
| D790,570 S | 6/2017 | Butcher et al. |
| 9,668,728 B2 | 6/2017 | Williams et al. |
| 9,668,729 B2 | 6/2017 | Williams et al. |
| 9,668,732 B2 | 6/2017 | Patel et al. |
| 9,668,733 B2 | 6/2017 | Williams |
| 9,668,734 B2 | 6/2017 | Kostrzewski et al. |
| 9,675,344 B2 | 6/2017 | Combrowski et al. |
| 9,675,351 B2 | 6/2017 | Hodgkinson et al. |
| 9,675,354 B2 | 6/2017 | Weir et al. |
| 9,675,355 B2 | 6/2017 | Shelton, IV et al. |
| 9,675,372 B2 | 6/2017 | Laurent et al. |
| 9,675,375 B2 | 6/2017 | Houser et al. |
| 9,675,405 B2 | 6/2017 | Trees et al. |
| 9,675,819 B2 | 6/2017 | Dunbar et al. |
| 9,681,870 B2 | 6/2017 | Baxter, III et al. |
| 9,681,873 B2 | 6/2017 | Smith et al. |
| 9,681,884 B2 | 6/2017 | Clem et al. |
| 9,687,230 B2 | 6/2017 | Leimbach et al. |
| 9,687,231 B2 | 6/2017 | Baxter, III et al. |
| 9,687,232 B2 | 6/2017 | Shelton, IV et al. |
| 9,687,233 B2 | 6/2017 | Fernandez et al. |
| 9,687,236 B2 | 6/2017 | Leimbach et al. |
| 9,687,237 B2 | 6/2017 | Schmid et al. |
| 9,687,253 B2 | 6/2017 | Detry et al. |
| 9,689,466 B2 | 6/2017 | Kanai et al. |
| 9,690,362 B2 | 6/2017 | Leimbach et al. |
| 9,693,772 B2 | 7/2017 | Ingmanson et al. |
| 9,693,774 B2 | 7/2017 | Gettinger et al. |
| 9,693,777 B2 | 7/2017 | Schellin et al. |
| 9,700,309 B2 | 7/2017 | Jaworek et al. |
| 9,700,310 B2 | 7/2017 | Morgan et al. |
| 9,700,312 B2 | 7/2017 | Kostrzewski et al. |
| 9,700,314 B2 | 7/2017 | Marczyk |
| 9,700,317 B2 | 7/2017 | Aronhalt et al. |
| 9,700,318 B2 | 7/2017 | Scirica et al. |
| 9,700,319 B2 | 7/2017 | Motooka et al. |
| 9,700,320 B2 | 7/2017 | Dinardo et al. |
| 9,700,321 B2 | 7/2017 | Shelton, IV et al. |
| 9,706,981 B2 | 7/2017 | Nicholas et al. |
| 9,706,991 B2 | 7/2017 | Hess et al. |
| 9,706,993 B2 | 7/2017 | Hessler et al. |
| 9,707,005 B2 | 7/2017 | Strobl et al. |
| 9,707,026 B2 | 7/2017 | Malackowski et al. |
| 9,707,033 B2 | 7/2017 | Parihar et al. |
| 9,707,043 B2 | 7/2017 | Bozung |
| 9,707,684 B2 | 7/2017 | Ruiz Morales et al. |
| 9,713,468 B2 | 7/2017 | Harris et al. |
| 9,713,470 B2 | 7/2017 | Scirica et al. |
| 9,713,474 B2 | 7/2017 | Lorenz |
| 9,717,497 B2 | 8/2017 | Zerkle et al. |
| 9,717,498 B2 | 8/2017 | Aranyi et al. |
| 9,718,190 B2 | 8/2017 | Larkin et al. |
| 9,722,236 B2 | 8/2017 | Sathrum |
| 9,724,091 B2 | 8/2017 | Shelton, IV et al. |
| 9,724,092 B2 | 8/2017 | Baxter, III et al. |
| 9,724,094 B2 | 8/2017 | Baber et al. |
| 9,724,095 B2 | 8/2017 | Gupta et al. |
| 9,724,096 B2 | 8/2017 | Thompson et al. |
| 9,724,098 B2 | 8/2017 | Baxter, III et al. |
| 9,724,118 B2 | 8/2017 | Schulte et al. |
| 9,724,163 B2 | 8/2017 | Orban |
| 9,730,692 B2 | 8/2017 | Shelton, IV et al. |
| 9,730,695 B2 | 8/2017 | Leimbach et al. |
| 9,730,697 B2 | 8/2017 | Morgan et al. |
| 9,730,717 B2 | 8/2017 | Katsuki et al. |
| 9,731,410 B2 | 8/2017 | Hirabayashi et al. |
| 9,733,663 B2 | 8/2017 | Leimbach et al. |
| 9,737,297 B2 | 8/2017 | Racenet et al. |
| 9,737,301 B2 | 8/2017 | Baber et al. |
| 9,737,302 B2 | 8/2017 | Shelton, IV et al. |
| 9,737,303 B2 | 8/2017 | Shelton, IV et al. |
| 9,737,365 B2 | 8/2017 | Hegeman et al. |
| 9,743,927 B2 | 8/2017 | Whitman |
| 9,743,928 B2 | 8/2017 | Shelton, IV et al. |
| 9,743,929 B2 | 8/2017 | Leimbach et al. |
| D798,319 S | 9/2017 | Bergstrand et al. |
| 9,750,498 B2 | 9/2017 | Timm et al. |
| 9,750,499 B2 | 9/2017 | Leimbach et al. |
| 9,750,501 B2 | 9/2017 | Shelton, IV et al. |
| 9,750,502 B2 | 9/2017 | Scirica et al. |
| 9,750,639 B2 | 9/2017 | Barnes et al. |
| 9,757,123 B2 | 9/2017 | Giordano et al. |
| 9,757,124 B2 | 9/2017 | Schellin et al. |
| 9,757,126 B2 | 9/2017 | Cappola |
| 9,757,128 B2 | 9/2017 | Baber et al. |
| 9,757,129 B2 | 9/2017 | Williams |
| 9,757,130 B2 | 9/2017 | Shelton, IV |
| 9,763,662 B2 | 9/2017 | Shelton, IV et al. |
| 9,763,668 B2 | 9/2017 | Whitfield et al. |
| 9,770,245 B2 | 9/2017 | Swayze et al. |
| 9,770,274 B2 | 9/2017 | Pool et al. |
| D798,886 S | 10/2017 | Prophete et al. |
| D800,742 S | 10/2017 | Rhodes |
| D800,744 S | 10/2017 | Jitkoff et al. |
| D800,766 S | 10/2017 | Park et al. |
| D800,904 S | 10/2017 | Leimbach et al. |
| 9,775,608 B2 | 10/2017 | Aronhalt et al. |
| 9,775,609 B2 | 10/2017 | Shelton, IV et al. |
| 9,775,610 B2 | 10/2017 | Nicholas et al. |
| 9,775,611 B2 | 10/2017 | Kostrzewski |
| 9,775,613 B2 | 10/2017 | Shelton, IV et al. |
| 9,775,614 B2 | 10/2017 | Shelton, IV et al. |
| 9,775,618 B2 | 10/2017 | Bettuchi et al. |
| 9,775,635 B2 | 10/2017 | Takei |
| 9,775,678 B2 | 10/2017 | Lohmeier |

(56) References Cited

U.S. PATENT DOCUMENTS

| | | |
|---|---|---|
| 9,782,169 B2 | 10/2017 | Kimsey et al. |
| 9,782,170 B2 | 10/2017 | Zemlok et al. |
| 9,782,180 B2 | 10/2017 | Smith et al. |
| 9,782,193 B2 | 10/2017 | Thistle |
| 9,782,214 B2 | 10/2017 | Houser et al. |
| 9,788,834 B2 | 10/2017 | Schmid et al. |
| 9,788,835 B2 | 10/2017 | Morgan et al. |
| 9,788,836 B2 | 10/2017 | Overmyer et al. |
| 9,788,847 B2 | 10/2017 | Jinno |
| 9,788,851 B2 | 10/2017 | Dannaher et al. |
| 9,788,902 B2 | 10/2017 | Inoue et al. |
| 9,795,379 B2 | 10/2017 | Leimbach et al. |
| 9,795,380 B2 | 10/2017 | Shelton, IV et al. |
| 9,795,381 B2 | 10/2017 | Shelton, IV |
| 9,795,382 B2 | 10/2017 | Shelton, IV |
| 9,795,383 B2 | 10/2017 | Aldridge et al. |
| 9,795,384 B2 | 10/2017 | Weaner et al. |
| 9,797,486 B2 | 10/2017 | Zergiebel et al. |
| 9,801,626 B2 | 10/2017 | Parihar et al. |
| 9,801,627 B2 | 10/2017 | Harris et al. |
| 9,801,628 B2 | 10/2017 | Harris et al. |
| 9,801,634 B2 | 10/2017 | Shelton, IV et al. |
| 9,802,033 B2 | 10/2017 | Hibner et al. |
| 9,804,618 B2 | 10/2017 | Leimbach et al. |
| D803,234 S | 11/2017 | Day et al. |
| D803,235 S | 11/2017 | Markson et al. |
| D803,850 S | 11/2017 | Chang et al. |
| 9,808,244 B2 | 11/2017 | Leimbach et al. |
| 9,808,246 B2 | 11/2017 | Shelton, IV et al. |
| 9,808,247 B2 | 11/2017 | Shelton, IV et al. |
| 9,808,248 B2 | 11/2017 | Hoffman |
| 9,808,249 B2 | 11/2017 | Shelton, IV |
| 9,814,460 B2 | 11/2017 | Kimsey et al. |
| 9,814,462 B2 | 11/2017 | Woodard, Jr. et al. |
| 9,814,463 B2 | 11/2017 | Williams et al. |
| 9,814,530 B2 | 11/2017 | Weir et al. |
| 9,814,561 B2 | 11/2017 | Forsell |
| 9,820,445 B2 | 11/2017 | Simpson et al. |
| 9,820,737 B2 | 11/2017 | Beardsley et al. |
| 9,820,738 B2 | 11/2017 | Lytle, IV et al. |
| 9,820,741 B2 | 11/2017 | Kostrzewski |
| 9,820,768 B2 | 11/2017 | Gee et al. |
| 9,825,455 B2 | 11/2017 | Sandhu et al. |
| 9,826,976 B2 | 11/2017 | Parihar et al. |
| 9,826,977 B2 | 11/2017 | Leimbach et al. |
| 9,826,978 B2 | 11/2017 | Shelton, IV et al. |
| 9,829,698 B2 | 11/2017 | Haraguchi et al. |
| D806,108 S | 12/2017 | Day |
| 9,833,236 B2 | 12/2017 | Shelton, IV et al. |
| 9,833,238 B2 | 12/2017 | Baxter, III et al. |
| 9,833,239 B2 | 12/2017 | Yates et al. |
| 9,833,241 B2 | 12/2017 | Huitema et al. |
| 9,833,242 B2 | 12/2017 | Baxter, III et al. |
| 9,839,420 B2 | 12/2017 | Shelton, IV et al. |
| 9,839,421 B2 | 12/2017 | Zerkle et al. |
| 9,839,422 B2 | 12/2017 | Schellin et al. |
| 9,839,423 B2 | 12/2017 | Vendely et al. |
| 9,839,427 B2 | 12/2017 | Swayze et al. |
| 9,839,428 B2 | 12/2017 | Baxter, III et al. |
| 9,839,429 B2 | 12/2017 | Weisenburgh, II et al. |
| 9,839,480 B2 | 12/2017 | Pribanic et al. |
| 9,844,368 B2 | 12/2017 | Boudreaux et al. |
| 9,844,369 B2 | 12/2017 | Huitema et al. |
| 9,844,372 B2 | 12/2017 | Shelton, IV et al. |
| 9,844,373 B2 | 12/2017 | Swayze et al. |
| 9,844,374 B2 | 12/2017 | Lytle, IV et al. |
| 9,844,375 B2 | 12/2017 | Overmyer et al. |
| 9,844,376 B2 | 12/2017 | Baxter, III et al. |
| 9,844,379 B2 | 12/2017 | Shelton, IV et al. |
| 9,848,871 B2 | 12/2017 | Harris et al. |
| 9,848,873 B2 | 12/2017 | Shelton, IV |
| 9,848,875 B2 | 12/2017 | Aronhalt et al. |
| 9,848,877 B2 | 12/2017 | Shelton, IV et al. |
| 9,850,994 B2 | 12/2017 | Schena |
| 9,855,039 B2 | 1/2018 | Racenet et al. |
| 9,855,040 B2 | 1/2018 | Kostrzewski |
| 9,855,662 B2 | 1/2018 | Ruiz Morales et al. |
| 9,861,261 B2 | 1/2018 | Shahinian |
| 9,861,359 B2 | 1/2018 | Shelton, IV et al. |
| 9,861,361 B2 | 1/2018 | Aronhalt et al. |
| 9,861,362 B2 | 1/2018 | Whitman et al. |
| 9,861,382 B2 | 1/2018 | Smith et al. |
| 9,861,446 B2 | 1/2018 | Lang |
| 9,867,612 B2 | 1/2018 | Parihar et al. |
| 9,867,615 B2 | 1/2018 | Fanelli et al. |
| 9,867,618 B2 | 1/2018 | Hall et al. |
| 9,867,620 B2 | 1/2018 | Fischvogt et al. |
| 9,868,198 B2 | 1/2018 | Nicholas et al. |
| 9,872,682 B2 | 1/2018 | Hess et al. |
| 9,872,683 B2 | 1/2018 | Hopkins et al. |
| 9,872,684 B2 | 1/2018 | Hall et al. |
| 9,872,722 B2 | 1/2018 | Lech |
| 9,877,721 B2 | 1/2018 | Schellin et al. |
| 9,877,723 B2 | 1/2018 | Hall et al. |
| 9,877,776 B2 | 1/2018 | Boudreaux |
| D810,099 S | 2/2018 | Riedel |
| 9,883,843 B2 | 2/2018 | Garlow |
| 9,883,860 B2 | 2/2018 | Leimbach |
| 9,883,861 B2 | 2/2018 | Shelton, IV et al. |
| 9,884,456 B2 | 2/2018 | Schellin et al. |
| 9,888,919 B2 | 2/2018 | Leimbach et al. |
| 9,888,921 B2 | 2/2018 | Williams et al. |
| 9,888,924 B2 | 2/2018 | Ebersole et al. |
| 9,889,230 B2 | 2/2018 | Bennett et al. |
| 9,895,147 B2 | 2/2018 | Shelton, IV |
| 9,895,148 B2 | 2/2018 | Shelton, IV et al. |
| 9,895,813 B2 | 2/2018 | Blumenkranz et al. |
| 9,901,339 B2 | 2/2018 | Farascioni |
| 9,901,341 B2 | 2/2018 | Kostrzewski |
| 9,901,342 B2 | 2/2018 | Shelton, IV et al. |
| 9,901,344 B2 | 2/2018 | Moore et al. |
| 9,901,345 B2 | 2/2018 | Moore et al. |
| 9,901,346 B2 | 2/2018 | Moore et al. |
| 9,901,406 B2 | 2/2018 | State et al. |
| 9,901,412 B2 | 2/2018 | Lathrop et al. |
| D813,899 S | 3/2018 | Erant et al. |
| 9,907,456 B2 | 3/2018 | Miyoshi |
| 9,907,553 B2 | 3/2018 | Cole et al. |
| 9,907,600 B2 | 3/2018 | Stulen et al. |
| 9,907,620 B2 | 3/2018 | Shelton, IV et al. |
| 9,913,641 B2 | 3/2018 | Takemoto et al. |
| 9,913,642 B2 | 3/2018 | Leimbach et al. |
| 9,913,644 B2 | 3/2018 | McCuen |
| 9,913,646 B2 | 3/2018 | Shelton, IV |
| 9,913,647 B2 | 3/2018 | Weisenburgh, II et al. |
| 9,913,648 B2 | 3/2018 | Shelton, IV et al. |
| 9,913,694 B2 | 3/2018 | Brisson |
| 9,913,733 B2 | 3/2018 | Piron et al. |
| 9,918,704 B2 | 3/2018 | Shelton, IV et al. |
| 9,918,714 B2 | 3/2018 | Gibbons, Jr. |
| 9,918,715 B2 | 3/2018 | Menn |
| 9,918,716 B2 | 3/2018 | Baxter, III et al. |
| 9,918,717 B2 | 3/2018 | Czernik |
| 9,918,730 B2 | 3/2018 | Trees et al. |
| 9,924,941 B2 | 3/2018 | Burbank |
| 9,924,942 B2 | 3/2018 | Swayze et al. |
| 9,924,944 B2 | 3/2018 | Shelton, IV et al. |
| 9,924,945 B2 | 3/2018 | Zheng et al. |
| 9,924,946 B2 | 3/2018 | Vendely et al. |
| 9,924,947 B2 | 3/2018 | Shelton, IV et al. |
| 9,924,961 B2 | 3/2018 | Shelton, IV et al. |
| 9,931,106 B2 | 4/2018 | Au et al. |
| 9,931,116 B2 | 4/2018 | Racenet et al. |
| 9,931,118 B2 | 4/2018 | Shelton, IV et al. |
| 9,931,120 B2 | 4/2018 | Chen et al. |
| 9,936,949 B2 | 4/2018 | Measamer et al. |
| 9,936,950 B2 | 4/2018 | Shelton, IV et al. |
| 9,936,951 B2 | 4/2018 | Hufnagel et al. |
| 9,936,954 B2 | 4/2018 | Shelton, IV et al. |
| 9,937,626 B2 | 4/2018 | Rockrohr |
| 9,943,309 B2 | 4/2018 | Shelton, IV et al. |
| 9,943,310 B2 | 4/2018 | Harris et al. |
| 9,943,312 B2 | 4/2018 | Posada et al. |
| D819,072 S | 5/2018 | Clediere |

(56) References Cited

U.S. PATENT DOCUMENTS

| | | |
|---|---|---|
| 9,955,954 B2 | 5/2018 | Destoumieux et al. |
| 9,955,965 B2 | 5/2018 | Chen et al. |
| 9,955,966 B2 | 5/2018 | Zergiebel |
| 9,962,129 B2 | 5/2018 | Jerebko et al. |
| 9,962,157 B2 | 5/2018 | Sapre |
| 9,962,158 B2 | 5/2018 | Hall et al. |
| 9,962,159 B2 | 5/2018 | Heinrich et al. |
| 9,962,161 B2 | 5/2018 | Scheib et al. |
| 9,968,354 B2 | 5/2018 | Shelton, IV et al. |
| 9,968,355 B2 | 5/2018 | Shelton, IV et al. |
| 9,968,356 B2 | 5/2018 | Shelton, IV et al. |
| 9,968,397 B2 | 5/2018 | Taylor et al. |
| 9,974,529 B2 | 5/2018 | Shelton, IV et al. |
| 9,974,538 B2 | 5/2018 | Baxter, III et al. |
| 9,974,539 B2 | 5/2018 | Yates et al. |
| 9,974,541 B2 | 5/2018 | Calderoni |
| 9,974,542 B2 | 5/2018 | Hodgkinson |
| 9,980,713 B2 | 5/2018 | Aronhalt et al. |
| 9,980,724 B2 | 5/2018 | Farascioni et al. |
| 9,980,729 B2 | 5/2018 | Moore et al. |
| 9,980,769 B2 | 5/2018 | Trees et al. |
| D819,680 S | 6/2018 | Nguyen |
| D819,682 S | 6/2018 | Howard et al. |
| D819,684 S | 6/2018 | Dart |
| D820,307 S | 6/2018 | Jian et al. |
| D820,867 S | 6/2018 | Dickens et al. |
| 9,987,000 B2 | 6/2018 | Shelton, IV et al. |
| 9,987,003 B2 | 6/2018 | Timm et al. |
| 9,987,006 B2 | 6/2018 | Morgan et al. |
| 9,987,095 B2 | 6/2018 | Chowaniec et al. |
| 9,987,099 B2 | 6/2018 | Chen et al. |
| 9,993,248 B2 | 6/2018 | Shelton, IV et al. |
| 9,993,258 B2 | 6/2018 | Shelton, IV et al. |
| 9,999,408 B2 | 6/2018 | Boudreaux et al. |
| 9,999,423 B2 | 6/2018 | Schuckmann et al. |
| 9,999,426 B2 | 6/2018 | Moore et al. |
| 9,999,431 B2 | 6/2018 | Shelton, IV et al. |
| 9,999,472 B2 | 6/2018 | Weir et al. |
| 10,004,497 B2 | 6/2018 | Overmyer et al. |
| 10,004,498 B2 | 6/2018 | Morgan et al. |
| 10,004,500 B2 | 6/2018 | Shelton, IV et al. |
| 10,004,501 B2 | 6/2018 | Shelton, IV et al. |
| 10,004,505 B2 | 6/2018 | Moore et al. |
| 10,004,506 B2 | 6/2018 | Shelton, IV et al. |
| D822,206 S | 7/2018 | Shelton, IV et al. |
| 10,010,322 B2 | 7/2018 | Shelton, IV et al. |
| 10,010,324 B2 | 7/2018 | Huitema et al. |
| 10,013,049 B2 | 7/2018 | Leimbach et al. |
| 10,016,199 B2 | 7/2018 | Baber et al. |
| 10,016,656 B2 | 7/2018 | Devor et al. |
| 10,022,125 B2 | 7/2018 | (Prommersberger) Stopek et al. |
| 10,024,407 B2 | 7/2018 | Aranyi et al. |
| 10,028,742 B2 | 7/2018 | Shelton, IV et al. |
| 10,028,743 B2 | 7/2018 | Shelton, IV et al. |
| 10,028,744 B2 | 7/2018 | Shelton, IV et al. |
| 10,028,761 B2 | 7/2018 | Leimbach et al. |
| 10,029,125 B2 | 7/2018 | Shapiro et al. |
| 10,034,344 B2 | 7/2018 | Yoshida |
| 10,034,668 B2 | 7/2018 | Ebner |
| D826,405 S | 8/2018 | Shelton, IV et al. |
| 10,039,440 B2 | 8/2018 | Fenech et al. |
| 10,039,529 B2 | 8/2018 | Kerr et al. |
| 10,039,532 B2 | 8/2018 | Srinivas et al. |
| 10,039,545 B2 | 8/2018 | Sadowski et al. |
| 10,041,822 B2 | 8/2018 | Zemlok |
| 10,045,769 B2 | 8/2018 | Aronhalt et al. |
| 10,045,776 B2 | 8/2018 | Shelton, IV et al. |
| 10,045,778 B2 | 8/2018 | Yates et al. |
| 10,045,779 B2 | 8/2018 | Savage et al. |
| 10,045,781 B2 | 8/2018 | Cropper et al. |
| 10,045,782 B2 | 8/2018 | Murthy Aravalli |
| 10,052,044 B2 | 8/2018 | Shelton, IV et al. |
| 10,052,099 B2 | 8/2018 | Morgan et al. |
| 10,052,100 B2 | 8/2018 | Morgan et al. |
| 10,052,102 B2 | 8/2018 | Baxter, III et al. |
| 10,052,104 B2 | 8/2018 | Shelton, IV et al. |
| 10,052,164 B2 | 8/2018 | Overmyer |
| 10,058,317 B2 | 8/2018 | Fan et al. |
| 10,058,327 B2 | 8/2018 | Weisenburgh, II et al. |
| 10,058,373 B2 | 8/2018 | Takashino et al. |
| 10,058,395 B2 | 8/2018 | Devengenzo et al. |
| 10,058,963 B2 | 8/2018 | Shelton, IV et al. |
| 10,064,620 B2 | 9/2018 | Gettinger et al. |
| 10,064,621 B2 | 9/2018 | Kerr et al. |
| 10,064,624 B2 | 9/2018 | Shelton, IV et al. |
| 10,064,639 B2 | 9/2018 | Ishida et al. |
| 10,064,649 B2 | 9/2018 | Golebieski et al. |
| 10,064,688 B2 | 9/2018 | Shelton, IV et al. |
| 10,070,861 B2 | 9/2018 | Spivey et al. |
| 10,070,863 B2 | 9/2018 | Swayze et al. |
| 10,071,452 B2 | 9/2018 | Shelton, IV et al. |
| 10,076,325 B2 | 9/2018 | Huang et al. |
| 10,076,326 B2 | 9/2018 | Yates et al. |
| 10,076,340 B2 | 9/2018 | Belagali et al. |
| D831,209 S | 10/2018 | Huitema et al. |
| D831,676 S | 10/2018 | Park et al. |
| D832,301 S | 10/2018 | Smith |
| 10,085,624 B2 | 10/2018 | Isoda et al. |
| 10,085,643 B2 | 10/2018 | Bandic et al. |
| 10,085,728 B2 | 10/2018 | Jogasaki et al. |
| 10,085,746 B2 | 10/2018 | Fischvogt |
| 10,085,748 B2 | 10/2018 | Morgan et al. |
| 10,085,749 B2 | 10/2018 | Cappola et al. |
| 10,085,751 B2 | 10/2018 | Overmyer et al. |
| 10,085,754 B2 | 10/2018 | Sniffin et al. |
| 10,085,806 B2 | 10/2018 | Hagn et al. |
| 10,092,290 B2 | 10/2018 | Yigit et al. |
| 10,092,292 B2 | 10/2018 | Boudreaux et al. |
| 10,098,635 B2 | 10/2018 | Burbank |
| 10,098,636 B2 | 10/2018 | Shelton, IV et al. |
| 10,098,640 B2 | 10/2018 | Bertolero et al. |
| 10,098,642 B2 | 10/2018 | Baxter, III et al. |
| 10,099,303 B2 | 10/2018 | Yoshida et al. |
| 10,101,861 B2 | 10/2018 | Kiyoto |
| 10,105,128 B2 | 10/2018 | Cooper et al. |
| 10,105,136 B2 | 10/2018 | Yates et al. |
| 10,105,139 B2 | 10/2018 | Yates et al. |
| 10,105,140 B2 | 10/2018 | Malinouskas et al. |
| 10,105,142 B2 | 10/2018 | Baxter, III et al. |
| 10,106,932 B2 | 10/2018 | Anderson et al. |
| 10,111,657 B2 | 10/2018 | McCuen |
| 10,111,679 B2 | 10/2018 | Baber et al. |
| 10,111,698 B2 | 10/2018 | Scheib et al. |
| 10,111,702 B2 | 10/2018 | Kostrzewski |
| 10,117,649 B2 | 11/2018 | Baxter et al. |
| 10,117,650 B2 | 11/2018 | Nicholas et al. |
| 10,117,652 B2 | 11/2018 | Schmid et al. |
| 10,117,653 B2 | 11/2018 | Leimbach et al. |
| 10,117,654 B2 | 11/2018 | Ingmanson et al. |
| 10,123,798 B2 | 11/2018 | Baxter, III et al. |
| 10,124,493 B2 | 11/2018 | Rothfuss et al. |
| 10,130,352 B2 | 11/2018 | Widenhouse et al. |
| 10,130,359 B2 | 11/2018 | Hess et al. |
| 10,130,361 B2 | 11/2018 | Yates et al. |
| 10,130,363 B2 | 11/2018 | Huitema et al. |
| 10,130,366 B2 | 11/2018 | Shelton, IV et al. |
| 10,130,367 B2 | 11/2018 | Cappola et al. |
| 10,130,738 B2 | 11/2018 | Shelton, IV et al. |
| 10,130,830 B2 | 11/2018 | Miret Carceller et al. |
| 10,133,248 B2 | 11/2018 | Fitzsimmons et al. |
| 10,135,242 B2 | 11/2018 | Baber et al. |
| 10,136,879 B2 | 11/2018 | Ross et al. |
| 10,136,887 B2 | 11/2018 | Shelton, IV et al. |
| 10,136,889 B2 | 11/2018 | Shelton, IV et al. |
| 10,136,890 B2 | 11/2018 | Shelton, IV et al. |
| 10,136,891 B2 | 11/2018 | Shelton, IV et al. |
| D835,659 S | 12/2018 | Anzures et al. |
| D836,124 S | 12/2018 | Fan |
| 10,143,474 B2 | 12/2018 | Bucciaglia et al. |
| 10,149,679 B2 | 12/2018 | Shelton, IV et al. |
| 10,149,680 B2 | 12/2018 | Parihar et al. |
| 10,149,682 B2 | 12/2018 | Shelton, IV et al. |
| 10,149,683 B2 | 12/2018 | Smith et al. |
| 10,149,712 B2 | 12/2018 | Manwaring et al. |

(56) References Cited

U.S. PATENT DOCUMENTS

| | | |
|---|---|---|
| 10,154,841 B2 | 12/2018 | Weaner et al. |
| 10,159,481 B2 | 12/2018 | Whitman et al. |
| 10,159,482 B2 | 12/2018 | Swayze et al. |
| 10,159,483 B2 | 12/2018 | Beckman et al. |
| 10,163,589 B2 | 12/2018 | Zergiebel et al. |
| D837,244 S | 1/2019 | Kuo et al. |
| D837,245 S | 1/2019 | Kuo et al. |
| 10,166,025 B2 | 1/2019 | Leimbach et al. |
| 10,166,026 B2 | 1/2019 | Shelton, IV et al. |
| 10,172,611 B2 | 1/2019 | Shelton, IV et al. |
| 10,172,615 B2 | 1/2019 | Marczyk et al. |
| 10,172,616 B2 | 1/2019 | Murray et al. |
| 10,172,617 B2 | 1/2019 | Shelton, IV et al. |
| 10,172,619 B2 | 1/2019 | Harris et al. |
| 10,172,620 B2 | 1/2019 | Harris et al. |
| 10,172,636 B2 | 1/2019 | Stulen et al. |
| 10,175,127 B2 | 1/2019 | Collins et al. |
| 10,178,992 B2 | 1/2019 | Wise et al. |
| 10,180,463 B2 | 1/2019 | Beckman et al. |
| 10,182,813 B2 | 1/2019 | Leimbach et al. |
| 10,182,815 B2 | 1/2019 | Williams et al. |
| 10,182,816 B2 | 1/2019 | Shelton, IV et al. |
| 10,182,818 B2 | 1/2019 | Hensel et al. |
| 10,182,819 B2 | 1/2019 | Shelton, IV |
| 10,188,385 B2 | 1/2019 | Kerr et al. |
| 10,188,393 B2 | 1/2019 | Smith et al. |
| 10,188,394 B2 | 1/2019 | Shelton, IV et al. |
| D839,900 S | 2/2019 | Gan |
| D841,667 S | 2/2019 | Coren |
| 10,194,801 B2 | 2/2019 | Elhawary et al. |
| 10,194,904 B2 | 2/2019 | Viola et al. |
| 10,194,907 B2 | 2/2019 | Marczyk et al. |
| 10,194,910 B2 | 2/2019 | Shelton, IV et al. |
| 10,194,913 B2 | 2/2019 | Nalagatla et al. |
| 10,194,976 B2 | 2/2019 | Boudreaux |
| 10,194,992 B2 | 2/2019 | Robinson |
| 10,201,348 B2 | 2/2019 | Scheib et al. |
| 10,201,349 B2 | 2/2019 | Leimbach et al. |
| 10,201,363 B2 | 2/2019 | Shelton, IV |
| 10,201,364 B2 | 2/2019 | Leimbach et al. |
| 10,201,365 B2 | 2/2019 | Boudreaux et al. |
| 10,201,381 B2 | 2/2019 | Zergiebel et al. |
| 10,206,605 B2 | 2/2019 | Shelton, IV et al. |
| 10,206,676 B2 | 2/2019 | Shelton, IV |
| 10,206,677 B2 | 2/2019 | Harris et al. |
| 10,206,678 B2 | 2/2019 | Shelton, IV et al. |
| 10,206,748 B2 | 2/2019 | Burbank |
| 10,210,244 B1 | 2/2019 | Branavan et al. |
| 10,211,586 B2 | 2/2019 | Adams et al. |
| 10,213,198 B2 | 2/2019 | Aronhalt et al. |
| 10,213,201 B2 | 2/2019 | Shelton, IV et al. |
| 10,213,202 B2 | 2/2019 | Flanagan et al. |
| 10,213,203 B2 | 2/2019 | Swayze et al. |
| 10,213,262 B2 | 2/2019 | Shelton, IV et al. |
| D842,328 S | 3/2019 | Jian et al. |
| 10,219,811 B2 | 3/2019 | Haider et al. |
| 10,219,832 B2 | 3/2019 | Bagwell et al. |
| 10,220,522 B2 | 3/2019 | Rockrohr |
| 10,226,239 B2 | 3/2019 | Nicholas et al. |
| 10,226,249 B2 | 3/2019 | Jaworek et al. |
| 10,226,250 B2 | 3/2019 | Beckman et al. |
| 10,226,251 B2 | 3/2019 | Scheib et al. |
| 10,226,274 B2 | 3/2019 | Worrell et al. |
| 10,231,634 B2 | 3/2019 | Zand et al. |
| 10,231,653 B2 | 3/2019 | Bohm et al. |
| 10,231,734 B2 | 3/2019 | Thompson et al. |
| 10,231,794 B2 | 3/2019 | Shelton, IV et al. |
| 10,238,385 B2 | 3/2019 | Yates et al. |
| 10,238,386 B2 | 3/2019 | Overmyer et al. |
| 10,238,387 B2 | 3/2019 | Yates et al. |
| 10,238,389 B2 | 3/2019 | Yates et al. |
| 10,238,390 B2 | 3/2019 | Harris et al. |
| 10,238,391 B2 | 3/2019 | Leimbach et al. |
| D844,666 S | 4/2019 | Espeleta et al. |
| D844,667 S | 4/2019 | Espeleta et al. |
| D845,342 S | 4/2019 | Espeleta et al. |
| 10,245,027 B2 | 4/2019 | Shelton, IV et al. |
| 10,245,028 B2 | 4/2019 | Shelton, IV et al. |
| 10,245,029 B2 | 4/2019 | Hunter et al. |
| 10,245,030 B2 | 4/2019 | Hunter et al. |
| 10,245,032 B2 | 4/2019 | Shelton, IV |
| 10,245,033 B2 | 4/2019 | Overmyer et al. |
| 10,245,034 B2 | 4/2019 | Shelton, IV et al. |
| 10,245,035 B2 | 4/2019 | Swayze et al. |
| 10,245,038 B2 | 4/2019 | Hopkins et al. |
| 10,245,058 B2 | 4/2019 | Omori et al. |
| 10,251,648 B2 | 4/2019 | Harris et al. |
| 10,251,649 B2 | 4/2019 | Schellin et al. |
| 10,251,725 B2 | 4/2019 | Valentine et al. |
| 10,258,322 B2 | 4/2019 | Fanton et al. |
| 10,258,330 B2 | 4/2019 | Shelton, IV et al. |
| 10,258,331 B2 | 4/2019 | Shelton, IV et al. |
| 10,258,332 B2 | 4/2019 | Schmid et al. |
| 10,258,333 B2 | 4/2019 | Shelton, IV et al. |
| 10,258,336 B2 | 4/2019 | Baxter, III et al. |
| 10,258,418 B2 | 4/2019 | Shelton, IV et al. |
| 10,264,797 B2 | 4/2019 | Zhang et al. |
| 10,265,065 B2 | 4/2019 | Shelton, IV et al. |
| 10,265,067 B2 | 4/2019 | Yates et al. |
| 10,265,068 B2 | 4/2019 | Harris et al. |
| 10,265,072 B2 | 4/2019 | Shelton, IV et al. |
| 10,265,073 B2 | 4/2019 | Scheib et al. |
| 10,265,074 B2 | 4/2019 | Shelton, IV et al. |
| 10,265,090 B2 | 4/2019 | Ingmanson et al. |
| 10,271,844 B2 | 4/2019 | Valentine et al. |
| 10,271,845 B2 | 4/2019 | Shelton, IV |
| 10,271,846 B2 | 4/2019 | Shelton, IV et al. |
| 10,271,849 B2 | 4/2019 | Vendely et al. |
| 10,271,851 B2 | 4/2019 | Shelton, IV et al. |
| D847,989 S | 5/2019 | Shelton, IV et al. |
| D848,473 S | 5/2019 | Zhu et al. |
| D849,046 S | 5/2019 | Kuo et al. |
| 10,278,696 B2 | 5/2019 | Gurumurthy et al. |
| 10,278,697 B2 | 5/2019 | Shelton, IV et al. |
| 10,278,702 B2 | 5/2019 | Shelton, IV et al. |
| 10,278,703 B2 | 5/2019 | Nativ et al. |
| 10,278,707 B2 | 5/2019 | Thompson et al. |
| 10,278,722 B2 | 5/2019 | Shelton, IV et al. |
| 10,278,780 B2 | 5/2019 | Shelton, IV |
| 10,285,694 B2 | 5/2019 | Viola et al. |
| 10,285,695 B2 | 5/2019 | Jaworek et al. |
| 10,285,699 B2 | 5/2019 | Vendely et al. |
| 10,285,705 B2 | 5/2019 | Shelton, IV et al. |
| 10,292,701 B2 | 5/2019 | Scheib et al. |
| 10,292,704 B2 | 5/2019 | Harris et al. |
| 10,292,707 B2 | 5/2019 | Shelton, IV et al. |
| 10,293,100 B2 | 5/2019 | Shelton, IV et al. |
| 10,293,553 B2 | 5/2019 | Racenet et al. |
| 10,299,787 B2 | 5/2019 | Shelton, IV |
| 10,299,788 B2 | 5/2019 | Heinrich et al. |
| 10,299,789 B2 | 5/2019 | Marczyk et al. |
| 10,299,792 B2 | 5/2019 | Huitema et al. |
| 10,299,817 B2 | 5/2019 | Shelton, IV et al. |
| 10,299,818 B2 | 5/2019 | Riva |
| 10,299,878 B2 | 5/2019 | Shelton, IV et al. |
| D850,617 S | 6/2019 | Shelton, IV et al. |
| D851,676 S | 6/2019 | Foss et al. |
| D851,762 S | 6/2019 | Shelton, IV et al. |
| 10,307,159 B2 | 6/2019 | Harris et al. |
| 10,307,160 B2 | 6/2019 | Vendely et al. |
| 10,307,161 B2 | 6/2019 | Jankowski |
| 10,307,163 B2 | 6/2019 | Moore et al. |
| 10,307,170 B2 | 6/2019 | Parfett et al. |
| 10,307,202 B2 | 6/2019 | Smith et al. |
| 10,314,559 B2 | 6/2019 | Razzaque et al. |
| 10,314,577 B2 | 6/2019 | Laurent et al. |
| 10,314,582 B2 | 6/2019 | Shelton, IV et al. |
| 10,314,587 B2 | 6/2019 | Harris et al. |
| 10,314,588 B2 | 6/2019 | Turner et al. |
| 10,314,589 B2 | 6/2019 | Shelton, IV et al. |
| 10,314,590 B2 | 6/2019 | Shelton, IV et al. |
| 10,315,566 B2 | 6/2019 | Choi et al. |
| 10,321,907 B2 | 6/2019 | Shelton, IV et al. |
| 10,321,909 B2 | 6/2019 | Shelton, IV et al. |

(56) References Cited

U.S. PATENT DOCUMENTS

| | | |
|---|---|---|
| 10,321,927 B2 | 6/2019 | Hinman |
| 10,327,743 B2 | 6/2019 | St. Goar et al. |
| 10,327,764 B2 | 6/2019 | Harris et al. |
| 10,327,765 B2 | 6/2019 | Timm et al. |
| 10,327,767 B2 | 6/2019 | Shelton, IV et al. |
| 10,327,769 B2 | 6/2019 | Overmyer et al. |
| 10,327,776 B2 | 6/2019 | Harris et al. |
| 10,327,777 B2 | 6/2019 | Harris et al. |
| D854,032 S | 7/2019 | Jones et al. |
| D854,151 S | 7/2019 | Shelton, IV et al. |
| 10,335,144 B2 | 7/2019 | Shelton, IV et al. |
| 10,335,145 B2 | 7/2019 | Harris et al. |
| 10,335,147 B2 | 7/2019 | Rector et al. |
| 10,335,148 B2 | 7/2019 | Shelton, IV et al. |
| 10,335,149 B2 | 7/2019 | Baxter, III et al. |
| 10,335,150 B2 | 7/2019 | Shelton, IV |
| 10,335,151 B2 | 7/2019 | Shelton, IV et al. |
| 10,337,148 B2 | 7/2019 | Rouse et al. |
| 10,342,533 B2 | 7/2019 | Shelton, IV et al. |
| 10,342,535 B2 | 7/2019 | Scheib et al. |
| 10,342,541 B2 | 7/2019 | Shelton, IV et al. |
| 10,342,543 B2 | 7/2019 | Shelton, IV et al. |
| 10,342,623 B2 | 7/2019 | Huelman et al. |
| 10,349,939 B2 | 7/2019 | Shelton, IV et al. |
| 10,350,016 B2 | 7/2019 | Burbank et al. |
| 10,357,246 B2 | 7/2019 | Shelton, IV et al. |
| 10,357,247 B2 | 7/2019 | Shelton, IV et al. |
| 10,357,248 B2 | 7/2019 | Dalessandro et al. |
| 10,357,252 B2 | 7/2019 | Harris et al. |
| 10,363,031 B2 | 7/2019 | Alexander, III et al. |
| 10,363,033 B2 | 7/2019 | Timm et al. |
| 10,363,036 B2 | 7/2019 | Yates et al. |
| 10,363,037 B2 | 7/2019 | Aronhalt et al. |
| D855,634 S | 8/2019 | Kim |
| D856,359 S | 8/2019 | Huang et al. |
| 10,368,838 B2 | 8/2019 | Williams et al. |
| 10,368,861 B2 | 8/2019 | Baxter, III et al. |
| 10,368,863 B2 | 8/2019 | Timm et al. |
| 10,368,864 B2 | 8/2019 | Harris et al. |
| 10,368,865 B2 | 8/2019 | Harris et al. |
| 10,368,867 B2 | 8/2019 | Harris et al. |
| 10,368,892 B2 | 8/2019 | Stulen et al. |
| 10,376,263 B2 | 8/2019 | Morgan et al. |
| 10,383,626 B2 | 8/2019 | Soltz |
| 10,383,628 B2 | 8/2019 | Kang et al. |
| 10,383,629 B2 | 8/2019 | Ross et al. |
| 10,383,630 B2 | 8/2019 | Shelton, IV et al. |
| 10,383,633 B2 | 8/2019 | Shelton, IV et al. |
| 10,383,634 B2 | 8/2019 | Shelton, IV et al. |
| 10,390,823 B2 | 8/2019 | Shelton, IV et al. |
| 10,390,825 B2 | 8/2019 | Shelton, IV et al. |
| 10,390,828 B2 | 8/2019 | Vendely et al. |
| 10,390,829 B2 | 8/2019 | Eckert et al. |
| 10,390,830 B2 | 8/2019 | Schulz |
| 10,390,841 B2 | 8/2019 | Shelton, IV et al. |
| 10,390,897 B2 | 8/2019 | Kostrzewski |
| D860,219 S | 9/2019 | Rasmussen et al. |
| 10,398,433 B2 | 9/2019 | Boudreaux et al. |
| 10,398,434 B2 | 9/2019 | Shelton, IV et al. |
| 10,398,436 B2 | 9/2019 | Shelton, IV et al. |
| 10,405,854 B2 | 9/2019 | Schmid et al. |
| 10,405,857 B2 | 9/2019 | Shelton, IV et al. |
| 10,405,859 B2 | 9/2019 | Harris et al. |
| 10,405,863 B2 | 9/2019 | Wise et al. |
| 10,405,914 B2 | 9/2019 | Manwaring et al. |
| 10,405,932 B2 | 9/2019 | Overmyer |
| 10,413,291 B2 | 9/2019 | Worthington et al. |
| 10,413,293 B2 | 9/2019 | Shelton, IV et al. |
| 10,413,294 B2 | 9/2019 | Shelton, IV et al. |
| 10,413,297 B2 | 9/2019 | Harris et al. |
| 10,413,370 B2 | 9/2019 | Yates et al. |
| 10,413,373 B2 | 9/2019 | Yates et al. |
| 10,420,548 B2 | 9/2019 | Whitman et al. |
| 10,420,549 B2 | 9/2019 | Yates et al. |
| 10,420,550 B2 | 9/2019 | Shelton, IV |
| 10,420,552 B2 | 9/2019 | Shelton, IV et al. |
| 10,420,553 B2 | 9/2019 | Shelton, IV et al. |
| 10,420,555 B2 | 9/2019 | Shelton, IV et al. |
| 10,420,558 B2 | 9/2019 | Nalagatla et al. |
| 10,420,559 B2 | 9/2019 | Marczyk et al. |
| 10,420,560 B2 | 9/2019 | Shelton, IV et al. |
| 10,420,561 B2 | 9/2019 | Shelton, IV et al. |
| 10,420,577 B2 | 9/2019 | Chowaniec et al. |
| D861,707 S | 10/2019 | Yang |
| D863,343 S | 10/2019 | Mazlish et al. |
| D864,388 S | 10/2019 | Barber |
| 10,426,463 B2 | 10/2019 | Shelton, IV et al. |
| 10,426,466 B2 | 10/2019 | Contini et al. |
| 10,426,467 B2 | 10/2019 | Miller et al. |
| 10,426,468 B2 | 10/2019 | Contini et al. |
| 10,426,469 B2 | 10/2019 | Shelton, IV et al. |
| 10,426,471 B2 | 10/2019 | Shelton, IV et al. |
| 10,426,476 B2 | 10/2019 | Harris et al. |
| 10,426,477 B2 | 10/2019 | Harris et al. |
| 10,426,478 B2 | 10/2019 | Shelton, IV et al. |
| 10,426,481 B2 | 10/2019 | Aronhalt et al. |
| 10,433,837 B2 | 10/2019 | Worthington et al. |
| 10,433,839 B2 | 10/2019 | Scheib et al. |
| 10,433,840 B2 | 10/2019 | Shelton, IV et al. |
| 10,433,844 B2 | 10/2019 | Shelton, IV et al. |
| 10,433,845 B2 | 10/2019 | Baxter, III et al. |
| 10,433,846 B2 | 10/2019 | Vendely et al. |
| 10,433,849 B2 | 10/2019 | Shelton, IV et al. |
| 10,433,918 B2 | 10/2019 | Shelton, IV et al. |
| 10,441,279 B2 | 10/2019 | Shelton, IV et al. |
| 10,441,280 B2 | 10/2019 | Timm et al. |
| 10,441,281 B2 | 10/2019 | Shelton, IV et al. |
| 10,441,285 B2 | 10/2019 | Shelton, IV et al. |
| 10,441,286 B2 | 10/2019 | Shelton, IV et al. |
| 10,441,345 B2 | 10/2019 | Aldridge et al. |
| 10,441,369 B2 | 10/2019 | Shelton, IV et al. |
| 10,448,948 B2 | 10/2019 | Shelton, IV et al. |
| 10,448,950 B2 | 10/2019 | Shelton, IV et al. |
| 10,448,952 B2 | 10/2019 | Shelton, IV et al. |
| 10,456,122 B2 | 10/2019 | Koltz et al. |
| 10,456,132 B2 | 10/2019 | Gettinger et al. |
| 10,456,133 B2 | 10/2019 | Yates et al. |
| 10,456,137 B2 | 10/2019 | Vendely et al. |
| 10,456,140 B2 | 10/2019 | Shelton, IV et al. |
| D865,796 S | 11/2019 | Xu et al. |
| 10,463,367 B2 | 11/2019 | Kostrzewski et al. |
| 10,463,369 B2 | 11/2019 | Shelton, IV et al. |
| 10,463,370 B2 | 11/2019 | Yates et al. |
| 10,463,372 B2 | 11/2019 | Shelton, IV et al. |
| 10,463,373 B2 | 11/2019 | Mozdzierz et al. |
| 10,463,382 B2 | 11/2019 | Ingmanson et al. |
| 10,463,383 B2 | 11/2019 | Shelton, IV et al. |
| 10,463,384 B2 | 11/2019 | Shelton, IV et al. |
| 10,470,762 B2 | 11/2019 | Leimbach et al. |
| 10,470,763 B2 | 11/2019 | Yates et al. |
| 10,470,764 B2 | 11/2019 | Baxter, III et al. |
| 10,470,768 B2 | 11/2019 | Harris et al. |
| 10,470,769 B2 | 11/2019 | Shelton, IV et al. |
| 10,471,576 B2 | 11/2019 | Totsu |
| 10,471,607 B2 | 11/2019 | Butt et al. |
| 10,478,181 B2 | 11/2019 | Shelton, IV et al. |
| 10,478,182 B2 | 11/2019 | Taylor |
| 10,478,188 B2 | 11/2019 | Harris et al. |
| 10,478,189 B2 | 11/2019 | Bear et al. |
| 10,478,190 B2 | 11/2019 | Miller et al. |
| 10,478,207 B2 | 11/2019 | Lathrop |
| 10,485,536 B2 | 11/2019 | Ming et al. |
| 10,485,537 B2 | 11/2019 | Yates et al. |
| 10,485,539 B2 | 11/2019 | Shelton, IV et al. |
| 10,485,541 B2 | 11/2019 | Shelton, IV et al. |
| 10,485,542 B2 | 11/2019 | Shelton, IV et al. |
| 10,485,543 B2 | 11/2019 | Shelton, IV et al. |
| 10,485,546 B2 | 11/2019 | Shelton, IV et al. |
| 10,485,547 B2 | 11/2019 | Shelton, IV et al. |
| D869,655 S | 12/2019 | Shelton, IV et al. |
| D870,742 S | 12/2019 | Cornell |
| 10,492,783 B2 | 12/2019 | Shelton, IV et al. |
| 10,492,785 B2 | 12/2019 | Overmyer et al. |
| 10,492,787 B2 | 12/2019 | Smith et al. |

(56) References Cited

U.S. PATENT DOCUMENTS

| | | |
|---|---|---|
| 10,492,814 B2 | 12/2019 | Snow et al. |
| 10,492,847 B2 | 12/2019 | Godara et al. |
| 10,492,851 B2 | 12/2019 | Hughett, Sr. et al. |
| 10,498,269 B2 | 12/2019 | Zemlok et al. |
| 10,499,890 B2 | 12/2019 | Shelton, IV et al. |
| 10,499,914 B2 | 12/2019 | Huang et al. |
| 10,499,918 B2 | 12/2019 | Schellin et al. |
| 10,500,309 B2 | 12/2019 | Shah et al. |
| 10,512,461 B2 | 12/2019 | Gupta et al. |
| 10,517,590 B2 | 12/2019 | Giordano et al. |
| 10,517,594 B2 | 12/2019 | Shelton, IV et al. |
| 10,517,595 B2 | 12/2019 | Hunter et al. |
| 10,517,596 B2 | 12/2019 | Hunter et al. |
| 10,517,599 B2 | 12/2019 | Baxter, III et al. |
| 10,517,682 B2 | 12/2019 | Giordano et al. |
| 10,524,784 B2 | 1/2020 | Kostrzewski |
| 10,524,787 B2 | 1/2020 | Shelton, IV et al. |
| 10,524,788 B2 | 1/2020 | Vendely et al. |
| 10,524,789 B2 | 1/2020 | Swayze et al. |
| 10,524,790 B2 | 1/2020 | Shelton, IV et al. |
| 10,524,795 B2 | 1/2020 | Nalagatla et al. |
| 10,531,874 B2 | 1/2020 | Morgan et al. |
| 10,531,887 B2 | 1/2020 | Shelton, IV et al. |
| 10,537,324 B2 | 1/2020 | Shelton, IV et al. |
| 10,537,325 B2 | 1/2020 | Bakos et al. |
| 10,542,908 B2 | 1/2020 | Mei et al. |
| 10,542,974 B2 | 1/2020 | Yates et al. |
| 10,542,978 B2 | 1/2020 | Chowaniec et al. |
| 10,542,979 B2 | 1/2020 | Shelton, IV et al. |
| 10,542,982 B2 | 1/2020 | Beckman et al. |
| 10,542,985 B2 | 1/2020 | Zhan et al. |
| 10,542,988 B2 | 1/2020 | Schellin et al. |
| 10,542,991 B2 | 1/2020 | Shelton, IV et al. |
| 10,548,504 B2 | 2/2020 | Shelton, IV et al. |
| 10,548,600 B2 | 2/2020 | Shelton, IV et al. |
| 10,548,673 B2 | 2/2020 | Harris et al. |
| 10,561,418 B2 | 2/2020 | Richard et al. |
| 10,561,420 B2 | 2/2020 | Harris et al. |
| 10,561,422 B2 | 2/2020 | Schellin et al. |
| 10,561,432 B2 | 2/2020 | Estrella et al. |
| 10,561,474 B2 | 2/2020 | Adams et al. |
| 10,562,160 B2 | 2/2020 | Iwata et al. |
| 10,568,621 B2 | 2/2020 | Shelton, IV et al. |
| 10,568,624 B2 | 2/2020 | Shelton, IV et al. |
| 10,568,625 B2 | 2/2020 | Harris et al. |
| 10,568,626 B2 | 2/2020 | Shelton, IV et al. |
| 10,568,629 B2 | 2/2020 | Shelton, IV et al. |
| 10,568,632 B2 | 2/2020 | Miller et al. |
| 10,568,652 B2 | 2/2020 | Hess et al. |
| 10,569,071 B2 | 2/2020 | Harris et al. |
| 10,575,868 B2 | 3/2020 | Hall et al. |
| 10,580,320 B2 | 3/2020 | Kamiguchi et al. |
| 10,582,928 B2 | 3/2020 | Hunter et al. |
| 10,588,623 B2 | 3/2020 | Schmid et al. |
| 10,588,625 B2 | 3/2020 | Weaner et al. |
| 10,588,626 B2 | 3/2020 | Overmyer et al. |
| 10,588,629 B2 | 3/2020 | Malinouskas et al. |
| 10,588,630 B2 | 3/2020 | Shelton, IV et al. |
| 10,588,631 B2 | 3/2020 | Shelton, IV et al. |
| 10,588,632 B2 | 3/2020 | Shelton, IV et al. |
| 10,588,633 B2 | 3/2020 | Shelton, IV et al. |
| 2001/0000531 A1 | 4/2001 | Casscells et al. |
| 2001/0025183 A1 | 9/2001 | Shahidi |
| 2001/0025184 A1 | 9/2001 | Messerly |
| 2001/0034530 A1 | 10/2001 | Malackowski et al. |
| 2002/0014510 A1 | 2/2002 | Richter et al. |
| 2002/0022810 A1 | 2/2002 | Urich |
| 2002/0022836 A1 | 2/2002 | Goble et al. |
| 2002/0022861 A1 | 2/2002 | Jacobs et al. |
| 2002/0029032 A1 | 3/2002 | Arkin |
| 2002/0029036 A1 | 3/2002 | Goble et al. |
| 2002/0042620 A1 | 4/2002 | Julian et al. |
| 2002/0087048 A1 | 7/2002 | Brock et al. |
| 2002/0091374 A1 | 7/2002 | Cooper |
| 2002/0095175 A1 | 7/2002 | Brock et al. |
| 2002/0103494 A1 | 8/2002 | Pacey |
| 2002/0116063 A1 | 8/2002 | Giannetti et al. |
| 2002/0117534 A1 | 8/2002 | Green et al. |
| 2002/0127265 A1 | 9/2002 | Bowman et al. |
| 2002/0128633 A1 | 9/2002 | Brock et al. |
| 2002/0134811 A1 | 9/2002 | Napier et al. |
| 2002/0135474 A1 | 9/2002 | Sylliassen |
| 2002/0143340 A1 | 10/2002 | Kaneko |
| 2002/0151770 A1 | 10/2002 | Noll et al. |
| 2002/0158593 A1 | 10/2002 | Henderson et al. |
| 2002/0185514 A1 | 12/2002 | Adams et al. |
| 2002/0188170 A1 | 12/2002 | Santamore et al. |
| 2002/0188287 A1 | 12/2002 | Zvuloni et al. |
| 2003/0009193 A1 | 1/2003 | Corsaro |
| 2003/0011245 A1 | 1/2003 | Fiebig |
| 2003/0012805 A1 | 1/2003 | Chen et al. |
| 2003/0040670 A1 | 2/2003 | Govari |
| 2003/0045835 A1 | 3/2003 | Anderson et al. |
| 2003/0066858 A1 | 4/2003 | Holgersson |
| 2003/0078647 A1 | 4/2003 | Vallana et al. |
| 2003/0083648 A1 | 5/2003 | Wang et al. |
| 2003/0084983 A1 | 5/2003 | Rangachari et al. |
| 2003/0093103 A1 | 5/2003 | Malackowski et al. |
| 2003/0094356 A1 | 5/2003 | Waldron |
| 2003/0096158 A1 | 5/2003 | Takano et al. |
| 2003/0114851 A1 | 6/2003 | Truckai et al. |
| 2003/0121586 A1 | 7/2003 | Mitra et al. |
| 2003/0139741 A1 | 7/2003 | Goble et al. |
| 2003/0149406 A1 | 8/2003 | Martineau et al. |
| 2003/0153908 A1 | 8/2003 | Goble et al. |
| 2003/0153968 A1 | 8/2003 | Geis et al. |
| 2003/0163085 A1 | 8/2003 | Tanner et al. |
| 2003/0164172 A1 | 9/2003 | Chumas et al. |
| 2003/0181900 A1 | 9/2003 | Long |
| 2003/0190584 A1 | 10/2003 | Heasley |
| 2003/0195387 A1 | 10/2003 | Kortenbach et al. |
| 2003/0205029 A1 | 11/2003 | Chapolini et al. |
| 2003/0212005 A1 | 11/2003 | Petito et al. |
| 2003/0216732 A1 | 11/2003 | Truckai et al. |
| 2003/0236505 A1 | 12/2003 | Bonadio et al. |
| 2004/0006335 A1 | 1/2004 | Garrison |
| 2004/0006340 A1 | 1/2004 | Latterell et al. |
| 2004/0007608 A1 | 1/2004 | Ehrenfels et al. |
| 2004/0024457 A1 | 2/2004 | Boyce et al. |
| 2004/0028502 A1 | 2/2004 | Cummins |
| 2004/0030333 A1 | 2/2004 | Goble |
| 2004/0034357 A1 | 2/2004 | Beane et al. |
| 2004/0044295 A1 | 3/2004 | Reinert et al. |
| 2004/0044364 A1 | 3/2004 | DeVries et al. |
| 2004/0049121 A1 | 3/2004 | Yaron |
| 2004/0049172 A1 | 3/2004 | Root et al. |
| 2004/0059362 A1 | 3/2004 | Knodel et al. |
| 2004/0068161 A1 | 4/2004 | Couvillon |
| 2004/0068224 A1 | 4/2004 | Couvillon et al. |
| 2004/0068307 A1 | 4/2004 | Goble |
| 2004/0070369 A1 | 4/2004 | Sakakibara |
| 2004/0073222 A1 | 4/2004 | Koseki |
| 2004/0078037 A1 | 4/2004 | Batchelor et al. |
| 2004/0082952 A1 | 4/2004 | Dycus et al. |
| 2004/0085180 A1 | 5/2004 | Juang |
| 2004/0092992 A1 | 5/2004 | Adams et al. |
| 2004/0093024 A1 | 5/2004 | Lousararian et al. |
| 2004/0098040 A1 | 5/2004 | Taniguchi et al. |
| 2004/0101822 A1 | 5/2004 | Wiesner et al. |
| 2004/0102783 A1 | 5/2004 | Sutterlin et al. |
| 2004/0108357 A1 | 6/2004 | Milliman et al. |
| 2004/0110439 A1 | 6/2004 | Chaikof et al. |
| 2004/0115022 A1 | 6/2004 | Albertson et al. |
| 2004/0116952 A1 | 6/2004 | Sakurai et al. |
| 2004/0119185 A1 | 6/2004 | Chen |
| 2004/0122419 A1 | 6/2004 | Neuberger |
| 2004/0122423 A1 | 6/2004 | Dycus et al. |
| 2004/0133095 A1 | 7/2004 | Dunki-Jacobs et al. |
| 2004/0133189 A1 | 7/2004 | Sakurai |
| 2004/0143297 A1 | 7/2004 | Ramsey |
| 2004/0147909 A1 | 7/2004 | Johnston et al. |
| 2004/0153100 A1 | 8/2004 | Ahlberg et al. |
| 2004/0158261 A1 | 8/2004 | Vu |
| 2004/0164123 A1 | 8/2004 | Racenet et al. |

(56) References Cited

U.S. PATENT DOCUMENTS

| | | |
|---|---|---|
| 2004/0166169 A1 | 8/2004 | Malaviya et al. |
| 2004/0167572 A1 | 8/2004 | Roth et al. |
| 2004/0181219 A1 | 9/2004 | Goble et al. |
| 2004/0193189 A1 | 9/2004 | Kortenbach et al. |
| 2004/0197367 A1 | 10/2004 | Rezania et al. |
| 2004/0199181 A1 | 10/2004 | Knodel et al. |
| 2004/0204735 A1 | 10/2004 | Shiroff et al. |
| 2004/0218451 A1 | 11/2004 | Said et al. |
| 2004/0222268 A1 | 11/2004 | Bilotti et al. |
| 2004/0225186 A1 | 11/2004 | Horne et al. |
| 2004/0232201 A1 | 11/2004 | Wenchell et al. |
| 2004/0236352 A1 | 11/2004 | Wang et al. |
| 2004/0243147 A1 | 12/2004 | Lipow |
| 2004/0243151 A1 | 12/2004 | Demmy et al. |
| 2004/0243163 A1 | 12/2004 | Casiano et al. |
| 2004/0247415 A1 | 12/2004 | Mangone |
| 2004/0249366 A1 | 12/2004 | Kunz |
| 2004/0254455 A1 | 12/2004 | Iddan |
| 2004/0254566 A1 | 12/2004 | Plicchi et al. |
| 2004/0254590 A1 | 12/2004 | Hoffman et al. |
| 2004/0260315 A1 | 12/2004 | Dell et al. |
| 2004/0267310 A1 | 12/2004 | Racenet et al. |
| 2005/0010158 A1 | 1/2005 | Brugger et al. |
| 2005/0010213 A1 | 1/2005 | Stad et al. |
| 2005/0021078 A1 | 1/2005 | Vleugels et al. |
| 2005/0032511 A1 | 2/2005 | Malone et al. |
| 2005/0033352 A1 | 2/2005 | Zepf et al. |
| 2005/0051163 A1 | 3/2005 | Deem et al. |
| 2005/0054946 A1 | 3/2005 | Krzyzanowski |
| 2005/0057225 A1 | 3/2005 | Marquet |
| 2005/0058890 A1 | 3/2005 | Brazell et al. |
| 2005/0059997 A1 | 3/2005 | Bauman et al. |
| 2005/0070929 A1 | 3/2005 | Dalessandro et al. |
| 2005/0075561 A1 | 4/2005 | Golden |
| 2005/0080342 A1 | 4/2005 | Gilreath et al. |
| 2005/0085693 A1 | 4/2005 | Belson et al. |
| 2005/0090817 A1 | 4/2005 | Phan |
| 2005/0096683 A1 | 5/2005 | Ellins et al. |
| 2005/0116673 A1 | 6/2005 | Carl et al. |
| 2005/0124855 A1 | 6/2005 | Jaffe et al. |
| 2005/0125897 A1 | 6/2005 | Wyslucha et al. |
| 2005/0130682 A1 | 6/2005 | Takara et al. |
| 2005/0131173 A1 | 6/2005 | McDaniel et al. |
| 2005/0131211 A1 | 6/2005 | Bayley et al. |
| 2005/0131390 A1 | 6/2005 | Heinrich et al. |
| 2005/0131436 A1 | 6/2005 | Johnston et al. |
| 2005/0131457 A1 | 6/2005 | Douglas et al. |
| 2005/0137454 A1 | 6/2005 | Saadat et al. |
| 2005/0137455 A1 | 6/2005 | Ewers et al. |
| 2005/0139636 A1 | 6/2005 | Schwemberger et al. |
| 2005/0143759 A1 | 6/2005 | Kelly |
| 2005/0143769 A1 | 6/2005 | White et al. |
| 2005/0145671 A1 | 7/2005 | Viola |
| 2005/0150928 A1 | 7/2005 | Kameyama et al. |
| 2005/0154258 A1 | 7/2005 | Tartaglia et al. |
| 2005/0154406 A1 | 7/2005 | Bombard et al. |
| 2005/0159778 A1 | 7/2005 | Heinrich et al. |
| 2005/0165419 A1 | 7/2005 | Sauer et al. |
| 2005/0169974 A1 | 8/2005 | Tenerz et al. |
| 2005/0171522 A1 | 8/2005 | Christopherson |
| 2005/0177176 A1 | 8/2005 | Gerbi et al. |
| 2005/0177181 A1 | 8/2005 | Kagan et al. |
| 2005/0177249 A1 | 8/2005 | Kladakis et al. |
| 2005/0182298 A1 | 8/2005 | Ikeda et al. |
| 2005/0182443 A1 | 8/2005 | Jonn et al. |
| 2005/0184121 A1 | 8/2005 | Heinrich |
| 2005/0186240 A1 | 8/2005 | Ringeisen et al. |
| 2005/0187545 A1 | 8/2005 | Hooven et al. |
| 2005/0203550 A1 | 9/2005 | Laufer et al. |
| 2005/0209614 A1 | 9/2005 | Fenter et al. |
| 2005/0216055 A1 | 9/2005 | Scirica et al. |
| 2005/0222587 A1 | 10/2005 | Jinno et al. |
| 2005/0222611 A1 | 10/2005 | Weitkamp |
| 2005/0222616 A1 | 10/2005 | Rethy et al. |
| 2005/0222665 A1 | 10/2005 | Aranyi |
| 2005/0228224 A1 | 10/2005 | Okada et al. |
| 2005/0228446 A1 | 10/2005 | Mooradian et al. |
| 2005/0230453 A1 | 10/2005 | Viola |
| 2005/0240178 A1 | 10/2005 | Morley et al. |
| 2005/0245965 A1 | 11/2005 | Orban, III et al. |
| 2005/0246881 A1 | 11/2005 | Kelly et al. |
| 2005/0251063 A1 | 11/2005 | Basude |
| 2005/0256452 A1 | 11/2005 | DeMarchi et al. |
| 2005/0261676 A1 | 11/2005 | Hall et al. |
| 2005/0263563 A1 | 12/2005 | Racenet et al. |
| 2005/0267455 A1 | 12/2005 | Eggers et al. |
| 2005/0274034 A1 | 12/2005 | Hayashida et al. |
| 2005/0283188 A1 | 12/2005 | Loshakove et al. |
| 2006/0008787 A1 | 1/2006 | Hayman et al. |
| 2006/0015009 A1 | 1/2006 | Jaffe et al. |
| 2006/0020258 A1 | 1/2006 | Strauss et al. |
| 2006/0020336 A1 | 1/2006 | Liddicoat |
| 2006/0025812 A1 | 2/2006 | Shelton |
| 2006/0041188 A1 | 2/2006 | Dirusso et al. |
| 2006/0047275 A1 | 3/2006 | Goble |
| 2006/0049229 A1 | 3/2006 | Milliman et al. |
| 2006/0052824 A1 | 3/2006 | Ransick et al. |
| 2006/0052825 A1 | 3/2006 | Ransick et al. |
| 2006/0064086 A1 | 3/2006 | Odom |
| 2006/0079735 A1 | 4/2006 | Martone et al. |
| 2006/0079879 A1 | 4/2006 | Faller et al. |
| 2006/0086032 A1 | 4/2006 | Valencic et al. |
| 2006/0087746 A1 | 4/2006 | Lipow |
| 2006/0089535 A1 | 4/2006 | Raz et al. |
| 2006/0097699 A1 | 5/2006 | Kamenoff |
| 2006/0100643 A1 | 5/2006 | Laufer et al. |
| 2006/0100649 A1 | 5/2006 | Hart |
| 2006/0111711 A1 | 5/2006 | Goble |
| 2006/0111723 A1 | 5/2006 | Chapolini et al. |
| 2006/0116634 A1 | 6/2006 | Shachar |
| 2006/0142772 A1 | 6/2006 | Ralph et al. |
| 2006/0154546 A1 | 7/2006 | Murphy et al. |
| 2006/0161050 A1 | 7/2006 | Butler et al. |
| 2006/0161185 A1 | 7/2006 | Saadat et al. |
| 2006/0167471 A1 | 7/2006 | Phillips |
| 2006/0173290 A1 | 8/2006 | Lavallee et al. |
| 2006/0173470 A1 | 8/2006 | Oray et al. |
| 2006/0176031 A1 | 8/2006 | Forman et al. |
| 2006/0178556 A1 | 8/2006 | Hasser et al. |
| 2006/0180633 A1 | 8/2006 | Emmons |
| 2006/0180634 A1 | 8/2006 | Shelton et al. |
| 2006/0185682 A1 | 8/2006 | Marczyk |
| 2006/0199999 A1 | 9/2006 | Ikeda et al. |
| 2006/0201989 A1 | 9/2006 | Ojeda |
| 2006/0206100 A1 | 9/2006 | Eskridge et al. |
| 2006/0217729 A1 | 9/2006 | Eskridge et al. |
| 2006/0235368 A1 | 10/2006 | Oz |
| 2006/0241666 A1 | 10/2006 | Briggs et al. |
| 2006/0244460 A1 | 11/2006 | Weaver |
| 2006/0252990 A1 | 11/2006 | Kubach |
| 2006/0252993 A1 | 11/2006 | Freed et al. |
| 2006/0258904 A1 | 11/2006 | Stefanchik et al. |
| 2006/0259073 A1 | 11/2006 | Miyamoto et al. |
| 2006/0261763 A1 | 11/2006 | Lott et al. |
| 2006/0263444 A1 | 11/2006 | Ming et al. |
| 2006/0264831 A1 | 11/2006 | Skwarek et al. |
| 2006/0264929 A1 | 11/2006 | Goble et al. |
| 2006/0271042 A1 | 11/2006 | Latterell et al. |
| 2006/0271102 A1 | 11/2006 | Bosshard et al. |
| 2006/0282064 A1 | 12/2006 | Shimizu et al. |
| 2006/0284730 A1 | 12/2006 | Schmid et al. |
| 2006/0287576 A1 | 12/2006 | Tsuji et al. |
| 2006/0289602 A1 | 12/2006 | Wales et al. |
| 2006/0291981 A1 | 12/2006 | Viola et al. |
| 2007/0009570 A1 | 1/2007 | Kim et al. |
| 2007/0010702 A1 | 1/2007 | Wang et al. |
| 2007/0010838 A1 | 1/2007 | Shelton et al. |
| 2007/0016235 A1 | 1/2007 | Tanaka et al. |
| 2007/0026039 A1 | 2/2007 | Drumheller et al. |
| 2007/0026040 A1 | 2/2007 | Crawley et al. |
| 2007/0027468 A1 | 2/2007 | Wales et al. |
| 2007/0027551 A1 | 2/2007 | Farnsworth et al. |
| 2007/0043387 A1 | 2/2007 | Vargas et al. |
| 2007/0049951 A1 | 3/2007 | Menn |

(56) References Cited

U.S. PATENT DOCUMENTS

| | | |
|---|---|---|
| 2007/0049966 A1 | 3/2007 | Bonadio et al. |
| 2007/0051375 A1 | 3/2007 | Milliman |
| 2007/0055228 A1 | 3/2007 | Berg et al. |
| 2007/0073341 A1 | 3/2007 | Smith et al. |
| 2007/0073389 A1 | 3/2007 | Bolduc et al. |
| 2007/0078328 A1 | 4/2007 | Ozaki et al. |
| 2007/0078484 A1 | 4/2007 | Talarico et al. |
| 2007/0084897 A1 | 4/2007 | Shelton et al. |
| 2007/0088376 A1 | 4/2007 | Zacharias |
| 2007/0090788 A1 | 4/2007 | Hansford et al. |
| 2007/0093869 A1 | 4/2007 | Bloom et al. |
| 2007/0102472 A1 | 5/2007 | Shelton |
| 2007/0106113 A1 | 5/2007 | Ravo |
| 2007/0106317 A1 | 5/2007 | Shelton et al. |
| 2007/0134251 A1 | 6/2007 | Ashkenazi et al. |
| 2007/0135686 A1 | 6/2007 | Pruitt et al. |
| 2007/0135803 A1 | 6/2007 | Belson |
| 2007/0152612 A1 | 7/2007 | Chen et al. |
| 2007/0155010 A1 | 7/2007 | Farnsworth et al. |
| 2007/0170225 A1 | 7/2007 | Shelton et al. |
| 2007/0173687 A1 | 7/2007 | Shima et al. |
| 2007/0173813 A1 | 7/2007 | Odom |
| 2007/0175950 A1 | 8/2007 | Shelton et al. |
| 2007/0175951 A1 | 8/2007 | Shelton et al. |
| 2007/0175955 A1 | 8/2007 | Shelton et al. |
| 2007/0179476 A1* | 8/2007 | Shelton, IV ..... A61B 17/07207 606/1 |
| 2007/0179477 A1 | 8/2007 | Danger |
| 2007/0185545 A1 | 8/2007 | Duke |
| 2007/0187857 A1 | 8/2007 | Riley et al. |
| 2007/0190110 A1 | 8/2007 | Pameijer et al. |
| 2007/0191868 A1 | 8/2007 | Theroux et al. |
| 2007/0194079 A1 | 8/2007 | Hueil et al. |
| 2007/0194082 A1 | 8/2007 | Morgan et al. |
| 2007/0197954 A1 | 8/2007 | Keenan |
| 2007/0198039 A1 | 8/2007 | Jones et al. |
| 2007/0203510 A1 | 8/2007 | Bettuchi |
| 2007/0207010 A1 | 9/2007 | Caspi |
| 2007/0208359 A1 | 9/2007 | Hoffman |
| 2007/0208375 A1 | 9/2007 | Nishizawa et al. |
| 2007/0213750 A1 | 9/2007 | Weadock |
| 2007/0225562 A1 | 9/2007 | Spivey et al. |
| 2007/0233163 A1 | 10/2007 | Bombard et al. |
| 2007/0243227 A1 | 10/2007 | Gertner |
| 2007/0244471 A1 | 10/2007 | Malackowski |
| 2007/0246505 A1 | 10/2007 | Pace-Floridia et al. |
| 2007/0262592 A1 | 11/2007 | Hwang et al. |
| 2007/0275035 A1 | 11/2007 | Herman et al. |
| 2007/0276409 A1 | 11/2007 | Ortiz et al. |
| 2007/0279011 A1 | 12/2007 | Jones et al. |
| 2007/0286892 A1 | 12/2007 | Herzberg et al. |
| 2007/0296286 A1 | 12/2007 | Avenell |
| 2008/0003196 A1 | 1/2008 | Jonn et al. |
| 2008/0015598 A1 | 1/2008 | Prommersberger |
| 2008/0021486 A1 | 1/2008 | Oyola et al. |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0030170 A1 | 2/2008 | Dacquay et al. |
| 2008/0039746 A1 | 2/2008 | Hissong et al. |
| 2008/0042861 A1 | 2/2008 | Dacquay et al. |
| 2008/0051833 A1 | 2/2008 | Gramuglia et al. |
| 2008/0064921 A1 | 3/2008 | Larkin et al. |
| 2008/0065153 A1 | 3/2008 | Allard et al. |
| 2008/0071328 A1 | 3/2008 | Haubrich et al. |
| 2008/0077158 A1 | 3/2008 | Haider et al. |
| 2008/0078802 A1 | 4/2008 | Hess et al. |
| 2008/0082114 A1 | 4/2008 | McKenna et al. |
| 2008/0082125 A1 | 4/2008 | Murray et al. |
| 2008/0082126 A1 | 4/2008 | Murray et al. |
| 2008/0083807 A1 | 4/2008 | Beardsley et al. |
| 2008/0085296 A1 | 4/2008 | Powell et al. |
| 2008/0086078 A1 | 4/2008 | Powell et al. |
| 2008/0091072 A1 | 4/2008 | Omori et al. |
| 2008/0108443 A1 | 5/2008 | Jinno et al. |
| 2008/0114250 A1 | 5/2008 | Urbano et al. |
| 2008/0125634 A1 | 5/2008 | Ryan et al. |
| 2008/0125749 A1 | 5/2008 | Olson |
| 2008/0128469 A1 | 6/2008 | Dalessandro et al. |
| 2008/0129253 A1 | 6/2008 | Shiue et al. |
| 2008/0135600 A1 | 6/2008 | Hiranuma et al. |
| 2008/0140115 A1 | 6/2008 | Stopek |
| 2008/0140159 A1 | 6/2008 | Bornhoft et al. |
| 2008/0154299 A1 | 6/2008 | Livneh |
| 2008/0154335 A1 | 6/2008 | Thrope et al. |
| 2008/0169328 A1 | 7/2008 | Shelton |
| 2008/0169332 A1 | 7/2008 | Shelton et al. |
| 2008/0169333 A1 | 7/2008 | Shelton et al. |
| 2008/0172087 A1 | 7/2008 | Fuchs et al. |
| 2008/0177392 A1 | 7/2008 | Williams et al. |
| 2008/0190989 A1 | 8/2008 | Crews et al. |
| 2008/0196253 A1 | 8/2008 | Ezra et al. |
| 2008/0196419 A1 | 8/2008 | Dube |
| 2008/0197167 A1 | 8/2008 | Viola et al. |
| 2008/0200755 A1 | 8/2008 | Bakos |
| 2008/0200762 A1 | 8/2008 | Stokes et al. |
| 2008/0200835 A1 | 8/2008 | Monson et al. |
| 2008/0200911 A1 | 8/2008 | Long |
| 2008/0200933 A1 | 8/2008 | Bakos et al. |
| 2008/0200934 A1 | 8/2008 | Fox |
| 2008/0206186 A1 | 8/2008 | Butler et al. |
| 2008/0234709 A1 | 9/2008 | Houser |
| 2008/0242939 A1 | 10/2008 | Johnston |
| 2008/0249536 A1 | 10/2008 | Stahler et al. |
| 2008/0249608 A1 | 10/2008 | Dave |
| 2008/0255413 A1 | 10/2008 | Zemlok et al. |
| 2008/0262654 A1 | 10/2008 | Omori et al. |
| 2008/0269596 A1 | 10/2008 | Revie et al. |
| 2008/0281171 A1 | 11/2008 | Fennell et al. |
| 2008/0287944 A1 | 11/2008 | Pearson et al. |
| 2008/0293910 A1 | 11/2008 | Kapiamba et al. |
| 2008/0294179 A1 | 11/2008 | Balbierz et al. |
| 2008/0296346 A1 | 12/2008 | Shelton, IV et al. |
| 2008/0297287 A1 | 12/2008 | Shachar et al. |
| 2008/0308602 A1 | 12/2008 | Timm et al. |
| 2008/0308603 A1 | 12/2008 | Shelton et al. |
| 2008/0308607 A1* | 12/2008 | Timm ............... A61B 17/07207 227/176.1 |
| 2008/0312686 A1 | 12/2008 | Ellingwood |
| 2008/0312687 A1 | 12/2008 | Blier |
| 2008/0315829 A1 | 12/2008 | Jones et al. |
| 2009/0001121 A1 | 1/2009 | Hess et al. |
| 2009/0001130 A1 | 1/2009 | Hess et al. |
| 2009/0004455 A1 | 1/2009 | Gravagna et al. |
| 2009/0005809 A1 | 1/2009 | Hess et al. |
| 2009/0012534 A1 | 1/2009 | Madhani et al. |
| 2009/0015195 A1 | 1/2009 | Loth-Krausser |
| 2009/0020958 A1 | 1/2009 | Soul |
| 2009/0048583 A1 | 2/2009 | Williams et al. |
| 2009/0048589 A1 | 2/2009 | Takashino et al. |
| 2009/0076506 A1 | 3/2009 | Baker |
| 2009/0078736 A1 | 3/2009 | Van Lue |
| 2009/0081313 A1 | 3/2009 | Aghion et al. |
| 2009/0088659 A1 | 4/2009 | Graham et al. |
| 2009/0090763 A1 | 4/2009 | Zemlok et al. |
| 2009/0099579 A1 | 4/2009 | Nentwick et al. |
| 2009/0099876 A1 | 4/2009 | Whitman |
| 2009/0112234 A1 | 4/2009 | Crainich et al. |
| 2009/0118762 A1 | 5/2009 | Crainch et al. |
| 2009/0119011 A1 | 5/2009 | Kondo et al. |
| 2009/0131819 A1 | 5/2009 | Ritchie et al. |
| 2009/0132400 A1 | 5/2009 | Conway |
| 2009/0143855 A1 | 6/2009 | Weber et al. |
| 2009/0149871 A9 | 6/2009 | Kagan et al. |
| 2009/0171147 A1 | 7/2009 | Lee et al. |
| 2009/0177226 A1 | 7/2009 | Reinprecht et al. |
| 2009/0181290 A1 | 7/2009 | Baldwin et al. |
| 2009/0188964 A1 | 7/2009 | Orlov |
| 2009/0192534 A1 | 7/2009 | Ortiz et al. |
| 2009/0198272 A1 | 8/2009 | Kerver et al. |
| 2009/0204108 A1 | 8/2009 | Steffen |
| 2009/0204109 A1 | 8/2009 | Grove et al. |
| 2009/0206125 A1 | 8/2009 | Huitema et al. |

(56) References Cited

U.S. PATENT DOCUMENTS

| | | |
|---|---|---|
| 2009/0206126 A1 | 8/2009 | Huitema et al. |
| 2009/0206131 A1 | 8/2009 | Weisenburgh, II et al. |
| 2009/0206133 A1 | 8/2009 | Morgan et al. |
| 2009/0206137 A1 | 8/2009 | Hall et al. |
| 2009/0206139 A1 | 8/2009 | Hall et al. |
| 2009/0206141 A1 | 8/2009 | Huitema et al. |
| 2009/0206142 A1 | 8/2009 | Huitema et al. |
| 2009/0221993 A1 | 9/2009 | Sohi et al. |
| 2009/0227834 A1 | 9/2009 | Nakamoto et al. |
| 2009/0234273 A1 | 9/2009 | Intoccia et al. |
| 2009/0242610 A1 | 10/2009 | Shelton, IV et al. |
| 2009/0246873 A1 | 10/2009 | Yamamoto et al. |
| 2009/0247368 A1 | 10/2009 | Chiang |
| 2009/0247901 A1 | 10/2009 | Zimmer |
| 2009/0253959 A1 | 10/2009 | Yoshie et al. |
| 2009/0255974 A1 | 10/2009 | Viola |
| 2009/0262078 A1 | 10/2009 | Pizzi |
| 2009/0270895 A1 | 10/2009 | Churchill et al. |
| 2009/0278406 A1 | 11/2009 | Hoffman |
| 2009/0290016 A1 | 11/2009 | Suda |
| 2009/0292283 A1 | 11/2009 | Odom |
| 2009/0306639 A1 | 12/2009 | Nevo et al. |
| 2009/0308907 A1 | 12/2009 | Nalagatla et al. |
| 2009/0318557 A1 | 12/2009 | Stockel |
| 2009/0325859 A1 | 12/2009 | Ameer et al. |
| 2010/0005035 A1 | 1/2010 | Carpenter et al. |
| 2010/0012703 A1 | 1/2010 | Calabrese et al. |
| 2010/0015104 A1 | 1/2010 | Fraser et al. |
| 2010/0016888 A1 | 1/2010 | Calabrese et al. |
| 2010/0017715 A1 | 1/2010 | Balassanian |
| 2010/0023024 A1 | 1/2010 | Zeiner et al. |
| 2010/0030233 A1 | 2/2010 | Whitman et al. |
| 2010/0036370 A1 | 2/2010 | Mirel et al. |
| 2010/0051668 A1 | 3/2010 | Milliman et al. |
| 2010/0057118 A1 | 3/2010 | Dietz et al. |
| 2010/0065604 A1 | 3/2010 | Weng |
| 2010/0069942 A1 | 3/2010 | Shelton, IV |
| 2010/0076483 A1 | 3/2010 | Imuta |
| 2010/0076489 A1 | 3/2010 | Stopek et al. |
| 2010/0081883 A1 | 4/2010 | Murray et al. |
| 2010/0093568 A1* | 4/2010 | Tagawa ............... C10M 101/02 508/133 |
| 2010/0094340 A1 | 4/2010 | Stopek et al. |
| 2010/0100123 A1 | 4/2010 | Bennett |
| 2010/0100124 A1 | 4/2010 | Calabrese et al. |
| 2010/0116519 A1 | 5/2010 | Gareis |
| 2010/0122339 A1 | 5/2010 | Boccacci |
| 2010/0133317 A1 | 6/2010 | Shelton, IV et al. |
| 2010/0137990 A1 | 6/2010 | Apatsidis et al. |
| 2010/0145146 A1 | 6/2010 | Melder |
| 2010/0147921 A1 | 6/2010 | Olson |
| 2010/0147922 A1 | 6/2010 | Olson |
| 2010/0179022 A1 | 7/2010 | Shirokoshi |
| 2010/0180711 A1 | 7/2010 | Kilibarda et al. |
| 2010/0191262 A1 | 7/2010 | Harris et al. |
| 2010/0191292 A1 | 7/2010 | DeMeo et al. |
| 2010/0193566 A1 | 8/2010 | Scheib et al. |
| 2010/0204717 A1 | 8/2010 | Knodel |
| 2010/0204721 A1 | 8/2010 | Young et al. |
| 2010/0217281 A1 | 8/2010 | Matsuoka et al. |
| 2010/0222901 A1 | 9/2010 | Swayze et al. |
| 2010/0228250 A1 | 9/2010 | Brogna |
| 2010/0241137 A1 | 9/2010 | Doyle et al. |
| 2010/0249497 A1 | 9/2010 | Peine et al. |
| 2010/0249947 A1 | 9/2010 | Lesh et al. |
| 2010/0256675 A1 | 10/2010 | Romans |
| 2010/0258327 A1 | 10/2010 | Esenwein et al. |
| 2010/0267662 A1 | 10/2010 | Fielder et al. |
| 2010/0274160 A1 | 10/2010 | Yachi et al. |
| 2010/0292540 A1 | 11/2010 | Hess et al. |
| 2010/0298636 A1 | 11/2010 | Castro et al. |
| 2010/0301097 A1 | 12/2010 | Scirica et al. |
| 2010/0310623 A1 | 12/2010 | Laurencin et al. |
| 2010/0312261 A1 | 12/2010 | Suzuki et al. |
| 2010/0318085 A1 | 12/2010 | Austin et al. |
| 2010/0331856 A1 | 12/2010 | Carlson et al. |
| 2011/0006101 A1 | 1/2011 | Hall et al. |
| 2011/0011916 A1 | 1/2011 | Levine |
| 2011/0016960 A1 | 1/2011 | Debrailly |
| 2011/0021871 A1 | 1/2011 | Berkelaar |
| 2011/0022032 A1 | 1/2011 | Zemlok et al. |
| 2011/0024477 A1 | 2/2011 | Hall |
| 2011/0024478 A1 | 2/2011 | Shelton, IV |
| 2011/0025311 A1 | 2/2011 | Chauvin et al. |
| 2011/0036891 A1 | 2/2011 | Zemlok et al. |
| 2011/0046667 A1 | 2/2011 | Culligan et al. |
| 2011/0052660 A1 | 3/2011 | Yang et al. |
| 2011/0060363 A1 | 3/2011 | Hess et al. |
| 2011/0066156 A1 | 3/2011 | McGahan et al. |
| 2011/0082538 A1 | 4/2011 | Dahlgren et al. |
| 2011/0087276 A1 | 4/2011 | Bedi et al. |
| 2011/0088921 A1 | 4/2011 | Forgues et al. |
| 2011/0091515 A1 | 4/2011 | Zilberman et al. |
| 2011/0095064 A1 | 4/2011 | Taylor et al. |
| 2011/0101069 A1 | 5/2011 | Bombard et al. |
| 2011/0101794 A1 | 5/2011 | Schroeder et al. |
| 2011/0112517 A1 | 5/2011 | Peine et al. |
| 2011/0112530 A1 | 5/2011 | Keller |
| 2011/0114697 A1 | 5/2011 | Baxter, III et al. |
| 2011/0125149 A1 | 5/2011 | El-Galley et al. |
| 2011/0125176 A1 | 5/2011 | Yates et al. |
| 2011/0127945 A1 | 6/2011 | Yoneda |
| 2011/0129706 A1 | 6/2011 | Takahashi et al. |
| 2011/0144764 A1 | 6/2011 | Bagga et al. |
| 2011/0147433 A1 | 6/2011 | Shelton, IV et al. |
| 2011/0160725 A1 | 6/2011 | Kabaya et al. |
| 2011/0163146 A1 | 7/2011 | Ortiz et al. |
| 2011/0172495 A1 | 7/2011 | Armstrong |
| 2011/0174861 A1 | 7/2011 | Shelton, IV et al. |
| 2011/0192882 A1 | 8/2011 | Hess et al. |
| 2011/0199225 A1 | 8/2011 | Touchberry et al. |
| 2011/0218400 A1 | 9/2011 | Ma et al. |
| 2011/0218550 A1 | 9/2011 | Ma |
| 2011/0225105 A1 | 9/2011 | Scholer et al. |
| 2011/0230713 A1 | 9/2011 | Kleemann et al. |
| 2011/0230875 A1* | 9/2011 | Walberg ................ A61B 17/29 606/33 |
| 2011/0238044 A1 | 9/2011 | Main et al. |
| 2011/0241597 A1 | 10/2011 | Zhu et al. |
| 2011/0271186 A1 | 11/2011 | Owens |
| 2011/0275901 A1 | 11/2011 | Shelton, IV |
| 2011/0276083 A1 | 11/2011 | Shelton, IV et al. |
| 2011/0278343 A1 | 11/2011 | Knodel et al. |
| 2011/0279268 A1 | 11/2011 | Konishi et al. |
| 2011/0290856 A1 | 12/2011 | Shelton, IV et al. |
| 2011/0293690 A1 | 12/2011 | Griffin et al. |
| 2011/0295295 A1 | 12/2011 | Shelton, IV et al. |
| 2011/0313894 A1 | 12/2011 | Dye et al. |
| 2011/0315413 A1 | 12/2011 | Fisher et al. |
| 2012/0004636 A1 | 1/2012 | Lo |
| 2012/0007442 A1 | 1/2012 | Rhodes et al. |
| 2012/0016239 A1 | 1/2012 | Barthe et al. |
| 2012/0016413 A1 | 1/2012 | Timm et al. |
| 2012/0016467 A1 | 1/2012 | Chen et al. |
| 2012/0029272 A1 | 2/2012 | Shelton, IV et al. |
| 2012/0033360 A1 | 2/2012 | Hsu |
| 2012/0059286 A1 | 3/2012 | Hastings et al. |
| 2012/0064483 A1 | 3/2012 | Lint et al. |
| 2012/0074200 A1 | 3/2012 | Schmid et al. |
| 2012/0078244 A1* | 3/2012 | Worrell ............ A61B 17/07207 606/33 |
| 2012/0080336 A1 | 4/2012 | Shelton, IV et al. |
| 2012/0080344 A1 | 4/2012 | Shelton, IV |
| 2012/0080478 A1 | 4/2012 | Morgan et al. |
| 2012/0080498 A1 | 4/2012 | Shelton, IV et al. |
| 2012/0086276 A1 | 4/2012 | Sawyers |
| 2012/0095458 A1 | 4/2012 | Cybulski et al. |
| 2012/0109186 A1 | 5/2012 | Parrott et al. |
| 2012/0116261 A1 | 5/2012 | Mumaw et al. |
| 2012/0116262 A1 | 5/2012 | Houser et al. |
| 2012/0116265 A1 | 5/2012 | Houser et al. |
| 2012/0116266 A1 | 5/2012 | Houser et al. |
| 2012/0116381 A1 | 5/2012 | Houser et al. |
| 2012/0118595 A1 | 5/2012 | Pellenc |

(56) References Cited

U.S. PATENT DOCUMENTS

| | | |
|---|---|---|
| 2012/0123463 A1 | 5/2012 | Jacobs |
| 2012/0125792 A1 | 5/2012 | Cassivi |
| 2012/0130217 A1 | 5/2012 | Kauphusman et al. |
| 2012/0132286 A1 | 5/2012 | Lim et al. |
| 2012/0171539 A1 | 7/2012 | Rejman et al. |
| 2012/0175398 A1 | 7/2012 | Sandborn et al. |
| 2012/0197272 A1 | 8/2012 | Oray et al. |
| 2012/0211542 A1 | 8/2012 | Racenet |
| 2012/0234895 A1 | 9/2012 | O'Connor et al. |
| 2012/0234897 A1 | 9/2012 | Shelton, IV et al. |
| 2012/0239068 A1 | 9/2012 | Morris et al. |
| 2012/0248169 A1 | 10/2012 | Widenhouse et al. |
| 2012/0251861 A1 | 10/2012 | Liang et al. |
| 2012/0253328 A1 | 10/2012 | Cunningham et al. |
| 2012/0283707 A1 | 11/2012 | Giordano et al. |
| 2012/0289811 A1 | 11/2012 | Viola et al. |
| 2012/0289979 A1 | 11/2012 | Eskaros et al. |
| 2012/0292367 A1 | 11/2012 | Morgan et al. |
| 2012/0298722 A1 | 11/2012 | Hess et al. |
| 2013/0006227 A1 | 1/2013 | Takashino |
| 2013/0008937 A1 | 1/2013 | Viola |
| 2013/0012983 A1 | 1/2013 | Kleyman |
| 2013/0018400 A1 | 1/2013 | Milton et al. |
| 2013/0020375 A1 | 1/2013 | Shelton, IV et al. |
| 2013/0020376 A1 | 1/2013 | Shelton, IV et al. |
| 2013/0023861 A1 | 1/2013 | Shelton, IV et al. |
| 2013/0023910 A1 | 1/2013 | Solomon et al. |
| 2013/0026208 A1 | 1/2013 | Shelton, IV et al. |
| 2013/0026210 A1 | 1/2013 | Shelton, IV et al. |
| 2013/0030462 A1 | 1/2013 | Keating et al. |
| 2013/0041292 A1 | 2/2013 | Cunningham |
| 2013/0057162 A1 | 3/2013 | Pollischansky |
| 2013/0068816 A1 | 3/2013 | Mandakolathur Vasudevan et al. |
| 2013/0087597 A1 | 4/2013 | Shelton, IV et al. |
| 2013/0090534 A1 | 4/2013 | Burns et al. |
| 2013/0096568 A1 | 4/2013 | Justis |
| 2013/0098970 A1 | 4/2013 | Racenet et al. |
| 2013/0105552 A1 | 5/2013 | Weir et al. |
| 2013/0106352 A1 | 5/2013 | Nagamine |
| 2013/0116669 A1 | 5/2013 | Shelton, IV et al. |
| 2013/0123816 A1 | 5/2013 | Hodgkinson et al. |
| 2013/0126202 A1 | 5/2013 | Oomori et al. |
| 2013/0131476 A1 | 5/2013 | Siu et al. |
| 2013/0131651 A1 | 5/2013 | Strobl et al. |
| 2013/0136969 A1 | 5/2013 | Yasui et al. |
| 2013/0153641 A1 | 6/2013 | Shelton, IV et al. |
| 2013/0158390 A1 | 6/2013 | Tan et al. |
| 2013/0162198 A1 | 6/2013 | Yokota et al. |
| 2013/0169217 A1 | 7/2013 | Watanabe et al. |
| 2013/0172878 A1 | 7/2013 | Smith |
| 2013/0175317 A1 | 7/2013 | Yates et al. |
| 2013/0211244 A1 | 8/2013 | Nathaniel |
| 2013/0214025 A1 | 8/2013 | Zemlok et al. |
| 2013/0233906 A1 | 9/2013 | Hess et al. |
| 2013/0238021 A1 | 9/2013 | Gross et al. |
| 2013/0248578 A1 | 9/2013 | Arteaga Gonzalez |
| 2013/0253480 A1 | 9/2013 | Kimball et al. |
| 2013/0256373 A1 | 10/2013 | Schmid et al. |
| 2013/0256380 A1 | 10/2013 | Schmid et al. |
| 2013/0267978 A1 | 10/2013 | Trissel |
| 2013/0270322 A1 | 10/2013 | Scheib et al. |
| 2013/0277410 A1 | 10/2013 | Fernandez et al. |
| 2013/0306704 A1 | 11/2013 | Balbierz et al. |
| 2013/0317753 A1 | 11/2013 | Kamen et al. |
| 2013/0327552 A1 | 12/2013 | Lovelass et al. |
| 2013/0333910 A1 | 12/2013 | Tanimoto et al. |
| 2013/0334280 A1 | 12/2013 | Krehel et al. |
| 2013/0334283 A1 | 12/2013 | Swayze et al. |
| 2013/0334285 A1 | 12/2013 | Swayze et al. |
| 2013/0341374 A1 | 12/2013 | Shelton, IV et al. |
| 2014/0001231 A1 | 1/2014 | Shelton, IV et al. |
| 2014/0001234 A1 | 1/2014 | Shelton, IV et al. |
| 2014/0005640 A1 | 1/2014 | Shelton, IV et al. |
| 2014/0005678 A1 | 1/2014 | Shelton, IV et al. |
| 2014/0005702 A1 | 1/2014 | Timm et al. |
| 2014/0005718 A1 | 1/2014 | Shelton, IV et al. |
| 2014/0012299 A1 | 1/2014 | Stoddard et al. |
| 2014/0014705 A1 | 1/2014 | Baxter, III |
| 2014/0014707 A1 | 1/2014 | Onukuri et al. |
| 2014/0018832 A1 | 1/2014 | Shelton, IV |
| 2014/0039549 A1 | 2/2014 | Belsky et al. |
| 2014/0048580 A1 | 2/2014 | Merchant et al. |
| 2014/0081176 A1 | 3/2014 | Hassan |
| 2014/0094681 A1 | 4/2014 | Valentine et al. |
| 2014/0100558 A1 | 4/2014 | Schmitz et al. |
| 2014/0107640 A1 | 4/2014 | Yates et al. |
| 2014/0115229 A1 | 4/2014 | Kothamasu et al. |
| 2014/0131418 A1 | 5/2014 | Kostrzewski |
| 2014/0135832 A1 | 5/2014 | Park et al. |
| 2014/0151433 A1 | 6/2014 | Shelton, IV et al. |
| 2014/0158747 A1 | 6/2014 | Measamer et al. |
| 2014/0166723 A1 | 6/2014 | Beardsley et al. |
| 2014/0166724 A1 | 6/2014 | Schellin et al. |
| 2014/0166725 A1 | 6/2014 | Schellin et al. |
| 2014/0166726 A1 | 6/2014 | Schellin et al. |
| 2014/0175147 A1 | 6/2014 | Manoux et al. |
| 2014/0175150 A1 | 6/2014 | Shelton, IV et al. |
| 2014/0175152 A1 | 6/2014 | Hess et al. |
| 2014/0181710 A1 | 6/2014 | Baalu et al. |
| 2014/0188091 A1 | 7/2014 | Vidal et al. |
| 2014/0188159 A1 | 7/2014 | Steege |
| 2014/0207124 A1 | 7/2014 | Aldridge et al. |
| 2014/0207125 A1 | 7/2014 | Applegate et al. |
| 2014/0209658 A1 | 7/2014 | Skalla et al. |
| 2014/0224857 A1 | 8/2014 | Schmid |
| 2014/0228632 A1 | 8/2014 | Sholev et al. |
| 2014/0228867 A1 | 8/2014 | Thomas et al. |
| 2014/0239047 A1 | 8/2014 | Hodgkinson et al. |
| 2014/0243865 A1 | 8/2014 | Swayze et al. |
| 2014/0246475 A1 | 9/2014 | Hall et al. |
| 2014/0248167 A1 | 9/2014 | Sugimoto et al. |
| 2014/0249557 A1 | 9/2014 | Koch et al. |
| 2014/0249573 A1 | 9/2014 | Arav |
| 2014/0263541 A1 | 9/2014 | Leimbach et al. |
| 2014/0263552 A1 | 9/2014 | Hall et al. |
| 2014/0263558 A1 | 9/2014 | Hausen et al. |
| 2014/0276730 A1 | 9/2014 | Boudreaux et al. |
| 2014/0284371 A1 | 9/2014 | Morgan et al. |
| 2014/0288460 A1 | 9/2014 | Ouyang et al. |
| 2014/0291379 A1 | 10/2014 | Schellin et al. |
| 2014/0291383 A1 | 10/2014 | Spivey et al. |
| 2014/0299648 A1 | 10/2014 | Shelton, IV et al. |
| 2014/0303645 A1 | 10/2014 | Morgan et al. |
| 2014/0303660 A1 | 10/2014 | Boyden et al. |
| 2014/0330161 A1 | 11/2014 | Swayze et al. |
| 2014/0330298 A1 | 11/2014 | Arshonsky et al. |
| 2014/0330579 A1 | 11/2014 | Cashman et al. |
| 2014/0367445 A1 | 12/2014 | Ingmanson et al. |
| 2014/0374130 A1 | 12/2014 | Nakamura et al. |
| 2014/0378950 A1 | 12/2014 | Chiu |
| 2015/0002089 A1 | 1/2015 | Rejman et al. |
| 2015/0008248 A1 | 1/2015 | Giordano et al. |
| 2015/0025549 A1 | 1/2015 | Kilroy et al. |
| 2015/0038961 A1 | 2/2015 | Clark et al. |
| 2015/0053737 A1 | 2/2015 | Leimbach et al. |
| 2015/0053742 A1 | 2/2015 | Shelton, IV et al. |
| 2015/0053743 A1 | 2/2015 | Yates et al. |
| 2015/0053746 A1 | 2/2015 | Shelton, IV et al. |
| 2015/0053748 A1 | 2/2015 | Yates et al. |
| 2015/0060518 A1 | 3/2015 | Shelton, IV et al. |
| 2015/0060519 A1 | 3/2015 | Shelton, IV et al. |
| 2015/0060520 A1 | 3/2015 | Shelton, IV et al. |
| 2015/0060521 A1 | 3/2015 | Weisenburgh, II et al. |
| 2015/0066000 A1 | 3/2015 | An et al. |
| 2015/0076208 A1 | 3/2015 | Shelton, IV |
| 2015/0076209 A1 | 3/2015 | Shelton, IV et al. |
| 2015/0076210 A1 | 3/2015 | Shelton, IV et al. |
| 2015/0076212 A1 | 3/2015 | Shelton, IV |
| 2015/0080868 A1 | 3/2015 | Kerr |
| 2015/0083781 A1 | 3/2015 | Giordano et al. |
| 2015/0083782 A1 | 3/2015 | Scheib et al. |
| 2015/0088547 A1 | 3/2015 | Balram et al. |
| 2015/0090760 A1 | 4/2015 | Giordano et al. |
| 2015/0090762 A1 | 4/2015 | Giordano et al. |

(56) References Cited

U.S. PATENT DOCUMENTS

| | | |
|---|---|---|
| 2015/0122870 A1 | 5/2015 | Zemlok et al. |
| 2015/0134077 A1 | 5/2015 | Shelton, IV et al. |
| 2015/0150620 A1 | 6/2015 | Miyamoto et al. |
| 2015/0173749 A1 | 6/2015 | Shelton, IV et al. |
| 2015/0173756 A1 | 6/2015 | Baxter, III et al. |
| 2015/0173789 A1 | 6/2015 | Baxter, III et al. |
| 2015/0196295 A1 | 7/2015 | Shelton, IV et al. |
| 2015/0196296 A1 | 7/2015 | Swayze et al. |
| 2015/0196299 A1 | 7/2015 | Swayze et al. |
| 2015/0201918 A1 | 7/2015 | Kumar et al. |
| 2015/0201932 A1 | 7/2015 | Swayze et al. |
| 2015/0201936 A1 | 7/2015 | Swayze et al. |
| 2015/0201937 A1 | 7/2015 | Swayze et al. |
| 2015/0201938 A1 | 7/2015 | Swayze et al. |
| 2015/0201939 A1 | 7/2015 | Swayze et al. |
| 2015/0201940 A1 | 7/2015 | Swayze et al. |
| 2015/0201941 A1 | 7/2015 | Swayze et al. |
| 2015/0222212 A1 | 8/2015 | Iwata |
| 2015/0223868 A1 | 8/2015 | Brandt et al. |
| 2015/0231409 A1 | 8/2015 | Racenet et al. |
| 2015/0238118 A1 | 8/2015 | Legassey et al. |
| 2015/0272557 A1 | 10/2015 | Overmyer et al. |
| 2015/0272571 A1 | 10/2015 | Leimbach et al. |
| 2015/0272580 A1 | 10/2015 | Leimbach et al. |
| 2015/0272582 A1 | 10/2015 | Leimbach et al. |
| 2015/0297200 A1 | 10/2015 | Fitzsimmons et al. |
| 2015/0297222 A1 | 10/2015 | Huitema et al. |
| 2015/0297223 A1 | 10/2015 | Huitema et al. |
| 2015/0297225 A1 | 10/2015 | Huitema et al. |
| 2015/0297228 A1 | 10/2015 | Huitema et al. |
| 2015/0297233 A1 | 10/2015 | Huitema et al. |
| 2015/0302539 A1 | 10/2015 | Mazar et al. |
| 2015/0303417 A1 | 10/2015 | Koeder et al. |
| 2015/0313594 A1 | 11/2015 | Shelton, IV et al. |
| 2015/0324317 A1 | 11/2015 | Collins et al. |
| 2015/0327864 A1 | 11/2015 | Hodgkinson et al. |
| 2015/0352699 A1 | 12/2015 | Sakai et al. |
| 2015/0366585 A1 | 12/2015 | Lemay et al. |
| 2015/0372265 A1 | 12/2015 | Morisaku et al. |
| 2015/0374369 A1 | 12/2015 | Yates et al. |
| 2015/0374372 A1 | 12/2015 | Zergiebel et al. |
| 2015/0374378 A1 | 12/2015 | Giordano et al. |
| 2016/0000431 A1 | 1/2016 | Giordano et al. |
| 2016/0000437 A1 | 1/2016 | Giordano et al. |
| 2016/0000438 A1 | 1/2016 | Swayze et al. |
| 2016/0000442 A1 | 1/2016 | Shelton, IV |
| 2016/0000452 A1 | 1/2016 | Yates et al. |
| 2016/0000453 A1 | 1/2016 | Yates et al. |
| 2016/0023342 A1 | 1/2016 | Koenig et al. |
| 2016/0030042 A1 | 2/2016 | Heinrich et al. |
| 2016/0051316 A1 | 2/2016 | Boudreaux |
| 2016/0058443 A1 | 3/2016 | Yates et al. |
| 2016/0066913 A1 | 3/2016 | Swayze et al. |
| 2016/0069449 A1 | 3/2016 | Kanai et al. |
| 2016/0074040 A1 | 3/2016 | Widenhouse et al. |
| 2016/0074103 A1 | 3/2016 | Sartor |
| 2016/0082161 A1 | 3/2016 | Zilberman et al. |
| 2016/0089137 A1 | 3/2016 | Hess et al. |
| 2016/0089198 A1 | 3/2016 | Arya et al. |
| 2016/0095585 A1 | 4/2016 | Zergiebel et al. |
| 2016/0106431 A1 | 4/2016 | Shelton, IV et al. |
| 2016/0113653 A1 | 4/2016 | Zingman |
| 2016/0120545 A1 | 5/2016 | Shelton, IV et al. |
| 2016/0135835 A1 | 5/2016 | Onuma |
| 2016/0166248 A1 | 6/2016 | Deville et al. |
| 2016/0166256 A1 | 6/2016 | Baxter, III et al. |
| 2016/0183939 A1 | 6/2016 | Shelton, IV et al. |
| 2016/0183943 A1 | 6/2016 | Shelton, IV |
| 2016/0183944 A1 | 6/2016 | Swensgard et al. |
| 2016/0192916 A1 | 7/2016 | Shelton, IV et al. |
| 2016/0192918 A1 | 7/2016 | Shelton, IV et al. |
| 2016/0192960 A1 | 7/2016 | Bueno et al. |
| 2016/0192977 A1 | 7/2016 | Manwaring et al. |
| 2016/0199063 A1 | 7/2016 | Mandakolathur Vasudevan et al. |
| 2016/0199956 A1 | 7/2016 | Shelton, IV et al. |
| 2016/0206314 A1 | 7/2016 | Scheib et al. |
| 2016/0235404 A1 | 8/2016 | Shelton, IV |
| 2016/0235409 A1 | 8/2016 | Shelton, IV et al. |
| 2016/0235494 A1 | 8/2016 | Shelton, IV et al. |
| 2016/0242783 A1 | 8/2016 | Shelton, IV et al. |
| 2016/0249910 A1 | 9/2016 | Shelton, IV et al. |
| 2016/0249922 A1 | 9/2016 | Morgan et al. |
| 2016/0256154 A1 | 9/2016 | Shelton, IV et al. |
| 2016/0256159 A1 | 9/2016 | Pinjala et al. |
| 2016/0256160 A1 | 9/2016 | Shelton, IV et al. |
| 2016/0256229 A1 | 9/2016 | Morgan et al. |
| 2016/0262745 A1 | 9/2016 | Morgan et al. |
| 2016/0262746 A1 | 9/2016 | Shelton, IV et al. |
| 2016/0262921 A1 | 9/2016 | Balbierz et al. |
| 2016/0278771 A1 | 9/2016 | Shelton, IV et al. |
| 2016/0278848 A1 | 9/2016 | Boudreaux et al. |
| 2016/0287265 A1 | 10/2016 | Macdonald et al. |
| 2016/0287279 A1 | 10/2016 | Bovay et al. |
| 2016/0310143 A1 | 10/2016 | Bettuchi |
| 2016/0314716 A1 | 10/2016 | Grubbs |
| 2016/0345976 A1 | 12/2016 | Gonzalez et al. |
| 2016/0346034 A1 | 12/2016 | Arya et al. |
| 2016/0354088 A1 | 12/2016 | Cabrera et al. |
| 2016/0367122 A1 | 12/2016 | Ichimura et al. |
| 2016/0374678 A1 | 12/2016 | Becerra et al. |
| 2017/0007236 A1 | 1/2017 | Shelton, IV et al. |
| 2017/0007243 A1 | 1/2017 | Shelton, IV et al. |
| 2017/0007244 A1 | 1/2017 | Shelton, IV et al. |
| 2017/0007245 A1 | 1/2017 | Shelton, IV et al. |
| 2017/0007248 A1 | 1/2017 | Shelton, IV et al. |
| 2017/0007250 A1 | 1/2017 | Shelton, IV et al. |
| 2017/0007347 A1 | 1/2017 | Jaworek et al. |
| 2017/0014125 A1 | 1/2017 | Shelton, IV et al. |
| 2017/0027572 A1 | 2/2017 | Nalagatla et al. |
| 2017/0049444 A1 | 2/2017 | Schellin et al. |
| 2017/0049447 A1 | 2/2017 | Barton et al. |
| 2017/0049448 A1 | 2/2017 | Widenhouse et al. |
| 2017/0056000 A1 | 3/2017 | Nalagatla et al. |
| 2017/0056002 A1 | 3/2017 | Nalagatla et al. |
| 2017/0056005 A1 | 3/2017 | Shelton, IV et al. |
| 2017/0079642 A1 | 3/2017 | Overmyer et al. |
| 2017/0086827 A1 | 3/2017 | Vendely et al. |
| 2017/0086829 A1 | 3/2017 | Vendely et al. |
| 2017/0086830 A1 | 3/2017 | Yates et al. |
| 2017/0086831 A1 | 3/2017 | Shelton, IV et al. |
| 2017/0086838 A1 | 3/2017 | Harris et al. |
| 2017/0086842 A1 | 3/2017 | Shelton, IV et al. |
| 2017/0086844 A1 | 3/2017 | Vendely et al. |
| 2017/0105733 A1 | 4/2017 | Scheib et al. |
| 2017/0119388 A1 | 5/2017 | Kostrzewski |
| 2017/0119397 A1 | 5/2017 | Harris et al. |
| 2017/0150965 A1 | 6/2017 | Williams |
| 2017/0172382 A1 | 6/2017 | Nir et al. |
| 2017/0172550 A1 | 6/2017 | Mukherjee et al. |
| 2017/0172662 A1 | 6/2017 | Panescu et al. |
| 2017/0172672 A1 | 6/2017 | Bailey et al. |
| 2017/0182211 A1 | 6/2017 | Raxworthy et al. |
| 2017/0196554 A1 | 7/2017 | Rousseau et al. |
| 2017/0196556 A1 | 7/2017 | Shah et al. |
| 2017/0196558 A1 | 7/2017 | Morgan et al. |
| 2017/0196637 A1 | 7/2017 | Shelton, IV et al. |
| 2017/0196648 A1 | 7/2017 | Ward et al. |
| 2017/0196649 A1 | 7/2017 | Yates et al. |
| 2017/0202571 A1 | 7/2017 | Shelton, IV et al. |
| 2017/0202596 A1 | 7/2017 | Shelton, IV et al. |
| 2017/0202770 A1 | 7/2017 | Friedrich et al. |
| 2017/0209145 A1 | 7/2017 | Swayze et al. |
| 2017/0209146 A1 | 7/2017 | Yates et al. |
| 2017/0215881 A1 | 8/2017 | Shelton, IV et al. |
| 2017/0215943 A1 | 8/2017 | Allen, IV |
| 2017/0224331 A1 | 8/2017 | Worthington et al. |
| 2017/0224332 A1 | 8/2017 | Hunter et al. |
| 2017/0224334 A1 | 8/2017 | Worthington et al. |
| 2017/0224339 A1 | 8/2017 | Huang et al. |
| 2017/0231627 A1 | 8/2017 | Shelton, IV et al. |
| 2017/0231628 A1 | 8/2017 | Shelton, IV et al. |
| 2017/0238928 A1 | 8/2017 | Morgan et al. |
| 2017/0238929 A1 | 8/2017 | Yates et al. |
| 2017/0245952 A1 | 8/2017 | Shelton, IV et al. |

(56) References Cited

U.S. PATENT DOCUMENTS

| | | |
|---|---|---|
| 2017/0249431 A1 | 8/2017 | Shelton, IV et al. |
| 2017/0258469 A1 | 9/2017 | Shelton, IV et al. |
| 2017/0265774 A1 | 9/2017 | Johnson et al. |
| 2017/0265856 A1 | 9/2017 | Shelton, IV et al. |
| 2017/0281164 A1 | 10/2017 | Harris et al. |
| 2017/0281167 A1 | 10/2017 | Shelton, IV et al. |
| 2017/0281169 A1 | 10/2017 | Harris et al. |
| 2017/0281171 A1 | 10/2017 | Shelton, IV et al. |
| 2017/0281173 A1 | 10/2017 | Shelton, IV et al. |
| 2017/0281174 A1 | 10/2017 | Harris et al. |
| 2017/0281186 A1 | 10/2017 | Shelton, IV et al. |
| 2017/0281187 A1 | 10/2017 | Shelton, IV et al. |
| 2017/0281189 A1 | 10/2017 | Nalagatla et al. |
| 2017/0290584 A1 | 10/2017 | Jasemian et al. |
| 2017/0290585 A1 | 10/2017 | Shelton, IV et al. |
| 2017/0290586 A1 | 10/2017 | Wellman |
| 2017/0296169 A1 | 10/2017 | Yates et al. |
| 2017/0296173 A1 | 10/2017 | Shelton, IV et al. |
| 2017/0296177 A1 | 10/2017 | Harris et al. |
| 2017/0296185 A1 | 10/2017 | Swensgard et al. |
| 2017/0296213 A1 | 10/2017 | Swensgard et al. |
| 2017/0311944 A1 | 11/2017 | Morgan et al. |
| 2017/0311949 A1 | 11/2017 | Shelton, IV |
| 2017/0312041 A1 | 11/2017 | Giordano et al. |
| 2017/0312042 A1 | 11/2017 | Giordano et al. |
| 2017/0319201 A1 | 11/2017 | Morgan et al. |
| 2017/0319207 A1 | 11/2017 | Shelton, IV et al. |
| 2017/0319209 A1 | 11/2017 | Morgan et al. |
| 2017/0325813 A1 | 11/2017 | Aranyi et al. |
| 2017/0333034 A1 | 11/2017 | Morgan et al. |
| 2017/0333035 A1 | 11/2017 | Morgan et al. |
| 2017/0333070 A1 | 11/2017 | Laurent et al. |
| 2017/0348010 A1 | 12/2017 | Chiang |
| 2017/0348043 A1 | 12/2017 | Wang et al. |
| 2017/0354413 A1 | 12/2017 | Chen et al. |
| 2017/0354415 A1 | 12/2017 | Casasanta, Jr. et al. |
| 2017/0358052 A1 | 12/2017 | Yuan |
| 2017/0360439 A1 | 12/2017 | Chen et al. |
| 2017/0360441 A1 | 12/2017 | Sgroi |
| 2017/0364183 A1 | 12/2017 | Xiao |
| 2017/0367695 A1 | 12/2017 | Shelton, IV et al. |
| 2017/0367696 A1 | 12/2017 | Shelton, IV et al. |
| 2017/0367697 A1 | 12/2017 | Shelton, IV et al. |
| 2017/0367698 A1 | 12/2017 | Shelton, IV et al. |
| 2017/0367700 A1 | 12/2017 | Leimbach et al. |
| 2017/0367991 A1 | 12/2017 | Widenhouse et al. |
| 2018/0000483 A1 | 1/2018 | Leimbach et al. |
| 2018/0000545 A1 | 1/2018 | Giordano et al. |
| 2018/0008270 A1 | 1/2018 | Moore et al. |
| 2018/0008271 A1 | 1/2018 | Moore et al. |
| 2018/0008356 A1 | 1/2018 | Giordano et al. |
| 2018/0008357 A1 | 1/2018 | Giordano et al. |
| 2018/0028184 A1 | 2/2018 | Shelton, IV et al. |
| 2018/0028185 A1 | 2/2018 | Shelton, IV et al. |
| 2018/0042611 A1 | 2/2018 | Swayze et al. |
| 2018/0049824 A1 | 2/2018 | Harris et al. |
| 2018/0049883 A1 | 2/2018 | Moskowitz et al. |
| 2018/0055513 A1 | 3/2018 | Shelton, IV et al. |
| 2018/0055524 A1 | 3/2018 | Shelton, IV et al. |
| 2018/0055525 A1 | 3/2018 | Shelton, IV et al. |
| 2018/0055526 A1 | 3/2018 | Shelton, IV et al. |
| 2018/0064440 A1 | 3/2018 | Shelton, IV et al. |
| 2018/0064441 A1 | 3/2018 | Shelton, IV et al. |
| 2018/0064442 A1 | 3/2018 | Shelton, IV et al. |
| 2018/0064443 A1 | 3/2018 | Shelton, IV et al. |
| 2018/0070942 A1 | 3/2018 | Shelton, IV et al. |
| 2018/0078248 A1 | 3/2018 | Swayze et al. |
| 2018/0078268 A1 | 3/2018 | Messerly et al. |
| 2018/0085116 A1 | 3/2018 | Yates et al. |
| 2018/0085117 A1 | 3/2018 | Shelton, IV et al. |
| 2018/0103953 A1 | 4/2018 | Shelton, IV et al. |
| 2018/0103955 A1 | 4/2018 | Shelton, IV et al. |
| 2018/0110516 A1 | 4/2018 | Baxter, III et al. |
| 2018/0110519 A1 | 4/2018 | Lytle, IV et al. |
| 2018/0110520 A1 | 4/2018 | Shelton, IV et al. |
| 2018/0110521 A1 | 4/2018 | Shelton, IV et al. |
| 2018/0110522 A1 | 4/2018 | Shelton, IV et al. |
| 2018/0110523 A1 | 4/2018 | Shelton, IV |
| 2018/0110574 A1 | 4/2018 | Shelton, IV et al. |
| 2018/0110575 A1 | 4/2018 | Shelton, IV et al. |
| 2018/0114591 A1 | 4/2018 | Pribanic et al. |
| 2018/0116658 A1 | 5/2018 | Aronhalt, IV et al. |
| 2018/0116662 A1 | 5/2018 | Shelton, IV et al. |
| 2018/0116665 A1 | 5/2018 | Hall et al. |
| 2018/0125481 A1 | 5/2018 | Yates et al. |
| 2018/0125484 A1 | 5/2018 | Kostrzewski |
| 2018/0125487 A1 | 5/2018 | Beardsley |
| 2018/0125488 A1 | 5/2018 | Morgan et al. |
| 2018/0125489 A1 | 5/2018 | Leimbach et al. |
| 2018/0125590 A1 | 5/2018 | Giordano et al. |
| 2018/0125594 A1 | 5/2018 | Beardsley |
| 2018/0126504 A1 | 5/2018 | Shelton, IV et al. |
| 2018/0132845 A1 | 5/2018 | Schmid et al. |
| 2018/0132849 A1 | 5/2018 | Miller et al. |
| 2018/0132850 A1 | 5/2018 | Leimbach et al. |
| 2018/0132851 A1 | 5/2018 | Hall et al. |
| 2018/0132926 A1 | 5/2018 | Asher et al. |
| 2018/0132952 A1 | 5/2018 | Spivey et al. |
| 2018/0133856 A1 | 5/2018 | Shelton, IV et al. |
| 2018/0140299 A1 | 5/2018 | Weaner et al. |
| 2018/0140368 A1 | 5/2018 | Shelton, IV et al. |
| 2018/0146960 A1 | 5/2018 | Shelton, IV et al. |
| 2018/0150153 A1 | 5/2018 | Yoon et al. |
| 2018/0153542 A1 | 6/2018 | Shelton, IV et al. |
| 2018/0161034 A1 | 6/2018 | Scheib et al. |
| 2018/0168575 A1 | 6/2018 | Simms et al. |
| 2018/0168577 A1 | 6/2018 | Aronhalt et al. |
| 2018/0168578 A1 | 6/2018 | Aronhalt et al. |
| 2018/0168579 A1 | 6/2018 | Aronhalt et al. |
| 2018/0168580 A1 | 6/2018 | Hunter et al. |
| 2018/0168584 A1 | 6/2018 | Harris et al. |
| 2018/0168586 A1 | 6/2018 | Shelton, IV et al. |
| 2018/0168589 A1 | 6/2018 | Swayze et al. |
| 2018/0168590 A1 | 6/2018 | Overmyer et al. |
| 2018/0168591 A1 | 6/2018 | Swayze et al. |
| 2018/0168592 A1 | 6/2018 | Overmyer et al. |
| 2018/0168593 A1 | 6/2018 | Overmyer et al. |
| 2018/0168594 A1 | 6/2018 | Shelton, IV et al. |
| 2018/0168597 A1 | 6/2018 | Fanelli et al. |
| 2018/0168598 A1 | 6/2018 | Shelton, IV et al. |
| 2018/0168600 A1 | 6/2018 | Shelton, IV et al. |
| 2018/0168601 A1 | 6/2018 | Bakos et al. |
| 2018/0168602 A1 | 6/2018 | Bakos et al. |
| 2018/0168603 A1 | 6/2018 | Morgan et al. |
| 2018/0168604 A1 | 6/2018 | Shelton, IV et al. |
| 2018/0168605 A1 | 6/2018 | Baber et al. |
| 2018/0168606 A1 | 6/2018 | Shelton, IV et al. |
| 2018/0168607 A1 | 6/2018 | Shelton, IV et al. |
| 2018/0168608 A1 | 6/2018 | Shelton, IV et al. |
| 2018/0168609 A1 | 6/2018 | Fanelli et al. |
| 2018/0168610 A1 | 6/2018 | Shelton, IV et al. |
| 2018/0168614 A1 | 6/2018 | Shelton, IV et al. |
| 2018/0168615 A1 | 6/2018 | Shelton, IV et al. |
| 2018/0168616 A1 | 6/2018 | Shelton, IV et al. |
| 2018/0168617 A1 | 6/2018 | Shelton, IV et al. |
| 2018/0168618 A1 | 6/2018 | Scott et al. |
| 2018/0168619 A1 | 6/2018 | Scott et al. |
| 2018/0168621 A1 | 6/2018 | Shelton, IV et al. |
| 2018/0168623 A1 | 6/2018 | Simms et al. |
| 2018/0168624 A1 | 6/2018 | Shelton, IV et al. |
| 2018/0168625 A1 | 6/2018 | Posada et al. |
| 2018/0168626 A1 | 6/2018 | Shelton, IV et al. |
| 2018/0168627 A1 | 6/2018 | Weaner et al. |
| 2018/0168628 A1 | 6/2018 | Hunter et al. |
| 2018/0168629 A1 | 6/2018 | Shelton, IV et al. |
| 2018/0168630 A1 | 6/2018 | Shelton, IV et al. |
| 2018/0168631 A1 | 6/2018 | Harris et al. |
| 2018/0168632 A1 | 6/2018 | Harris et al. |
| 2018/0168633 A1 | 6/2018 | Shelton, IV et al. |
| 2018/0168637 A1 | 6/2018 | Harris et al. |
| 2018/0168638 A1 | 6/2018 | Harris et al. |
| 2018/0168639 A1 | 6/2018 | Shelton, IV et al. |
| 2018/0168641 A1 | 6/2018 | Harris et al. |
| 2018/0168642 A1 | 6/2018 | Shelton, IV et al. |

(56) References Cited

U.S. PATENT DOCUMENTS

| | | |
|---|---|---|
| 2018/0168643 A1 | 6/2018 | Shelton, IV et al. |
| 2018/0168644 A1 | 6/2018 | Shelton, IV et al. |
| 2018/0168646 A1 | 6/2018 | Shelton, IV et al. |
| 2018/0168647 A1 | 6/2018 | Shelton, IV et al. |
| 2018/0168648 A1 | 6/2018 | Shelton, IV et al. |
| 2018/0168649 A1 | 6/2018 | Shelton, IV et al. |
| 2018/0168650 A1 | 6/2018 | Shelton, IV et al. |
| 2018/0168651 A1 | 6/2018 | Shelton, IV et al. |
| 2018/0168715 A1 | 6/2018 | Strobl |
| 2018/0199940 A1 | 7/2018 | Zergiebel et al. |
| 2018/0206843 A1 | 7/2018 | Yates et al. |
| 2018/0206906 A1 | 7/2018 | Moua et al. |
| 2018/0214147 A1 | 8/2018 | Merchant et al. |
| 2018/0221046 A1 | 8/2018 | Demmy et al. |
| 2018/0221050 A1 | 8/2018 | Kostrzewski et al. |
| 2018/0228490 A1 | 8/2018 | Richard et al. |
| 2018/0242962 A1 | 8/2018 | Walen et al. |
| 2018/0249999 A1 | 9/2018 | Parihar et al. |
| 2018/0250001 A1 | 9/2018 | Aronhalt et al. |
| 2018/0250020 A1 | 9/2018 | Carusillo |
| 2018/0250086 A1 | 9/2018 | Grubbs |
| 2018/0271520 A1 | 9/2018 | Shelton, IV et al. |
| 2018/0271604 A1 | 9/2018 | Grout et al. |
| 2018/0273597 A1 | 9/2018 | Stimson |
| 2018/0280020 A1 | 10/2018 | Hess et al. |
| 2018/0289369 A1 | 10/2018 | Shelton, IV et al. |
| 2018/0296211 A1 | 10/2018 | Timm et al. |
| 2018/0296213 A1 | 10/2018 | Strobl |
| 2018/0296215 A1 | 10/2018 | Baxter, III et al. |
| 2018/0296216 A1 | 10/2018 | Shelton, IV et al. |
| 2018/0296217 A1 | 10/2018 | Moore et al. |
| 2018/0303481 A1 | 10/2018 | Shelton, IV et al. |
| 2018/0303482 A1 | 10/2018 | Shelton, IV et al. |
| 2018/0310931 A1 | 11/2018 | Hall et al. |
| 2018/0311002 A1 | 11/2018 | Giordano et al. |
| 2018/0317916 A1 | 11/2018 | Wixey |
| 2018/0317917 A1 | 11/2018 | Huang et al. |
| 2018/0317919 A1 | 11/2018 | Shelton, IV et al. |
| 2018/0325528 A1 | 11/2018 | Windolf et al. |
| 2018/0325611 A1 | 11/2018 | Robinson et al. |
| 2018/0333155 A1 | 11/2018 | Hall et al. |
| 2018/0333169 A1 | 11/2018 | Leimbach et al. |
| 2018/0344319 A1 | 12/2018 | Shelton, IV et al. |
| 2018/0353170 A1 | 12/2018 | Overmyer et al. |
| 2018/0353176 A1 | 12/2018 | Shelton, IV et al. |
| 2018/0353177 A1 | 12/2018 | Shelton, IV et al. |
| 2018/0353178 A1 | 12/2018 | Shelton, IV et al. |
| 2018/0353179 A1 | 12/2018 | Shelton, IV et al. |
| 2018/0360443 A1 | 12/2018 | Shelton, IV et al. |
| 2018/0360445 A1 | 12/2018 | Shelton, IV et al. |
| 2018/0360446 A1 | 12/2018 | Shelton, IV et al. |
| 2018/0360447 A1 | 12/2018 | Shelton, IV et al. |
| 2018/0360448 A1 | 12/2018 | Harris et al. |
| 2018/0360449 A1 | 12/2018 | Shelton, IV et al. |
| 2018/0360450 A1 | 12/2018 | Shelton, IV et al. |
| 2018/0360452 A1 | 12/2018 | Shelton, IV et al. |
| 2018/0360454 A1 | 12/2018 | Shelton, IV et al. |
| 2018/0360455 A1 | 12/2018 | Shelton, IV et al. |
| 2018/0360456 A1 | 12/2018 | Shelton, IV et al. |
| 2018/0360471 A1 | 12/2018 | Parfett et al. |
| 2018/0360472 A1 | 12/2018 | Harris et al. |
| 2018/0360473 A1 | 12/2018 | Shelton, IV et al. |
| 2018/0360549 A1 | 12/2018 | Hares et al. |
| 2018/0368822 A1 | 12/2018 | Shelton, IV et al. |
| 2018/0368833 A1 | 12/2018 | Shelton, IV et al. |
| 2018/0368837 A1 | 12/2018 | Morgan et al. |
| 2018/0368838 A1 | 12/2018 | Shelton, IV et al. |
| 2018/0368839 A1 | 12/2018 | Shelton, IV et al. |
| 2018/0368840 A1 | 12/2018 | Shelton, IV et al. |
| 2018/0368841 A1 | 12/2018 | Shelton, IV et al. |
| 2018/0368842 A1 | 12/2018 | Shelton, IV et al. |
| 2018/0368843 A1 | 12/2018 | Shelton, IV et al. |
| 2018/0368844 A1 | 12/2018 | Bakos et al. |
| 2018/0368845 A1 | 12/2018 | Bakos et al. |
| 2018/0368846 A1 | 12/2018 | Shelton, IV et al. |
| 2018/0368847 A1 | 12/2018 | Shelton, IV et al. |
| 2019/0000446 A1 | 1/2019 | Shelton, IV et al. |
| 2019/0000448 A1 | 1/2019 | Shelton, IV et al. |
| 2019/0000450 A1 | 1/2019 | Shelton, IV et al. |
| 2019/0000454 A1 | 1/2019 | Swayze et al. |
| 2019/0000456 A1 | 1/2019 | Shelton, IV et al. |
| 2019/0000457 A1 | 1/2019 | Shelton, IV et al. |
| 2019/0000459 A1 | 1/2019 | Shelton, IV et al. |
| 2019/0000460 A1 | 1/2019 | Shelton, IV et al. |
| 2019/0000461 A1 | 1/2019 | Shelton, IV et al. |
| 2019/0000462 A1 | 1/2019 | Shelton, IV et al. |
| 2019/0000463 A1 | 1/2019 | Shelton, IV et al. |
| 2019/0000464 A1 | 1/2019 | Shelton, IV et al. |
| 2019/0000465 A1 | 1/2019 | Shelton, IV et al. |
| 2019/0000466 A1 | 1/2019 | Shelton, IV et al. |
| 2019/0000467 A1 | 1/2019 | Shelton, IV et al. |
| 2019/0000468 A1 | 1/2019 | Adams et al. |
| 2019/0000469 A1 | 1/2019 | Shelton, IV et al. |
| 2019/0000470 A1 | 1/2019 | Yates et al. |
| 2019/0000471 A1 | 1/2019 | Shelton, IV et al. |
| 2019/0000472 A1 | 1/2019 | Shelton, IV et al. |
| 2019/0000473 A1 | 1/2019 | Shelton, IV et al. |
| 2019/0000474 A1 | 1/2019 | Shelton, IV et al. |
| 2019/0000475 A1 | 1/2019 | Shelton, IV et al. |
| 2019/0000476 A1 | 1/2019 | Shelton, IV et al. |
| 2019/0000477 A1 | 1/2019 | Shelton, IV et al. |
| 2019/0000478 A1 | 1/2019 | Messerly et al. |
| 2019/0000479 A1 | 1/2019 | Harris et al. |
| 2019/0000525 A1 | 1/2019 | Messerly et al. |
| 2019/0000528 A1 | 1/2019 | Yates et al. |
| 2019/0000530 A1 | 1/2019 | Yates et al. |
| 2019/0000531 A1 | 1/2019 | Messerly et al. |
| 2019/0000534 A1 | 1/2019 | Messerly et al. |
| 2019/0000538 A1 | 1/2019 | Widenhouse et al. |
| 2019/0000555 A1 | 1/2019 | Schings et al. |
| 2019/0000565 A1 | 1/2019 | Shelton, IV et al. |
| 2019/0003292 A1 | 1/2019 | Balan et al. |
| 2019/0008509 A1 | 1/2019 | Shelton, IV et al. |
| 2019/0008511 A1 | 1/2019 | Kerr et al. |
| 2019/0015096 A1 | 1/2019 | Shelton, IV et al. |
| 2019/0015102 A1 | 1/2019 | Baber et al. |
| 2019/0015165 A1 | 1/2019 | Giordano et al. |
| 2019/0029675 A1 | 1/2019 | Yates et al. |
| 2019/0029676 A1 | 1/2019 | Yates et al. |
| 2019/0029677 A1 | 1/2019 | Yates et al. |
| 2019/0029678 A1 | 1/2019 | Shelton, IV et al. |
| 2019/0029681 A1 | 1/2019 | Swayze et al. |
| 2019/0029682 A1 | 1/2019 | Huitema et al. |
| 2019/0029701 A1 | 1/2019 | Shelton, IV et al. |
| 2019/0033955 A1 | 1/2019 | Leimbach et al. |
| 2019/0038279 A1 | 2/2019 | Shelton, IV et al. |
| 2019/0038281 A1 | 2/2019 | Shelton, IV et al. |
| 2019/0038282 A1 | 2/2019 | Shelton, IV et al. |
| 2019/0038283 A1 | 2/2019 | Shelton, IV et al. |
| 2019/0038292 A1 | 2/2019 | Zhang |
| 2019/0038371 A1 | 2/2019 | Wixey et al. |
| 2019/0046181 A1 | 2/2019 | McCuen |
| 2019/0046187 A1 | 2/2019 | Yates et al. |
| 2019/0059886 A1 | 2/2019 | Shelton, IV et al. |
| 2019/0090870 A1 | 3/2019 | Shelton, IV et al. |
| 2019/0090871 A1 | 3/2019 | Shelton, IV et al. |
| 2019/0091183 A1 | 3/2019 | Tomat et al. |
| 2019/0099177 A1 | 4/2019 | Yates et al. |
| 2019/0099178 A1 | 4/2019 | Leimbach et al. |
| 2019/0099179 A1 | 4/2019 | Leimbach et al. |
| 2019/0099180 A1 | 4/2019 | Leimbach et al. |
| 2019/0099181 A1 | 4/2019 | Shelton, IV et al. |
| 2019/0099182 A1 | 4/2019 | Bakos et al. |
| 2019/0099183 A1 | 4/2019 | Leimbach et al. |
| 2019/0099184 A1 | 4/2019 | Setser et al. |
| 2019/0099224 A1 | 4/2019 | Leimbach et al. |
| 2019/0099229 A1 | 4/2019 | Spivey et al. |
| 2019/0102930 A1 | 4/2019 | Leimbach et al. |
| 2019/0105035 A1 | 4/2019 | Shelton, IV et al. |
| 2019/0105036 A1 | 4/2019 | Morgan et al. |
| 2019/0105037 A1 | 4/2019 | Morgan et al. |
| 2019/0105038 A1 | 4/2019 | Schmid et al. |
| 2019/0105039 A1 | 4/2019 | Morgan et al. |
| 2019/0105043 A1 | 4/2019 | Jaworek et al. |

(56) References Cited

U.S. PATENT DOCUMENTS

| | | |
|---|---|---|
| 2019/0105044 A1 | 4/2019 | Shelton, IV et al. |
| 2019/0105049 A1 | 4/2019 | Moore et al. |
| 2019/0110791 A1 | 4/2019 | Shelton, IV et al. |
| 2019/0110792 A1 | 4/2019 | Shelton, IV et al. |
| 2019/0110793 A1 | 4/2019 | Parihar et al. |
| 2019/0117216 A1 | 4/2019 | Overmyer et al. |
| 2019/0117217 A1 | 4/2019 | Overmyer et al. |
| 2019/0117222 A1 | 4/2019 | Shelton, IV et al. |
| 2019/0117224 A1 | 4/2019 | Setser et al. |
| 2019/0117225 A1 | 4/2019 | Moore et al. |
| 2019/0125343 A1 | 5/2019 | Wise et al. |
| 2019/0125344 A1 | 5/2019 | DiNardo et al. |
| 2019/0125345 A1 | 5/2019 | Baber et al. |
| 2019/0125365 A1 | 5/2019 | Parfett et al. |
| 2019/0125380 A1 | 5/2019 | Hunter et al. |
| 2019/0125475 A1 | 5/2019 | Wise et al. |
| 2019/0133585 A1 | 5/2019 | Smith et al. |
| 2019/0142421 A1 | 5/2019 | Shelton, IV |
| 2019/0183490 A1 | 6/2019 | Shelton, IV et al. |
| 2019/0183491 A1 | 6/2019 | Shelton, IV et al. |
| 2019/0183492 A1 | 6/2019 | Shelton, IV et al. |
| 2019/0183493 A1 | 6/2019 | Shelton, IV et al. |
| 2019/0183494 A1 | 6/2019 | Shelton, IV et al. |
| 2019/0183495 A1 | 6/2019 | Shelton, IV et al. |
| 2019/0183496 A1 | 6/2019 | Shelton, IV et al. |
| 2019/0183497 A1 | 6/2019 | Shelton, IV et al. |
| 2019/0183498 A1 | 6/2019 | Shelton, IV et al. |
| 2019/0183499 A1 | 6/2019 | Shelton, IV et al. |
| 2019/0183500 A1 | 6/2019 | Shelton, IV et al. |
| 2019/0183501 A1 | 6/2019 | Shelton, IV et al. |
| 2019/0183502 A1 | 6/2019 | Shelton, IV et al. |
| 2019/0183503 A1 | 6/2019 | Shelton, IV et al. |
| 2019/0183504 A1 | 6/2019 | Shelton, IV et al. |
| 2019/0183505 A1 | 6/2019 | Vendely et al. |
| 2019/0183592 A1 | 6/2019 | Shelton, IV et al. |
| 2019/0183594 A1 | 6/2019 | Shelton, IV et al. |
| 2019/0183597 A1 | 6/2019 | Shelton, IV et al. |
| 2019/0192137 A1 | 6/2019 | Shelton, IV et al. |
| 2019/0192138 A1 | 6/2019 | Shelton, IV et al. |
| 2019/0192141 A1 | 6/2019 | Shelton, IV et al. |
| 2019/0192144 A1 | 6/2019 | Parfett et al. |
| 2019/0192145 A1 | 6/2019 | Shelton, IV et al. |
| 2019/0192146 A1 | 6/2019 | Widenhouse et al. |
| 2019/0192147 A1 | 6/2019 | Shelton, IV et al. |
| 2019/0192148 A1 | 6/2019 | Shelton, IV et al. |
| 2019/0192149 A1 | 6/2019 | Shelton, IV et al. |
| 2019/0192150 A1 | 6/2019 | Widenhouse et al. |
| 2019/0192151 A1 | 6/2019 | Shelton, IV et al. |
| 2019/0192152 A1 | 6/2019 | Morgan et al. |
| 2019/0192153 A1 | 6/2019 | Shelton, IV et al. |
| 2019/0192154 A1 | 6/2019 | Shelton, IV et al. |
| 2019/0192155 A1 | 6/2019 | Shelton, IV et al. |
| 2019/0192156 A1 | 6/2019 | Simms et al. |
| 2019/0192157 A1 | 6/2019 | Scott et al. |
| 2019/0192158 A1 | 6/2019 | Scott et al. |
| 2019/0192159 A1 | 6/2019 | Simms et al. |
| 2019/0192227 A1 | 6/2019 | Shelton, IV et al. |
| 2019/0192235 A1 | 6/2019 | Harris et al. |
| 2019/0192236 A1 | 6/2019 | Shelton, IV et al. |
| 2019/0200895 A1 | 7/2019 | Shelton, IV et al. |
| 2019/0200991 A1 | 7/2019 | Moore et al. |
| 2019/0200992 A1 | 7/2019 | Moore et al. |
| 2019/0200993 A1 | 7/2019 | Moore et al. |
| 2019/0200994 A1 | 7/2019 | Moore et al. |
| 2019/0201028 A1 | 7/2019 | Shelton, IV et al. |
| 2019/0206562 A1 | 7/2019 | Shelton, IV et al. |
| 2019/0209164 A1 | 7/2019 | Timm et al. |
| 2019/0209165 A1 | 7/2019 | Timm et al. |
| 2019/0209171 A1 | 7/2019 | Shelton, IV et al. |
| 2019/0209172 A1 | 7/2019 | Shelton, IV et al. |
| 2019/0209247 A1 | 7/2019 | Giordano et al. |
| 2019/0209248 A1 | 7/2019 | Giordano et al. |
| 2019/0209249 A1 | 7/2019 | Giordano et al. |
| 2019/0209250 A1 | 7/2019 | Giordano et al. |
| 2019/0216558 A1 | 7/2019 | Giordano et al. |
| 2019/0223865 A1 | 7/2019 | Shelton, IV et al. |
| 2019/0223871 A1 | 7/2019 | Moore et al. |
| 2019/0261984 A1 | 8/2019 | Nelson et al. |
| 2019/0261991 A1 | 8/2019 | Beckman et al. |
| 2019/0267403 A1 | 8/2019 | Li et al. |
| 2019/0269400 A1 | 9/2019 | Mandakolathur Vasudevan et al. |
| 2019/0269402 A1 | 9/2019 | Murray et al. |
| 2019/0269403 A1 | 9/2019 | Baxter, III et al. |
| 2019/0269407 A1 | 9/2019 | Swensgard et al. |
| 2019/0269428 A1 | 9/2019 | Allen et al. |
| 2019/0274677 A1 | 9/2019 | Shelton, IV |
| 2019/0274678 A1 | 9/2019 | Shelton, IV |
| 2019/0274679 A1 | 9/2019 | Shelton, IV |
| 2019/0274680 A1 | 9/2019 | Shelton, IV |
| 2019/0274685 A1 | 9/2019 | Olson et al. |
| 2019/0290263 A1 | 9/2019 | Morgan et al. |
| 2019/0290264 A1 | 9/2019 | Morgan et al. |
| 2019/0290265 A1 | 9/2019 | Shelton, IV et al. |
| 2019/0290267 A1 | 9/2019 | Baxter, III et al. |
| 2019/0290274 A1 | 9/2019 | Shelton, IV |
| 2019/0290281 A1 | 9/2019 | Aronhalt et al. |
| 2019/0298348 A1 | 10/2019 | Harris et al. |
| 2019/0298360 A1 | 10/2019 | Shelton, IV et al. |
| 2019/0298361 A1 | 10/2019 | Shelton, IV et al. |
| 2019/0298362 A1 | 10/2019 | Shelton, IV et al. |
| 2019/0307452 A1 | 10/2019 | Shelton, IV et al. |
| 2019/0307453 A1 | 10/2019 | Shelton, IV et al. |
| 2019/0307454 A1 | 10/2019 | Shelton, IV et al. |
| 2019/0307455 A1 | 10/2019 | Shelton, IV et al. |
| 2019/0307456 A1 | 10/2019 | Shelton, IV et al. |
| 2019/0307476 A1 | 10/2019 | Shelton, IV et al. |
| 2019/0307477 A1 | 10/2019 | Shelton, IV et al. |
| 2019/0307478 A1 | 10/2019 | Shelton, IV et al. |
| 2019/0307479 A1 | 10/2019 | Shelton, IV et al. |
| 2019/0314016 A1 | 10/2019 | Huitema et al. |
| 2019/0314017 A1 | 10/2019 | Huitema et al. |
| 2019/0314018 A1 | 10/2019 | Huitema et al. |
| 2019/0321039 A1 | 10/2019 | Harris et al. |
| 2019/0321040 A1 | 10/2019 | Shelton, IV |
| 2019/0321041 A1 | 10/2019 | Shelton, IV |
| 2019/0328386 A1 | 10/2019 | Harris et al. |
| 2019/0328387 A1 | 10/2019 | Overmyer et al. |
| 2019/0328390 A1 | 10/2019 | Harris et al. |
| 2019/0336128 A1 | 11/2019 | Harris et al. |
| 2019/0343514 A1 | 11/2019 | Shelton, IV et al. |
| 2019/0343515 A1 | 11/2019 | Morgan et al. |
| 2019/0343518 A1 | 11/2019 | Shelton, IV |
| 2019/0343525 A1 | 11/2019 | Shelton, IV et al. |
| 2019/0350582 A1 | 11/2019 | Shelton, IV et al. |
| 2019/0357909 A1 | 11/2019 | Huitema et al. |
| 2019/0365384 A1 | 12/2019 | Baxter, III et al. |
| 2019/0374224 A1 | 12/2019 | Huitema et al. |
| 2020/0000461 A1 | 1/2020 | Yates et al. |
| 2020/0000468 A1 | 1/2020 | Shelton, IV et al. |
| 2020/0000469 A1 | 1/2020 | Shelton, IV et al. |
| 2020/0000471 A1 | 1/2020 | Shelton, IV et al. |
| 2020/0000531 A1 | 1/2020 | Giordano et al. |
| 2020/0008800 A1 | 1/2020 | Shelton, IV et al. |
| 2020/0008802 A1 | 1/2020 | Aronhalt et al. |
| 2020/0008809 A1 | 1/2020 | Shelton, IV et al. |
| 2020/0015819 A1 | 1/2020 | Shelton, IV et al. |
| 2020/0022702 A1 | 1/2020 | Shelton, IV et al. |
| 2020/0029964 A1 | 1/2020 | Overmyer et al. |
| 2020/0030050 A1 | 1/2020 | Shelton, IV et al. |
| 2020/0038016 A1 | 2/2020 | Shelton, IV et al. |
| 2020/0038018 A1 | 2/2020 | Shelton, IV et al. |
| 2020/0038020 A1 | 2/2020 | Yates et al. |
| 2020/0046348 A1 | 2/2020 | Shelton, IV et al. |
| 2020/0046893 A1 | 2/2020 | Shelton, IV et al. |
| 2020/0054320 A1 | 2/2020 | Harris et al. |
| 2020/0054321 A1 | 2/2020 | Harris et al. |
| 2020/0054322 A1 | 2/2020 | Harris et al. |
| 2020/0054323 A1 | 2/2020 | Harris et al. |
| 2020/0054324 A1 | 2/2020 | Shelton, IV et al. |
| 2020/0054325 A1 | 2/2020 | Harris et al. |
| 2020/0054326 A1 | 2/2020 | Harris et al. |
| 2020/0054327 A1 | 2/2020 | Harris et al. |
| 2020/0054328 A1 | 2/2020 | Harris et al. |
| 2020/0054329 A1 | 2/2020 | Shelton, IV et al. |

(56) References Cited

U.S. PATENT DOCUMENTS

| | | | |
|---|---|---|---|
| 2020/0054330 A1 | 2/2020 | Harris et al. |
| 2020/0054331 A1 | 2/2020 | Harris et al. |
| 2020/0054332 A1 | 2/2020 | Shelton, IV et al. |
| 2020/0054333 A1 | 2/2020 | Shelton, IV et al. |
| 2020/0054334 A1 | 2/2020 | Shelton, IV et al. |
| 2020/0054355 A1 | 2/2020 | Laurent et al. |
| 2020/0060680 A1 | 2/2020 | Shelton, IV et al. |
| 2020/0060681 A1 | 2/2020 | Shelton, IV et al. |
| 2020/0060713 A1 | 2/2020 | Leimbach et al. |
| 2020/0077994 A1 | 3/2020 | Shelton, IV et al. |
| 2020/0078015 A1 | 3/2020 | Miller et al. |
| 2020/0078016 A1 | 3/2020 | Swayze et al. |

FOREIGN PATENT DOCUMENTS

| | | |
|---|---|---|
| AU | 2012200178 B2 | 7/2013 |
| BR | 112013027777 A2 | 1/2017 |
| CA | 1015829 A | 8/1977 |
| CA | 1125615 A | 6/1982 |
| CA | 2520413 A1 | 3/2007 |
| CA | 2725181 A1 | 11/2007 |
| CA | 2851239 A1 | 11/2007 |
| CA | 2664874 A1 | 11/2009 |
| CA | 2813230 A1 | 4/2012 |
| CA | 2940510 A1 | 8/2015 |
| CA | 2698728 C | 8/2016 |
| CN | 1163558 A | 10/1997 |
| CN | 2488482 Y | 5/2002 |
| CN | 1634601 A | 7/2005 |
| CN | 2716900 Y | 8/2005 |
| CN | 2738962 Y | 11/2005 |
| CN | 1777406 A | 5/2006 |
| CN | 2796654 Y | 7/2006 |
| CN | 2868212 Y | 2/2007 |
| CN | 200942099 Y | 9/2007 |
| CN | 200984209 Y | 12/2007 |
| CN | 200991269 Y | 12/2007 |
| CN | 201001747 Y | 1/2008 |
| CN | 101143105 A | 3/2008 |
| CN | 201029899 Y | 3/2008 |
| CN | 101378791 A | 3/2009 |
| CN | 101522120 A | 9/2009 |
| CN | 101669833 A | 3/2010 |
| CN | 101721236 A | 6/2010 |
| CN | 101828940 A | 9/2010 |
| CN | 101873834 A | 10/2010 |
| CN | 201719298 U | 1/2011 |
| CN | 102038532 A | 5/2011 |
| CN | 201879759 U | 6/2011 |
| CN | 201949071 U | 8/2011 |
| CN | 102217961 A | 10/2011 |
| CN | 102217963 A | 10/2011 |
| CN | 102247183 A | 11/2011 |
| CN | 101779977 B | 12/2011 |
| CN | 101912284 B | 7/2012 |
| CN | 102125450 B | 7/2012 |
| CN | 202313537 U | 7/2012 |
| CN | 202397539 U | 8/2012 |
| CN | 202426586 U | 9/2012 |
| CN | 202489990 U | 10/2012 |
| CN | 102228387 B | 11/2012 |
| CN | 102835977 A | 12/2012 |
| CN | 202568350 U | 12/2012 |
| CN | 103690212 A | 4/2014 |
| CN | 203564285 U | 4/2014 |
| CN | 203564287 U | 4/2014 |
| CN | 203597997 U | 5/2014 |
| CN | 103829981 A | 6/2014 |
| CN | 103829983 A | 6/2014 |
| CN | 103908313 A | 7/2014 |
| CN | 203693685 U | 7/2014 |
| CN | 203736251 U | 7/2014 |
| CN | 103981635 A | 8/2014 |
| CN | 203815517 U | 9/2014 |
| CN | 102783741 B | 10/2014 |
| CN | 102973300 B | 10/2014 |
| CN | 104337556 A | 2/2015 |
| CN | 204158440 U | 2/2015 |
| CN | 204158441 U | 2/2015 |
| CN | 102469995 B | 3/2015 |
| CN | 204636451 U | 9/2015 |
| CN | 103860225 B | 3/2016 |
| CN | 103750872 B | 5/2016 |
| DE | 273689 C | 5/1914 |
| DE | 1775926 A | 1/1972 |
| DE | 3036217 A1 | 4/1982 |
| DE | 3210466 A1 | 9/1983 |
| DE | 3709067 A1 | 9/1988 |
| DE | 19534043 A1 | 3/1997 |
| DE | 19851291 A1 | 1/2000 |
| DE | 19924311 A1 | 11/2000 |
| DE | 20016423 U1 | 2/2001 |
| DE | 20112837 U1 | 10/2001 |
| DE | 20121753 U1 | 4/2003 |
| DE | 202004012389 U1 | 9/2004 |
| DE | 10314072 A1 | 10/2004 |
| DE | 102004014011 A1 | 10/2005 |
| DE | 102004063606 A1 | 7/2006 |
| DE | 202007003114 U1 | 6/2007 |
| DE | 102010013150 A1 | 9/2011 |
| EP | 0000756 A1 | 2/1979 |
| EP | 0122046 A1 | 10/1984 |
| EP | 0129442 B1 | 11/1987 |
| EP | 0255631 A1 | 2/1988 |
| EP | 0169044 B1 | 6/1991 |
| EP | 0541950 A1 | 5/1993 |
| EP | 0548998 A1 | 6/1993 |
| EP | 0594148 A1 | 4/1994 |
| EP | 0646357 A1 | 4/1995 |
| EP | 0505036 B1 | 5/1995 |
| EP | 0669104 A1 | 8/1995 |
| EP | 0705571 A1 | 4/1996 |
| EP | 0528478 B1 | 5/1996 |
| EP | 0770355 A1 | 5/1997 |
| EP | 0625335 B1 | 11/1997 |
| EP | 0879742 A1 | 11/1998 |
| EP | 0650701 B1 | 3/1999 |
| EP | 0923907 A1 | 6/1999 |
| EP | 0484677 B2 | 7/2000 |
| EP | 1034747 A1 | 9/2000 |
| EP | 1034748 A1 | 9/2000 |
| EP | 0726632 B1 | 10/2000 |
| EP | 1053719 A1 | 11/2000 |
| EP | 1055399 A1 | 11/2000 |
| EP | 1055400 A1 | 11/2000 |
| EP | 1080694 A1 | 3/2001 |
| EP | 1090592 A1 | 4/2001 |
| EP | 1095627 A1 | 5/2001 |
| EP | 0806914 B1 | 9/2001 |
| EP | 1234587 A1 | 8/2002 |
| EP | 1284120 A1 | 2/2003 |
| EP | 0717967 B1 | 5/2003 |
| EP | 0869742 B1 | 5/2003 |
| EP | 1374788 A1 | 1/2004 |
| EP | 1407719 A2 | 4/2004 |
| EP | 0996378 B1 | 6/2004 |
| EP | 1157666 B1 | 9/2005 |
| EP | 0880338 B1 | 10/2005 |
| EP | 1158917 B1 | 11/2005 |
| EP | 1344498 B1 | 11/2005 |
| EP | 1330989 B1 | 12/2005 |
| EP | 1632191 A2 | 3/2006 |
| EP | 1082944 B1 | 5/2006 |
| EP | 1253866 B1 | 7/2006 |
| EP | 1723914 A1 | 11/2006 |
| EP | 1285633 B1 | 12/2006 |
| EP | 1011494 B1 | 1/2007 |
| EP | 1767163 A1 | 3/2007 |
| EP | 1837041 A1 | 9/2007 |
| EP | 0922435 B1 | 10/2007 |
| EP | 1599146 B1 | 10/2007 |
| EP | 1330201 B1 | 6/2008 |
| EP | 2039302 A2 | 3/2009 |
| EP | 1719461 B1 | 6/2009 |

(56) References Cited

FOREIGN PATENT DOCUMENTS

| | | |
|---|---|---|
| EP | 2116196 A2 | 11/2009 |
| EP | 1769754 B1 | 6/2010 |
| EP | 1627605 B1 | 12/2010 |
| EP | 2316345 A1 | 5/2011 |
| EP | 1962711 B1 | 2/2012 |
| EP | 2486862 A2 | 8/2012 |
| EP | 2486868 A2 | 8/2012 |
| EP | 2517638 A1 | 10/2012 |
| EP | 2606812 A1 | 6/2013 |
| EP | 2649948 A1 | 10/2013 |
| EP | 2649949 A1 | 10/2013 |
| EP | 2668910 A2 | 12/2013 |
| EP | 2687164 A2 | 1/2014 |
| EP | 2713902 A1 | 4/2014 |
| EP | 2743042 A2 | 6/2014 |
| EP | 2764827 A2 | 8/2014 |
| EP | 2777524 A2 | 9/2014 |
| EP | 2842500 A1 | 3/2015 |
| EP | 2853220 A1 | 4/2015 |
| EP | 2298220 B1 | 6/2016 |
| EP | 2510891 B1 | 6/2016 |
| EP | 3031404 A1 | 6/2016 |
| EP | 3047806 A1 | 7/2016 |
| EP | 3078334 A1 | 10/2016 |
| EP | 2364651 B1 | 11/2016 |
| EP | 2747235 B1 | 11/2016 |
| EP | 3095399 A2 | 11/2016 |
| EP | 2789299 B1 | 5/2017 |
| EP | 3225190 A2 | 10/2017 |
| EP | 3363378 A1 | 8/2018 |
| FR | 459743 A | 11/1913 |
| FR | 999646 A | 2/1952 |
| FR | 1112936 A | 3/1956 |
| FR | 2598905 A1 | 11/1987 |
| FR | 2689749 B1 | 7/1994 |
| FR | 2765794 A1 | 1/1999 |
| FR | 2815842 A1 | 5/2002 |
| GB | 939929 A | 10/1963 |
| GB | 1210522 A | 10/1970 |
| GB | 1217159 A | 12/1970 |
| GB | 1339394 A | 12/1973 |
| GB | 2024012 A | 1/1980 |
| GB | 2109241 A | 6/1983 |
| GB | 2090534 B | 6/1984 |
| GB | 2272159 A | 5/1994 |
| GB | 2336214 A | 10/1999 |
| GB | 2509523 A | 7/2014 |
| GR | 930100110 A | 11/1993 |
| JP | S4711908 Y1 | 5/1972 |
| JP | S5033988 U | 4/1975 |
| JP | S5367286 A | 6/1978 |
| JP | S56112235 A | 9/1981 |
| JP | S60113007 A | 6/1985 |
| JP | S62170011 U | 10/1987 |
| JP | S63270040 A | 11/1988 |
| JP | H0129503 B2 | 6/1989 |
| JP | H0378514 U | 8/1991 |
| JP | H0385009 U | 8/1991 |
| JP | H04215747 A | 8/1992 |
| JP | H04131860 U | 12/1992 |
| JP | H0584252 A | 4/1993 |
| JP | H05123325 A | 5/1993 |
| JP | H05226945 A | 9/1993 |
| JP | H0630945 A | 2/1994 |
| JP | H06237937 A | 8/1994 |
| JP | H06327684 A | 11/1994 |
| JP | H079622 U | 2/1995 |
| JP | H07124166 A | 5/1995 |
| JP | H07163573 A | 6/1995 |
| JP | H07255735 A | 10/1995 |
| JP | H07285089 A | 10/1995 |
| JP | H0833642 A | 2/1996 |
| JP | H08164141 A | 6/1996 |
| JP | H08182684 A | 7/1996 |
| JP | H08507708 A | 8/1996 |
| JP | H08229050 A | 9/1996 |
| JP | H08289895 A | 11/1996 |
| JP | H09-323068 A | 12/1997 |
| JP | H10118090 A | 5/1998 |
| JP | H10-200699 A | 7/1998 |
| JP | H10296660 A | 11/1998 |
| JP | 2000014632 A | 1/2000 |
| JP | 2000033071 A | 2/2000 |
| JP | 2000112002 A | 4/2000 |
| JP | 2000166932 A | 6/2000 |
| JP | 2000171730 A | 6/2000 |
| JP | 2000271141 A | 10/2000 |
| JP | 2000287987 A | 10/2000 |
| JP | 2000325303 A | 11/2000 |
| JP | 2001087272 A | 4/2001 |
| JP | 2001514541 A | 9/2001 |
| JP | 2001276091 A | 10/2001 |
| JP | 2002051974 A | 2/2002 |
| JP | 2002054903 A | 2/2002 |
| JP | 2002085415 A | 3/2002 |
| JP | 2002143078 A | 5/2002 |
| JP | 2002153481 A | 5/2002 |
| JP | 2002528161 A | 9/2002 |
| JP | 2002314298 A | 10/2002 |
| JP | 2003135473 A | 5/2003 |
| JP | 2003521301 A | 7/2003 |
| JP | 3442423 B2 | 9/2003 |
| JP | 2003300416 A | 10/2003 |
| JP | 2004147701 A | 5/2004 |
| JP | 2004162035 A | 6/2004 |
| JP | 2004229976 A | 8/2004 |
| JP | 2005013573 A | 1/2005 |
| JP | 2005080702 A | 3/2005 |
| JP | 2005131163 A | 5/2005 |
| JP | 2005131164 A | 5/2005 |
| JP | 2005131173 A | 5/2005 |
| JP | 2005131211 A | 5/2005 |
| JP | 2005131212 A | 5/2005 |
| JP | 2005137423 A | 6/2005 |
| JP | 2005187954 A | 7/2005 |
| JP | 2005211455 A | 8/2005 |
| JP | 2005328882 A | 12/2005 |
| JP | 2005335432 A | 12/2005 |
| JP | 2005342267 A | 12/2005 |
| JP | 3791856 B2 | 6/2006 |
| JP | 2006187649 A | 7/2006 |
| JP | 2006218228 A | 8/2006 |
| JP | 2006281405 A | 10/2006 |
| JP | 2006346445 A | 12/2006 |
| JP | 2008220032 A | 9/2008 |
| JP | 2009507526 A | 2/2009 |
| JP | 2009189838 A | 8/2009 |
| JP | 2009189846 A | 8/2009 |
| JP | 2009207260 A | 9/2009 |
| JP | 2009226028 A | 10/2009 |
| JP | 2009538684 A | 11/2009 |
| JP | 2009539420 A | 11/2009 |
| JP | 2010069307 A | 4/2010 |
| JP | 2010069310 A | 4/2010 |
| JP | 2010098844 A | 4/2010 |
| JP | 2010214128 A | 9/2010 |
| JP | 2011072574 A | 4/2011 |
| JP | 4722849 B2 | 7/2011 |
| JP | 4728996 B2 | 7/2011 |
| JP | 2011524199 A | 9/2011 |
| JP | D1432094 | 12/2011 |
| JP | 2012143283 A | 8/2012 |
| JP | 5154710 B1 | 2/2013 |
| JP | 2013126430 A | 6/2013 |
| JP | 2014121599 A | 7/2014 |
| JP | 2016512057 A | 4/2016 |
| KR | 20100110134 A | 10/2010 |
| KR | 20110003229 A | 1/2011 |
| RU | 1814161 C | 5/1993 |
| RU | 2008830 C1 | 3/1994 |
| RU | 2052979 C1 | 1/1996 |
| RU | 2066128 C1 | 9/1996 |
| RU | 2069981 C1 | 12/1996 |
| RU | 2098025 C1 | 12/1997 |

(56) References Cited

FOREIGN PATENT DOCUMENTS

| | | |
|---|---|---|
| RU | 2104671 C1 | 2/1998 |
| RU | 2110965 C1 | 5/1998 |
| RU | 2141279 C1 | 11/1999 |
| RU | 2144791 C1 | 1/2000 |
| RU | 2161450 C1 | 1/2001 |
| RU | 2181566 C2 | 4/2002 |
| RU | 2187249 C2 | 8/2002 |
| RU | 32984 U1 | 10/2003 |
| RU | 2225170 C2 | 3/2004 |
| RU | 42750 U1 | 12/2004 |
| RU | 61114 U1 | 2/2007 |
| RU | 61122 U1 | 2/2007 |
| RU | 2430692 C2 | 10/2011 |
| SU | 189517 A | 1/1967 |
| SU | 297156 A | 5/1971 |
| SU | 328636 A | 9/1972 |
| SU | 511939 A1 | 4/1976 |
| SU | 674747 A1 | 7/1979 |
| SU | 728848 A1 | 4/1980 |
| SU | 1009439 A | 4/1983 |
| SU | 1271497 A1 | 11/1986 |
| SU | 1333319 A2 | 8/1987 |
| SU | 1377052 A1 | 2/1988 |
| SU | 1377053 A1 | 2/1988 |
| SU | 1443874 A1 | 12/1988 |
| SU | 1509051 A1 | 9/1989 |
| SU | 1561964 A1 | 5/1990 |
| SU | 1708312 A1 | 1/1992 |
| SU | 1722476 A1 | 3/1992 |
| SU | 1752361 A1 | 8/1992 |
| SU | 1814161 A1 | 5/1993 |
| WO | WO-9315648 A1 | 8/1993 |
| WO | WO-9420030 A1 | 9/1994 |
| WO | WO-9517855 A1 | 7/1995 |
| WO | WO-9520360 A1 | 8/1995 |
| WO | WO-9623448 A1 | 8/1996 |
| WO | WO-9635464 A1 | 11/1996 |
| WO | WO-9639086 A1 | 12/1996 |
| WO | WO-9639088 A1 | 12/1996 |
| WO | WO-9724073 A1 | 7/1997 |
| WO | WO-9734533 A1 | 9/1997 |
| WO | WO-9827870 A1 | 7/1998 |
| WO | WO-9903407 A1 | 1/1999 |
| WO | WO-9903409 A1 | 1/1999 |
| WO | WO-9948430 A1 | 9/1999 |
| WO | WO-0024322 A1 | 5/2000 |
| WO | WO-0024330 A1 | 5/2000 |
| WO | WO-0053112 A2 | 9/2000 |
| WO | WO-0057796 A1 | 10/2000 |
| WO | WO-0105702 A1 | 1/2001 |
| WO | WO-0154594 A1 | 8/2001 |
| WO | WO-0158371 A1 | 8/2001 |
| WO | WO-0162164 A2 | 8/2001 |
| WO | WO-0162169 A2 | 8/2001 |
| WO | WO-0191646 A1 | 12/2001 |
| WO | WO-0219932 A1 | 3/2002 |
| WO | WO-0226143 A1 | 4/2002 |
| WO | WO-0236028 A1 | 5/2002 |
| WO | WO-02065933 A2 | 8/2002 |
| WO | WO-03055402 A1 | 7/2003 |
| WO | WO-03094747 A1 | 11/2003 |
| WO | WO-03079909 A3 | 3/2004 |
| WO | WO-2004019803 A1 | 3/2004 |
| WO | WO-2004032783 A1 | 4/2004 |
| WO | WO-2004047626 A1 | 6/2004 |
| WO | WO-2004047653 A2 | 6/2004 |
| WO | WO-2004056277 A1 | 7/2004 |
| WO | WO-2004078050 A2 | 9/2004 |
| WO | WO-2004078051 A2 | 9/2004 |
| WO | WO-2004096015 A2 | 11/2004 |
| WO | WO-2006044581 A2 | 4/2006 |
| WO | WO-2006051252 A1 | 5/2006 |
| WO | WO-2006059067 A1 | 6/2006 |
| WO | WO-2006073581 A2 | 7/2006 |
| WO | WO-2006085389 A1 | 8/2006 |
| WO | WO-2007015971 A2 | 2/2007 |
| WO | WO-2007074430 A1 | 7/2007 |
| WO | WO-2007129121 A1 | 11/2007 |
| WO | WO-2007137304 A2 | 11/2007 |
| WO | WO-2007142625 A2 | 12/2007 |
| WO | WO-2008021969 A2 | 2/2008 |
| WO | WO-2008061566 A1 | 5/2008 |
| WO | WO-2008089404 A2 | 7/2008 |
| WO | WO-2009005969 A2 | 1/2009 |
| WO | WO-2009067649 A2 | 5/2009 |
| WO | WO-2009091497 A2 | 7/2009 |
| WO | WO-2010126129 A1 | 11/2010 |
| WO | WO-2010134913 A1 | 11/2010 |
| WO | WO-2011008672 A2 | 1/2011 |
| WO | WO-2011044343 A2 | 4/2011 |
| WO | WO-2012006306 A2 | 1/2012 |
| WO | WO-2012013577 A1 | 2/2012 |
| WO | WO-2012044606 A2 | 4/2012 |
| WO | WO-2012061725 A1 | 5/2012 |
| WO | WO-2012072133 A1 | 6/2012 |
| WO | WO-2012166503 A1 | 12/2012 |
| WO | WO-2013087092 A1 | 6/2013 |
| WO | WO-2013151888 A1 | 10/2013 |
| WO | WO-2014004209 A2 | 1/2014 |
| WO | WO-2014113438 A1 | 7/2014 |
| WO | WO-2015032797 A1 | 3/2015 |
| WO | WO-2015138760 A1 | 9/2015 |
| WO | WO-2015187107 A1 | 12/2015 |

OTHER PUBLICATIONS

ASTM procedure D2240-05, "Standard Test Method for Rubber Property-Durometer Hardness," (Published Apr. 2010).
Van Meer et al., "A Disposable Plastic Compact Wrist for Smart Minimally Invasive Surgical Tools," LAAS/CNRS (Aug. 2005).
Breedveld et al., "A New, Easily Miniaturized Sterrable Endoscope," IEEE Engineering in Medicine and Biology Magazine (Nov./Dec. 2005).
Disclosed Anonymously, "Motor-Driven Surgical Stapler Improvements," Research Disclosure Database No. 526041, Published: Feb. 2008.
B.R. Coolman, DVM, MS et al., "Comparison of Skin Staples With Sutures for Anastomosis of the Small Intestine in Dogs," Abstract; http://www.blackwell-synergy.com/doi/abs/10.1053/jvet.2000.7539?cookieSet=1&journalCode=vsu which redirects to http://www3.interscience.wiley.com/journal/119040681/abstract?CRETRY=1&SRETRY=0; [online] accessed: Sep. 22, 2008 (2 pages).
D. Tuite, Ed., "Get the Lowdown on Ultracapacitors," Nov. 15, 2007; [online] URL: http://electronicdesign.com/Articles/Print.cfm?ArticleID=17465, accessed Jan. 15, 2008 (5 pages).
Datasheet for Panasonic TK Relays Ultra Low Profile 2 A Polarized Relay, Copyright Matsushita Electric Works, Ltd. (Known of at least as early as Aug. 17, 2010), 5 pages.
Schellhammer et al., "Poly-Lactic-Acid for Coating of Endovascular Stents: Preliminary Results in Canine Experimental Av-Fistulae," Mat.-wiss. u. Werkstofftech., 32, pp. 193-199 (2001).
Miyata et al., "Biomolecule-Sensitive Hydrogels," Advanced Drug Delivery Reviews, 54 (2002) pp. 79-98.
Jeong et al., "Thermosensitive Sol-Gel Reversible Hydrogels," Advanced Drug Delivery Reviews, 54 (2002) pp. 37-51.
Covidien Brochure, "Endo GIA™ Ultra Universal Stapler," (2010), 2 pages.
Qiu et al., "Environment-Sensitive Hydrogels for Drug Delivery," Advanced Drug Delivery Reviews, 53 (2001) pp. 321-339.
Hoffman, "Hydrogels for Biomedical Applications," Advanced Drug Delivery Reviews, 43 (2002) pp. 3-12.
Hoffman, "Hydrogels for Biomedical Applications," Advanced Drug Delivery Reviews, 54 (2002) pp. 3-12.
Peppas, "Physiologically Responsive Hydrogels," Journal of Bioactive and Compatible Polymers, vol. 6 (Jul. 1991) pp. 241-246.
Peppas, Editor "Hydrogels in Medicine and Pharmacy," vol. I, Fundamentals, CRC Press, 1986.
Young, "Microcellular foams via phase separation," Journal of Vacuum Science & Technology A 4(3), (May/Jun. 1986).

(56) References Cited

OTHER PUBLICATIONS

Ebara, "Carbohydrate-Derived Hydrogels and Microgels," Engineered Carbohydrate-Based Materials for Biomedical Applications: Polymers, Surfaes, Dendrimers, Nanoparticles, and Hydrogels, Edited by Ravin Narain, 2011, pp. 337-345.
http://ninpgan.net/publications/51-100/89.pdf; 2004, Ning Pan, On Uniqueness of Fibrous Materials, Design & Nature II. Eds: Colins, M. and Brebbia, C. WIT Press, Boston, 493-504.
Solorio et al., "Gelatin Microspheres Crosslinked with Genipin for Local Delivery of Growth Factors," J. Tissue Eng. Regen. Med. (2010), 4(7): pp. 514-523.
Covidien iDrive™ Ultra in Service Reference Card, "iDrive™ Ultra Powered Stapling Device," (4 pages).
Covidien iDrive™ Ultra Powered Stapling System ibrochure, "The Power of iDrive™ Ultra Powered Stapling System and Tri-Staple™ Technology," (23 pages).
Covidien "iDrive™ Ultra Powered Stapling System, A Guide for Surgeons," (6 pages).
Covidien "iDrive™ Ultra Powered Stapling System, Cleaning and Sterilization Guide," (2 pages).
Covidien Brochure "iDrive™ Ultra Powered Stapling System," (6 pages).
Covidien Brochure, "Endo GIA™ Reloads with Tri-Staple™ Technology," (2010), 1 page.
Covidien Brochure, "Endo GIA™ Reloads with Tri-Staple™ Technology and Endo GIA™ Ultra Universal Staplers," (2010), 2 pages.
Covidien Brochure, "Endo GIA™ Curved Tip Reload with Tri-Staple™ Technology," (2012), 2 pages.
Covidien Brochure, "Endo GIA™ Reloads with Tri-Staple™ Technology," (2010), 2 pages.
Pitt et al., "Attachment of Hyaluronan to Metallic Surfaces," J. Biomed. Mater. Res. 68A: pp. 95-106, 2004.
Indian Standard: Automotive Vehicles—Brakes and Braking Systems (IS 11852-1:2001), Mar. 1, 2001.
Patrick J. Sweeney: "RFID for Dummies", Mar. 11, 2010, pp. 365-365, XP055150775, ISBN: 978-1-11-805447-5, Retrieved from the Internet: URL: books.google.de/books?isbn=1118054474 [retrieved on Nov. 4, 2014]—book not attached.
Allegro MicroSystems, LLC, Automotive Full Bridge MOSFET Driver, A3941-DS, Rev. 5, 21 pages, http://www.allegromicro.com/~/media/Files/Datasheets/A3941-Datasheet.ashx?la=en.
Data Sheet of LM4F230H5QR, 2007.
Seils et al., Covidien Summary: Clinical Study "UCONN Biodynamics: Final Report on Results," (2 pages).
Byrne et al., "Molecular Imprinting Within Hydrogels," Advanced Drug Delivery Reviews, 54 (2002) pp. 149-161.
Fast, Versatile Blackfin Processors Handle Advanced RFID Reader Applications; Analog Dialogue: vol. 40—Sep. 2006; http://www.analog.com/library/analogDialogue/archives/40-09/rfid.pdf; Wayback Machine to Feb. 15, 2012.
Chen et al., "Elastomeric Biomaterials for Tissue Engineering," Progress in Polymer Science 38 (2013), pp. 584-671.
Matsuda, "Thermodynamics of Formation of Porous Polymeric Membrane from Solutions," Polymer Journal, vol. 23, No. 5, pp. 435-444 (1991).
Covidien Brochure, "Endo GIA™ Black Reload with Tri-Staple™ Technology," (2012), 2 pages.
Biomedical Coatings, Fort Wayne Metals, Research Products Corporation, obtained online at www.fwmetals.com on Jun. 21, 2010 (1 page).
The Sodem Aseptic Battery Transfer Kit, Sodem Systems, 2000, 3 pages.
C.C. Thompson et al., "Peroral Endoscopic Reduction of Dilated Gastrojejunal Anastomosis After Roux-en-Y Gastric Bypass: A Possible New Option for Patients with Weight Regain," Surg Endosc (2006) vol. 20., pp. 1744-1748.
Serial Communication Protocol; Michael Lemmon Feb. 1, 2009; http://www3.nd.edu/~lemmon/courses/ee224/web-man ual/web-manual/lab12/node2.html; Wayback Machine to Apr. 29, 2012.
Lyon et al. "The Relationship Between Current Load and Temperature for Quasi-Steady State and Transient Conditions," SPIE—International Society for Optical Engineering. Proceedings, vol. 4020, (pp. 62-70), Mar. 30, 2000.
Anonymous: "Sense & Control Application Note Current Sensing Using Linear Hall Sensors," Feb. 3, 2009, pp. 1-18. Retrieved from the Internet: URL: http://www.infineon.com/dgdl/Current_Sensing_Rev.1.1.pdf?fileId=db3a304332d040720132d939503e5f17 [retrieved on Oct. 18, 2016].
Mouser Electronics, "LM317M 3—Terminal Adjustable Regulator with Overcurrent/Overtemperature Self Protection", Mar. 31, 2014 (Mar. 31, 2014), XP0555246104, Retrieved from the Internet: URL: http://www.mouser.com/ds/2/405/lm317m-440423.pdf, pp. 1-8.
Mouser Electronics, "LM317 3—Terminal Adjustable Regulator with Overcurrent/Overtemperature Self Protection", Sep. 30, 2016 (Sep. 30, 2016), XP0555246104, Retrieved from the Internet: URL: http://www.mouser.com/ds/2/405/lm317m-440423.pdf, pp. 1-9.
Cuper et al., "The Use of Near-Infrared Light for Safe and Effective Visualization of Subsurface Blood Vessels to Facilitate Blood Withdrawal in Children," Medical Engineering & Physics, vol. 35, No. 4, pp. 433-440 (2013).
Anonymous, Analog Devices Wiki, Chapter 11: The Current Mirror, Aug. 20, 2017, 22 pages. https://wiki.analog.com/university/courses/electronics/text/chapter-11?rev=1503222341.
Yan et al, Comparison of the effects of Mg—6Zn and Ti—3Al—2.5V alloys on TGF-$\beta$/TNF-$\alpha$/VEGF/b-FGF in the healing of the intestinal track in vivo, Biomed. Mater. 9 (2014), 11 pages.
Yan et al., "Comparison of the effects of Mg—6Zn and titanium on intestinal tract in vivo," J Mater Sci: Mater Med (2013), 11 pages.
Brar et al., "Investigation of the mechanical and degradation properties of Mg—Sr and Mg—Zn—Sr alloys for use as potential biodegradable implant materials," J. Mech. Behavior of Biomed. Mater. 7 (2012) pp. 87-95.
Pellicer et al. "On the biodegradability, mechanical behavior, and cytocompatibility of amorphous Mg72Zn23Ca5 and crystalline Mg70Zn23Ca5Pd2 alloys as temporary implant materials," J Biomed Mater Res Part A ,2013:101A:502-517.
Texas Instruments: "Current Recirculation and Decay Modes," Application Report SLVA321—Mar. 2009; Retrieved from the Internet: URL:http://www.ti.com/lit/an/slva321/slva321 [retrieved on Apr. 25, 2017], 7 pages.
Qiu Li Loh et al.: "Three-Dimensional Scaffolds for Tissue Engineering Applications: Role of Porosity and Pore Size", Tissue Engineering Part B—Reviews, vol. 19, No. 6, Dec. 1, 2013, pp. 485-502.
Gao et al., "Mechanical Signature Enhancement of Response Vibrations in the Time Lag Domain," Fifth International Congress on Sound and Vibration, Dec. 15-18, 1997, pp. 1-8.
Trendafilova et al., "Vibration-based Methods for Structural and Machinery Fault Diagnosis Based on Nonlinear Dynamics Tools," In: Fault Diagnosis in Robotic and Industrial Systems, IConcept Press LTD, 2012, pp. 1-29.
Youtube.com; video by Fibran (retrieved from URL https://www.youtube.com/watch?v=vN2Qjt51gFQ); (Year: 2018).
Foot and Ankle: Core Knowledge in Orthopaedics; by DiGiovanni MD, Elsevier; (p. 27, left column, heading "Materials for Soft Orthoses", 7th bullet point); (Year: 2007).
Lee, Youbok, "Antenna Circuit Design for RFID Applications," 2003, pp. 1-50, DS00710C, Microchip Technology Inc., Available: http://ww1.microchip.com/downloads/en/AppNotes/00710c.pdf.
Kawamura, Atsuo, et al. "Wireless Transmission of Power and Information Through One High-Frequency Resonant AC Link Inverter for Robot Manipulator Applications," Journal, May/Jun. 1996, pp. 503-508, vol. 32, No. 3, IEEE Transactions on Industry Applications.
Honda HS1332AT and ATD Model Info, powerequipment.honda.com [online], published on or before Mar. 22, 2016, [retrieved on May 31, 2019], retrieved from the Internet [URL: https://powerequipment.honda.com/snowblowers/models/hss1332at-hss1332atd] {Year: 2016).
Slow Safety Sign, shutterstock.com [online], published on or before May 9, 2017, [retrieved on May 31, 2019], retrieved from the

(56) References Cited

OTHER PUBLICATIONS https://www.shutterstock.com/image-victor/slow-safety-sign-twodimensional-turtle-symbolizing- . . . see PDF in file for full URL] (Year: 2017).
Warning Sign Beveled Buttons, by Peter, flarestock.com [online], published on or before Jan. 1, 2017, [retrieved on Jun. 4, 2019], retrieved from the Internet [URL: https://www.flarestock.com/stock-images/warning-sign-beveled-buttons/70257] (Year: 2017).
Arrow Sign Icon Next Button, by Blan-k, shutterstock.com [online], published on or before Aug. 6, 2014, [retrieved on Jun. 4, 2019], retrieved from the Internet [URL:https://www.shutterstock.com/de/image-vector/arrow-sign-icon-next-button-navigation-207700303?irgwc=1&utm . . . see PDF in file for full URL] (Year: 2014).
Elite Icons, by smart/icons, iconfinder.com [online], published on Aug. 18, 2016, [retrieved on Jun. 4, 2019], retrieved from the Internet [URL: https://www.iconfinder.com/iconsets/elite] (Year: 2016).
Tutorial overview of inductively coupled RFID Systems, UPM, May 2003, pp. 1-7, UPM Rafsec,<http://cdn.mobiusconsulting.com/papers/rfidsystems.pdf>.
Schroeter, John, "*Demystifying UHF Gen 2 RFID, HF RFID,*" Online Article, Jun. 2, 2008, pp. 1-3, <https://www.edn.com/design/industrial-control/4019123/Demystifying-UHF-Gen-2-RFID-HF-RFID>.
Adeeb, et al., "*An Inductive Link-Based Wireless Power Transfer System for Biomedical Applications,*" Research Article, Nov. 14, 2011, pp. 1-12, vol. 2012, Article ID 879294, Hindawi Publishing Corporation.
Pushing Pixels (GIF), published on dribble.com, 2013.
Sodium stearate C18H35NaO2, Chemspider Search and Share Chemistry, Royal Society of Chemistry, pp. 1-3, 2015, http://www.chemspider.com/Chemical-Structure.12639.html, accessed May 23, 2016.
NF Monographs: Sodium Stearate, U.S. Pharmacopeia, http://www.pharmacopeia.cn/v29240/usp29nf24s0_m77360.html, accessed May 23, 2016.
Fischer, Martin H, "Colloid-Chemical Studies on Soaps", The Chemical Engineer, pp. 184-193, Aug. 1919.
V.K. Ahluwalia and Madhuri Goyal, A Textbook of Organic Chemistry, Section 19.11.3, p. 356, 2000.
A.V. Kasture and S.G. Wadodkar, Pharmaceutical Chemistry—II: Second Year Diploma in Pharmacy, Nirali Prakashan, p. 339, 2007.
Forum discussion regarding "Speed Is Faster", published on Oct 1, 2014 and retrieved on Nov. 8, 2019 from URL https://english.stackexchange.com/questions/199018/how-is-that-correct-speed-is-faster-or-prices-are-cheaper (Year: 2014).
"Understanding the Requirements of ISO/IEC 14443 for Type B Proximity Contactless Identification Cards," retrieved from https://www.digchip.com/application-notes/22/15746.php on Mar. 2, 2020, pp. 1-28 (Nov. 2005).

* cited by examiner

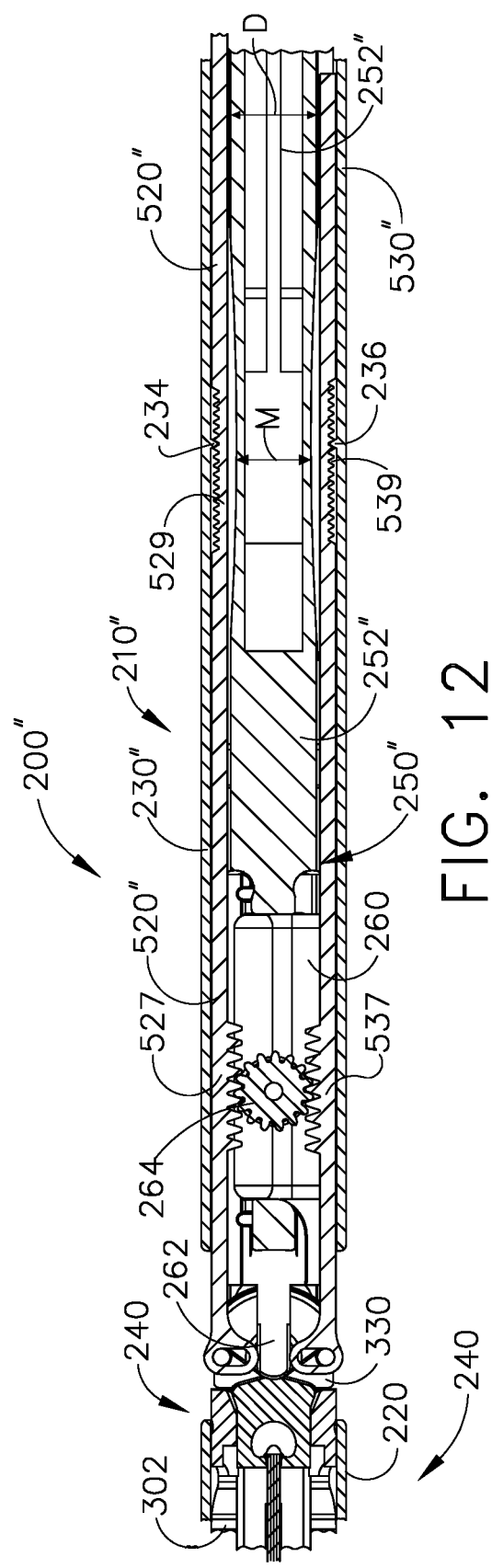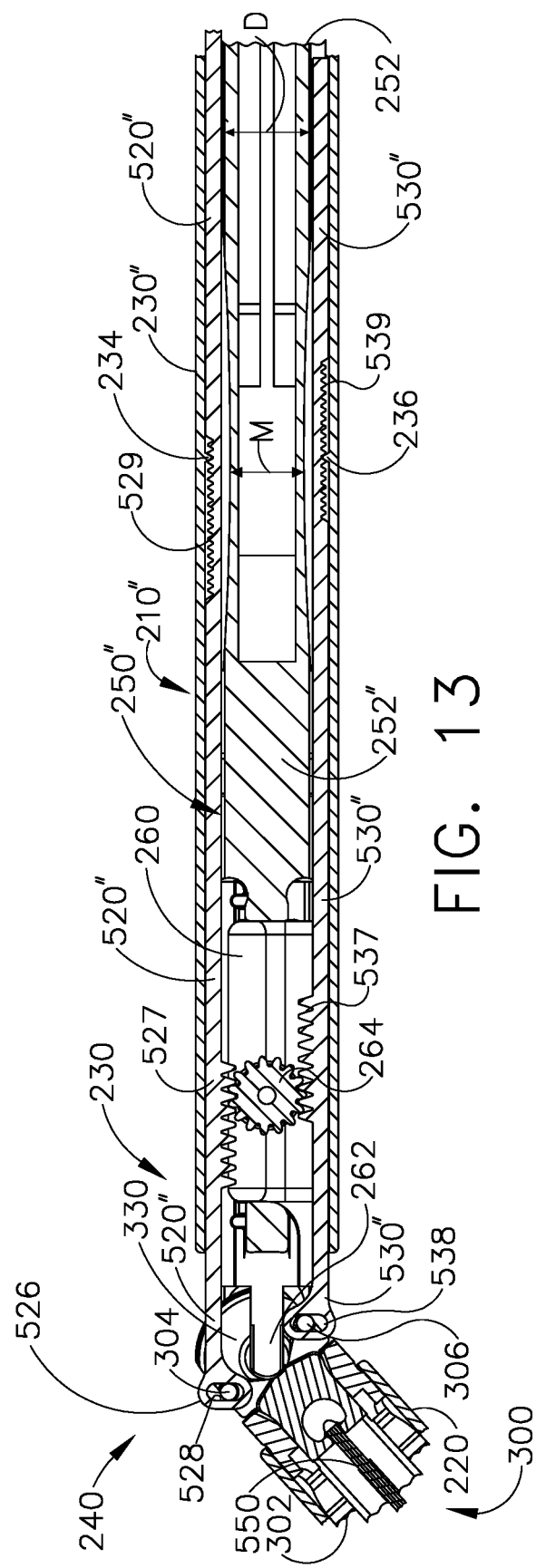

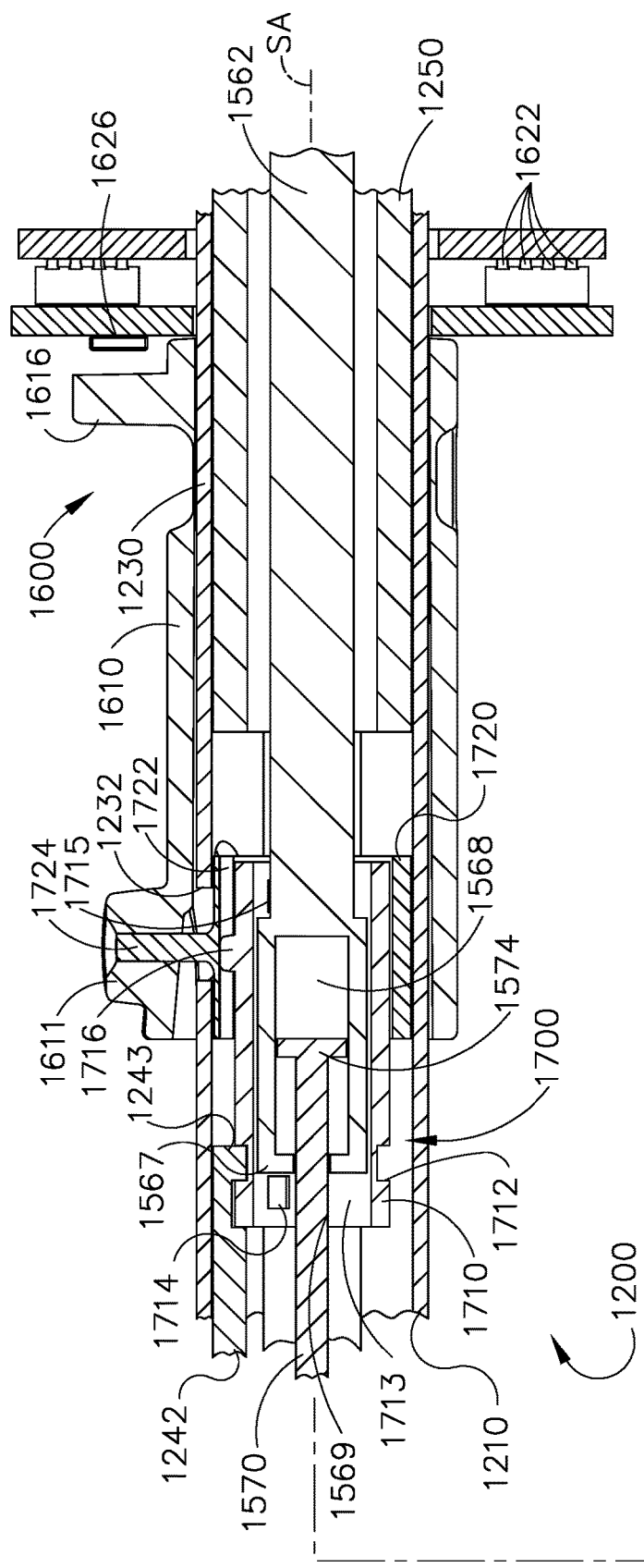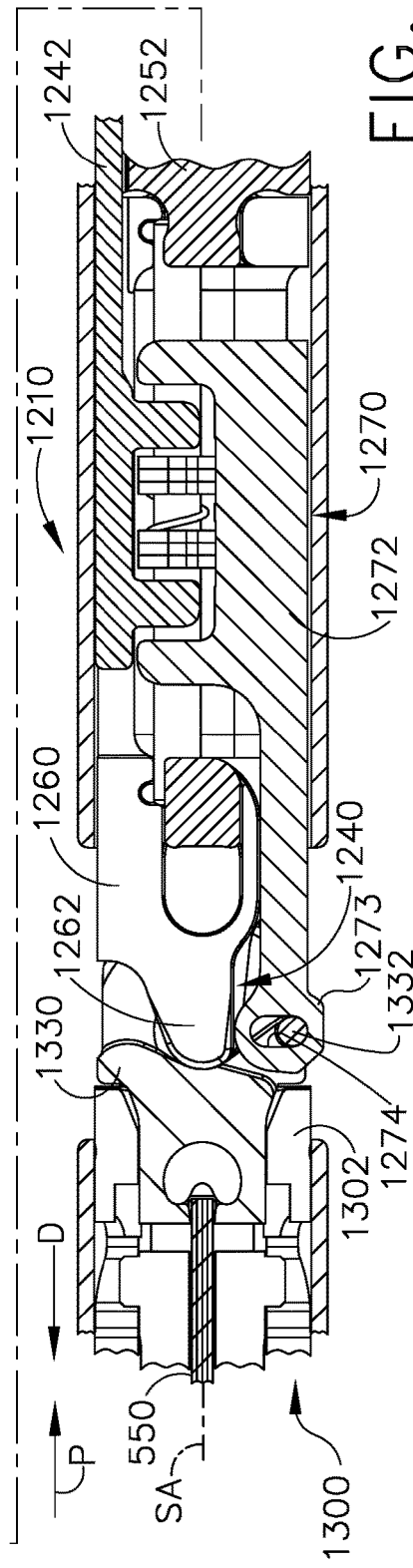
FIG. 20

DRIVE ARRANGEMENTS FOR ARTICULATABLE SURGICAL INSTRUMENTS

CROSS-REFERENCE TO RELATED APPLICATION

This application is a continuation application claiming priority under 35 U.S.C. § 120 to U.S. patent application Ser. No. 14/575,139, entitled DRIVE ARRANGEMENTS FOR ARTICULATABLE SURGICAL INSTRUMENTS, filed Dec. 18, 2014, which issued on Dec. 19, 2017 as U.S. Pat. No. 9,844,375, the entire disclosure of which is hereby incorporated by reference herein.

BACKGROUND

The present invention relates to surgical instruments and, in various embodiments, to surgical stapling and cutting instruments and staple cartridges for use therewith.

BRIEF DESCRIPTION OF THE DRAWINGS

The features and advantages of this invention, and the manner of attaining them, will become more apparent and the invention itself will be better understood by reference to the following description of embodiments of the invention taken in conjunction with the accompanying drawings, wherein:

FIG. 12 is a partial cross-sectional view of a portion of another interchangeable shaft assembly in an unarticulated configuration;

FIG. 13 is another partial cross-sectional view of the interchangeable shaft assembly of FIG. 12 in an articulated configuration;

FIG. 20 is another cross-sectional view of a portion of the interchangeable shaft assembly of FIGS. 14-19 with the end effector in an unarticulated orientation;

Corresponding reference characters indicate corresponding parts throughout the several views. The exemplifications set out herein illustrate certain embodiments of the invention, in one form, and such exemplifications are not to be construed as limiting the scope of the invention in any manner.

DETAILED DESCRIPTION

Figure 1:
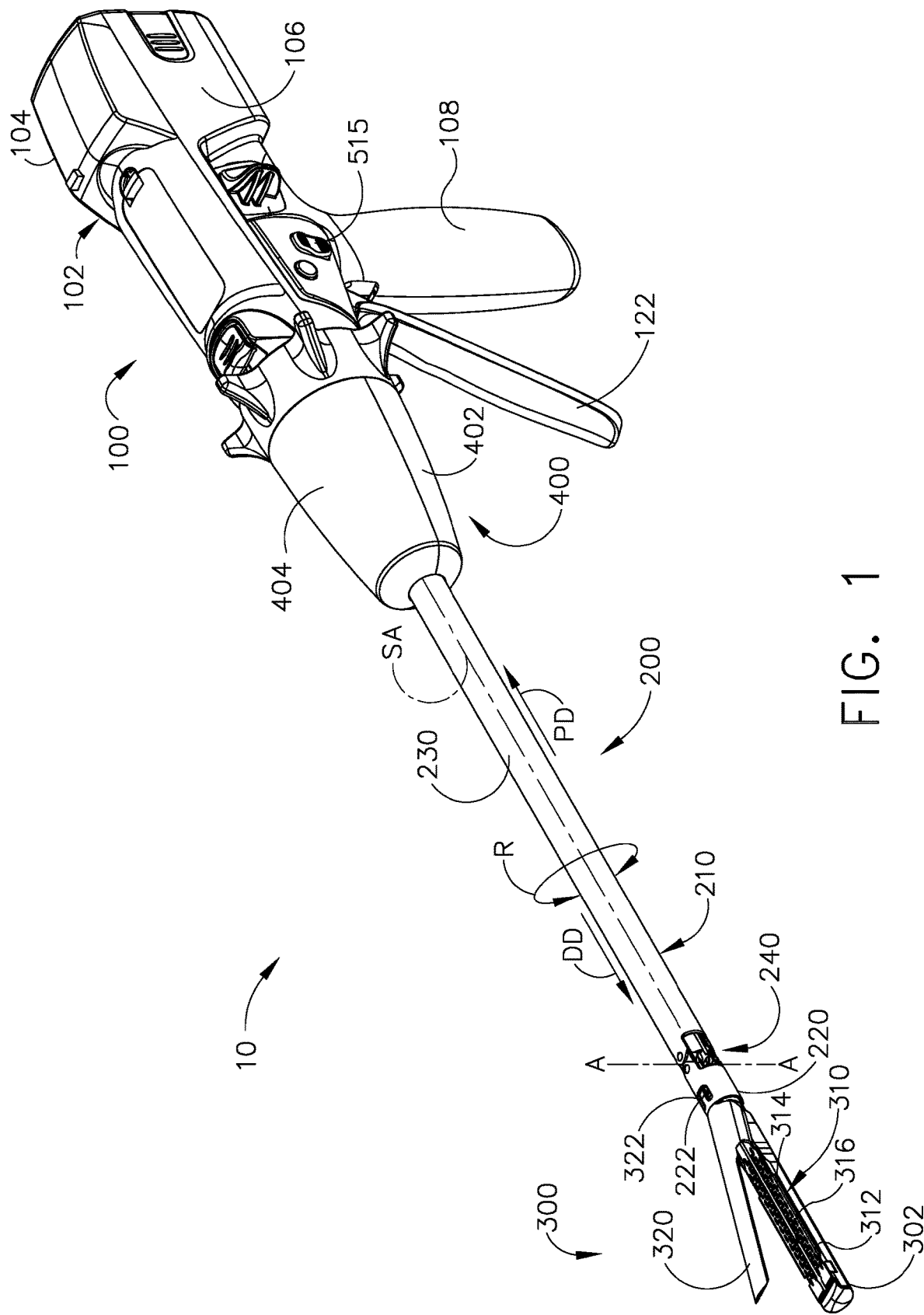
FIG. 1 is a perspective view of a powered surgical instrument comprising a handle, a shaft, and an articulatable end effector.

Applicant of the present application owns the following patent applications that were filed on Mar. 1, 2013 and which are each herein incorporated by reference in their respective entireties:

U.S. patent application Ser. No. 13/782,295, entitled ARTICULATABLE SURGICAL INSTRUMENTS WITH CONDUCTIVE PATHWAYS FOR SIGNAL COMMUNICATION, now U.S. Pat. No. 9,700,309;

U.S. patent application Ser. No. 13/782,323, entitled ROTARY POWERED ARTICULATION JOINTS FOR SURGICAL INSTRUMENTS, now U.S. Pat. No. 9,782,169;

U.S. patent application Ser. No. 13/782,338, entitled THUMBWHEEL SWITCH ARRANGEMENTS FOR SURGICAL INSTRUMENTS, now U.S. Patent Application Publication No. 2014/0249557;

U.S. patent application Ser. No. 13/782,499, entitled ELECTROMECHANICAL SURGICAL DEVICE WITH SIGNAL RELAY ARRANGEMENT, now U.S. Pat. No. 9,358,003;

U.S. patent application Ser. No. 13/782,460, entitled MULTIPLE PROCESSOR MOTOR CONTROL FOR MODULAR SURGICAL INSTRUMENTS, now U.S. Pat. No. 9,554,794;

U.S. patent application Ser. No. 13/782,358, entitled JOYSTICK SWITCH ASSEMBLIES FOR SURGICAL INSTRUMENTS, now U.S. Pat. No. 9,326,767;

U.S. patent application Ser. No. 13/782,481, entitled SENSOR STRAIGHTENED END EFFECTOR DURING REMOVAL THROUGH TROCAR, now U.S. Pat. No. 9,468,438;

U.S. patent application Ser. No. 13/782,518, entitled CONTROL METHODS FOR SURGICAL INSTRUMENTS WITH REMOVABLE IMPLEMENT PORTIONS, now U.S. Patent Application Publication No. 2014/0246475;

U.S. patent application Ser. No. 13/782,375, entitled ROTARY POWERED SURGICAL INSTRUMENTS WITH MULTIPLE DEGREES OF FREEDOM, now U.S. Pat. No. 9,398,911; and U.S. patent application Ser. No. 13/782,536, entitled SURGICAL INSTRUMENT SOFT STOP, now U.S. Pat. No. 9,307,986.

Applicant of the present application also owns the following patent applications that were filed on Mar. 14, 2013 and which are each herein incorporated by reference in their respective entireties:

U.S. patent application Ser. No. 13/803,097, entitled ARTICULATABLE SURGICAL INSTRUMENT COMPRISING A FIRING DRIVE, now U.S. Pat. No. 9,687,230;

U.S. patent application Ser. No. 13/803,193, entitled CONTROL ARRANGEMENTS FOR A DRIVE MEMBER OF A SURGICAL INSTRUMENT, now U.S. Pat. No. 9,332,987;

U.S. patent application Ser. No. 13/803,053, entitled INTERCHANGEABLE SHAFT ASSEMBLIES FOR USE WITH A SURGICAL INSTRUMENT, now U.S. Patent Application Publication No. 2014/0263564;

U.S. patent application Ser. No. 13/803,086, entitled ARTICULATABLE SURGICAL INSTRUMENT COMPRISING AN ARTICULATION LOCK, now U.S. Patent Application Publication No. 2014/0263541;

U.S. patent application Ser. No. 13/803,210, entitled SENSOR ARRANGEMENTS FOR ABSOLUTE POSITIONING SYSTEM FOR SURGICAL INSTRUMENTS, now U.S. Pat. No. 9,808,244;

U.S. patent application Ser. No. 13/803,148, entitled MULTI-FUNCTION MOTOR FOR A SURGICAL INSTRUMENT, now U.S. Patent Application Publication No. 2014/0263554;

U.S. patent application Ser. No. 13/803,066, entitled DRIVE SYSTEM LOCKOUT ARRANGEMENTS FOR MODULAR SURGICAL INSTRUMENTS, now U.S. Pat. No. 9,629,623;

U.S. patent application Ser. No. 13/803,117, entitled ARTICULATION CONTROL SYSTEM FOR ARTICULATABLE SURGICAL INSTRUMENTS, now U.S. Pat. No. 9,351,726;

U.S. patent application Ser. No. 13/803,130, entitled DRIVE TRAIN CONTROL ARRANGEMENTS FOR MODULAR SURGICAL INSTRUMENTS, now U.S. Pat. No. 9,351,727; and U.S. patent application Ser. No. 13/803,159, entitled METHOD AND SYSTEM FOR OPERATING A SURGICAL INSTRUMENT, now U.S. Patent Application Publication No. 2014/0277017.

Applicant of the present application also owns the following patent application that was filed on Mar. 7, 2014 and is herein incorporated by reference in its entirety:

U.S. patent application Ser. No. 14/200,111, entitled CONTROL SYSTEMS FOR SURGICAL INSTRUMENTS, now U.S. Pat. No. 9,629,629.

Applicant of the present application also owns the following patent applications that were filed on Mar. 26, 2014 and are each herein incorporated by reference in their respective entireties:

U.S. patent application Ser. No. 14/226,106, entitled POWER MANAGEMENT CONTROL SYSTEMS FOR SURGICAL INSTRUMENTS, now U.S. Patent Application Publication No. 2015/0272582;

U.S. patent application Ser. No. 14/226,099, entitled STERILIZATION VERIFICATION CIRCUIT, now U.S. Patent Application Publication No. 2015/0272581;

U.S. patent application Ser. No. 14/226,094, entitled VERIFICATION OF NUMBER OF BATTERY EXCHANGES/PROCEDURE COUNT, now U.S. Patent Application Publication No. 2015/0272580;

U.S. patent application Ser. No. 14/226,117, entitled POWER MANAGEMENT THROUGH SLEEP OPTIONS OF SEGMENTED CIRCUIT AND WAKE UP CONTROL, now U.S. Patent Application Publication No. 2015/0272574;

U.S. patent application Ser. No. 14/226,075, entitled MODULAR POWERED SURGICAL INSTRUMENT WITH DETACHABLE SHAFT ASSEMBLIES, now U.S. Pat. No. 9,743,929;

U.S. patent application Ser. No. 14/226,093, entitled FEEDBACK ALGORITHMS FOR MANUAL BAILOUT SYSTEMS FOR SURGICAL INSTRUMENTS, now U.S. Patent Application Publication No. 2015/0272569;

U.S. patent application Ser. No. 14/226,116, entitled SURGICAL INSTRUMENT UTILIZING SENSOR ADAPTATION, now U.S. Patent Application Publication No. 2015/0272571;

U.S. patent application Ser. No. 14/226,071, entitled SURGICAL INSTRUMENT CONTROL CIRCUIT HAVING A SAFETY PROCESSOR, now U.S. Pat. No. 9,690,362;

U.S. patent application Ser. No. 14/226,097, entitled SURGICAL INSTRUMENT COMPRISING INTERACTIVE SYSTEMS, now U.S. Patent Application Publication No. 2015/0272570;

U.S. patent application Ser. No. 14/226,126, entitled INTERFACE SYSTEMS FOR USE WITH SURGICAL INSTRUMENTS, now U.S. Patent Application Publication No. 2015/0272572;

U.S. patent application Ser. No. 14/226,133, entitled MODULAR SURGICAL INSTRUMENT SYSTEM, now U.S. Patent Application Publication No. 2015/0272557;

U.S. patent application Ser. No. 14/226,081, entitled SYSTEMS AND METHODS FOR CONTROLLING A SEGMENTED CIRCUIT, now U.S. Pat. No. 9,804,618;

U.S. patent application Ser. No. 14/226,076, entitled POWER MANAGEMENT THROUGH SEGMENTED CIRCUIT AND VARIABLE VOLTAGE PROTECTION, now U.S. Pat. No. 9,733,663;

U.S. patent application Ser. No. 14/226,111, entitled SURGICAL STAPLING INSTRUMENT SYSTEM, now U.S. Pat. No. 9,750,499; and U.S. patent application Ser. No. 14/226,125, entitled SURGICAL INSTRUMENT COMPRISING A ROTATABLE SHAFT, now U.S. Patent Application Publication No. 2015/0280384.

Applicant of the present application also owns the following patent applications that were filed on Sep. 5, 2014 and which are each herein incorporated by reference in their respective entireties:

U.S. patent application Ser. No. 14/479,103, entitled CIRCUITRY AND SENSORS FOR POWERED MEDICAL DEVICE, now U.S. Patent Application Publication No. 2016/0066912;

U.S. patent application Ser. No. 14/479,119, entitled ADJUNCT WITH INTEGRATED SENSORS TO QUANTIFY TISSUE COMPRESSION, now U.S. Pat. No. 9,724,094;

U.S. patent application Ser. No. 14/478,908, entitled MONITORING DEVICE DEGRADATION BASED ON COMPONENT EVALUATION, now U.S. Pat. No. 9,737,301;

U.S. patent application Ser. No. 14/478,895, entitled MULTIPLE SENSORS WITH ONE SENSOR AFFECTING A SECOND SENSOR'S OUTPUT OR INTERPRETATION, now U.S. Pat. No. 9,757,128;

U.S. patent application Ser. No. 14/479,110, entitled USE OF POLARITY OF HALL MAGNET DETECTION TO DETECT MISLOADED CARTRIDGE, now U.S. Patent Application Publication No. 2016/0066915;

U.S. patent application Ser. No. 14/479,098, entitled SMART CARTRIDGE WAKE UP OPERATION AND DATA RETENTION, now U.S. Patent Application Publication No. 2016/0066911;

U.S. patent application Ser. No. 14/479,115, entitled MULTIPLE MOTOR CONTROL FOR POWERED MEDICAL DEVICE, now U.S. Pat. No. 9,788,836; and U.S. patent application Ser. No. 14/479,108, entitled LOCAL DISPLAY OF TISSUE PARAMETER STABILIZATION, now U.S. Patent Application Publication No. 2016/0066913.

Applicant of the present application also owns the following patent applications that were filed on Apr. 9, 2014 and which are each herein incorporated by reference in their respective entireties:

U.S. patent application Ser. No. 14/248,590, entitled MOTOR DRIVEN SURGICAL INSTRUMENTS WITH LOCKABLE DUAL DRIVE SHAFTS, now U.S. Patent Application Publication No. 2014/0305987;

U.S. patent application Ser. No. 14/248,581, entitled SURGICAL INSTRUMENT COMPRISING A CLOSING DRIVE AND A FIRING DRIVE OPERATED FROM THE SAME ROTATABLE OUTPUT, now U.S. Pat. No. 9,649,110;

U.S. patent application Ser. No. 14/248,595, entitled SURGICAL INSTRUMENT SHAFT INCLUDING SWITCHES FOR CONTROLLING THE OPERATION OF THE SURGICAL INSTRUMENT, now U.S. Patent Application Publication No. 2014/0305988;

U.S. patent application Ser. No. 14/248,588, entitled POWERED LINEAR SURGICAL STAPLER, now U.S. Patent Application Publication No. 2014/0309666;

U.S. patent application Ser. No. 14/248,591, entitled TRANSMISSION ARRANGEMENT FOR A SURGICAL INSTRUMENT, now U.S. Patent Application Publication No. 2014/0305991;

U.S. patent application Ser. No. 14/248,584, entitled MODULAR MOTOR DRIVEN SURGICAL INSTRUMENTS WITH ALIGNMENT FEATURES FOR ALIGNING ROTARY DRIVE SHAFTS WITH SURGICAL END EFFECTOR SHAFTS, now U.S. Pat. No. 9,801,626;

U.S. patent application Ser. No. 14/248,587, entitled POWERED SURGICAL STAPLER, now U.S. Patent Application Publication No. 2014/0309665;

U.S. patent application Ser. No. 14/248,586, entitled DRIVE SYSTEM DECOUPLING ARRANGEMENT FOR A SURGICAL INSTRUMENT, now U.S. Patent Application Publication No. 2014/0305990; and U.S. patent application Ser. No. 14/248,607, entitled MODULAR MOTOR DRIVEN SURGICAL INSTRUMENTS WITH STATUS INDICATION ARRANGEMENTS, now U.S. Patent Application Publication No. 2014/0305992.

Applicant of the present application also owns the following patent applications that were filed on Apr. 16, 2013 and which are each herein incorporated by reference in their respective entireties:

U.S. Provisional Patent Application Ser. No. 61/812,365, entitled SURGICAL INSTRUMENT WITH MULTIPLE FUNCTIONS PERFORMED BY A SINGLE MOTOR;

U.S. Provisional Patent Application Ser. No. 61/812,376, entitled LINEAR CUTTER WITH POWER;

U.S. Provisional Patent Application Ser. No. 61/812,382, entitled LINEAR CUTTER WITH MOTOR AND PISTOL GRIP;

U.S. Provisional Patent Application Ser. No. 61/812,385, entitled SURGICAL INSTRUMENT HANDLE WITH MULTIPLE ACTUATION MOTORS AND MOTOR CONTROL; and U.S. Provisional Patent Application Ser. No. 61/812,372, entitled SURGICAL INSTRUMENT WITH MULTIPLE FUNCTIONS PERFORMED BY A SINGLE MOTOR.

Applicant of the present application owns the following patent applications that were filed on Dec. 18, 2014 which are each herein incorporated by reference in their respective entireties:

U.S. patent application Ser. No. 14/574,478, entitled SURGICAL INSTRUMENT SYSTEMS COMPRISING AN ARTICULATABLE END EFFECTOR AND MEANS FOR ADJUSTING THE FIRING STROKE OF A FIRING MEMBER; now U.S. Patent Application Publication No. 2016/0174977;

U.S. patent application Ser. No. 14/574,483, entitled SURGICAL INSTRUMENT ASSEMBLY COMPRISING LOCKABLE SYSTEMS; now U.S. Patent Application Publication No. 2016/0174969;

U.S. patent application Ser. No. 14/575,148, entitled LOCKING ARRANGEMENTS FOR DETACHABLE SHAFT ASSEMBLIES WITH ARTICULATABLE SURGICAL END EFFECTORS, now U.S. Patent Application Publication No. 2016/0174976;

U.S. patent application Ser. No. 14/575,130, entitled SURGICAL INSTRUMENT WITH AN ANVIL THAT IS SELECTIVELY MOVABLE ABOUT A DISCRETE NONMOVABLE AXIS RELATIVE TO A STAPLE CARTRIDGE, now U.S. Patent Application Publication No. 2016/0174972;

U.S. patent application Ser. No. 14/575,143, entitled SURGICAL INSTRUMENTS WITH IMPROVED CLO- SURE ARRANGEMENTS; now U.S. Patent Application Publication No. 2016/0174983;

U.S. patent application Ser. No. 14/575,117, entitled SURGICAL INSTRUMENTS WITH ARTICULATABLE END EFFECTORS AND MOVABLE FIRING BEAM SUPPORT ARRANGEMENTS, now U.S. Patent Application Publication No. 2016/0174975;

U.S. patent application Ser. No. 14/575,154, entitled SURGICAL INSTRUMENTS WITH ARTICULATABLE END EFFECTORS AND IMPROVED FIRING BEAM SUPPORT ARRANGEMENTS, now U.S. Patent Application Publication No. 2016/0174973;

U.S. patent application Ser. No. 14/574,493, entitled SURGICAL INSTRUMENT ASSEMBLY COMPRISING A FLEXIBLE ARTICULATION SYSTEM;

now U.S. Patent Application Publication No. 2016/0174970; and

U.S. patent application Ser. No. 14/574,500, entitled SURGICAL INSTRUMENT ASSEMBLY COMPRISING A LOCKABLE ARTICULATION SYSTEM;

now U.S. Patent Application Publication No. 2016/0174971.

Numerous specific details are set forth to provide a thorough understanding of the overall structure, function, manufacture, and use of the embodiments as described in the specification and illustrated in the accompanying drawings. Well-known operations, components, and elements have not been described in detail so as not to obscure the embodiments described in the specification. The reader will understand that the embodiments described and illustrated herein are non-limiting examples, and thus it can be appreciated that the specific structural and functional details disclosed herein may be representative and illustrative. Variations and changes thereto may be made without departing from the scope of the claims.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a surgical system, device, or apparatus that "comprises," "has," "includes" or "contains" one or more elements possesses those one or more elements, but is not limited to possessing only those one or more elements. Likewise, an element of a system, device, or apparatus that "comprises," "has," "includes" or "contains" one or more features possesses those one or more features, but is not limited to possessing only those one or more features.

The terms "proximal" and "distal" are used herein with reference to a clinician manipulating the handle portion of the surgical instrument. The term "proximal" referring to the portion closest to the clinician and the term "distal" referring to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Various exemplary devices and methods are provided for performing laparoscopic and minimally invasive surgical procedures. However, the reader will readily appreciate that the various methods and devices disclosed herein can be used in numerous surgical procedures and applications including, for example, in connection with open surgical procedures. As the present Detailed Description proceeds, the reader will further appreciate that the various instruments disclosed herein can be inserted into a body in any way, such as through a natural orifice, through an incision or puncture hole formed in tissue, etc. The working portions or "end effector" portions of the instruments can be inserted directly into a patient's body or can be inserted through an access device that has a working channel through which the end effector and elongated shaft of a surgical instrument can be advanced.

A surgical stapling system can comprise a shaft and an end effector extending from the shaft. The end effector comprises a first jaw and a second jaw. The first jaw comprises a staple cartridge. The staple cartridge is insertable into and removable from the first jaw; however, other embodiments are envisioned in which a staple cartridge is not removable from, or at least readily replaceable from, the first jaw. The second jaw comprises an anvil configured to deform staples ejected from the staple cartridge. The second jaw is pivotable relative to the first jaw about a closure axis; however, other embodiments are envisioned in which first jaw is pivotable relative to the second jaw. The surgical stapling system further comprises an articulation joint configured to permit the end effector to be rotated, or articulated, relative to the shaft. The end effector is rotatable about an articulation axis extending through the articulation joint. Other embodiments are envisioned which do not include an articulation joint.

The staple cartridge comprises a cartridge body. The cartridge body includes a proximal end, a distal end, and a deck extending between the proximal end and the distal end. In use, the staple cartridge is positioned on a first side of the tissue to be stapled and the anvil is positioned on a second side of the tissue. The anvil is moved toward the staple cartridge to compress and clamp the tissue against the deck. Thereafter, staples removably stored in the cartridge body can be deployed into the tissue. The cartridge body includes staple cavities defined therein wherein staples are removably stored in the staple cavities. The staple cavities are arranged in six longitudinal rows. Three rows of staple cavities are positioned on a first side of a longitudinal slot and three rows of staple cavities are positioned on a second side of the longitudinal slot. Other arrangements of staple cavities and staples may be possible.

The staples are supported by staple drivers in the cartridge body. The drivers are movable between a first, or unfired position, and a second, or fired, position to eject the staples from the staple cavities. The drivers are retained in the cartridge body by a retainer which extends around the bottom of the cartridge body and includes resilient members configured to grip the cartridge body and hold the retainer to the cartridge body. The drivers are movable between their unfired positions and their fired positions by a sled. The sled is movable between a proximal position adjacent the proximal end and a distal position adjacent the distal end. The sled comprises a plurality of ramped surfaces configured to slide under the drivers and lift the drivers, and the staples supported thereon, toward the anvil.

Further to the above, the sled is moved distally by a firing member. The firing member is configured to contact the sled and push the sled toward the distal end. The longitudinal slot defined in the cartridge body is configured to receive the firing member. The anvil also includes a slot configured to receive the firing member. The firing member further comprises a first cam which engages the first jaw and a second cam which engages the second jaw. As the firing member is advanced distally, the first cam and the second cam can control the distance, or tissue gap, between the deck of the staple cartridge and the anvil. The firing member also comprises a knife configured to incise the tissue captured intermediate the staple cartridge and the anvil. It is desirable for the knife to be positioned at least partially proximal to the ramped surfaces such that the staples are ejected ahead of the knife.

FIG. 1 illustrates an exemplary motor driven (or "powered") surgical instrument 10 which includes a housing 100, an elongate interchangeable shaft assembly 200 and a surgical end effector 300 that is operably connected to the interchangeable elongate shaft assembly 200. While the depicted shaft assembly is detachable from the housing 100, various unique and novel features may be equally enjoyed with arrangements that employ a dedicated (non-interchangeable) shaft assembly. The surgical end effector 300 as shown is configured to act as an endocutter for clamping, severing and stapling tissue. However, it will be appreciated that various embodiments may include end effectors configured to act as other surgical devices including, for example, graspers, cutters, staplers, clip appliers, access devices, drug/gene therapy delivery devices, ultrasound, RF, and/or laser energy devices, etc. As indicated above and will be describe further below, various portions of the surgical instrument 10 are motor driven. Further details regarding many aspects of the motor driven components of surgical instrument 10 may be found, for example, in U.S. patent application Ser. No. 13/803,086, entitled ARTICULATABLE SURGICAL INSTRUMENT COMPRISING AN ARTICULATION LOCK, now U.S. Patent Application Publication No. 2014/0263541 which has been incorporated by reference in its entirety herein. However, it will be understood that the various arrangements and features disclosed herein may be effectively employed in connection with robotically-controlled surgical systems. For example, various arrangements disclosed herein may be employed with various robotic systems, instruments, components and methods disclosed in U.S. patent application Ser. No. 13/118,241, entitled SURGICAL STAPLING INSTRUMENTS WITH ROTATABLE STAPLE DEPLOYMENT ARRANGEMENTS, now U.S. Pat. No. 9,072,535, as well as in U.S. Pat. No. 6,132,368, entitled MULTI-COMPONENT TELEPRESENCE SYSTEM AND METHOD, U.S. Pat. No. 5,878,193, entitled AUTOMATED ENDOSCOPE SYSTEM FOR OPTIMAL POSITIONING, U.S. Pat. No. 5,792,135, entitled ARTICULATED SURGICAL INSTRUMENT FOR PERFORMING MINIMALLY INVASIVE SURGERY WITH ENHANCED DEXTERITY AND SENSITIVITY, U.S. Pat. No. 6,231,565, entitled ROBOTIC ARM DLUS FOR PERFORMING SURGICAL TASKS, U.S. Pat. No. 6,783,524, entitled ROBOTIC SURGICAL TOOL WITH ULTRASOUND CAUTERIZING AND CUTTING INSTRUMENT, U.S. Pat. No. 6,364,888, entitled ALIGNMENT OF MASTER AND SLAVE IN A MINIMALLY INVASIVE SURGICAL APPARATUS, U.S. Pat. No. 7,524,320, entitled MECHANICAL ACTUATOR INTERFACE SYSTEM FOR ROBOTIC SURGICAL TOOLS, U.S. Pat. No. 7,691,098, entitled PLATFORM LINK WRIST MECHANISM, U.S. Pat. No. 7,806,891, entitled REPOSITIONING AND REORIENTATION OF MASTER/SLAVE RELATIONSHIP IN MINIMALLY INVASIVE TELESURGERY, and U.S. Pat. No. 7,824,401, entitled SURGICAL TOOL WITH WRISTED MONOPOLAR ELECTROSURGICAL END EFFECTORS the entire disclosures of each being hereby incorporated by reference herein.

Thus, as used herein, the term "housing" may also encompass a housing or similar portion of a robotic system that houses or otherwise operably supports at least one drive system that is configured to generate and apply at least one control motion which could be used to actuate the interchangeable shaft assemblies disclosed herein and their respective equivalents. The term "frame" may refer to a portion of a handheld surgical instrument, e.g., a "handle". The term "frame" may also represent a portion of a robotically-controlled surgical instrument and/or a portion of the robotic system that may be used to operably control a surgical instrument.

It should be appreciated that spatial terms such as vertical, horizontal, right, left, etc. are given herein with reference to the Figures assuming that the longitudinal or "shaft axis" of the surgical instrument 10 is co-axial to the central axis of the shaft 200. In actual practice, however, the surgical instrument 10 may be oriented at various angles and as such these spatial terms are used relative to the surgical instrument itself. Further, for a hand-held housing, "proximal" is used to denote a perspective of a clinician who is behind the handle who places the end effector 300 distal, or away from him or herself. As used herein, the phrase, "substantially transverse to the longitudinal axis" where the "longitudinal axis" is the axis of the shaft, refers to a direction that is nearly perpendicular to the longitudinal axis. It will be appreciated, however, that directions that deviate some from perpendicular to the longitudinal axis are also substantially transverse to the longitudinal axis.

As can be seen in FIG. 1, the end effector 300 is pivotally connected to the shaft assembly 200 at articulation joint 240. A variety of articulation joints and control systems are disclosed in various patents and patent applications that have been incorporated by reference herein and may be employed in connection with various features disclosed and claimed herein. Other articulation joints and articulation systems are disclosed in U.S. Pat. No. 7,753,245, entitled SURGICAL STAPLING INSTRUMENTS and U.S. Pat. No. 7,670,334, entitled SURGICAL INSTRUMENT HAVING AN ARTICULATING END EFFECTOR, the entire disclosures of each being hereby incorporated by reference herein. Various other means for articulating the end effector 300 are discussed in greater detail below.

The illustrated end effector 300 includes an elongate channel 302 that is configured to operably support a surgical staple cartridge 310 therein. The staple cartridge 310 includes a cartridge body 312 that operably supports a plurality of surgical staples or fasteners (not shown) therein. In one implementation, the staples are operably supported on drivers that are movably supported within corresponding staple pockets 314 formed in the cartridge body 312. The cartridge body 312 further includes an elongate slot 316 that is centrally disposed between lines of staple pockets 314. The elongate slot 316 is configured to accommodate a tissue cutting member (not shown) that is supported for longitudinal travel through the cartridge body 312 upon application of a firing motion thereto from a firing system as will be discussed in further detail below. In certain implementations, the tissue cutting member may interface with an actuator member, sometimes referred to as a "wedge sled" or simply "sled" that is configured to apply an upward motion to the staple drivers as the wedge sled is driven distally with the tissue cutting member. As can also be seen in FIG. 1, the end effector 300 includes an anvil 320 that is movably supported on the elongate channel 302 for selective travel toward and away from the elongate channel 302 and the staple cartridge 310 supported therein. The elongate channel and the anvil may also be referred to as "jaws" that are movable between open and closed positions. The anvil 320 has a staple-forming undersurface (not shown) that serves to form the ends of the staples as they are driven into forming contact therewith. The anvil 320 is movable between an open and closed positions by a closure member assembly 210 that interfaces with a closure system that is operably supported by the housing 100 as will be discussed in further detail below. In the illustrated embodiment, the anvil 320 is moved toward the staple cartridge 310 to a closed position when the closure member assembly 210 is driven in the distal direction "DD" and returned to an open position when the closure member assembly 210 is moved in a proximal direction "PD". A variety of different end effector arrangements and constructions are known and may be employed with various unique and novel features disclosed herein. Thus, many of the claims presented herein may not be limited to the particular end effector arrangement depicted in FIG. 1, for example. More details concerning the specific construction and operation of alternative end effectors may be found in various U.S. patent Applications and Patents that have been incorporated by reference herein.

In the illustrated form, the surgical instrument 10 includes a housing 100 that comprises a handle 102. In at least one form, the handle 102 comprises a pair of interconnectable housing segments 104, 106 that are interconnected by screws, snap features, adhesive, etc. In the illustrated arrangement, the handle housing segments 104, 106 cooperate to form a pistol grip portion 108 that can be gripped and manipulated by the clinician. As will be discussed in further detail below, the handle 102 operably supports a plurality of drive systems therein that are configured to generate and apply various control motions to corresponding portions of the interchangeable shaft assembly that is operably attached thereto.

Figure 2:
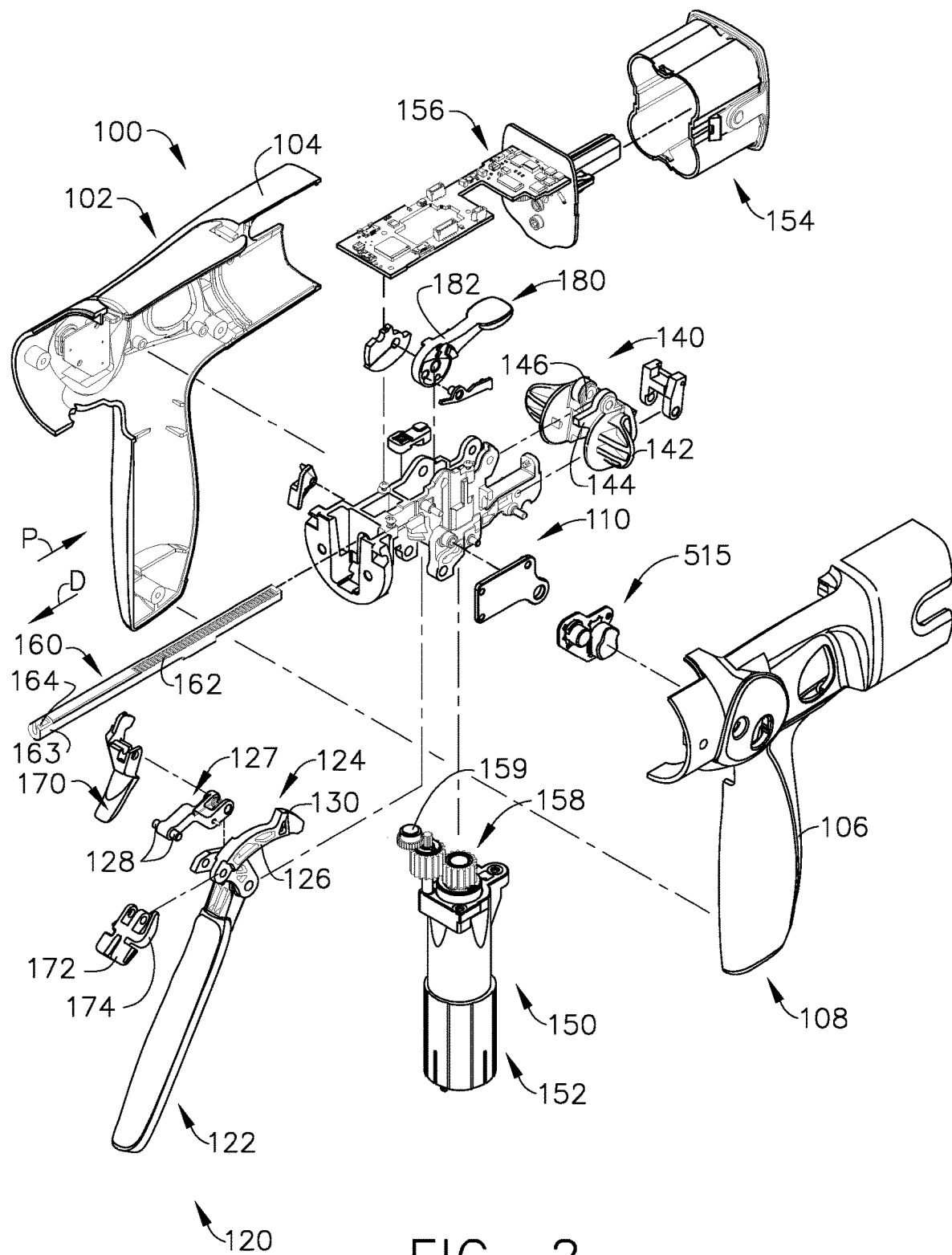
FIG. 2 is an exploded assembly view of a surgical instrument housing.

Referring now to FIG. 2, the handle 102 may further include a frame 110 that operably supports a plurality of drive systems. For example, the frame 110 can operably support a first or closure drive system, generally designated as 120, which may be employed to apply closing and opening motions to the interchangeable shaft assembly 200 that is operably attached or coupled thereto. In at least one form, the closure drive system 120 may include an actuator in the form of a closure trigger 122 that is pivotally supported by the frame 110. More specifically, as illustrated in FIG. 2, the closure trigger 122 may be pivotally supported by frame 110 such that when the clinician grips the pistol grip portion 108 of the handle 102, the closure trigger 122 may be easily pivoted from a starting or unactuated position to an actuated position and more particularly to a fully compressed or fully actuated position. The closure trigger 122 may be biased into the unactuated position by spring or other biasing arrangement (not shown). In various forms, the closure drive system 120 further includes a closure linkage assembly 124 that is pivotally coupled to the closure trigger 122. As can be seen in FIG. 2, the closure linkage assembly 124 may include a closure link 126 that that is pivotally coupled to the closure trigger 122. In addition, the closure linkage assembly 124 includes another closure link 127 that has a pair of laterally extending attachment lugs or portions 128 protruding therefrom.

Still referring to FIG. 2, it can be observed that the closure link 126 may have a locking wall 130 thereon that is configured to cooperate with a closure release assembly 140 that is pivotally coupled to the frame 110. In at least one form, the closure release assembly 140 may comprise a release button assembly 142 that has a distally protruding cam follower arm 144 formed thereon. The release button assembly 142 may be pivoted in a counterclockwise direction by a release spring 146. As the clinician depresses the closure trigger 122 from its unactuated position towards the pistol grip portion 108 of the handle 102, the closure link 126 pivots upward to a point wherein the cam follower arm 144 drops into retaining engagement with the locking wall 130 on the closure link 126 thereby preventing the closure trigger 122 from returning to the unactuated position. Thus, the closure release assembly 140 serves to lock the closure trigger 122 in the fully actuated position. When the clinician desires to unlock the closure trigger 122 to permit it to be biased to the unactuated position, the clinician simply pivots the closure release button assembly 142 such that the cam follower arm 144 is moved out of engagement with the locking wall 130 on the closure link 126. When the cam follower arm 144 has been moved out of engagement with the closure link 126, the closure trigger 122 may pivot back to the unactuated position. Other closure trigger locking and release arrangements may also be employed.

In at least one form, the handle 102 and the frame 110 may operably support another drive system referred to herein as firing drive system 150 that is configured to apply firing motions to corresponding portions of the interchangeable shaft assembly 200 attached thereto. The firing drive system may also be referred to herein as a "second drive system". The firing drive system 150 may employ an electric motor ("firing motor") 152, located in the pistol grip portion 108 of the handle 102. In various forms, the firing motor 152 may be a DC brushed driving motor having a maximum rotation of, approximately, 25,000 RPM, for example. In other arrangements, the firing motor may include a brushless motor, a cordless motor, a synchronous motor, a stepper motor, or any other suitable electric motor. A battery 154 (or "power source" or "power pack"), such as a Li ion battery, for example, may be coupled to the handle 102 to supply power to a control circuit board assembly 156 and ultimately to the firing motor 152.

The firing motor 152 can include a rotatable shaft (not shown) that operably interfaces with a gear reducer assembly 158 that is mounted in meshing engagement with a with a set, or rack, of drive teeth 162 on a longitudinally-movable drive member 160. In use, a voltage polarity provided by the battery can operate the firing motor 152 in a clockwise direction wherein the voltage polarity applied to the electric motor by the battery can be reversed in order to operate the electric motor 152 in a counter-clockwise direction. When the electric motor 152 is rotated in one direction, the drive member 160 will be axially driven in the distal direction "DD". When the motor 152 is driven in the opposite rotary direction, the drive member 160 will be axially driven in a proximal direction "PD". The handle 102 can include a switch which can be configured to reverse the polarity applied to the firing motor 152 by the battery. As with the other forms described herein, the handle 102 can also include a sensor or sensors that are configured to detect the position(s) of the drive member 160 and/or the direction(s) in which the drive member 160 is being moved.

In the illustrated instrument, actuation of the firing motor 152 is controlled by a firing trigger 170 that is pivotally supported on the handle 102. The firing trigger 170 may be pivoted between an unactuated position and an actuated position. The firing trigger 170 may be biased into the unactuated position by a spring (not shown) or other biasing arrangement such that when the clinician releases the firing trigger 170, it may be pivoted or otherwise returned to the unactuated position by the spring or biasing arrangement. In the illustrated form, the firing trigger 170 is positioned "outboard" of the closure trigger 122 as was discussed above. In at least one form, a firing trigger safety button 172 is pivotally mounted to the closure trigger 122. The safety button 172 is positioned between the firing trigger 170 and the closure trigger 122 and has a pivot arm 174 protruding therefrom. When the closure trigger 122 is in the unactuated position, the safety button 172 is contained in the handle housing 100 where the clinician cannot readily access it and move it between a safety position preventing actuation of the firing trigger 170 and a firing position wherein the firing trigger 170 may be fired. As the clinician depresses the closure trigger 122, the safety button 172 and the firing trigger 170 pivot down wherein they can then be manipulated by the clinician.

As indicated above, in at least one form, the longitudinally movable drive member 160 has a rack of teeth 162 formed thereon for meshing engagement with a corresponding drive gear 159 of the gear reducer assembly 158. At least one form may also include a manually-actuatable "bailout" assembly 180 that is configured to enable the clinician to manually retract the longitudinally movable drive member 160 should the firing motor 152 become disabled. The bailout assembly 180 may include a lever or bailout handle assembly 182 that is configured to be manually pivoted into ratcheting engagement with the teeth 162 in the drive member 160. Thus, the clinician can manually retract the drive member 160 by using the bailout handle assembly 182 to ratchet the drive member in the proximal direction "PD". U.S. Patent Application Publication No. 2010/0089970, now U.S. Pat. No. 9,072,535, discloses bailout arrangements and other components, arrangements and systems that may also be employed with the various instruments disclosed herein. U.S. patent application Ser. No. 12/249,117, entitled POWERED SURGICAL CUTTING AND STAPLING APPARATUS WITH MANUALLY RETRACTABLE FIRING SYSTEM, now U.S. Pat. No. 8,608,045, is hereby incorporated by reference in its entirety herein.

FIG. 1 illustrates the surgical instrument 10 with an interchangeable shaft assembly 200 operably coupled thereto. As indicated above, the shaft assembly 200 may be configured for quick attachment and detachment to the housing 100. The closure member assembly 210 includes a distal closure member segment 220 that is pivotally attached to a proximal closure member segment 230 at the articulation joint 240. The distal closure member segment 220 includes a U-shaped opening 222 that is configured to operably engage an upstanding anvil tab 322 on the anvil 320 when the closure member assembly is drawn in the proximal direction "PD". When the U-shaped opening 222 engages the anvil tab 322, the anvil 320 is pivoted to an open position. Specific details regarding examples of the articulation joint 240 and or other suitable articulation joint arrangements may be found in the various documents that have been herein incorporated by reference.

Figure 3:
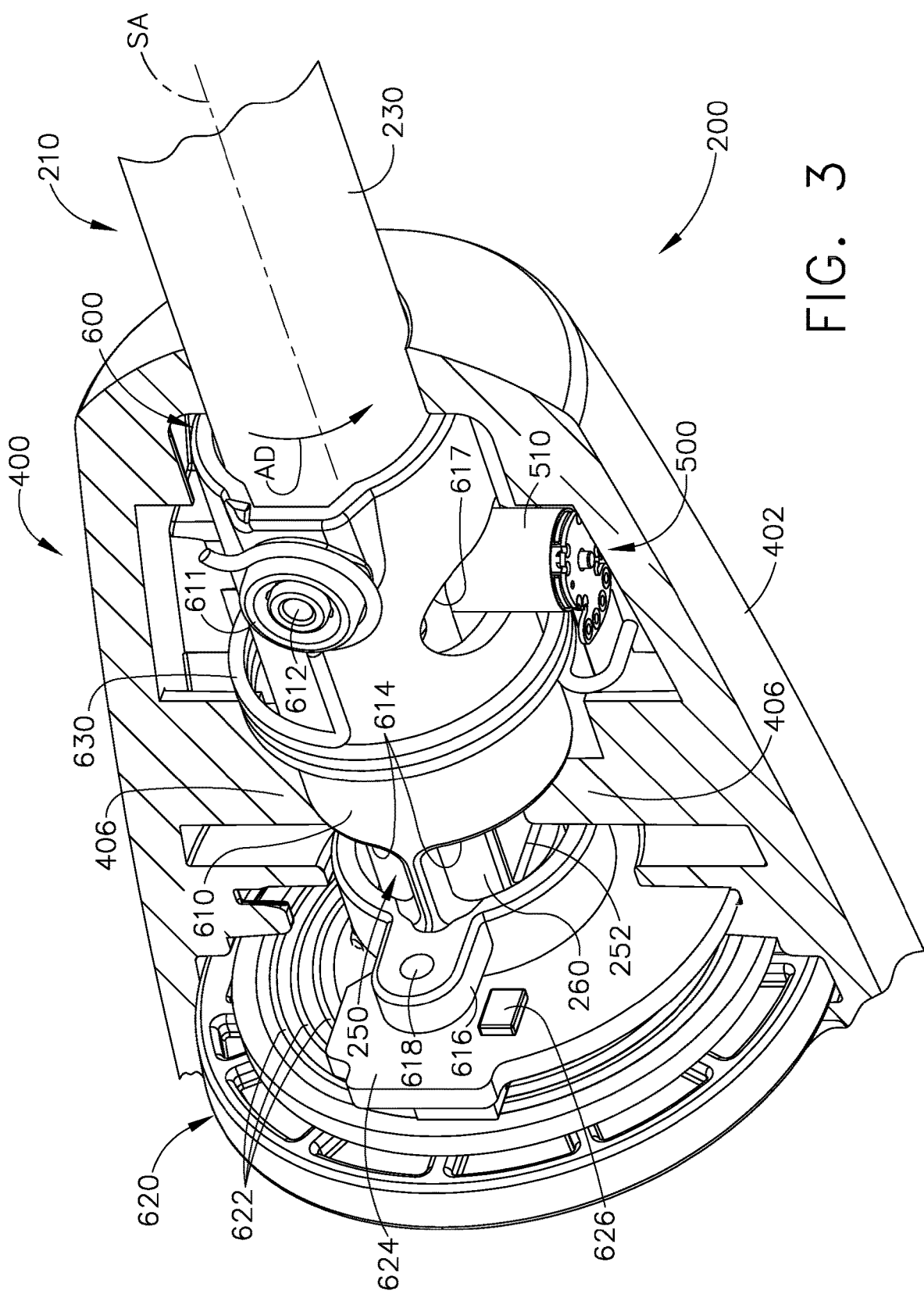
FIG. 3 is a cross-sectional view of a portion of an interchangeable shaft assembly.
Figure 7:
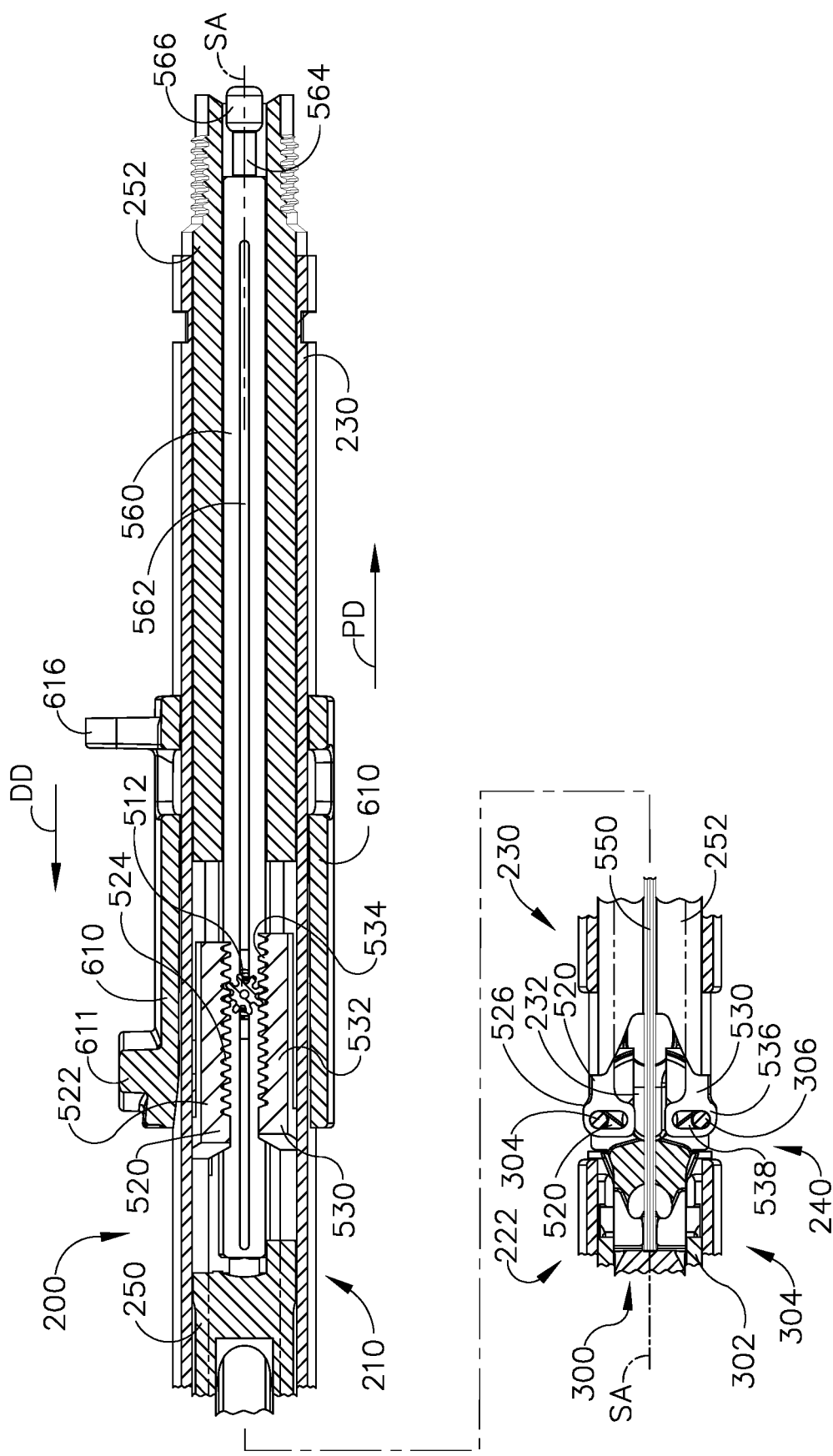
FIG. 7 is another cross-sectional view of the interchangeable shaft assembly and portion of the surgical end effector with the end effector in an unarticulated orientation.
Figure 8:
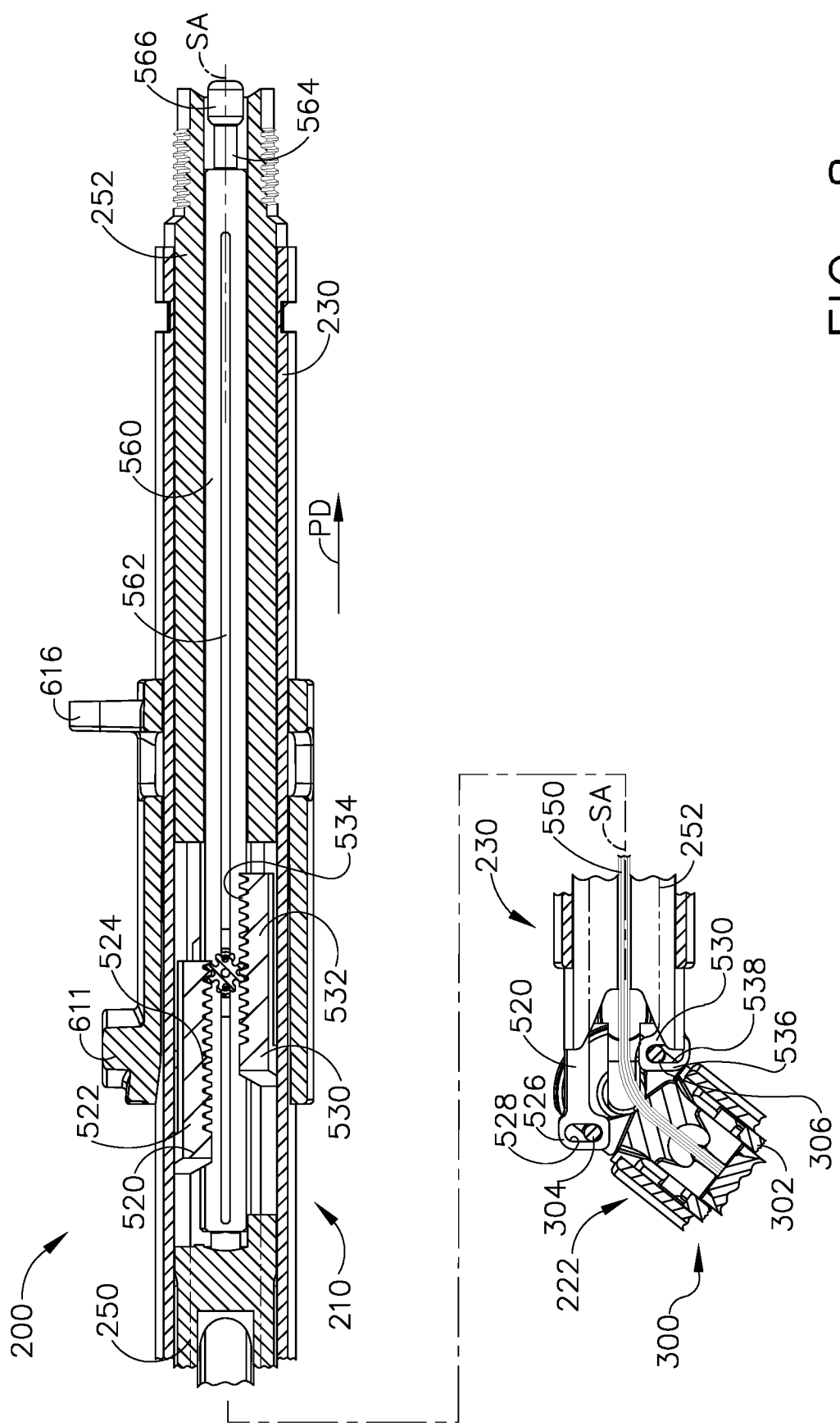
FIG. 8 is another cross-sectional view of the interchangeable shaft assembly of FIG. 7 with the end effector in an articulated orientation.

Referring now to FIGS. 3 and 7, the shaft assembly 200 includes a spine assembly 250 upon which the closure member assembly 210 is movably supported. The spine assembly 250 includes a distal end 252 that is pivotally attached to a proximal end 304 of the elongate channel 302. See FIG. 7. Such arrangement facilitates pivotal articulation of the end effector 300 relative to the distal end 252 of the spine assembly 250 about an articulation axis A-A which is transverse to the shaft axis SA-SA. See FIG. 1. In various implementations, the end effector 300 may also be selectively rotatable relative to the housing 100 about the shaft axis SA-SA (represented by arrow "R" in FIG. 1). Because the end effector 300 is directly attached to the distal end 252 of the spine assembly 250, rotation of the spine assembly 250 relative to the housing 100 results in rotation of the end effector 300 as well. In the illustrated implementation, the interchangeable shaft assembly 200 includes a rotation nozzle 400 that is rotatably journaled or otherwise rotationally supported by the handle 102. In the illustrated implementation, for example, the rotation nozzle 400 comprises two nozzle portions 402, 404 that are coupled together by snap features, screws, adhesive, etc. and include two opposed, inwardly extending lugs 406 that are seated in corresponding notches 254 in the proximal end 252 of the spine assembly 250. See FIG. 3. Such arrangement facilitates rotation of the spine assembly 250 when the nozzle 400 is rotated.

Figure 5:
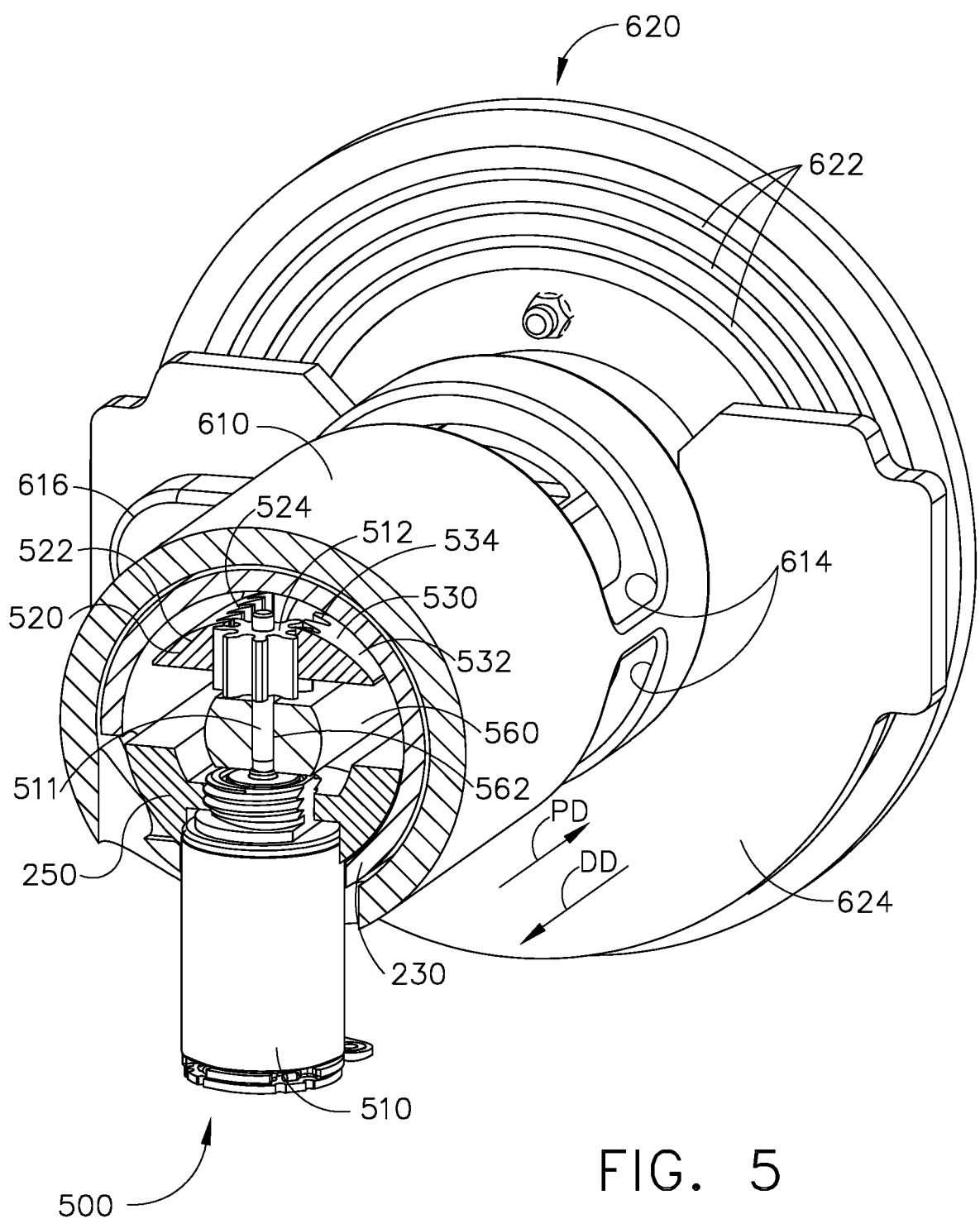
FIG. 5 is a cross-sectional perspective view of the interchangeable shaft assembly of FIG. 4.
Figure 6:
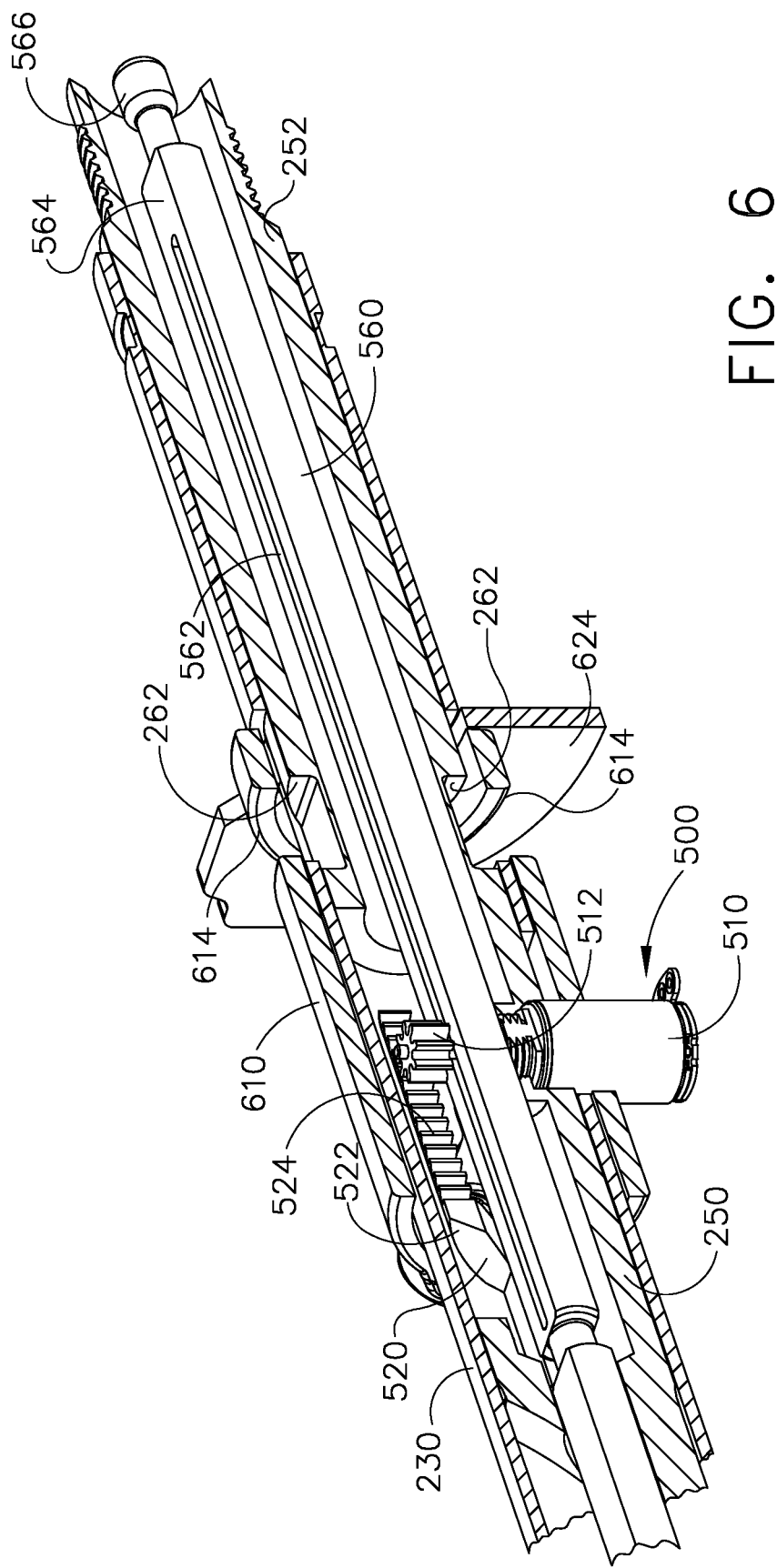
FIG. 6 is a cross-sectional perspective view of a portion of the interchangeable shaft assembly of FIG. 5.

Articulation of the end effector 300 about the articulation axis A-A is accomplished by actuation of an articulation system 500. In the illustrated implementation, for example, the articulation system 500 includes an articulation motor 510 that is used to actuate first and second articulation drivers 520, 530. See FIGS. 5 and 6. The articulation motor 510 may comprise a motor similar to the firing motor or any one of the various motor configurations discussed herein and includes an articulation drive gear 512 that is in meshing engagement with a first gear rack 524 on the proximal end 522 of the first articulation driver 520. The articulation gear 512 is also in meshing engagement with a second gear rack 534 on the proximal end 532 of the second articulation driver 530. As can be most particularly seen in FIG. 5, the articulation gear 512 is centrally disposed between the first and second gear racks 524, 534 such that rotation of the articulation gear in a first direction will result in the axial movement of the first articulation driver 520 in a distal direction "DD" and the simultaneous axial movement of the second articulation driver 530 in the proximal "PD" or opposite axial direction. Likewise, rotation of the articulation gear 512 in a second rotary direction will result in the axial movement of the second articulation driver 530 in the distal direction "DD" and the simultaneous axial movement of the first articulation driver 520 in the proximal or opposite direction "PD". Referring to FIG. 7, the distal end 526 of the first articulation driver 520 includes a slot 528 that is configured to receive a corresponding pin 304 formed on the elongate channel 302. Likewise, the distal end 536 of the second articulation driver 530 includes a slot 538 that is configured to receive a corresponding pin 306 formed on the elongate channel 302. Thus, axial movement of the articulation drivers 520, 530 in the above described manner will applying simultaneous "pushing and pulling" motions to the elongate channel 302 and thereby result in pivotal articulation of the end effector 300 about the articulation axis A-A.

As indicated above, the surgical instrument 10 also includes a tissue cutting member that is configured for axial travel through the elongate slot 316 in the surgical staple cartridge 310. In the illustrated implementation, for example, the tissue cutting member or tissue cutting surface (not shown) is formed on or otherwise attached to a distal firing member 550. The distal firing member 550 may be of laminated construction to facilitate bending about the articulation axis A-A while remaining sufficiently rigid to enable the tissue cutting edge to be driven through tissue that is clamped between the surgical staple cartridge and the anvil as well as driving the wedge sled therethrough. Various distal firing member and tissue cutting member configurations are known and are disclosed in the patents and/or patent applications that have been herein incorporated by reference. The distal firing member 550 is attached to a proximal firing member 560 that is supported for axial travel relative to the spine assembly 250. The proximal firing member 560 has a centrally disposed axial slot 562 therein to accommodate the drive shaft 511 of the articulation motor 510. See FIG. 5. Such arrangement facilitates axial travel of the proximal firing member 560 in response to firing motions applied thereto by the firing system. The proximal end 564 of the proximal firing member 560 includes a lug 566 that is configured to be receive in a firing rod attachment cradle 164 provided in the distal end 162 of the movable drive member 160. See FIG. 2. Thus, actuation of the firing motor 152 will result in the axial movement of the movable drive member 160 and the proximal firing member 560 and the distal firing member 550.

The firing motor 152 and the articulation motor 510 communicate with the control circuit 156 (FIG. 2) and are interlocked by a switching arrangement generally designated as 600. In the illustrated configuration, the switching arrangement 600 includes a switch drum 610 that is rotatably supported on the proximal closure member segment 230. See FIG. 3. The switch drum 610 includes a laterally extending boss 611 that has an inwardly extending cam pin 612 mounted (press-fit) therein. The cam pin 612 extends inwardly into a cam slot 232 provided in the proximal closure member segment 230. See FIG. 4. The switch drum 610 further includes opposed slots 614 that are configured to accommodate rotation of the nozzle lugs 406 therethrough. An articulation slot 617 is also provided to facilitate rotation of the switch drum 610 relative to the articulation motor 510. See FIG. 3. The switching arrangement 600 also includes a slip ring assembly 620 which is configured to conduct electrical power and/or signals to and/or from the end effector 300 to the handle 102 and more particularly to the control circuit 156 within the handle 102. The slip ring assembly 620 includes a plurality of concentric, or at least substantially concentric, conductors 622 on opposing sides thereof which can be configured to permit relative rotation between the halves of the slip ring assembly 620 while still maintaining electrically conductive pathways therebetween. Examples of such slip ring assemblies are disclosed U.S. patent application Ser. No. 13/800,067, entitled STAPLE CARTRIDGE TISSUE THICKNESS SENSOR SYSTEM, now U.S. Patent Application Publication No. 2014/0263552 and U.S. patent application Ser. No. 13/800,025, entitled STAPLE CARTRIDGE TISSUE THICKNESS SENSOR SYSTEM, now U.S. Pat. No. 9,345,481, and which are each hereby incorporated by reference herein in their respective entireties. In the illustrated implementation, the slip ring assembly 620 includes a bulkhead 624 that has a switch component 626 that communicates through the slip ring assembly 620 to the control circuit 156. The switch arrangement 600 also includes a movable switch component 618 that is mounted to a switch arm portion 616 of the switch drum 610.

Figure 4:
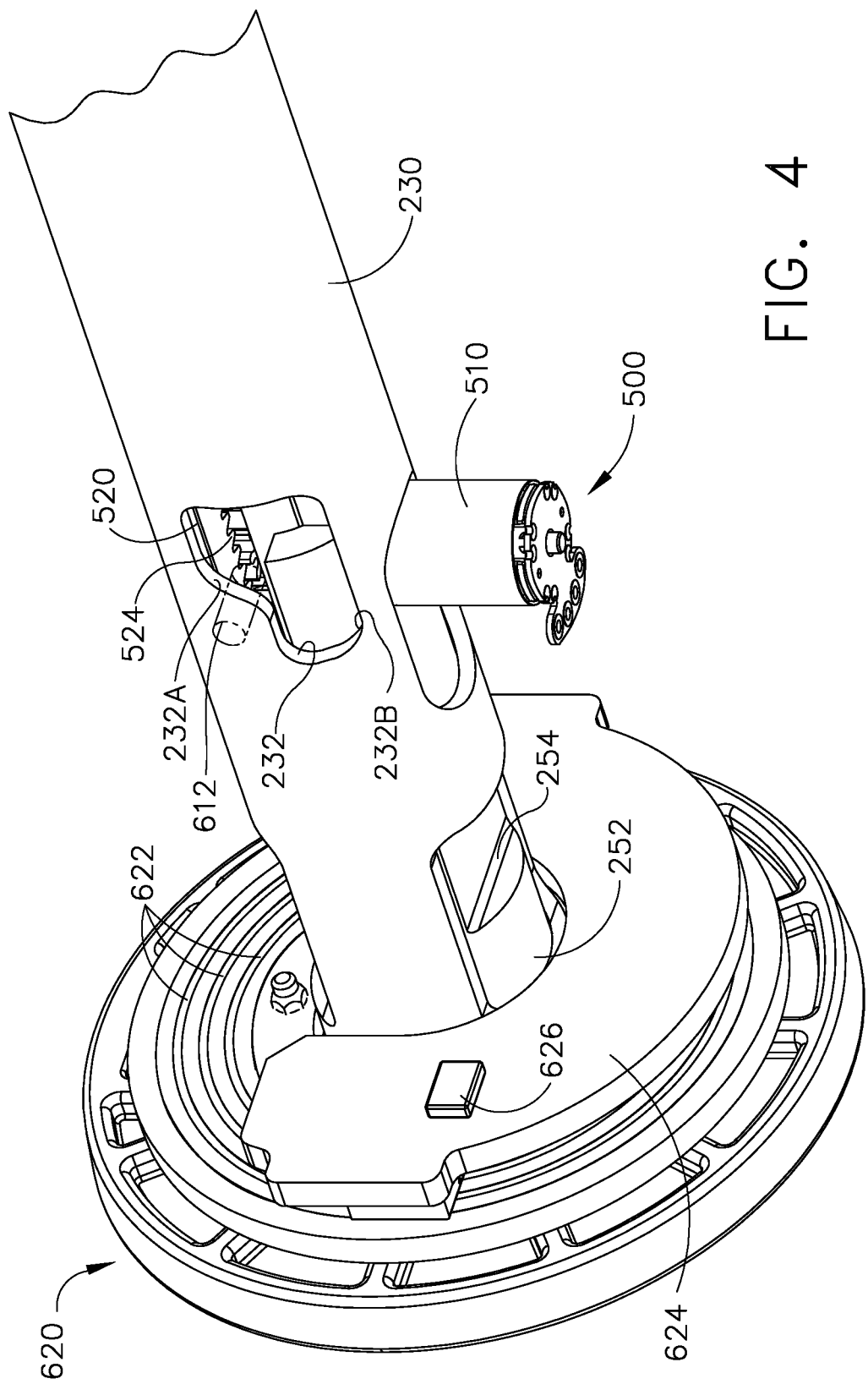
FIG. 4 is a partial perspective view of a portion of the interchangeable shaft assembly of FIG. 3 with the lock drum and nozzle removed for clarity.

Referring to FIG. 4, it can be seen that the cam slot 232 has a first portion 232A and a second portion 232B. When the closure member 230 is in the proximal (unactuated) position, the cam pin 612 is in the first portion 232A of the cam slot 232. A lock out spring 630 is mounted on the switch drum boss 611 to bias the switch drum 610 into that first position wherein the cam pin 612 is in the first portion 232A of the cam slot 232. See FIG. 3. When in that first position, the movable switch component 618 is not in contact or in "actuation proximity" with switch component 626. When in this "firing lock" position, the control circuit prevents actuation of the firing motor 152. Stated another way, unless the movable switch component 618 actuates switch component 626, no power is supplied to the firing motor 152. Thus, even if the clinician were to actuate the firing trigger 170 in an attempt to actuate the firing motor 152, the firing motor 152 would not actuate.

During a typical surgical procedure, the clinician may introduce the end effector 300 into the surgical site through a trocar or other opening in the patient to access the target tissue. In an effort to position the end effector in a desired position relative to the target tissue, the clinician may actuate the articulation motor 510 by actuating a rocker switch 515 mounted on the handle 102. The rocker switch 515 communicates with the control circuit 156 and by rocking the rocker switch 515 in a first direction will cause the articulation motor 510 to rotate in a first direction and result in articulation of the end effector 300 in a first articulation direction. Rocking the switch 515 in a second direction will result in rotation of the articulation motor 510 in an opposite rotary direction and cause the end effector 300 to articulate in a second opposite articulation direction. Once the clinician has positioned the end effector 300 in a desired position, the clinician can release the switch 515 to stop the articulation. At this point, the target tissue may be positioned between the surgical staple cartridge 310 and the anvil 320. The clinician may then move the anvil 320 to a closed position wherein the target tissue is clamped between the staple cartridge 310 and the anvil 320.

The closure member assembly 210 is actuated by actuating the closure trigger 122. The proximal end of the proximal closure member segment 230 is supported in a closure member attachment yoke (not shown) that is movably supported in a frame portion (not shown) of the shaft assembly 200. Examples of the closure member attachment yoke and the frame portion of the shaft assembly are described in further detail in U.S. patent application Ser. No. 13/803,097, entitled ARTICULATABLE SURGICAL INSTRUMENT COMPRISING A FIRING DRIVE, now U.S. Pat. No. 9,687,230, which has been herein incorporated by reference in its entirety. As the clinician depresses the closure trigger 122, the closure member assembly 210 is moved in the distal direction "DD" which ultimately causes the anvil 320 to pivot to the clamped position onto the target tissue. As the closure member assembly 210 moves distally, the cam pin 612 interacts with the cam slot 232 and is cammed into portion 232B of the cam slot 232. Movement of the cam pin 612 into the portion 232B of the cam slot 232 results in the rotational movement of the switch drum assembly 610 in actuation direction (represented by arrow "AD" in FIG. 3). As the switch drum 610 is biased into the actuation direction "AD" against the force of the spring 630, the switch component 618 is brought into activation/registration with switch component 626 which causes the control circuit board 156 to permit power to flow to the firing motor 152 upon actuation of the firing trigger 170. When in that closed position, the closure member assembly 210 and the anvil 320 are locked in the closed position in the manner described above. The control circuit 156 may also be configured such that when the switch components 618 and 626 are in actuation registration, the control circuit 156 prevents any flow of power to the articulation motor 510 should the rocker switch 515 be inadvertently actuated. Once the closure member assembly 210 and anvil 320 are locked in clamped position, the clinician may actuate the firing trigger 170 to drive the cutting member through the end effector 300 and cut the target tissue clamped therein and fire the surgical fasteners on each side of the tissue cut line. The end effector 300 may also be equipped with sensors that communicate with the control circuit 156 to detect when the tissue cutting member has reached its distal-most position to thereby signal the firing motor 152 to stop and reverse its direction to retract the tissue cutting member to its starting position. Other sensors may be employed to detect when the tissue cutting member has returned to the starting position and communicate with the control circuit 156 to thereby provide the clinician with an indication of the status of the tissue cutting member and/or enable the closure member assembly to be unlocked. Once the closure member assembly 210 has been unlocked, the lock out spring 630, acting on the switch drum 610, will urge the cam pin 612 to rotatably return to the portion 232A of the cam slot 232. Rotation of the switch drum 610 back to that starting position will deactivate the switch 626 which will once again prevent actuation of the firing motor 152.

Figure 9:
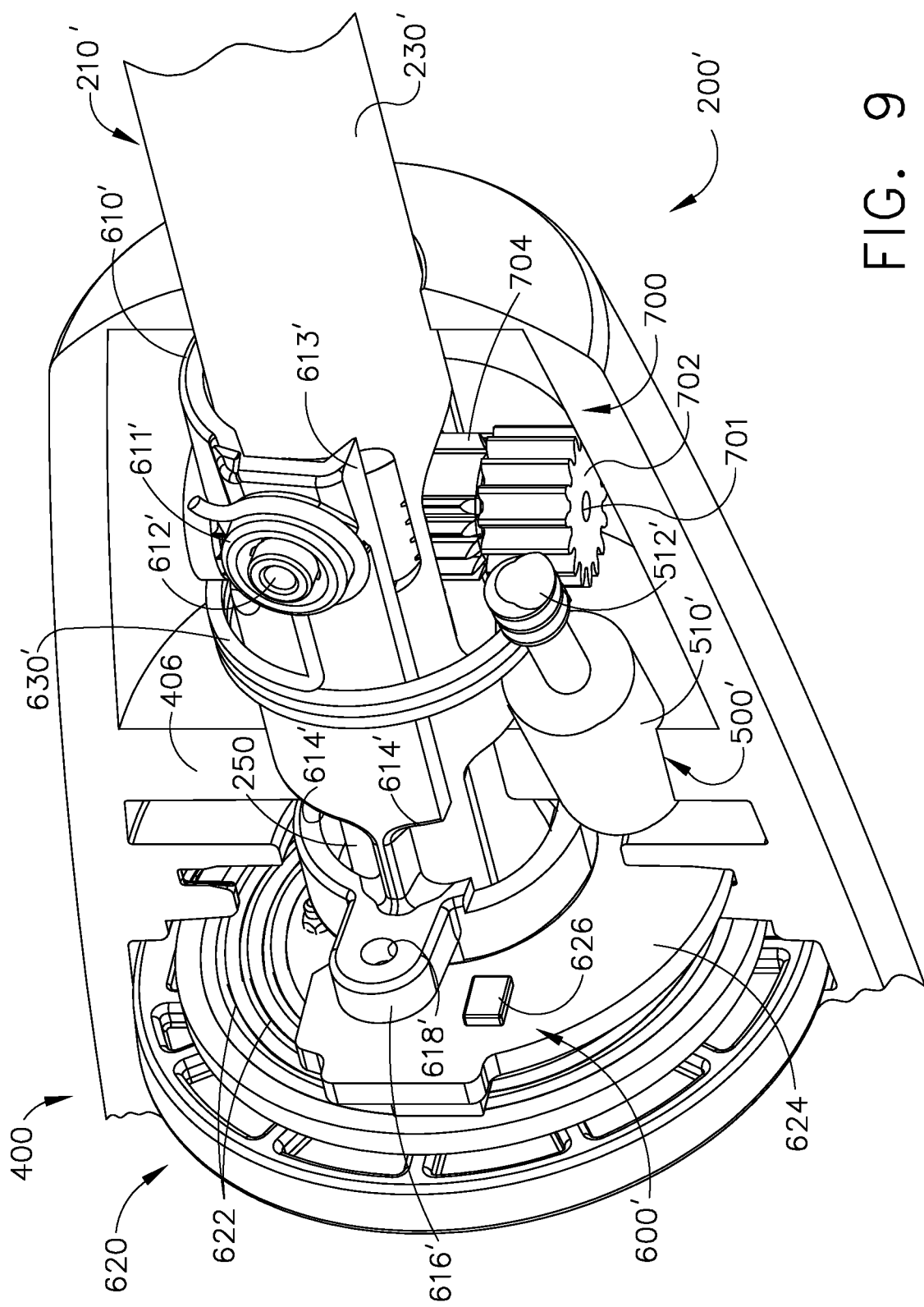
FIG. 9 is a partial perspective view of a portion of another interchangeable shaft assembly.
Figure 10:
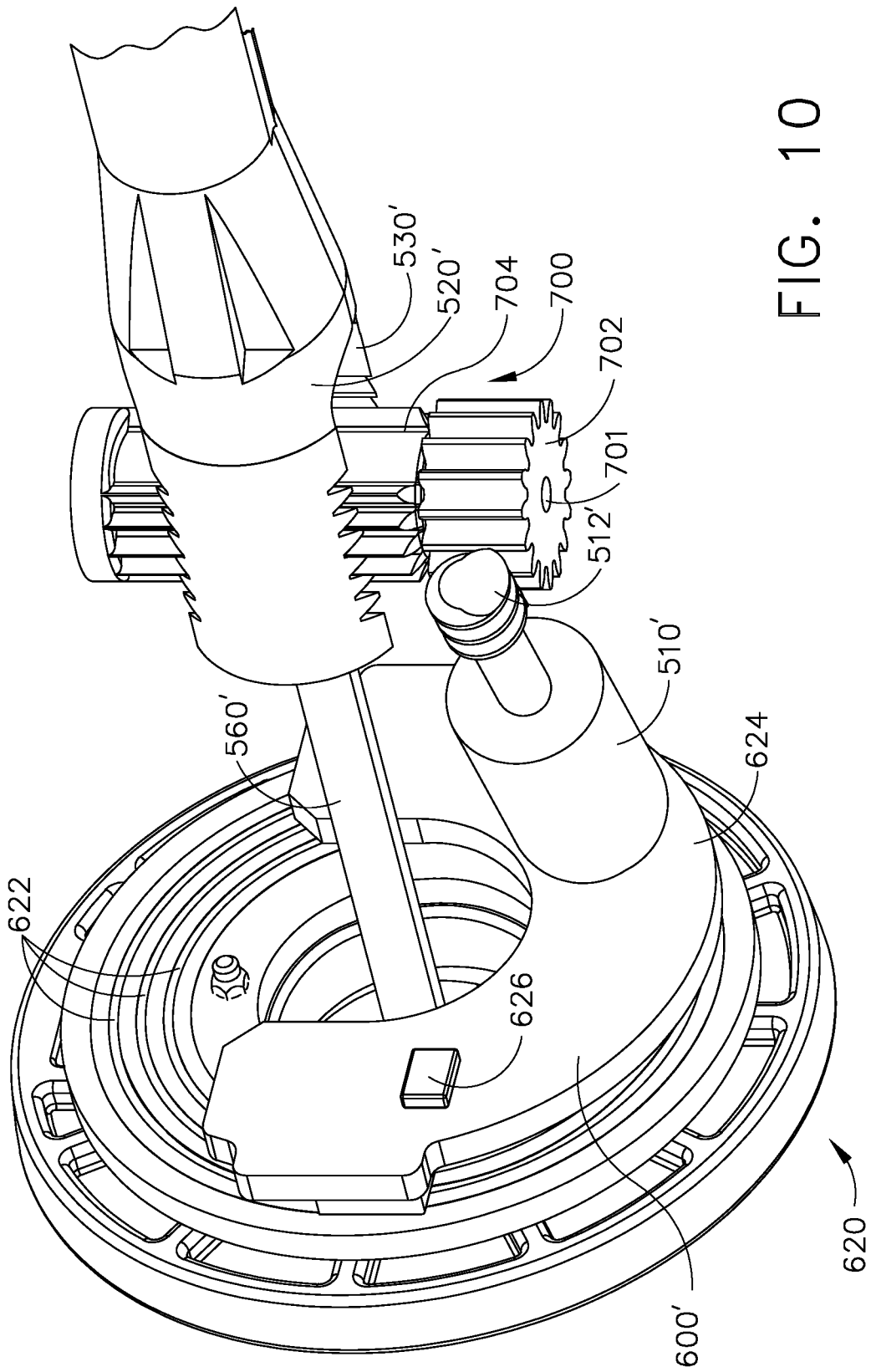
FIG. 10 is another perspective view of a portion of the interchangeable shaft assembly of FIG. 9 with various components omitted for clarity.
Figure 11:
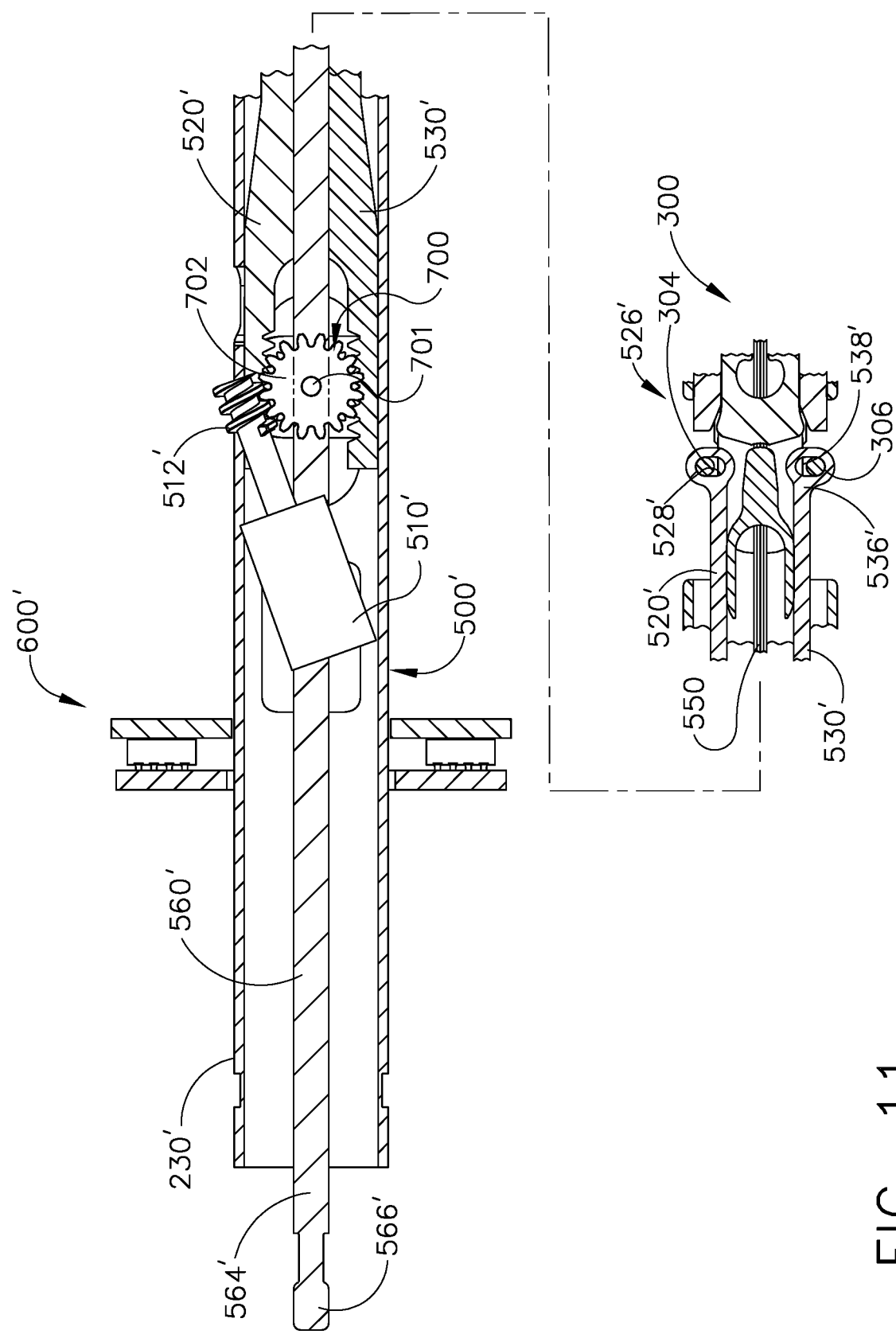
FIG. 11 is a partial cross-sectional view of a portion of the interchangeable shaft assembly of FIG. 10 with some components omitted for clarity.

FIGS. 9-11 illustrate another shaft assembly 200' that is substantially similar to shaft assembly 200 except for the differences discussed below. Those portions/components of shaft assembly 200' that are also found in shaft assembly 200 will be designated with like element numbers. As can be seen FIGS. 9-11, the shaft assembly 200' includes an articulation system 500' that comprises an articulation motor 510' that is used to actuate first and second articulation drivers 520', 530'. See FIGS. 10 and 11. The articulation motor 510' includes an articulation worm gear 512' that is in meshing engagement with an articulation gear assembly 700. In one form, the articulation gear assembly comprises an articulation spur gear 702 that is in meshing engagement with the articulation worm gear 512' and an articulation drive gear 704 that is in meshing engagement with portions of the first and second articulation drivers 520', 530'. The articulation gear assembly 700 and, more particularly, drive gear 704 is centrally disposed between a first gear rack 524' on the first articulation driver 520' and a second articulation gear rack 534' on the second articulation driver 530'. Rotation of the articulation drive gear 704 in a first direction will result in the axial movement of the first articulation driver 520' in a distal direction "DD" and the simultaneous axial movement of the second articulation driver 530' in the proximal "PD" or opposite axial direction. Likewise, rotation of the articulation drive gear 704 in a second rotary direction will result in the axial movement of the second articulation driver 530' in the distal direction "DD" and the simultaneous axial movement of the first articulation driver 520' in the proximal or opposite direction "PD".

Referring to FIG. 11, the distal end 526' of the first articulation driver 520' includes a slot 528' that is configured to receive a corresponding pin 304 formed on the elongate channel of the end effector 300. Likewise, the distal end 536' of the second articulation driver 530' includes a slot 538' that is configured to receive a corresponding pin 306 formed on the elongate channel. Thus, axial movement of the articulation drivers 520', 530' in the above described manner will applying simultaneous "pushing and pulling" motions to the elongate channel of the end effector 300 and thereby result in pivotal articulation of the end effector 300 about the articulation axis. As indicated above, the surgical instrument 10 also includes a tissue cutting member that is configured for axial travel through the elongate slot in the surgical staple cartridge that is supported in the end effector 300. The tissue cutting member or tissue cutting surface (not shown) is formed on or otherwise attached to the distal firing member 550. The distal firing member 550 is attached to a firing rod 560' that is supported for axial travel within the spine assembly 250. The proximal firing member 560' has a centrally disposed axial slot therein (not shown) to accommodate the gear drive shaft 701 upon which articulation spur gear 702 and articulation drive gear 704 are mounted. See FIGS. 9 and 10. Such arrangement facilitates axial travel of the proximal firing member 560' in response to firing motions applied thereto by the firing system. The proximal end 564' of the proximal firing member 560' includes a lug 566' that is configured to be receive in a firing rod attachment cradle 164 provided in the distal end 163 of the drive member 160. See FIG. 2. Thus, actuation of the firing motor 152 will result in the axial movement of the drive member 160 and the proximal firing member 560' and the distal firing member 550.

The firing motor 152 and the articulation motor 510 communicate with the control circuit 156 (FIG. 2) and are interlocked by a switching arrangement generally designated as 600. In the illustrated configuration, the switching arrangement 600 includes a switch drum 610' that is rotatably supported on the closure member 230'. The switch drum 610' includes a laterally extending boss 611' that has an inwardly extending cam pin 612' mounted therein. Similar to the arrangement described above, the cam pin 612' extends inwardly into a cam slot provided in the closure member 230'. The switch drum 610' further includes opposed slots 614' that are configured to accommodate rotation of the nozzle lugs 406 therethrough. The switch drum 610' has an open bottom portion 613' to facilitate rotation of the switch drum 610' relative to the articulation motor 510' and the articulation gear assembly 700. See FIG. 9. The switch arrangement 600' also includes a movable switch component 618' that is mounted to a switch arm portion 616' of the switch drum 610'.

As discussed above, when the closure member 230' is in the proximal (unactuated) position, the cam pin 612' is in a first portion of the cam slot. A lock out spring 630' is mounted on the switch drum boss 611' to bias the switch drum 610' into that first position wherein the cam pin 612' is in the first portion of the cam slot. When in that first position, the movable switch component 618' is not in contact or in "actuation proximity" with switch component 626. When in this "firing lock" position, the control circuit prevents actuation of the firing motor 152. Stated another way, unless the movable switch component actuates switch component 626, no power is supplied to the firing motor 152. Thus, even if the clinician were to actuate the firing trigger 170 in an attempt to actuate the firing motor 152, the firing motor 152 would not actuate.

In the illustrated example, closure member assembly 230' is actuated by actuating the closure trigger 122. As the clinician depresses the closure trigger 122, the closure member assembly 230' is moved in the distal direction "DD" which ultimately causes the anvil to pivot to the clamped position onto the target tissue. As the closure member assembly 230' moves distally, the cam pin 612' interacts with the cam slot which results in the rotational movement of the switch drum assembly 610'. As the switch drum 610' is biased into an actuation direction against the force of the spring 612', the switch component 618' is brought into activation/registration with switch component 626 which causes the control circuit board 156 to permit power to flow to the firing motor 152 upon actuation of the firing trigger 170. When in that closed position, the closure member assembly 210' and the anvil are locked in the closed position in the manner described above. The control circuit 156 may also be configured such that when the switch components 618' and 626 are in actuation registration, the control circuit 156 prevents any flow of power to the articulation motor 510' should the rocker switch 515 be inadvertently actuated. Once the closure member assembly 210' and anvil are locked in clamped position, the clinician may actuate the firing trigger 170 to drive the cutting member through the end effector 300 and cut the target tissue clamped therein and fire the surgical fasteners on each side of the tissue cut line. The end effector 300 may also be quipped with sensor (s) (not shown) that communicate with the control circuit 156 to detect when the tissue cutting member has reached its distal-most position to thereby provide the control circuit with inputs to cause the firing motor 152 to stop and reverse its direction to retract the tissue cutting member to its starting position. Other sensor(s) may be employed to detect when the tissue cutting member has returned to the starting position and communicate with the control circuit 156 to thereby communicate that information to the clinician and/or enable the closure member assembly to be unlocked. Once the closure member assembly 210' has been unlocked, the lock out spring 630', acting on the switch drum 610', will urge the cam pin 612' to rotatably return the switch drum 610' back to that starting position which will deactivate the switch 626 and once again actuation of the firing motor 152 will be prevented by the control circuit.

FIGS. 12 and 13 illustrate an alternative shaft assembly 200" that is substantially similar to shaft assembly 200 except for the differences discussed below. Those portions/components of shaft assembly 200" that are also found in shaft assembly 200 will be designated with like element numbers. As can be seen in those Figures, the shaft assembly 200" comprises a spine assembly 250" that comprises a proximal frame end or proximal frame member 252" that is attached to a shaft frame 260 that is pivotally coupled to an end effector frame insert 330 that is attached to the elongate channel 302. The shaft frame 260 includes a pivot pin 262 that is configured to be rotatably received within a pivot aperture (not shown) in the end effector frame insert 330. Such arrangement serves to define the articulation joint 240 about which the end effector 300 may articulate.

The illustrated shaft assembly 200" includes first and second articulation drivers 520", 530" that are similar to articulation drivers 520, 530 as discussed above, except for the differences described below. As can be seen in FIGS. 12 and 13, for example, the first and second articulation drivers 520", 530" are slidably supported between the spine assembly 250" and a closure member assembly 210". Thus, the articulation drivers 520", 530" slide axially between those components when actuated to articulate the end effector 300 about the articulation joint 240. To provide support to the first and second articulation drivers 520", 530" during actuation thereof, an idler gear 264 is centrally disposed between the articulation drivers 520" and 530". The first articulation driver 520" includes a first distal gear rack 527 and the second articulation driver 530" include a second distal gear rack 537. The first and second distal gear racks 527, 537 are in meshing engagement with the idler gear 264 as shown. In addition, the proximal closure member segment 230" includes a first friction generating detent or locking tooth 234 that is configured to slidably engage a first toothed or serrated portion 529 on the first articulation driver 520". The proximal closure member segment 230" also includes a second friction generating detent or locking tooth 236 that is configured to slidably engage a second toothed or serrated portion 539 on the second articulation driver 530". To facilitate some flexing of the serrated portions 529, 539 of the first and second articulation drivers 520", 530", respectively during articulation of the end effector 300, an amount of clearance is provided between the corresponding portion of the proximal frame member 252" and the serrated portions 529, 539 of the articulation drivers 520", 530". For example, the portions of the proximal frame member 252" that do not correspond to the serrated portions 529, 539 may have a diameter "D" and the portion of the proximal frame member 252" that corresponds to the serrated portions 529, 539 may have a smallest diameter of "M" wherein M<D. Such arrangement provides clearance for flexing of the articulation drivers 520", 530" as the drivers 520", 530" are axially advanced. During such axial advancement, the detent teeth 234, 236 engage the corresponding serrated portions 529, 539 to prevent the articulation drivers 520", 530" from moving and essentially "lock" the end effector in position. This is not only advantageous for holding the end effector in an articulated orientation during performance of a surgical procedure, but also during shipping of the device which may prevent portions thereof from inadvertently becoming damaged. In addition, such locking arrangements serve to retain the articulation drivers in their respective attachment positions prior to the attachment of the shaft assembly to the handle or housing. In alternative arrangements, the friction generating detent or locking teeth may each be spring biased into contact with the corresponding serrated portions of the articulation drivers. For example, each tooth may be separately movable in directions transverse to the serrated portions. A biasing member or spring may be situated in connection with each locking tooth to bias the tooth into retaining engagement with the corresponding serrated portion.

FIGS. 14-24 illustrate portions of another interchangeable shaft assembly 1200 that may be employed with surgical instrument 10. Those components of the interchangeable shaft assembly 1200 that are identical to components of the interchangeable shaft assembly 200 described above will be described below with like element numbers. In the illustrated arrangement, the shaft assembly 1200 includes a spine assembly 1250 upon which a closure member assembly 1210 is movably supported. The spine assembly 1250 includes a proximal spine segment 1252 that rotatably supported in a frame portion of the shaft assembly 1200. The proximal spine segment 1252 has two diametrically opposed notches 1253 that are configured to receive corresponding lug portions 1406 extending inwardly from the nozzle portions 1402. Further details concerning the shaft frame assembly and the rotary attachment of the proximal spine segment 1252 therein as well as the rotary attachment of the nozzle portions 1402 thereto may be found in U.S. patent application Ser. No. 13/803,097, entitled ARTICULATABLE SURGICAL INSTRUMENT COMPRISING A FIRING DRIVE, U.S. Pat. No. 9,687,230, which has been herein incorporated by reference in its entirety.

Figure 21:
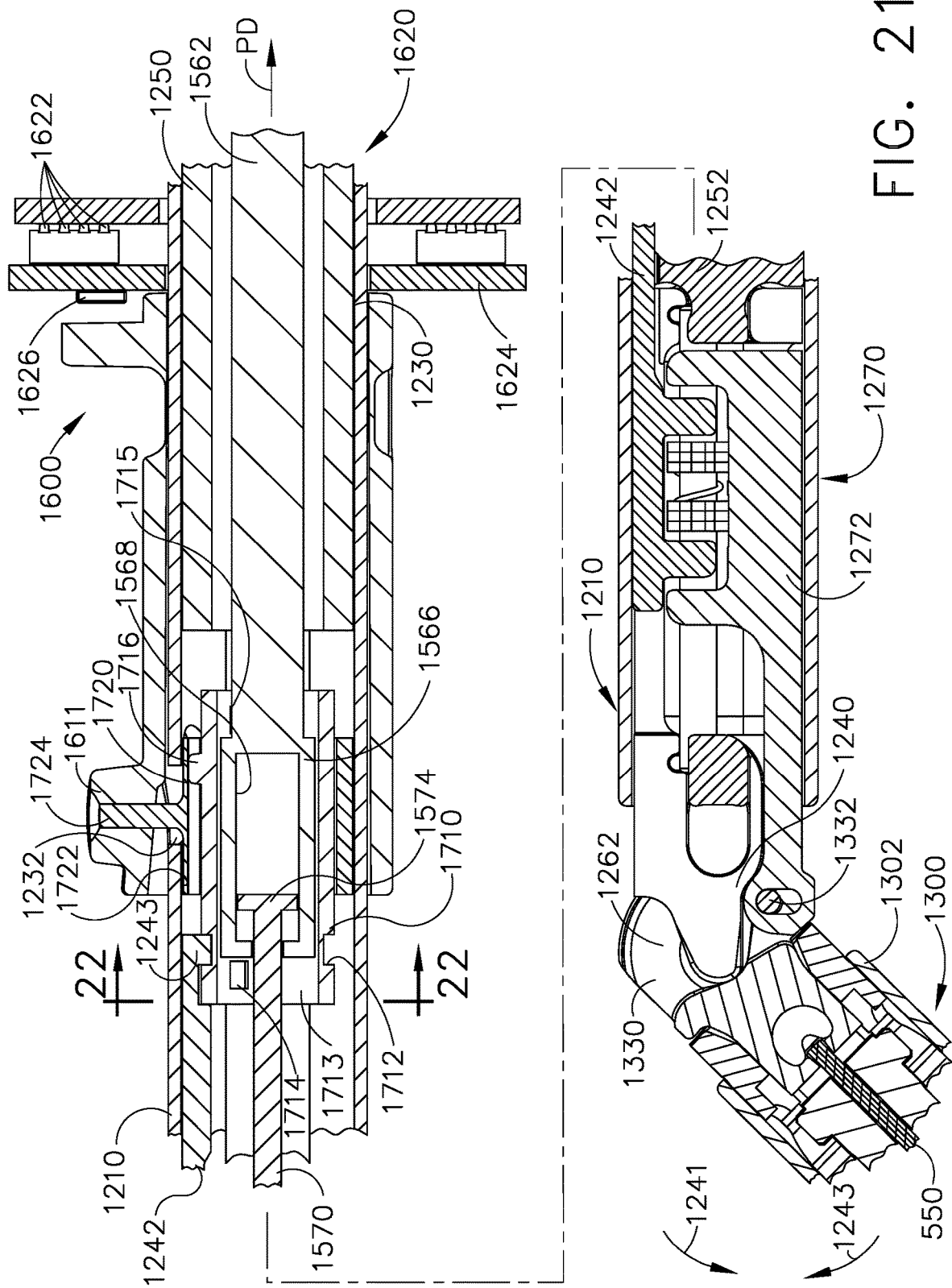
FIG. 21 is another cross-sectional view of a portion of the interchangeable shaft assembly of FIGS. 14-20 with the end effector in an articulated orientation.

Referring to FIGS. 16, 17, 18, 19, 22 and 24, the proximal spine segment 1252 is coupled to a distal frame member 1256 by a frame rib 1254 that extends therebetween within the closure member assembly 1210. As can be seen in FIGS. 20 and 21, the distal frame member 1256 is coupled to a frame 1260. The end effector 1300 is similar to end effector 300 and is configured to cut and staple/tissue in the above-described manners. The end effector 1300 includes an elongate channel 1302 that has an end effector frame insert 1330 attached thereto. Further details concerning the frame and end effector frame insert may also be found in U.S. patent application Ser. No. 13/803,097, entitled ARTICULATABLE SURGICAL INSTRUMENT COMPRISING A FIRING DRIVE, U.S. Pat. No. 9,687,230. The shaft frame 1260 includes a pivot pin 1262 that is configured to be rotatably received within a pivot aperture (not shown) in the end effector frame insert 1330. Such arrangement serves to define the articulation joint 1240 about which the end effector 1300 may articulate. In the illustrated implementation, the interchangeable shaft assembly 1200 includes a proximal articulation driver 1242 that interfaces with an articulation lock 1270. Further details regarding the articulation lock 1270 may also be found in U.S. patent application Ser. No. 13/803,097, entitled ARTICULATABLE SURGICAL INSTRUMENT COMPRISING A FIRING DRIVE, U.S. Pat. No. 9,687,230. As discussed in greater detail in that patent application, movement of the proximal articulation driver 1240, whether it be proximal or distal, can unlock the articulation lock 1270.

Figure 19:
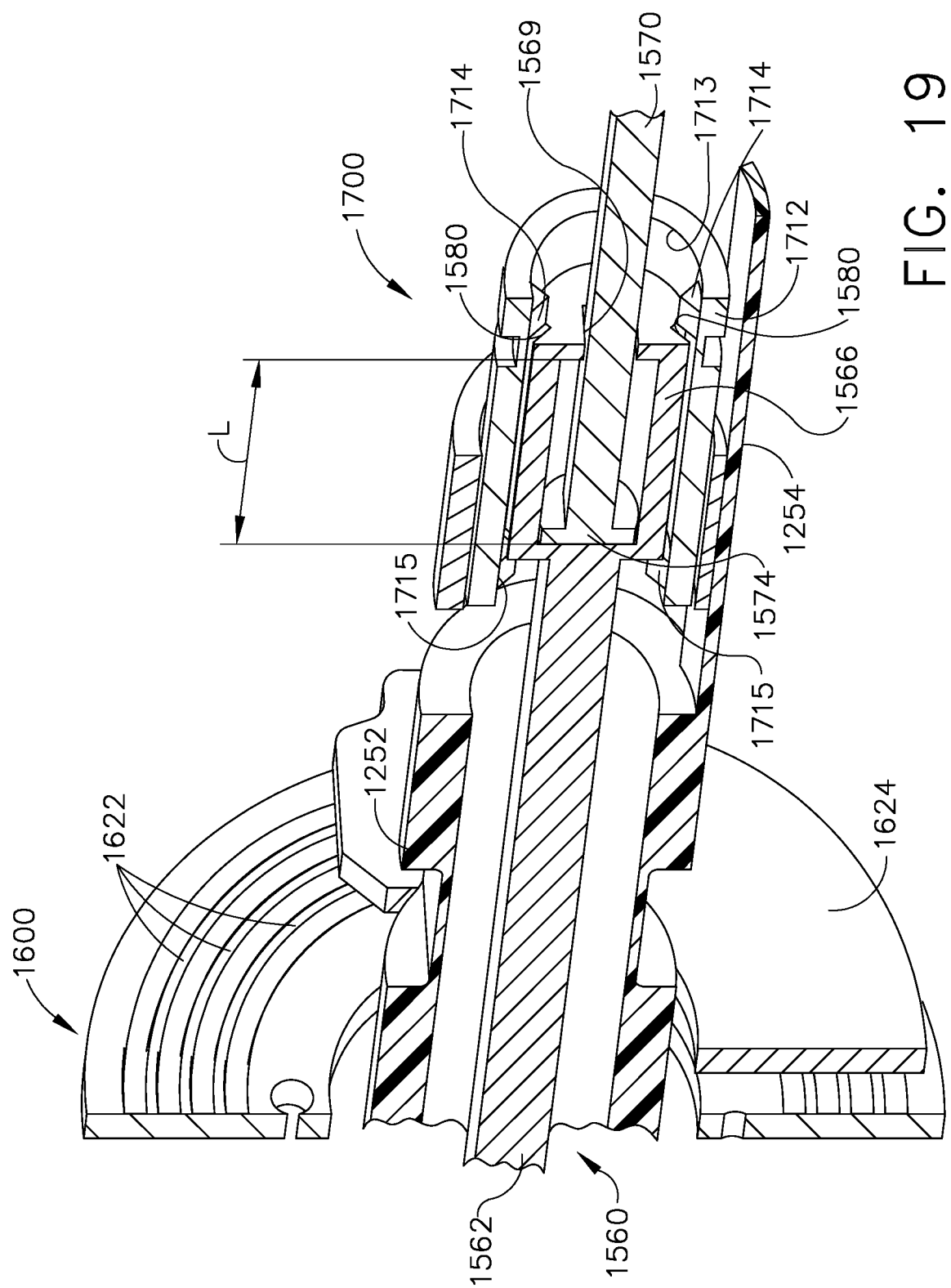
FIG. 19 is another cross-sectional perspective view of a portion of the interchangeable shaft assembly of FIGS. 14-18 with various components omitted for clarity and wherein the clutch assembly is in a firing orientation.

Still referring to FIGS. 19 and 20, the articulation lock 1270 includes a distal articulation driver 1272 that is movably coupled to a drive pin 1332 on the end effector frame insert 1330. For example, the drive pin 1332 is closely received within a pin slot 1274 defined in the distal end 1273 of the distal articulation driver 1272 such that the drive pin 1332 can bear against a proximal sidewall of the pin slot 1274 and transmit a proximal pushing force P to the distal articulation driver 1272. Such proximal pushing force P will only serve to bolster the locking engagement achieved by the articulation lock 1270. In order to release the locking engagement, and permit the end effector 1300 to be rotated in the direction indicated by arrow 1241, referring now to FIG. 21, the proximal articulation driver 1242 is pulled proximally to sufficiently unlock the lock components and permit the distal articulation driver 1272 to be moved proximally. In various circumstances, the proximal articulation driver 1242 can continue to be pulled proximally until a portion thereof pulls the distal articulation driver 1272 proximally to articulate the end effector 1300. After the end effector 1300 has been suitably articulated in the direction of arrow 1241, the proximal articulation driver 10040 can be released, in various circumstances, to permit the articulation lock 1270 to re-lock the distal articulation member 1272 in position. Further details regarding the construction and operation of the articulation lock 1270 may be found in U.S. patent application Ser. No. 13/803,097, entitled ARTICULATABLE SURGICAL INSTRUMENT COMPRISING A FIRING DRIVE, U.S. Pat. No. 9,687,230, which has been herein incorporated by reference in its entirety.

As discussed above, one form of the interchangeable shaft assembly 1200 comprises an articulation driver system including a proximal articulation driver 1242 and a distal articulation driver 1272. When a drive force is transmitted to the proximal articulation driver 1242, whether it be in the proximal direction or the distal direction, the drive force can be transmitted to the distal articulation driver 1272 through the articulation lock 1270. In various circumstances, further to the above, the drive member 160 of the surgical instrument 10 can be utilized to impart such a drive force to the proximal articulation driver 1242. For instance, the interchangeable shaft assembly 1200 includes a clutch system 1700 which can be configured to selectively connect the proximal articulation driver 1242 to the drive member 160 of the surgical instrument 10 such that the movement of the drive member 160 is imparted to the proximal articulation driver 1242. In use, the clutch system 1700 is movable between an engaged state (FIG. 22) in which the proximal articulation driver 1242 is operably engaged with a proximal firing member 1560 (and drive member 160) and a disengaged state (FIG. 24) in which the proximal articulation driver 1242 is not operably engaged with the proximal firing member 1560 (and the drive member 160).

Figure 16:
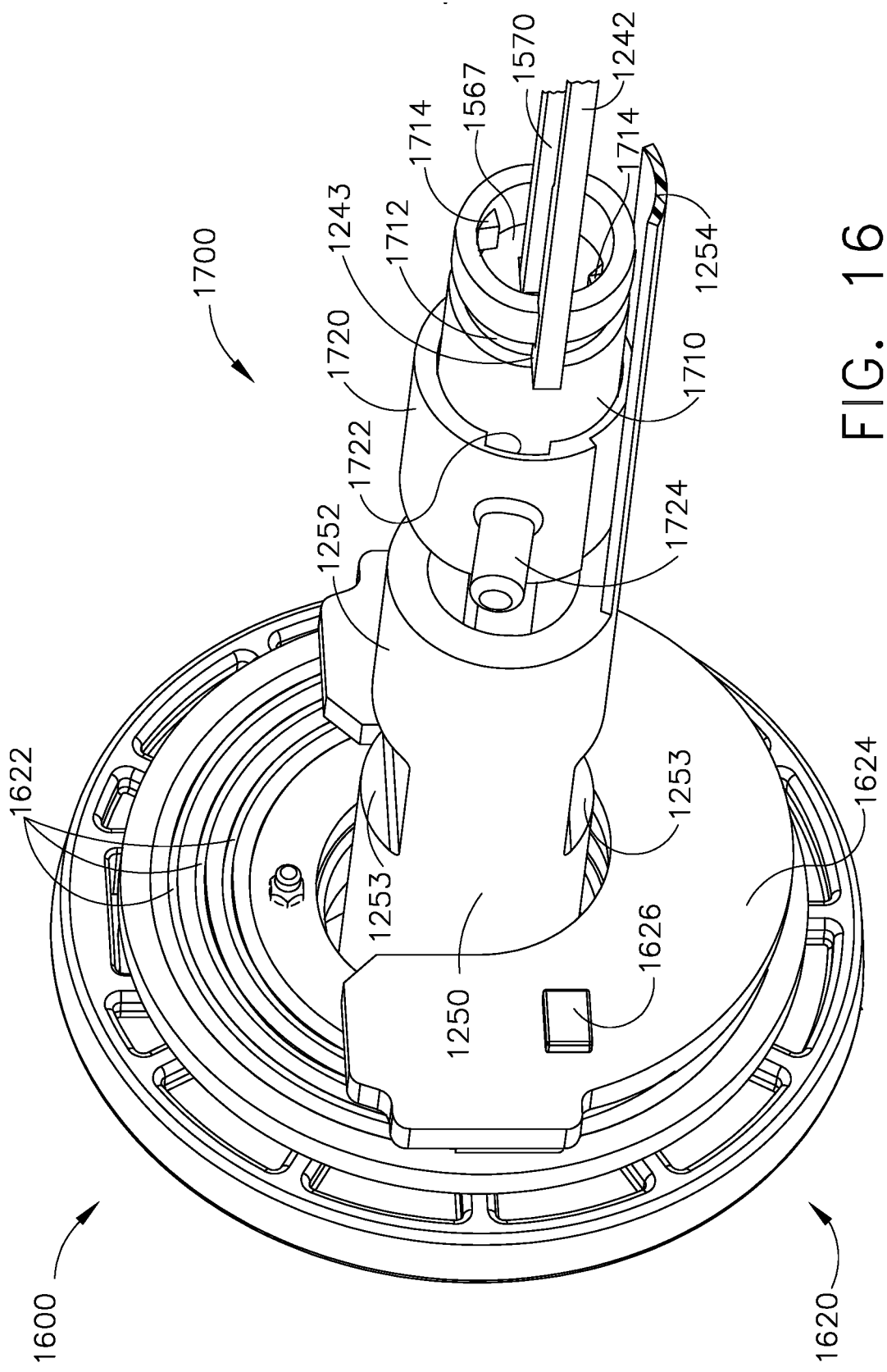
FIG. 16 is another perspective view of a portion of the interchangeable shaft assembly of FIGS. 14 and 15 with various components omitted for clarity.
Figure 17:
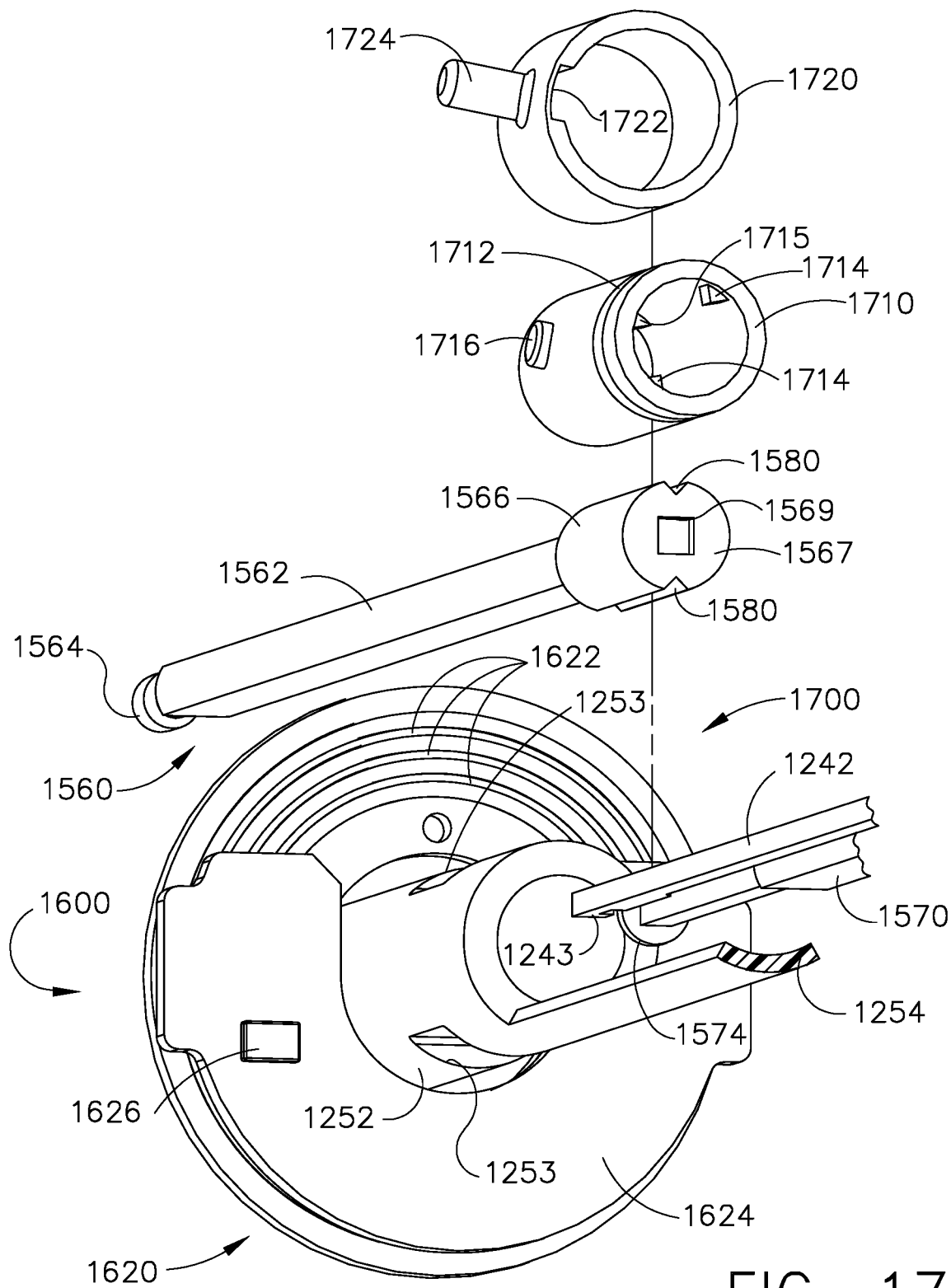
FIG. 17 is a partial exploded assembly view of a portion of the interchangeable shaft assembly of FIGS. 14-16.

In one form, the clutch system 1700 comprises an engagement member 1710 which can be configured to directly connect the proximal articulation driver 1242 to the proximal firing member 1560. As can be seen in FIG. 16, for example, the proximal articulation driver 1242 includes a proximal tab 1243 that is received within an annular groove 1712 provided in the perimeter of the engagement member 1710 to link the proximal articulation driver 1242 to the engagement member 1710 while permitting relative rotation therebetween. As can be seen in FIG. 17, the proximal firing member 1560 includes an elongate rod portion 1562 that has an attachment lug 1564 formed on the proximal end thereof. The attachment lug 1564 is configured to be rotatably supported in the cradle 162 on the drive member 160. See FIG. 2. As can be further seen in FIG. 17, the proximal firing member 1560 further comprises a firing rod coupler 1566 that is formed on the distal end of the rod 1562. The firing rod coupler 1566 includes a closed distal end 1567 that defines a cylindrical passage 1568. An aperture 1569 is formed through the closed distal end 1567 that is adapted to slidably receive a proximal end 1572 of an intermediate firing member 1570 therethrough. In the illustrated example, the intermediate firing member 1570 includes a stop member in the form of a disc 1574 that is formed on the proximal end 1572 thereof and is sized for sliding travel within the cylindrical passage 1568 in the firing rod coupler 1566. The distal end of the intermediate firing member 1570 is coupled to the proximal end of the distal firing member 550 in the various manners disclosed in, for example, U.S. patent application Ser. No. 13/803,097, entitled ARTICULATABLE SURGICAL INSTRUMENT COMPRISING A FIRING DRIVE, now U.S. Pat. No. 9,687,230, which has been herein incorporated by reference. In the illustrated arrangement, two diametrically-opposed, V-shaped engagement grooves 1580 are formed in the perimeter of the firing rod coupler 1566. See FIGS. 17-19. The V-shaped grooves 1580 are configured to slidably receive corresponding V-shaped articulation detents 1714, 1715 formed on the inner surface 1713 of the engagement member 1710.

Further to the above, referring again to FIGS. 16-24, the clutch system 1700 also comprises an actuator member 1720 that is configured to axially move on the engagement member 1710. As can be most particularly seen in FIG. 17, for example, a first engagement pin 1716 extends outward from the engagement member 1710 and is configured to be slidably received within a slot 1722 extending through the actuator member 1720. Such arrangement facilitates relative axial movement of the actuator member 1720 and the engagement member 1710 while also enabling the actuator member 1720 and engagement member 1710 to rotate as a unit. Also in the illustrated arrangement, the clutch system 1700 includes a cam pin 1724 that protrudes from the actuator member 1720. As with the arrangement described above, the cam pin 1724 extends out through a cam slot 1232 in a proximal closure member segment 1230. See FIG. 15.

The firing motor 152 communicates with the control circuit 156 and a switching arrangement generally designated as 1600. In the illustrated configuration, the switching arrangement 1600 includes a switch drum 1610 that is rotatably supported on the proximal closure member segment 1230. The switch drum 1610 includes a laterally extending boss 1611 that is adapted to receive an end of the cam pin 1724 therein. The switch drum 1610 further includes opposed slots 1614 that are configured to accommodate rotation of the nozzle lugs 1406 therethrough. See FIG. 14. The switching arrangement 1600 also includes a slip ring assembly 1620 which is configured to conduct electrical power and/or signals to and/or from the end effector 1300 to the handle 102 and more particularly to the control circuit 156 within the handle 102. The slip ring assembly 1620 includes a plurality of concentric, or at least substantially concentric, conductors 1622 on opposing sides thereof which can be configured to permit relative rotation between the halves of the slip ring assembly 1620 while still maintaining electrically conductive pathways therebetween. In the illustrated implementation, the slip ring assembly 1620 includes a bulkhead 1624 that has a switch component 1626 that communicates through the slip ring 1620 to the control circuit 156. The switch arrangement 1600 also includes a movable switch component 1618 that is mounted to a switch arm portion 1616 of the switch drum 1610. See FIG. 14.

Figure 14:
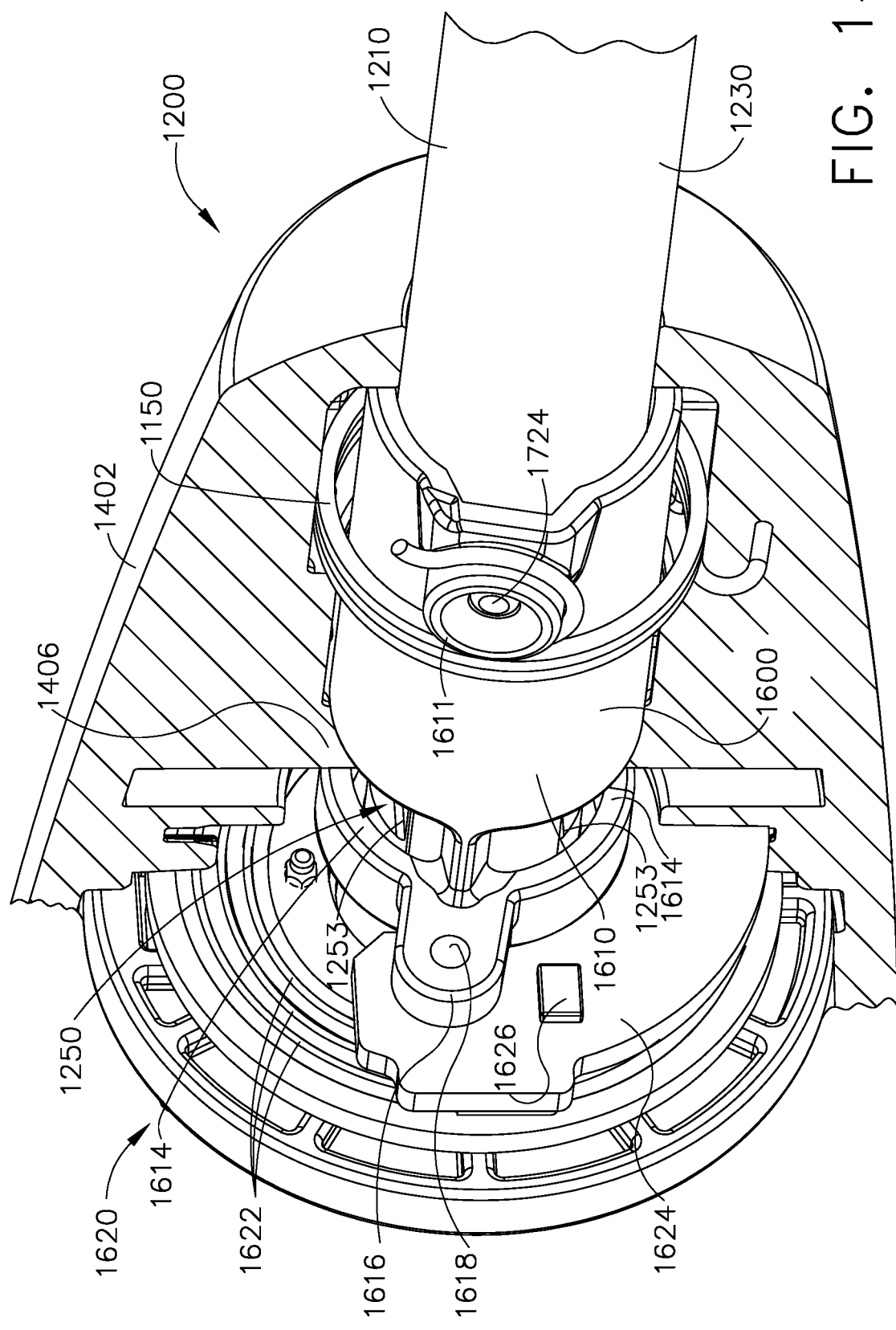
FIG. 14 is a perspective view of a portion of another interchangeable shaft assembly.
Figure 15:
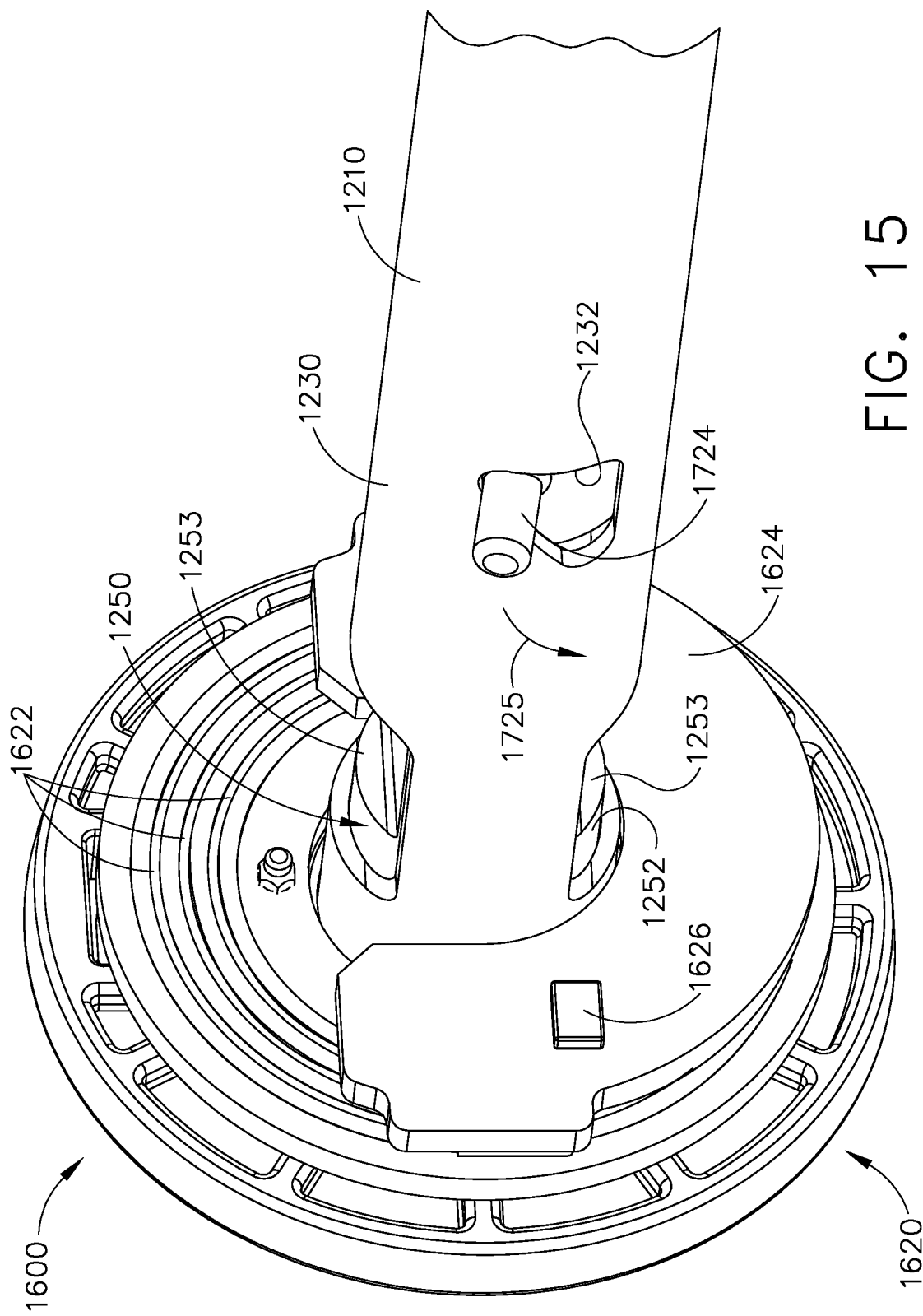
FIG. 15 is another perspective view of a portion of the interchangeable shaft assembly of FIG. 14 with various components omitted for clarity.

As discussed above, during a typical surgical procedure, the clinician may introduce the end effector 1300 into the surgical site through a trocar or other opening in the patient to access the target tissue. FIG. 20 illustrates the position of the end effector 1300 for insertion through a trocar port or otherwise into the patient to access the target tissue. As can be seen in that Figure, the end effector 1300 is unarticulated or stated another way is axially aligned with the shaft axis SA-SA. Once the end effector 1300 has passed through the trocar port, for example, the clinician may need to articulate the end effector 1300 to advantageously position it adjacent the target tissue. FIGS. 15, 18, 20, 21 and 22 illustrate the positions of the clutch system components when the clutch system 1700 is in the articulation orientation. During the articulation process, the end effector 1300 is in an open position. Stated another way, the closure member assembly 1210 is positioned in its proximal "unactuated" position such that the distal end of the anvil of the end effector 1300 is spaced away from the surgical staple cartridge. FIG. 15 illustrates the position of the proximal closure member segment 1230 when in the unactuated or open position. As can be seen in that Figure, the cam pin 1724 is located in the upper portion of the cam slot 1232. When in that position, the cam pin 1724 locates the switch drum 1610 such that the switch component 1618 on the switch arm 1616 is not in actuation proximity or alignment with the switch component 1626 on the switch bulkhead 1624. Thus, when the switch 1626 is not actuated by switch 1618, the control circuit 156 may be configured to permit the firing motor 152 to fire for a limited closing stroke but unable to fire for a period that is sufficient to actuate or advance the intermediate firing member 1570 and the distal firing member 550 as will be discussed in further detail below. As can be seen in FIG. 14, a firing system lockout spring 1150 is provided on the boss 1611 of the switch drum 1610 to bias the switch drum 1610 and ultimately the cam pin 1724 into the upper portion of the cam slot 1232 in the unactuated or open position. See FIG. 14. Thus, when the closure member assembly 1210 and ultimately the anvil of the end effector 1300 is in the open position, actuation of the firing motor 152 will not result in the advancement of the intermediate firing member 1570 and the distal firing member 550 through the end effector 1300.

Figure 18:
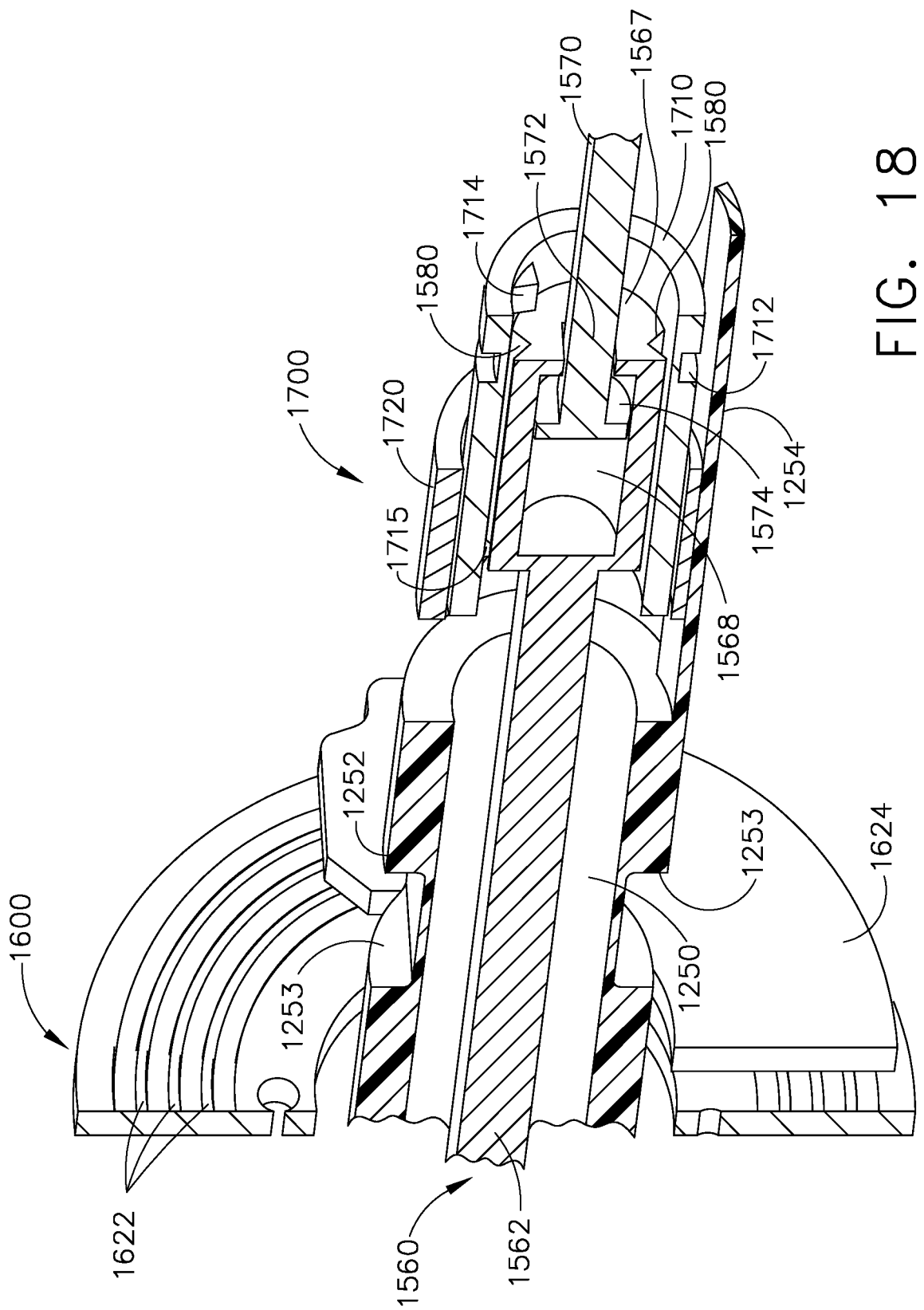
FIG. 18 is a cross-sectional perspective view of a portion of the interchangeable shaft assembly of FIGS. 14-17 with various components omitted for clarity and wherein the clutch assembly is in an articulation orientation.
Figure 22:
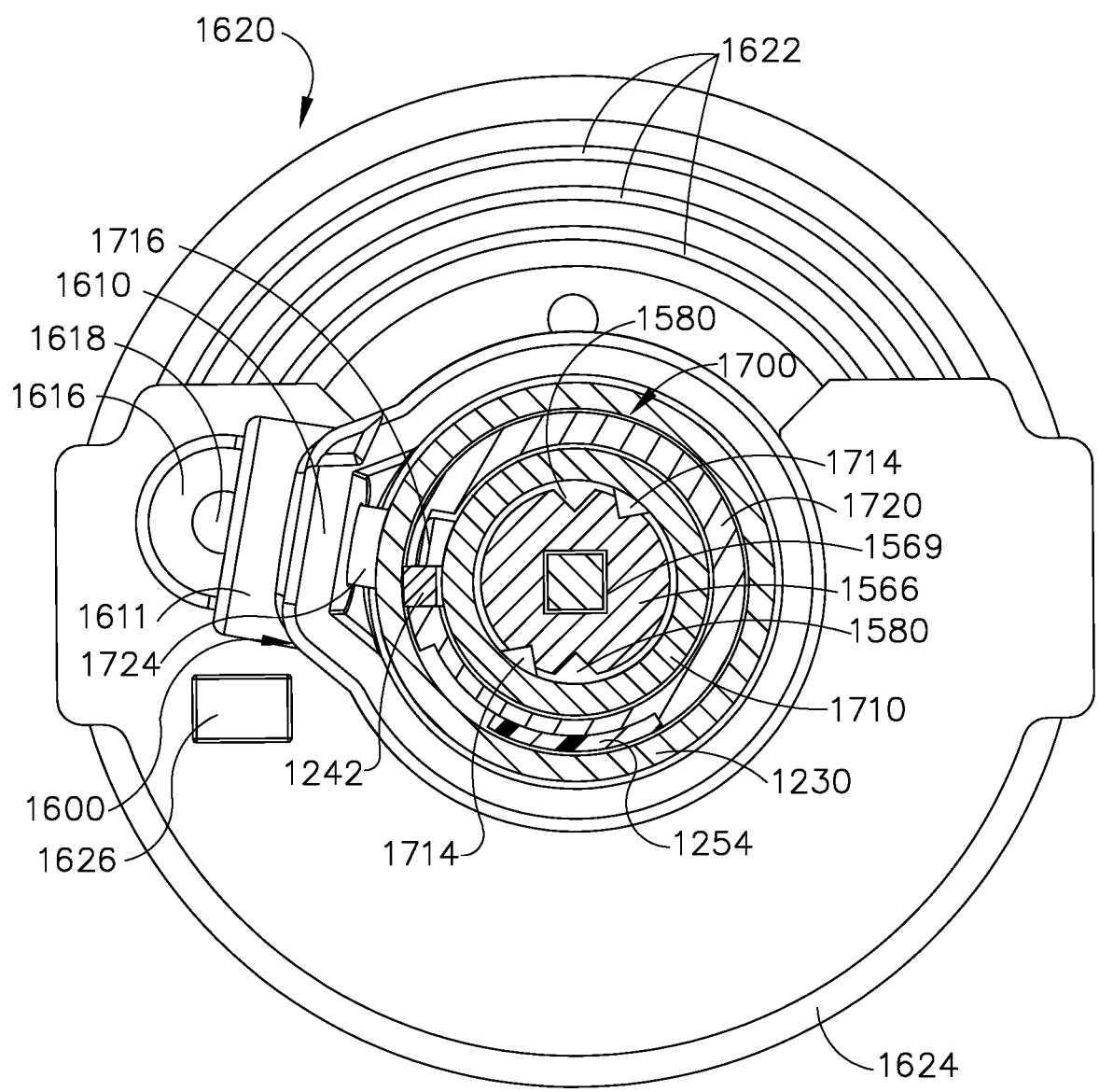
FIG. 22 is a cross-sectional view of the interchangeable shaft assembly of FIGS. 14-21 taken along lines 22-22 in FIG. 21.

Referring to FIGS. 18 and 22, when the clutch system 1700 is in the articulation orientation, the V-shaped detents 1714, 1715 are not aligned with the corresponding V-shaped slots 1580 in the firing rod coupler 1566. Thus, advancement of the drive member 160 and the proximal firing member 1560 in the distal direction "DD" will result in the distal advancement of the proximal articulation driver 1242 as shown in FIG. 21, for example. Such arrangement serves to pivot the end effector 1300 in the direction represented by arrow 1241 in FIG. 21. The drive member 160 and the proximal firing member 1560 are advanced distally by actuating the firing motor 152 in a first direction. In one implementation, the firing motor 152 may be actuated by actuating a rocker switch 515 mounted on the handle 102 in a first direction. To pivot the end effector 1300 in a second opposite direction (represented by arrow 1243 in FIG. 21) the rocker switch 515 is actuated in a second or opposite direction. In either case, however, because the closure member assembly 1210 is in the open position and the switch 1618 on the switch drum 1610 is out of actuation orientation with the switch 1626 on the switch bulkhead 1624, the control circuit 156 only permits actuation of the firing motor 152 for the time necessary to attain the desired articulation stroke but not of sufficient duration so as to advance the intermediate firing member 1570 distally. FIG. 20 illustrates the position of the stop member 1574 located on the distal end of the intermediate firing member 1570 within the cylindrical passage 1568 in the firing rod coupler 1566 when the clutch system 1700 is in the articulation mode, but prior to actuation of the firing motor 152. FIG. 21 illustrates the position of the stop member 1574 within the cylindrical passage 1568 after the firing motor 152 has been actuated to drive the proximal firing member 1560 in the proximal direction "PD". Because the V-shaped detents 1714 and 1715 are not aligned with the corresponding V-shaped slots 1580, movement of the proximal firing member 1560 and the firing rod coupler 1566 in the proximal direction "PD" causes the bottom of the firing rod coupler 1566 to contact the proximal detents 1715 and drive the engagement member 1710 in the proximal direction "PD" as well. Movement of the firing rod coupler 1566 also drives the articulation driver 1242 in the proximal direction thereby causing the end effector 1300 to articulate in the direction represented by arrow 1241 in FIG. 21. Actuation of the firing motor 152 in an opposite rotary direction will cause the proximal firing member 1560 to move in the distal direction "DD" such that the end 1567 thereof contacts the distal detents 1714 to drive the engagement member 1710 distally. Such distal movement of the engagement member 1710 also causes the articulation driver 1242 in the distal direction "DD" which results in the articulation of the end effector 1300 in an opposite articulation direction (represented by arrow 1243 in FIG. 21). Thus, it may be appreciated from the foregoing discussion that the proximal firing member 1560 may move axially for a predetermined amount of axial travel without axially advancing the intermediate firing member 1570 and the distal firing member 550 attached thereto. This predetermined amount of axial travel may be defined by the axial length "L" of the cylindrical passage 1568 in the firing rod coupler 1566. See FIG. 19.

Figure 23:
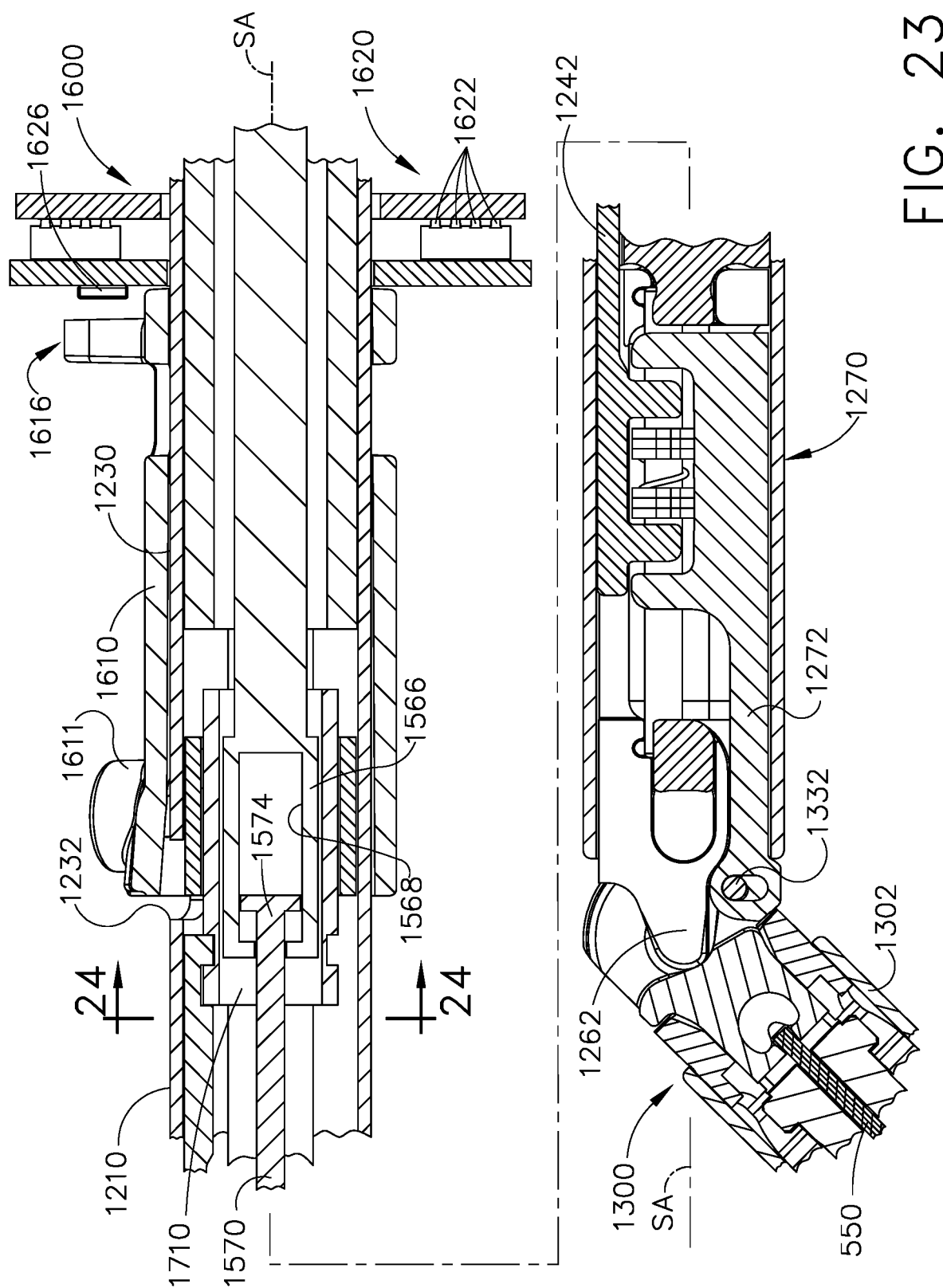
FIG. 23 is another cross-sectional view of a portion of the interchangeable shaft assembly of FIGS. 14-22 with the end effector in an articulated orientation and the clutch assembly in a firing orientation.
Figure 24:
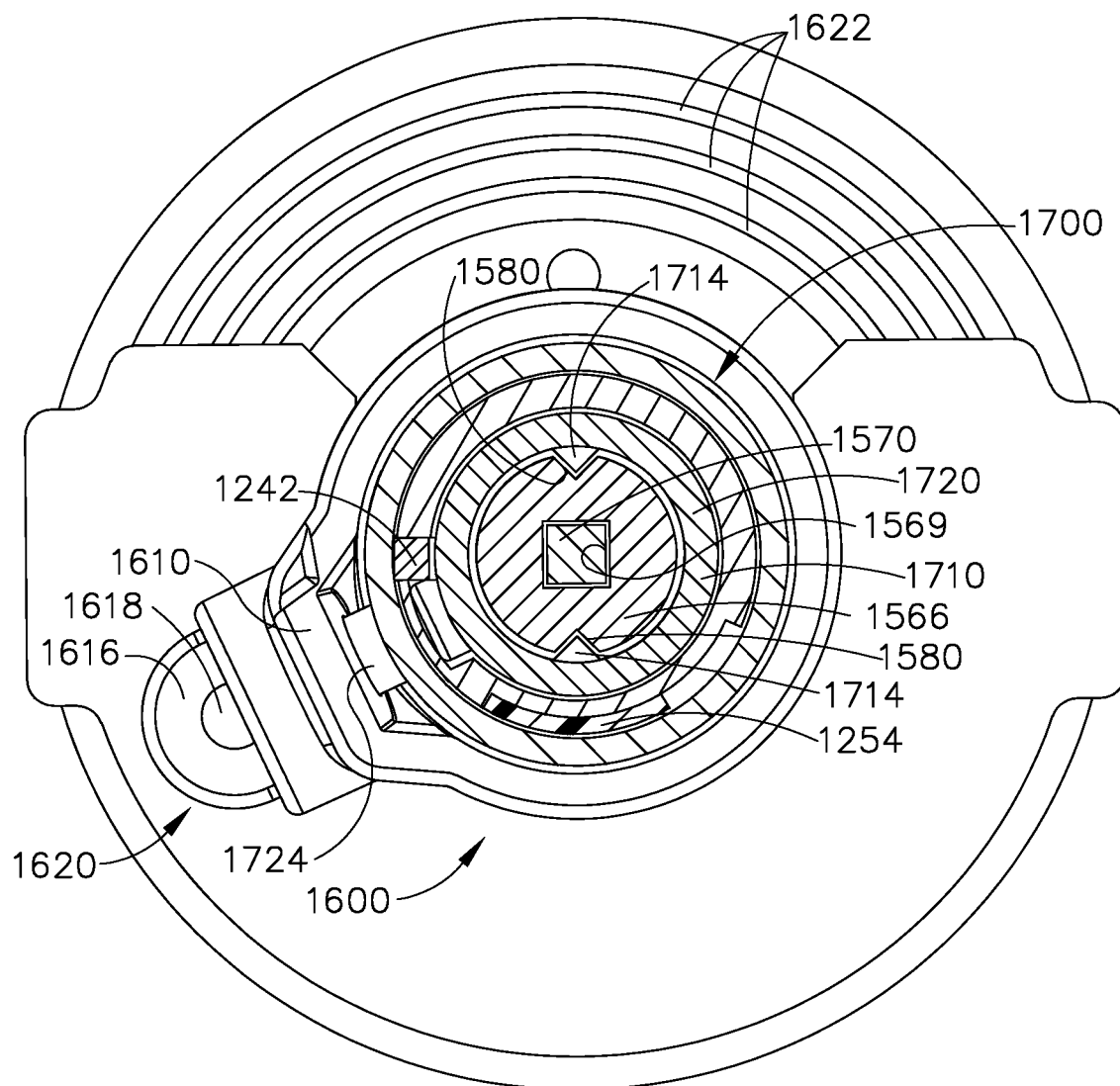
FIG. 24 is a cross-sectional view of the interchangeable shaft assembly of FIGS. 14-23 taken along lines 24-24 in FIG. 23.

Once the clinician has positioned the end effector 1300 in the desired orientation wherein the target tissue is located between the anvil and the staple cartridge, the clinician may then close the anvil to clamp the target tissue between the anvil and the staple cartridge. As discussed above, the anvil may be closed by actuating the closure trigger 122 to axially advance the closure member assembly 1210 in the distal direction "DD". As the closure member assembly 1210 moves distally, the cam slot 1232 in the proximal closure member segment 1230 causes the cam pin 1724 to move to the bottom of the cam slot 1232 (this movement is represented by arrow 1725 in FIG. 15). As the cam pin 1724 moves in the direction 1725, the switch drum 1610 is rotated on the closure member assembly 1210 such that the switch arm 1616 moves switch component 1618 into actuation registration with switch component 1626 to thereby provide the control circuit 156 with a signal indicating that the closure member assembly 1210 and, more precisely, that the anvil is in a closed position and ready for firing. The control circuit 156 will then enable the firing motor 152 to, upon actuation of the firing trigger 170, rotate for a sufficient firing time as to drive the distal firing member 550 (and cutting instrument attached thereto or otherwise mounted thereon) to its ending or completely fired position within the end effector 1300. FIGS. 19, 23 and 24 illustrate the positions of the various components of the clutch system 1700 in the firing orientation.

Many motorized surgical cutting and fastening instruments utilize a separate drive rod for articulation and for firing the device. Although that method employs a somewhat simple architecture, it can prove costly and have increased reliability concerns due to the fact that full drive systems are replicated in the design. Various arrangements disclosed herein employ a single drive mechanism to do both articulation and firing that also provide a means to lock the articulation before firing.

Figure 25:
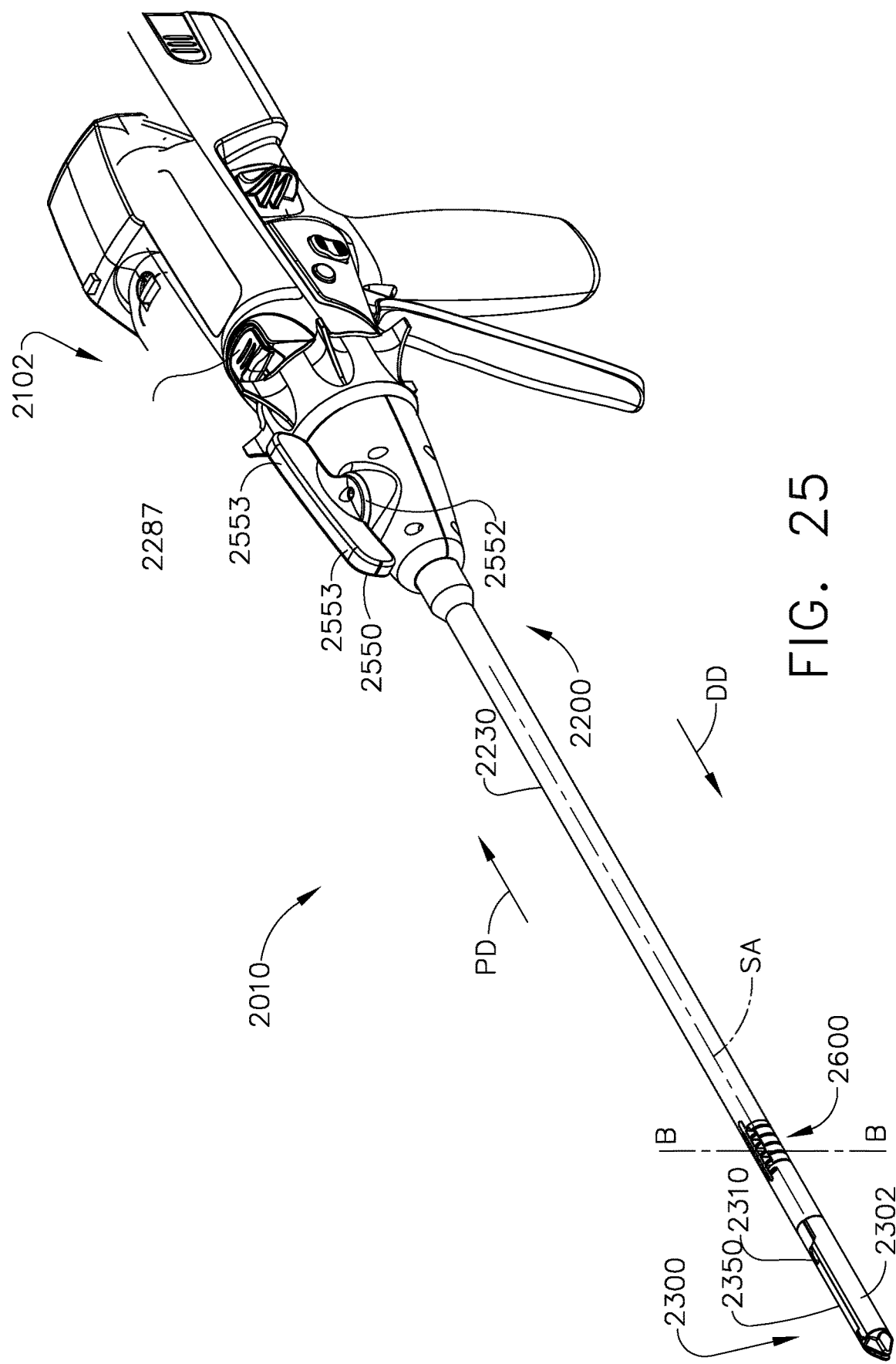
FIG. 25 is a perspective view of another surgical instrument with an articulatable surgical end effector operably coupled thereto.

When an articulatable end effector is used in surgery, it is desirable to prevent inadvertent detachment of the end effector from the surgical instrument, particularly when the end effector is in an articulated orientation. This problem can be exacerbated when using surgical instruments that employ interchangeable shaft assemblies that are detachable from the instrument handle or housing. For example, during use it is important to avoid inadvertent or in some cases careless detachment of the shaft assembly or end effector from the instrument when the end effector is in an articulated orientation. FIG. 25 illustrates another articulatable surgical instrument 2010 that includes an interchangeable shaft assembly 2200 that is removably mounted to the handle 2102 of the instrument 2010. An end effector 2300 is attached to the interchangeable shaft assembly 2200 and is selectively articulatable about an articulation axis B-B. The shaft assembly 2200 includes a unique and novel locking system for preventing detachment of the interchangeable shaft assembly 2200 from the handle 2102 when the end effector is in an articulated orientation. The surgical instrument 2010 is identical to surgical instrument 10 described above except for at least the differences discussed below. As can be seen in that Figure, the depicted surgical instrument 2010 is motor driven (or "powered") and includes a housing or handle 2102 that has interchangeable shaft assembly 2200 operably attached thereto. Various features and details regarding interchangeable shaft assemblies may be found in U.S. patent application Ser. No. 13/803,053, entitled INTERCHANGEABLE SHAFT ASSEMBLIES FOR USE WITH A SURGICAL INSTRUMENT, U.S. Patent Application Publication No. 2014/0263564, the entire disclosure of which is hereby incorporated by reference herein and in U.S. patent application Ser. No. 14/226,075, filed Mar. 26, 2014, entitled MODULAR POWERED SURGICAL INSTRUMENT WITH DETACHABLE SHAFT ASSEMBLIES, now U.S. Pat. No. 9,743,929, the entire disclosure of which is also hereby incorporated by reference herein.

Still referring to FIG. 25, an end effector 2300 is operably attached to the interchangeable shaft assembly 2200. The end effector 2300 may be identical to end effector 300, for example and include, among other things, an elongate channel 2302 that is configured to operably support a staple cartridge 2310 therein. The end effector 2300 further includes an anvil 2350 that has a staple forming undersurface thereon. The anvil 2350 is moved between open and closed positions by a closure tube assembly 2120 that is axially advanced in the distal and proximal directions by actuating a closure trigger 2122. The closure tube assembly 2120 includes a proximal closure tube shaft segment 2230 that is operably coupled to a distal closure tube segment 2220 by an articulation joint 2240 to facilitate articulation of the end effector 2300 about an articulation axis B-B that is transverse to a shaft axis SA-SA defined by the interchangeable shaft assembly 2200.

Figure 26:
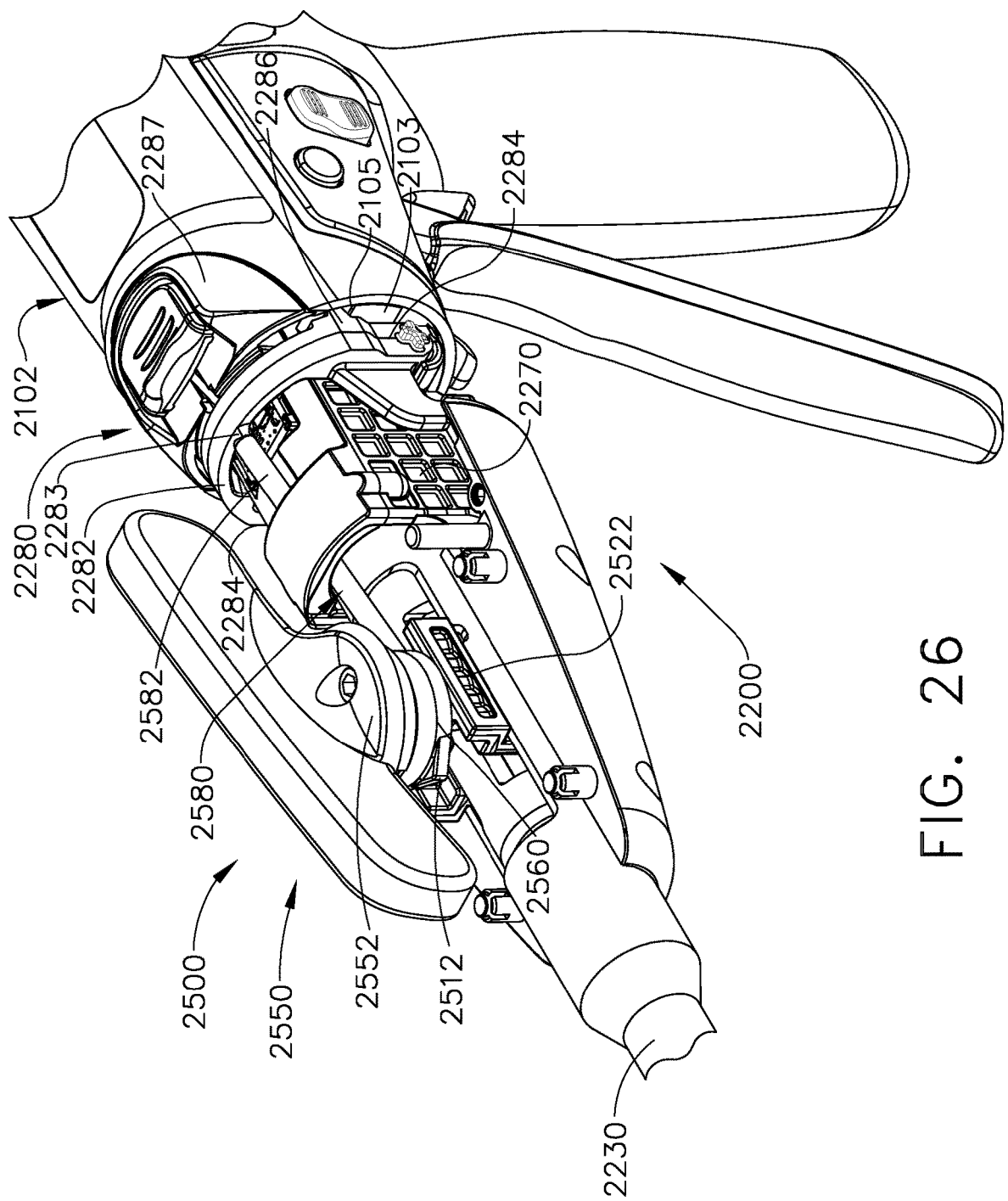
FIG. 26 is a perspective view of a handle portion of the surgical instrument of FIG. 25 with a portion of the nozzle housing omitted for clarity.
Figure 27:
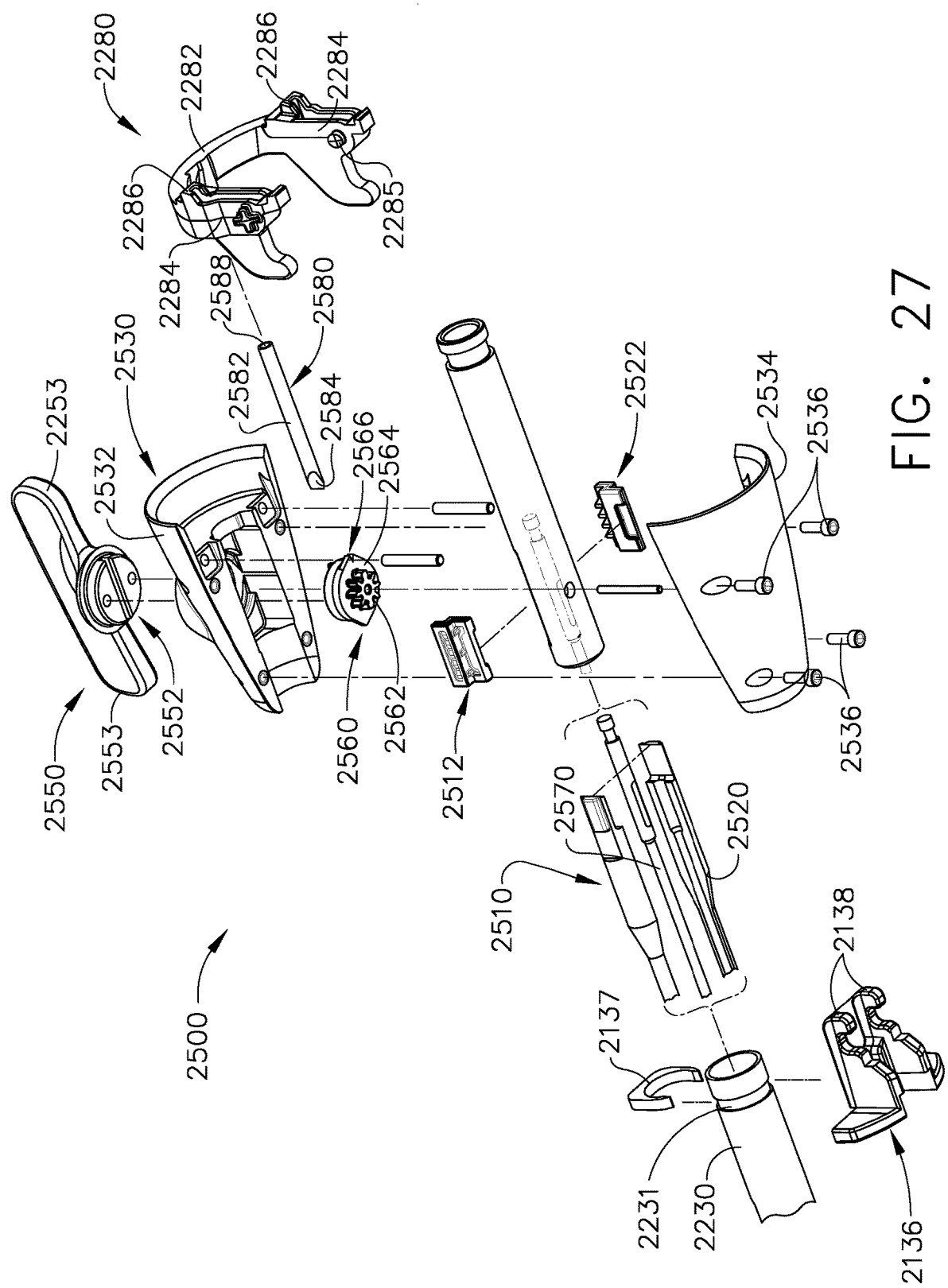
FIG. 27 is an exploded perspective view of a portion of the surgical instrument of FIGS. 25 and 26.

Referring to FIG. 26, the shaft assembly 2200 includes a chassis 2270 that is configured to be removably coupled to the handle 2102. Various shaft assembly embodiments employ a latch system 2280 for removably coupling the shaft assembly 2200 to the handle 2102 and more specifically to the handle frame. As can be seen in FIG. 26, for example, in at least one form, the latch system 2280 includes a lock member or lock yoke 2282 that is movably coupled to the chassis 2270. In the illustrated embodiment, for example, the lock yoke 2282 has a U-shape with two spaced downwardly extending legs 2284. The legs 2284 each have a pivot lug 2285 formed thereon that is adapted to be received in corresponding holes (not shown) that are formed in the chassis 2270. See FIG. 27. Such arrangement facilitates pivotal attachment of the lock yoke 2282 to the chassis 2270. The lock yoke 2282 may include two proximally protruding lock lugs 2286 that are configured for releasable engagement with corresponding lock detents or grooves 2105 in the distal attachment flange 2103 of the frame. See FIG. 27. The lock yoke 2282 may be biased in the proximal direction "PD" by a first spring or biasing member (not shown). Actuation of the lock yoke 2282 may be accomplished by a latch button 2287 that is slidably mounted on a latch actuator assembly that is mounted to the chassis 2270. The latch button 2287 may be biased in a proximal direction relative to the lock yoke 2282. As will be discussed in further detail below, the lock yoke 2282 may be moved to an unlocked position by biasing the latch button 2287 in the distal direction "DD" which also causes the lock yoke 2282 to pivot out of retaining engagement with the distal attachment flange 2103 of the frame. When the lock yoke 2282 is in "retaining engagement" with the distal attachment flange 2103 of the frame, the lock lugs 2286 are retainingly seated within the corresponding lock detents or grooves 2105 in the distal attachment flange 2103.

The interchangeable shaft assembly 2200 includes a closure shuttle 2136 that is slidably supported within the chassis 2270. The proximal closure tube segment 2230 is coupled to the closure shuttle 2136 for relative rotation thereto. For example, a U shaped connector 2137 is inserted into an annular slot 2231 in the proximal closure tube segment 2230 and is retained within vertical slots in the closure shuttle 2136. Such an arrangement serves to attach the proximal closure tube segment 2230 to the closure shuttle 2136 for axial travel therewith while enabling the proximal closure tube segment 2230 to rotate relative to the closure shuttle 2136 about the shaft axis SA-SA. The proximal closure shuttle 2136 includes hooks 2138 that are adapted to hookingly engage an attachment pin (not shown) that is attached to a second closure link (not shown) that is operably coupled to the closure trigger 2122 as described in detail in U.S. patent application Ser. No. 14/226,075. As described in that reference, actuation of the closure trigger 2122 will distally advance the closure link and apply a distal closure motion to the proximal closure shuttle 2136 and ultimately to the proximal closure tube segment 2230. A closure spring (not shown) is journaled on the proximal closure tube segment 2230 and serves to bias the proximal closure tube segment 2230 in the proximal direction "PD" which can serve to pivot the closure trigger 2122 into the unactuated position when the shaft assembly 2200 is operably coupled to the handle 2102.

The interchangeable shaft assembly 2200 further includes an articulation system 2500 for applying articulation motions to the first and second articulation bars 2510, 2520 that extend through the shaft assembly to operably interface with the end effector 2300. In the illustrated example, the articulation system 2500 further includes an articulation actuator 2550 that is rotatably supported on a nozzle housing 2530 that is supported on the chassis 2270. The nozzle housing may comprise two nozzle segments 2532, 2534 that are coupled together by a plurality of fasteners 2536. The articulation actuator 2550 comprises an articulation knob 2552 that is coupled to an articulation gear assembly 2560 that has an articulation pivot gear 2562 thereon. The articulation pivot gear 2562 is supported in meshing engagement with a first articulation gear rack 2512 that is attached to the first articulation bar 2510 and a second articulation gear rack 2522 that is attached to the second articulation bar 2520. Rotation of the articulation knob 2552 drivingly advances one of the articulation bars 2510, 2520 in a proximal or distal direction and the other of the articulation bars 2510, 2520 in the opposite direction to cause the end effector 2300 to articulate about the articulation axis in the desired direction.

The surgical end effector 2300 includes a firing member in the form of a tissue cutting member (not shown). The interchangeable shaft assembly 2200 also includes a firing rod segment 2570 that is configured to apply firing motions to the firing member. In the illustrated example, the firing rod segment is moved axially through the shaft assembly 2200 by the motor-driven firing system in the various manners described in further detail in the various references incorporated herein.

To prevent inadvertent detachment of the interchangeable shaft assembly 2200 from the handle 2102 when the end effector 2300 is in an articulated orientation, the shaft assembly 2200 further includes a unique and novel lock assembly generally designated as 2580. In the illustrated example, the gear assembly 2560 further includes a locking flange 2564 that has a lock notch 2566 therein. The lock assembly 2580 further includes a lock member 2582 that has pointed or tapered distal end 2584 that is configured for locking engagement with the lock notch 2566. The lock member 2582 is attached to the lock yoke 2282. In the illustrated example the lock member 2582 has an aperture 2588 that is adapted to receive a lock boss 2283 formed on the lock yoke 2282 to facilitate attachment of the lock member 2582 to the lock yoke 2282. See FIG. 26. T In the illustrated example, the articulation knob 2552 is attached to the articulation lock assembly 2560 such that the lock notch 2566 is aligned for locking engagement with the lock member 2582 when the actuator fin portions 2553 of the articulation knob 2552 are axially aligned with the shaft axis A-A. See FIG. 25. When in such arrangement, the fin portions indicate to the clinician that the end effector 2300 is unarticulated and essentially in axial alignment with the shaft axis SA. Also when in that position, the distal end 2584 of the lock member 2582 is received in the lock notch 2566. When in that position, sufficient clearance is provided between the distal end 2584 of the lock member 2582 and the lock notch 2566 to enable the lock yoke 2282 to be moved in the distal direction to thereby detach the interchangeable shaft assembly 2200 from the handle. Thus, when the end effector is in the unarticulated orientation, the shaft assembly 2200 is detachable from the handle or housing.

When the clinician desires to articulate the end effector 2300, the clinician applies a rotary force to the articulation fin portions 2553 that is sufficient to cause rotation of the gear assembly 2560. As gear assembly 2560 is rotated, the lock member 2582 moves in the proximal direction to permit the end 2584 of the lock member 2582 to move out of the lock notch 2566. The end 2584 rides around the rim of the locking flange 2564 during articulation. When in that position, the lock member 2582 prevents the lock yoke 2282 from moving sufficiently far enough in the distal direction to permit detachment of the shaft assembly 2200 from the handle. As such, when the end effector is in an articulated position, the lock yoke is prevented from moving to a detached or unlocked position. This arrangement not only prevents inadvertent detachment of the shaft assembly from the handle (i.e., by accident) but also prevents the clinician from detaching the shaft assembly 2200 using the latch button 2287.

Figure 28:
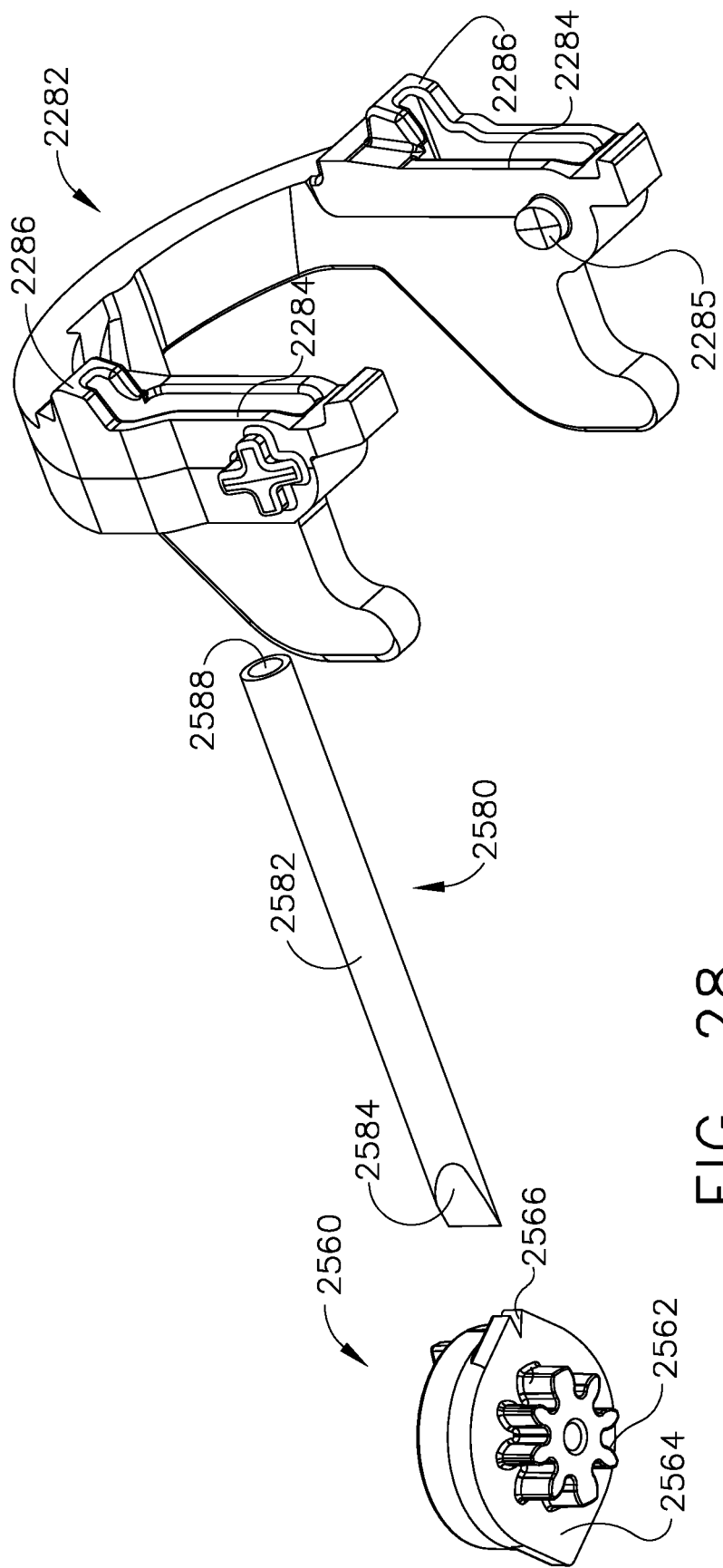
FIG. 28 is an exploded assembly view of portions of a lock assembly of the surgical instrument of FIGS. 25-27.

FIG. 28 is a cross-sectional view through a flexible articulation joint member 2600 of the type, for example, shown in FIG. 25. The joint member comprises a flexible body 2602 that has a centrally disposed passage 2604 that is configured to slidably support a flexible firing beam 2610 therethrough. In this arrangement, the body 2602 includes two upper passages 2606 that are sized and arranged to accommodate a corresponding articulation cable 2620 therethrough. The articulation cables 2620 perform the same functions as the articulation drivers disclosed herein. For example, each of the cables 2620 is attached to or otherwise interface with the surgical end effector. The proximal ends or portions of the cables 2620 interface with an articulation control system for actuating the cables to articulate the end effector. The body 2602 further includes two lower passages 2608 that are adapted to accommodate corresponding portions of a frame assembly 2630. In this example, the frame assembly includes a first frame band 2640 and a second frame band 2650. The bands 2640, 2650 are located on each lateral side of the flexible firing beam 2610 and extend back to the handle or housing. Each band 2640, 2650 may comprise a cantilever spring arm that extends through the corresponding lower passages 2608 and be coupled to or otherwise interface with the end effector. For example, the distal end of each band 2640, 2650 may be attached to corresponding portions of the elongate channel of the end effector. The bands 2640, 2650 will flex to accommodate articulation of the end effector. As can be seen in FIG. 28 however, each band 2640, 2650 is configured for frictional engagement with corresponding portions of the walls 2609 of each of the lower passages 2608. In the illustrated example, each band 2640, 2650 includes a friction lug or formation 2642, 2652 thereon as shown. Such arrangement serves to frictionally retain the body portion 2602 in the articulated orientation.

Figure 29:
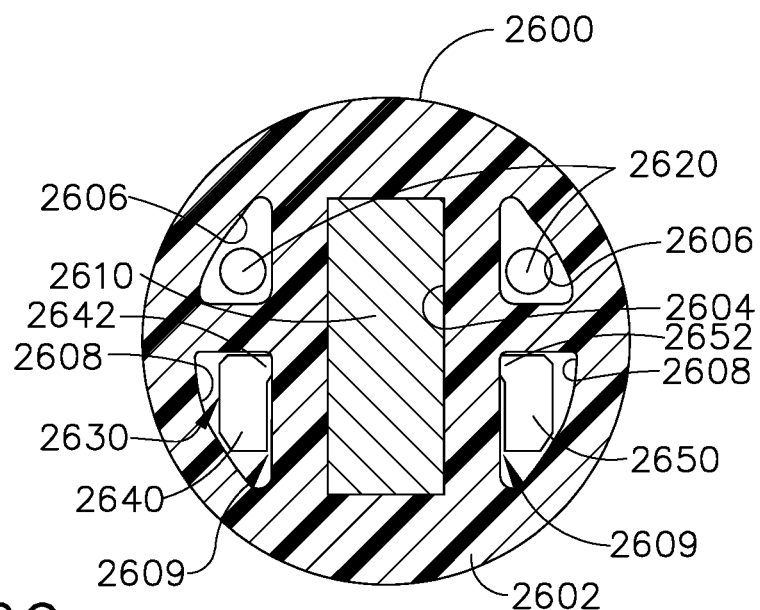
FIG. 29 is a cross-sectional view of an elongate shaft assembly of a surgical instrument.
Figure 30:
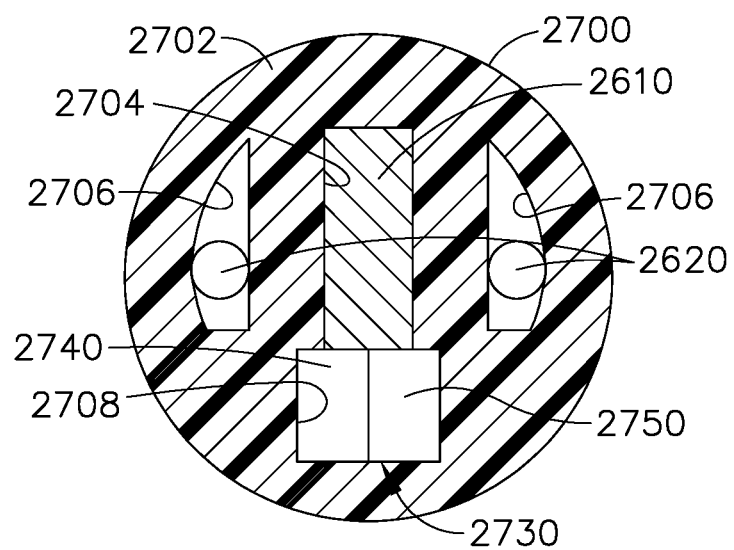
FIG. 30 is a cross-sectional view of another elongate shaft assembly of another surgical instrument.

FIG. 29 is a cross-sectional view through a flexible articulation joint member 2700 of the type, for example, shown in FIG. 25. The joint member comprises a flexible body 2702 that has a centrally disposed passage 2704 that is configured to slidably support a flexible firing beam 2610 therethrough. In this arrangement, the body 2702 includes two lateral passages 2706 that are sized and arranged to accommodate a corresponding articulation cable 2620 therethrough. In the illustrated arrangement, the passages 2706 are sized relative to the cables 2620 such that friction is generated between each cable and the walls of the corresponding passage 2706. The body 2702 further includes a lower passage 2708 that are adapted to accommodate corresponding portions of a frame assembly 2730. In this example, the frame assembly includes a first frame band 2740 and a second frame band 2750. The bands 2740, 2750 are located below the flexible firing beam 2610 and extend back to the handle or housing. Each band 2740, 2750 may comprise a cantilever spring arm that extends through the corresponding lower passages 2708 and be coupled to or otherwise interface with the end effector. For example, the distal end of each band 2740, 2750 may be attached to corresponding portions of the elongate channel of the end effector. The bands 2740, 7650 will flex to accommodate articulation of the end effector. As can be seen in FIG. 29, the bands 2740, 2750 are in frictional engagement with the firing beam 2610 as well as with the walls of the lower passage 2708. Such arrangement serves to frictionally retain the body portion 2702 in the articulated orientation.

Figure 31:
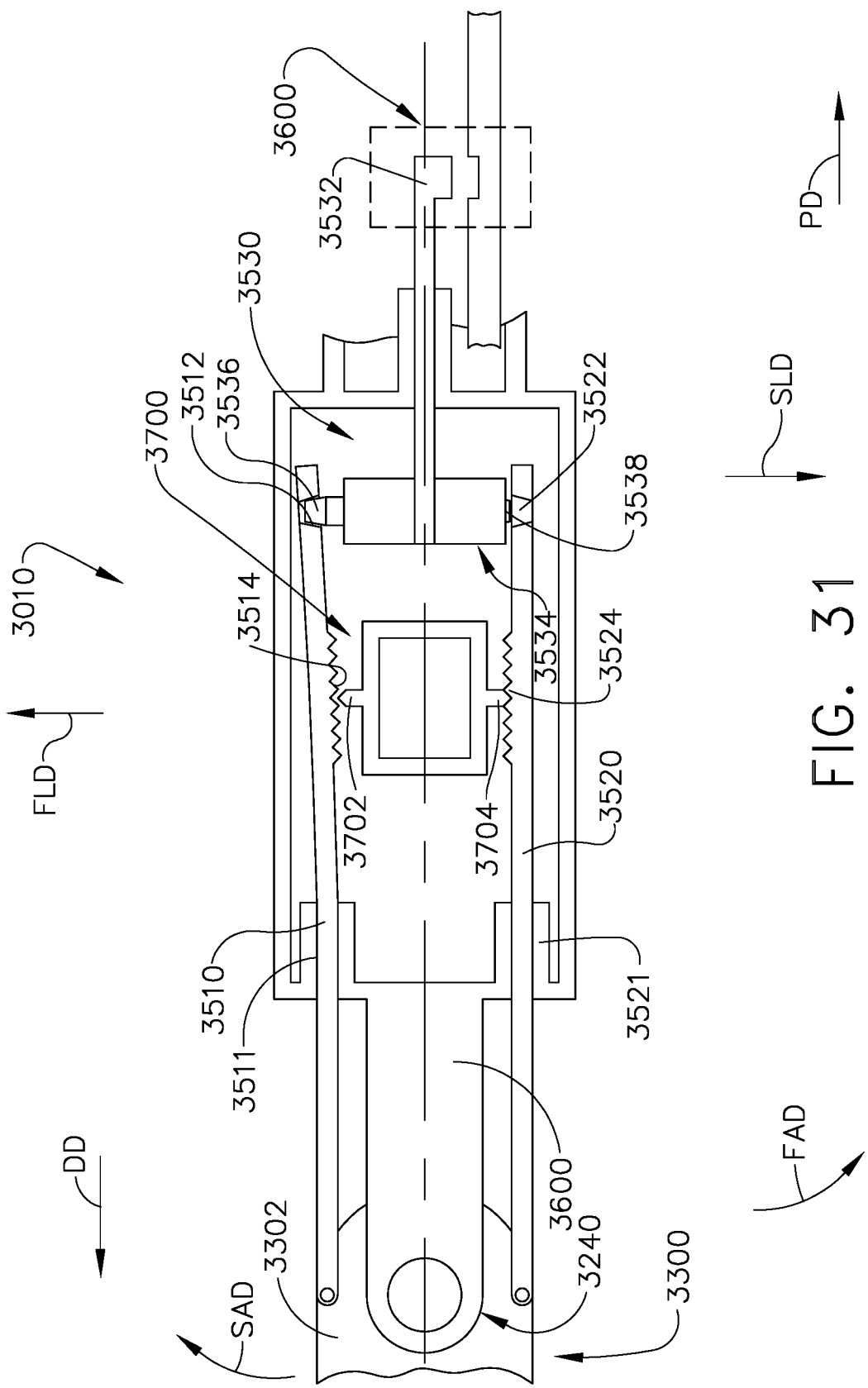
FIG. 31 is a diagrammatical view of a portion of another surgical instrument.

FIG. 31 illustrates in somewhat diagrammatical form, a surgical instrument 3010 with an articulatable end effector 3300 that employs a unique and novel articulation system 3500 for articulating the end effector 3300 about an articulation joint generally designated as 3240. In particular, the surgical instrument 3010 includes a frame assembly 3600 that is attached to the elongate channel 3302 of the surgical end effector 3300 such that the surgical end effector 3300 may be selectively articulated about the articulation joint 3240. The articulation system 3500 includes a first articulation member or bar 3510 and a second articulation member or bar 3520. Each of the first and second articulation bars 3510, 3520 are attached to the elongate channel 3302 of the surgical end effector 3300 and are arranged for axial movement relative to the frame assembly 3600. For example, the first articulation bar 3510 may be supported for axial movement relative to the frame assembly 3600 by a first bearing 3511 and the second articulation bar 3520 may be supported for axial movement relative to the frame assembly 3600 by a second bearing 3521.

The surgical end effector 3300 may comprise a surgical cutting and stapling device and include a firing member (not shown) that is configured for axial travel within the end effector 3300 as is taught in many of the references that have been herein incorporated by reference. The surgical instrument 3010 is equipped with a firing member or rod 3560 that is configured to move axially in response to drive motions from a firing drive system of the various types disclosed herein as well as disclosed in the various references incorporated herein. The articulation system 3500 as generally depicted in FIG. 31 includes an articulation drive assembly 3530 that is configured to operably interface with firing drive system to receive firing motions therefrom. For example, the articulation driver 3532 of the articulation drive assembly 3530 may operably interface with the firing rod 3560 through a switching or clutching arrangement 3600 of the type disclosed herein and/or in the referenced incorporated herein. Thus, when in the switching arrangement 3600 is in the "articulation mode", operation of the firing drive is transferred to the articulation driver 3532 to apply an axial articulation motion thereto. When the switching arrangement 3600 is in the "firing mode", actuation of the firing drive will result in the axial advancement of the firing member within the surgical end effector 3300.

As can be further seen in FIG. 31, the articulation drive assembly 3532 further includes a dual-acting solenoid assembly 3534 that is attached to the articulation driver 3532. The solenoid assembly 3534 includes articulation engagement member 3536 that is arranged for selective driving engagement with a portion of the first articulation driver 3510. In addition, the solenoid assembly 3534 includes a second articulation engagement member 3538 that is arranged for selective driving engagement with the second articulation bar 3520. For example, FIG. 31 illustrates a portion of the first driver 3536 received in a first drive aperture 3512 in the first articulation driver 3510. A similar second drive aperture 3522 is shown in the second articulation driver 3520, however, in FIG. 31, the second driver 3538 is in a retracted or disengaged position. Other arrangements for drivingly engaging and disengaging the articulation drive assembly 3530 may also be employed. Thus, when the first articulation engagement member 3536 is in driving engagement with the first articulation driver 3510, actuation of the firing drive system will result in the axial advancement of the first articulation driver 3510 and when the second articulation engagement member 3538 is in driving engagement with the second articulation driver 3520, actuation of the firing drive system will result in the axial advancement of the second articulation driver 3520.

As was discussed in further detail herein, it may be desirable for the surgical instrument to employ means for locking the articulation drivers in position prior to use of the device and/or after the end effector has been articulated into a desired position. To that end, the surgical instrument 3010 is shown with an articulation lock system 3700. The articulation lock system 3700 comprises a first lock member 3702 configured for locking engagement with a first serrated or toothed locking portion 3514 of the first articulation driver 3510 and a second lock member 3704 configured for locking engagement with a second toothed or locking portion 3524 of the second articulation driver 3520. When the first lock member 3702 is engaged with the first serrated portion 3514 of the first articulation driver 3510, the first articulation driver 3510 will be retained in that axial position. Similarly, when the second lock member 3704 is engaged with the second serrated portion 3524 of the second articulation driver 3520, the second articulation driver 3520 will be retained in that axial position.

FIG. 31 illustrates the first articulation engagement member 3536 in driving engagement with the aperture 3512. As can be seen in that Figure, at least a corresponding portion 3516 of the first articulation driver 3510 is moved laterally in the first lateral direction "FLD" such that the first serrated portion 3514 is moved out of engagement with the first locking member 3702. As can also be seen in FIG. 31, the second articulation engagement member 3538 is retracted out of engagement with the articulation aperture 3522. When in that position, the first articulation driver 3510 is in an unlocked orientation and is free to be axially advanced in the distal direction "DD" to articulate the surgical end effector 3300 in a first articulation direction "FAD" about the articulation joint 3240. As the first articulation driver 3510 is moved distally, the second articulation driver 3520 necessarily will move in the proximal direction "PD" due to its connection to the elongate channel 3302 of the surgical end effector 3300. Such proximal movement of the second articulation driver 3520 will be accommodated by the second lock member 3704 "bumping" or riding or slipping over the corresponding serrations 3524. Likewise, to articulate the surgical end effector in a second articulation direction "SAD" about the articulation joint 3240, the first articulation engagement member 3536 is retracted out of engagement with the first articulation aperture 3512 and the second articulation engagement member 3538 is moved laterally in the second lateral direction "SLD" into engagement with the second articulation aperture 3522 to bias or otherwise move the second serrated portion 3524 of the second articulation driver 3520 out of engagement with the second lock member 3707. When in that position, the second articulation driver 3520 is in an unlocked orientation and is free to be axially advanced in the distal direction "DD" to articulate the surgical end effector 3300 in a second articulation direction "SAD" about the articulation joint 3240. As the second articulation driver 3520 is moved distally, the first articulation driver 3510 necessarily will move in the proximal direction "PD" due to its connection to the elongate channel 3302 of the surgical end effector 3300. Such proximal movement of the first articulation driver 3510 will be accommodated by the first lock member 3702 "bumping" or riding or slipping over the corresponding serrations 3514.

Figure 32:
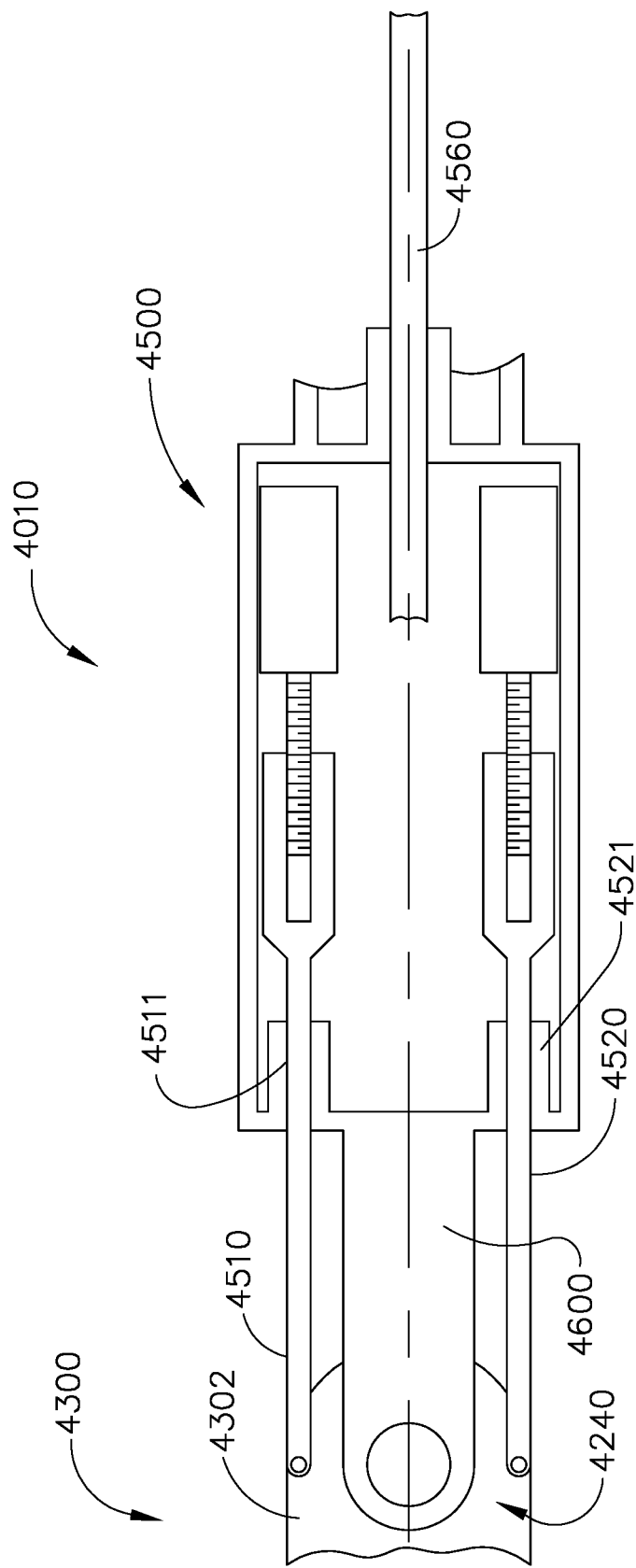
FIG. 32 is a diagrammatical view of a portion of another surgical instrument.

FIG. 32 illustrates in somewhat diagrammatical form, a surgical instrument 4010 with an articulatable end effector 4300 that employs a unique and novel articulation system 4500 for articulating the end effector 4300 about an articulation joint generally designated as 4240. In particular, the surgical instrument 4010 includes a frame assembly 4600 that is attached to the elongate channel 4302 of the surgical end effector 4300 such that the surgical end effector 4300 may be selectively articulated about the articulation joint 4240. The articulation system 4500 includes a first articulation member or bar 4510 and a second articulation member or bar 4520. Each of the first and second articulation bars 4510, 4520 are attached to the elongate channel 4302 of the surgical end effector 4300 and are arranged for axial movement relative to the frame assembly 4600. For example, the first articulation bar 4510 may be supported for axial movement relative to the frame assembly 4600 by a first bearing 4511 and the second articulation bar 4520 may be supported for axial movement relative to the frame assembly 4600 by a second bearing 4521.

The surgical end effector 4300 may comprise a surgical cutting and stapling device and include a firing member (not shown) that is configured for axial travel within the end effector 4300 as is taught in many of the references that have been herein incorporated by reference. The surgical instrument 4010 is equipped with a firing member or rod 4560 that is configured to move axially in response to drive motions from a firing drive system of the various types disclosed herein as well as the various references incorporated herein. The articulation system 4500 as generally depicted in FIG. 32 includes a first articulation drive motor 4530 that is configured to operably interface with the first articulation driver 4510 such that operation of the first articulation motor in one direction results in axial advancement of the first articulation bar 4510 in the distal direction "DD" and operation of the first articulation drive system in an opposite direction results in the axial movement of the first articulation bar 4510 in a proximal direction "PD". Similarly, the articulation system 4500 further comprises a second articulation drive motor 4540 that is configured to operably interface with the second articulation driver 4520 such that operation of the second articulation drive motor 4540 in one direction will result in the axial advancement of the second articulation driver in the distal direction "DD" and operation of the second articulation motor in an opposite direction will result in the axial advancement of the second articulation driver in the proximal direction "PD". The first and second articulation drive motors 4530, 4540 are controlled by a control circuit and controller arrangement, such that when one of the drive motors 4530 is operated to drive the articulation driver operably attached thereto in one axial direction for a first axial distance, the other articulation drive motor is operated in an opposite direction to move the other articulation driver operably coupled thereto in an opposite axial direction for a second axial distance that is equal to the first axial distance to accommodate articulation of the surgical end effector.

EXAMPLES

Example 1

A shaft assembly for a surgical instrument that comprises a movable drive member wherein the shaft assembly comprises a spine assembly that is operably couplable to the surgical instrument. A surgical end effector is coupled to the spine assembly by an articulation joint. A proximal firing member interfaces with the movable drive member and is supported for movable travel relative to the spine assembly. An intermediate firing member is supported for movable travel relative to the spine assembly and a distal firing member interfaces with the intermediate firing member and is supported for selective axial travel through at least a portion of the surgical end effector. An articulation driver interfaces with the end effector to apply articulation motions thereto. The surgical instrument further comprises a clutch system that is selectively movable between an articulation orientation and a firing orientation such that when the clutch system is in the articulation orientation, movement of the movable drive member is transmitted to the articulation driver through the proximal firing member and when the clutch system is in the firing orientation, movement of the movable drive member is transmitted to the distal firing member through the proximal firing member and the intermediate firing member.

Example 2

The shaft assembly of Example 1, wherein the intermediate firing member is coupled to the proximal firing member such that when the clutch system is in the articulation orientation, the proximal firing member is movable relative to the intermediate firing member and when the clutch system is in the firing orientation, the intermediate firing member moves axially with the proximal firing member.

Example 3

The shaft assembly of Example 2, wherein the intermediate firing member is coupled to the proximal firing member by a coupler comprising a proximal coupler end attached to a distal end of the proximal firing member and distal coupler end spaced from the proximal coupler end to define an enclosed axial passage therebetween for movably receiving a proximal end of the intermediate firing member therein.

Example 4

The shaft assembly of Example 3, wherein the clutch system comprises an engagement member that is supported for rotational travel around an outer perimeter of the coupler and wherein the articulation driver is coupled to the engagement member for axial travel therewith. A first proximal detent and a first distal detent are located on the engagement member. The first distal detent is spaced from the first proximal detent and is oriented in axial alignment therewith. The clutch system further comprises a first axial groove in an outer surface of the coupler such that when the first proximal and distal detents are aligned with the first axial groove, the coupler is axially movable relative to the engagement member and when the first proximal and distal detents are misaligned from the first axial groove, axial movement of the coupler in a distal direction will move the articulation driver in the distal direction and movement of the coupler in a proximal direction will move the articulation driver in the proximal direction.

Example 5

The shaft assembly of Example 4, wherein the shaft assembly further comprises a second proximal detent on the engagement member diametrically opposed from the first proximal detent. The shaft assembly further comprises a second distal detent on the engagement member diametrically opposed from the first distal detent and axially aligned with the second proximal detent. A second axial groove is provided in the outer surface of the coupler in an orientation that it is diametrically opposite from the first axial groove, such that when the first proximal and distal detents are misaligned with the first axial groove, the second proximal and distal detents are misaligned with the second axial groove and when the first proximal and distal detents are axially aligned with the first axial groove, the second proximal and distal detents are axially aligned with the second axial groove.

Example 6

The shaft assembly of Examples 4 or 5, wherein the articulation driver comprises a tab on a proximal end of the articulation driver that is received within an annular groove in a perimeter of the engagement member to facilitate rotation of the engagement member relative to the articulation driver.

Example 7

The shaft assembly of Example 5 further comprising means for rotating the engagement member on the coupler between the articulation orientation wherein the first proximal and distal detents are aligned with the first axial groove and the second proximal and distal detents are aligned with the second axial groove and the firing orientation wherein the first proximal and distal detents are not aligned with the first axial groove and the second proximal and distal detents are not aligned with the second axial groove.

Example 8

The shaft assembly of Examples 1, 2, 3, 4, 5, 6 or 7 wherein the surgical end effector comprises a first jaw coupled to the articulation joint and a second jaw that is supported adjacent to the first jaw. The first and second jaws are supported relative to each other such that one of the first and second jaws is selectively movable toward and away from the other of the first and second jaws between open and closed positions by axial travel of a closure member interfacing therewith.

Example 9

The shaft assembly of Example 8, wherein the means for rotating comprises an actuation member that is supported on the engagement member such that rotation of the actuation member causes rotation of the engagement member. The means for rotating further comprising a cam pin that is located on the actuation member and is configured to interface with a cam slot in the closure member such that when the closure member is in an unactuated position corresponding to the open position of the first and second jaws, the cam pin permits the engagement member to be biased into the articulation position and when the closure member is in an actuated position corresponding to the closed positions of the first and second jaws, the clam slot causes the cam pin to rotate the actuation member and the engagement member to the firing position.

Example 10

The shaft assembly of Example 9, further comprising a switch drum that interfaces with the actuation member to send a signal to a control circuit in the surgical instrument when the engagement member is in the firing orientation.

Example 11

A shaft assembly for a surgical instrument comprising a movable drive member, the shaft assembly comprising a spine assembly that is operably couplable to the surgical instrument. A surgical end effector is coupled to the spine assembly by an articulation joint. A proximal firing member interfaces with the movable drive member and is supported for movable travel relative to the spine assembly. A distal firing member interfaces with the proximal firing member and is supported for selective axial travel through at least a portion of the surgical end effector. At least one articulation driver interfaces with the end effector to apply articulation motions thereto. An articulation motor is supported by the spine assembly and drivingly interfaces with the at least one articulation driver. The shaft assembly further comprises means for preventing actuation of the movable drive member when the articulation motor is being actuated.

Example 12

The shaft assembly of Example 11, wherein the movable drive member is actuated by a firing motor and wherein the means for preventing actuation comprises a switch assembly that comprises a slip ring assembly that communicates with a control circuit for the surgical instrument. The control circuit communicates with the firing motor and the articulation motor. A switch drum is supported for movable travel on the frame assembly between a first position that corresponds to an articulation position and a second position that corresponds to a firing position such that when the switch drum is in the second position, the slip ring assembly communicates a firing status of the switch drum to the control circuit which enables the firing motor to be actuated and when the switch drum is in the first position, the control circuit prevents actuation of the firing motor and permits actuation of the articulation motor.

Example 13

The shaft assembly of Example 12 further comprising means for moving the switch drum between the first and second positions.

Example 14

The shaft assembly of Example 13, wherein the means for moving the switch drum comprises a spring member that is configured to bias the switch drum into the first position.

Example 15

The shaft assembly of Examples 11, 12, 13 or 14, wherein the surgical end effector comprises a first jaw that is coupled to the articulation joint and a second jaw that is supported adjacent to the first jaw. The first and second jaws are supported relative to each other such that one of the first and second jaws is selectively movable toward and away from the other of the first and second jaws between open and closed positions by axial travel of a closure member that interfaces therewith.

Example 16

The shaft assembly of Example 15, wherein the means for moving the switch drum further comprises a cam pin that is located on the switch drum and interfaces with a cam slot in the closure member such that when the closure member is in an unactuated position that corresponds to the open position of the first and second jaws, the cam pin permits the switch drum to be biased into the articulation position by the spring and when the closure member is in an actuated position that corresponds to the closed positions of the first and second jaws, the clam slot causes the cam pin to move the switch drum to the second position.

Example 17

The shaft assembly of Examples 11, 12, 13, 14, 15 or 16, wherein the at least one articulation driver comprises first and second articulation drivers that interface with the articulation motor such that actuation of the articulation motor drives the first and second articulation drivers in opposite directions.

Example 18

The shaft assembly of Example 17, further comprising means for supporting distal portions of the first and second articulation drivers during actuation thereof in opposite directions.

Example 19

The shaft assembly of Example 18, wherein the means for supporting comprises a distal idler gear that is centrally disposed between the distal portions of the first and second articulation drivers and in meshing engagement therewith.

Example 20

The shaft assembly of Examples 18 or 19, wherein the shaft assembly further comprises a first detent tooth that protrudes inwardly from the closure member into engagement with a first serrated portion of the first articulation driver. The shaft assembly further comprising a second detent tooth that protrudes inwardly from the closure member into engagement with a second serrated portion of the second articulation driver.

The entire disclosures of:

U.S. Pat. No. 5,403,312, entitled ELECTROSURGICAL HEMOSTATIC DEVICE, which issued on Apr. 4, 1995;

U.S. Pat. No. 7,000,818, entitled SURGICAL STAPLING INSTRUMENT HAVING SEPARATE DISTINCT CLOSING AND FIRING SYSTEMS, which issued on Feb. 21, 2006;

U.S. Pat. No. 7,422,139, entitled MOTOR-DRIVEN SURGICAL CUTTING AND FASTENING INSTRUMENT WITH TACTILE POSITION FEEDBACK, which issued on Sep. 9, 2008;

U.S. Pat. No. 7,464,849, entitled ELECTRO-MECHANICAL SURGICAL INSTRUMENT WITH CLOSURE SYSTEM AND ANVIL ALIGNMENT COMPONENTS, which issued on Dec. 16, 2008;

U.S. Pat. No. 7,670,334, entitled SURGICAL INSTRUMENT HAVING AN ARTICULATING END EFFECTOR, which issued on Mar. 2, 2010;

U.S. Pat. No. 7,753,245, entitled SURGICAL STAPLING INSTRUMENTS, which issued on Jul. 13, 2010;

U.S. Pat. No. 8,393,514, entitled SELECTIVELY ORIENTABLE IMPLANTABLE FASTENER CARTRIDGE, which issued on Mar. 12, 2013;

U.S. Pat. No. 7,845,537, entitled SURGICAL INSTRUMENT HAVING RECORDING CAPABILITIES; which issued on Dec. 7, 2010;

U.S. patent application Ser. No. 12/031,573, entitled SURGICAL CUTTING AND FASTENING INSTRUMENT HAVING RF ELECTRODES, filed Feb. 14, 2008;

U.S. Pat. No. 7,980,443, entitled END EFFECTORS FOR A SURGICAL CUTTING AND STAPLING INSTRUMENT, which issued on Jul. 19, 2011;

U.S. Pat. No. 8,210,411, entitled MOTOR-DRIVEN SURGICAL CUTTING INSTRUMENT, which issued on Jul. 3, 2012;

U.S. Pat. No. 8,608,045, entitled POWERED SURGICAL CUTTING AND STAPLING APPARATUS WITH MANUALLY RETRACTABLE FIRING SYSTEM, which issued on Dec. 17, 2013;

U.S. Pat. No. 8,220,688, entitled MOTOR-DRIVEN SURGICAL CUTTING INSTRUMENT WITH ELECTRIC ACTUATOR DIRECTIONAL CONTROL ASSEMBLY, which issued on Jul. 17, 2012;

U.S. Pat. No. 8,733,613, entitled STAPLE CARTRIDGE, which issued on May 27, 2014;

U.S. Pat. No. 8,561,870, entitled SURGICAL STAPLING INSTRUMENT, which issued on Oct. 22, 2013;

U.S. Patent Application Publication No. 2012/0298719, entitled SURGICAL STAPLING INSTRUMENTS WITH ROTATABLE STAPLE DEPLOYMENT ARRANGEMENTS, filed on May 27, 2011, now U.S. Pat. No. 9,072,535;

U.S. Patent Application Publication No. 2013/0334278, entitled ARTICULATABLE SURGICAL INSTRUMENT COMPRISING A FIRING DRIVE, filed on Jun. 15, 2012, now U.S. Pat. No. 9,101,358;

U.S. patent application Ser. No. 13/800,025, entitled STAPLE CARTRIDGE TISSUE THICKNESS SENSOR SYSTEM, filed on Mar. 13, 2013, now U.S. Pat. No. 9,345,481;

U.S. patent application Ser. No. 13/800,067, entitled STAPLE CARTRIDGE TISSUE THICKNESS SENSOR SYSTEM, filed on Mar. 13, 2013, now U.S. Patent Application Publication No. 2014/0263552;

U.S. Patent Application Publication No. 2007/0175955, entitled SURGICAL CUTTING AND FASTENING INSTRUMENT WITH CLOSURE TRIGGER LOCKING MECHANISM, filed Jan. 31, 2006; and U.S. Pat. No. 8,308,040, entitled SURGICAL STAPLING INSTRUMENT WITH AN ARTICULATABLE END EFFECTOR, which issued on Nov. 13, 2012, are hereby incorporated by reference herein.

Although the various embodiments of the devices have been described herein in connection with certain disclosed embodiments, many modifications and variations to those embodiments may be implemented. Also, where materials are disclosed for certain components, other materials may be used. Furthermore, according to various embodiments, a single component may be replaced by multiple components, and multiple components may be replaced by a single component, to perform a given function or functions. The foregoing description and following claims are intended to cover all such modification and variations.

With respect to the use of substantially any plural and/or singular terms herein, those having skill in the art can translate from the plural to the singular and/or from the singular to the plural as is appropriate to the context and/or application. The various singular/plural permutations are not expressly set forth herein for sake of clarity.

The herein described subject matter sometimes illustrates different components contained within, or connected with, different other components. It is to be understood that such depicted architectures are merely exemplary, and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components, and/or wirelessly interactable, and/or wirelessly interacting components, and/or logically interacting, and/or logically interactable components.

Although various embodiments have been described herein, many modifications, variations, substitutions, changes, and equivalents to those embodiments may be implemented and will occur to those skilled in the art. Also, where materials are disclosed for certain components, other materials may be used. It is therefore to be understood that the foregoing description and the appended claims are intended to cover all such modifications and variations as falling within the scope of the disclosed embodiments. The following claims are intended to cover all such modification and variations.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the invention described herein will be processed before surgery. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

In summary, numerous benefits have been described which result from employing the concepts described herein. The foregoing description of the one or more embodiments has been presented for purposes of illustration and description. It is not intended to be exhaustive or limiting to the precise form disclosed. Modifications or variations are possible in light of the above teachings. The one or more embodiments were chosen and described in order to illustrate principles and practical application to thereby enable one of ordinary skill in the art to utilize the various embodiments and with various modifications as are suited to the particular use contemplated. It is intended that the claims submitted herewith define the overall scope.

What is claimed is:

1. A shaft assembly configured to be removably connectable to a handle assembly of a surgical instrument, the shaft assembly comprising:
    an end effector pivotable between an unarticulated position and a plurality of articulated positions; and
    an articulation drive assembly comprising:
        a first articulation member coupled to the end effector, the first articulation member longitudinally movable from a first position to a second position to pivot the end effector in a first direction;
        a second articulation member coupled to the end effector, the second articulation member longitudinally movable from a third position to a fourth position to pivot the end effector in a second direction;
        an articulation lock system configured to engage with and thereby longitudinally retain at least one of the first articulation member or the second articulation member; and
        an articulation driver configured to selectively disengage either the first articulation member from the articulation lock system such that the first articulation member is longitudinally movable to pivot the end effector or the second articulation member from the articulation lock system such that the second articulation member is longitudinally movable to pivot the end effector.

2. The shaft assembly of claim 1, wherein the articulation lock system comprises:
    a first lock configured to engage with and thereby longitudinally retain the first articulation member; and
    a second lock configured to engage with and thereby longitudinally retain the second articulation member;
    wherein the articulation driver is configured to selectively disengage the first articulation member from the first lock or the second articulation member from the second lock.

3. The shaft assembly of claim 2, wherein each of the first lock and the second lock comprise a lock member configured to frictionally engage a serrated portion disposed on the respective first articulation member or the second articulation member.

4. The shaft assembly of claim 3, wherein articulation of the first articulation member from the first position to the second position causes the lock member of the second lock to slip over the serrated portion of the second articulation member.

5. The shaft assembly of claim 3, wherein the articulation driver is configured to flex the first articulation member or the second articulation member out of engagement with the first lock or the second lock respectively.

6. The shaft assembly of claim 1, wherein the articulation driver comprises a dual-acting solenoid.

7. The shaft assembly of claim 1, wherein the first position and the third position are proximal positions and the second position and the fourth position are distal positions.

8. The shaft assembly of claim 1, wherein the first articulation member and the second articulation member comprise cables.

9. The shaft assembly of claim 1, wherein the articulation drive assembly is positioned adjacently to an articulation joint about which the end effector pivots.

10. The shaft assembly of claim 1, wherein the first articulation member and the second articulation member comprise bars.

11. A shaft assembly configured to be removably connectable to a handle assembly of a surgical instrument, the shaft assembly comprising:
an end effector pivotable between an unarticulated position and a plurality of articulated positions; and
an articulation drive assembly comprising:
a first articulation member coupled to the end effector, the first articulation member longitudinally movable from a first position to a second position to pivot the end effector in a first direction;
a first motor comprising a first drive shaft threadably coupled to the first articulation member, the first motor configured to drive the first articulation member between the first position and the second position based on rotations of the first drive shaft;
a second articulation member coupled to the end effector, the second articulation member longitudinally movable from a third position to a fourth position to pivot the end effector in a second direction; and
a second motor comprising a second drive shaft threadably coupled to the second articulation member, the second motor configured to drive the second articulation member between the third position and the fourth position based on rotations of the second drive shaft;
wherein the first motor and the second motor are configured to selectively advance the first articulation member and the second articulation member respectively.

12. The shaft assembly of claim 11, further comprising a control circuit configured to selectively control the first motor and the second motor to drive the first articulation member and the second articulation member.

13. The shaft assembly of claim 11, wherein the first position and the third position are proximal positions and the second position and the fourth position are distal positions.

14. The shaft assembly of claim 11, wherein the first articulation member and the second articulation member comprise cables.

15. The shaft assembly of claim 11, wherein the articulation drive assembly is positioned adjacently to an articulation joint about which the end effector pivots.

16. The shaft assembly of claim 11, wherein the first articulation member and the second articulation member comprise bars.

17. A surgical instrument comprising:
a shaft assembly that is configured to be removably connectable to a handle assembly of the surgical instrument;
an articulation joint;
an end effector attached to the shaft assembly at the articulation joint, the end effector pivotable between an unarticulated position and a plurality of articulated positions about the articulation joint; and
an articulation drive assembly housed within the shaft assembly, the articulation drive assembly comprising:
a first articulation member coupled to the end effector, the first articulation member longitudinally movable from a first position to a second position to pivot the end effector about the articulation joint in a first direction;
a second articulation member coupled to the end effector, the second articulation member longitudinally movable from a third position to a fourth position to pivot the end effector about the articulation joint in a second direction;
an articulation lock system configured to longitudinally retain at least one of the first articulation member or the second articulation member; and
an articulation driver configured to selectively disengage either the first articulation member from the articulation lock system such that the first articulation member is longitudinally movable to pivot the end effector or the second articulation member from the articulation lock system such that the second articulation member is longitudinally movable to pivot the end effector.

18. The shaft assembly of claim 17, wherein the articulation lock system comprises:
a first lock configured to engage with and thereby longitudinally retain the first articulation member; and
a second lock configured to engage with and thereby longitudinally retain the second articulation member;
wherein the articulation driver is configured to selectively disengage the first articulation member from the first lock or the second articulation member from the second lock.

19. The shaft assembly of claim 17, wherein the first position and the third position are proximal positions and the second position and the fourth position are distal positions.

20. The shaft assembly of claim 17, wherein the first articulation member and the second articulation member comprise cables.

21. The shaft assembly of claim 17, wherein the articulation drive assembly is positioned within the shaft assembly adjacently to the articulation joint.

22. The shaft assembly of claim 17, wherein the first articulation member and the second articulation member comprise bars.

* * * * *